United States Patent [19]
Clauser

[11] Patent Number: 5,812,629
[45] Date of Patent: Sep. 22, 1998

[54] ULTRAHIGH RESOLUTION INTERFEROMETRIC X-RAY IMAGING

[76] Inventor: John F. Clauser, 817 Hawthorne Dr., Walnut Creek, Calif. 94596-6112

[21] Appl. No.: 846,742

[22] Filed: Apr. 30, 1997

[51] Int. Cl.$^6$ .............................. G01N 23/04; A61B 6/03
[52] U.S. Cl. .................................. 378/62; 378/7; 378/37
[58] Field of Search .............................. 378/2, 7, 37, 62, 378/71, 145, 147

[56] References Cited

U.S. PATENT DOCUMENTS

| | | | |
|---|---|---|---|
| 4,651,002 | 3/1987 | Anno | 250/336.1 |
| 4,677,681 | 6/1987 | Klausz | 382/6 |
| 5,684,851 | 11/1997 | Kurbatov et al. | 378/87 |

*Primary Examiner*—David P. Porta
*Assistant Examiner*—David Vernon Bruce

[57] ABSTRACT

The Invention provides practical apparatus and methods for significant improvements to conventional radiography practice. It can image objects having negligible x-ray absorption contrast e.g. otherwise x-ray transparent low-Z artifacts such as human soft-tissue, by obtaining edge-enhanced contrast from an object's (BDY) x-ray refractive-index gradients. In mammography, the contrast of small micro-calcifications is increased typically 4-fold, or more. It can be "tuned" to obtain element-selective refractive-index enhanced contrast to resonantly image minute quantities of a specific element with $Z \approx 35-56$ and only that element. With only a single brief x-ray exposure it can produce two independent images, e.g. of the object's x-ray absorption and refractive-index distributions. It virtually eliminates the blurring and contrast reducing effects of x-ray scatter, especially of very small-angle scatter. It does not use a Bucky grid, and the associated increase in effective detector quantum efficiency results in a significant decrease in image quantum mottle. It can produce CT scan 3D images with a much reduced scanning time. The Invention provides radiograms with greatly improved resolution, contrast and versatility, and edge-enhanced features. It operates via the fractional Talbot effect using two pre-object microfabricated gratings (G1, G2) and a detector (D) preferably containing a periodic pixel array. It further includes an in-situ laser interferometer for aligning the gratings (G1, G2) to the detector (D). While the Invention has a wide range of application, it is ideally suited for medical imaging of biological soft-tissue, and especially for mammography, angiography, and CT (or CAT) scans.

100 Claims, 28 Drawing Sheets

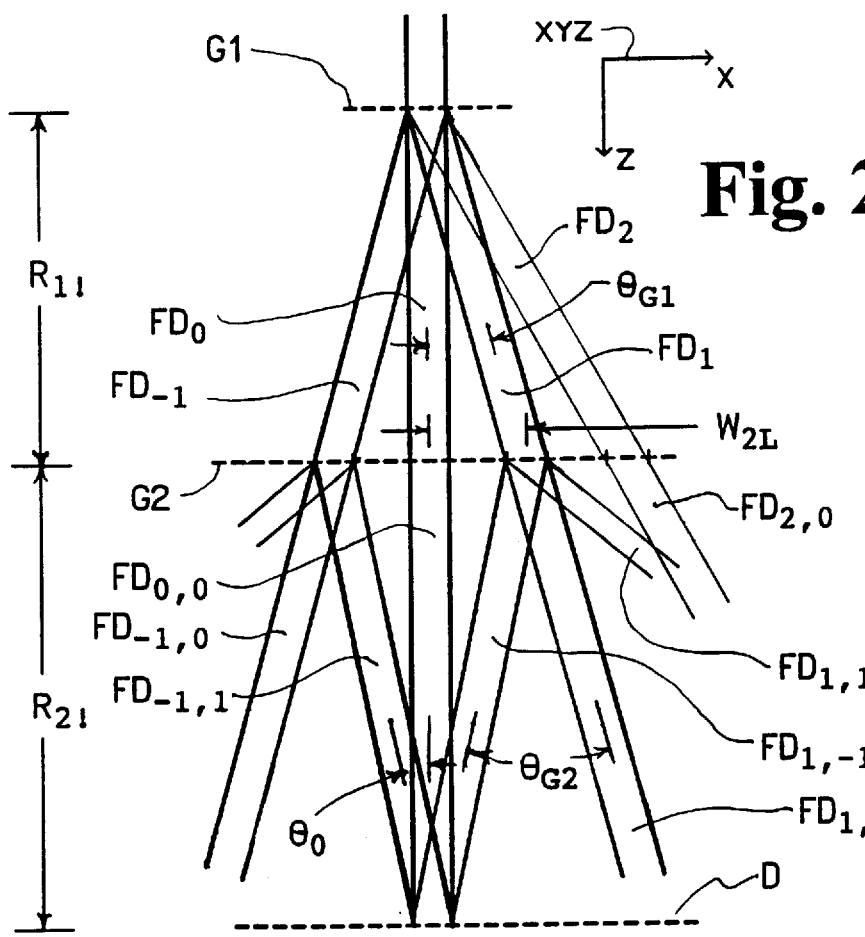

ULTRAHIGH RESOLUTION INTERFEROMETRIC X-RAY IMAGING

TABLE OF CONTENTS

References cited
Part I. Technical field of the Invention
I.1 Notation and mathematical definitions
I.2 General physics background
Part II.
II.1 Prior art for reducing of scatter-induced image blur
II.2 Prior art for refractive-index imaging
II.3 Prior art for x-ray element-selective imaging
Part III. Disclosure
III.1 The Invention's teaching
III.2 Calculation of pattern Q using physical optics principles
III.3 Action of grating G2 when configured as a binary absorption grating
III.4 Action of grating G2 when configured as a phase grating
III.5 Action of grating G1
III.6 Harmonically matching the phase and period of pattern P to the detector pixel array
   III.6.1 Detector pixel, grating G3, and resolution-element layouts
   III.6.2 Pattern P' and image subtraction under the absorption contrast methodology
   III.6.3 Design requirements for period and phase harmonic matching
   III.6.4 Catalog selection of $a_D$
III.7 Refractive-index-gradient contrast methodology
III.8 Element-selective contrast methodology
III.9 Obtaining two independent images from one exposure
III.10 Apparatus alignment system
   III.10.1 Alignment system components
   III.10.2 Operational principles of the optical interferometer
   III.10.3 Alignment methods
Part IV: Brief descriptions of the drawings
Part V. Preferred Embodiments
V.1 The Invention's parameter window
V.2 Apparatus dimensional and temperature stability
V.3 X-ray tubes and filters
V.4 Grating structures and their fabrication
V.5 Available detector sizes
V.6 Variant detector configuration using continuous detector media
V.7 Positionally scanned configurations
Part VI. Industrial applicability
Part VII. Abstract
Part VIII. Claims

REFERENCES CITED

U.S. PATENT DOCUMENTS:
Anno, U.S. Pat. No. 4,651,002.
Barnea, U.S. Pat. No. 4,433,427.
Ema U.S. Pat. Nos. 4,688,242 and 4,837,796.
OTHER PUBLICATIONS:
M. V. Bazylenko and M. Gross (1996). J. Vac. Sci. Technol. A, 14(6), November/December.
M. V. Berry and S. Klein (1996). J. Mod. Opt., 43, 2139–2164.
F. Biggs and R. Lighthill (1971). *Analytical approximations for x-ray cross sections II* (Sandia Laboratory report SC-RR-71 0507).
M. M. Blouke (1995). Photonics Spectra, November 118–120.
U. Bonse and H. Hellkötter (1969). Z. Physik, 223, 345–352; see also U. Bonse (1969), in *Vth international congress on x-ray optics and microanalysis,* ed. by G. M öllenstedt and K. H. Gaukler (Springer Verlag, Berlin) pp.1–10.
M. Born and E. Wolf (1967). *Principles of Optics* (Pergamon Press, Oxford).
J. F. Clauser and M. W. Reinsch (1992). Appl. Phys., B54, 380–395.
J. F. Clauser and S. Li (1997), in *Atom Interferometry,* ed. by P. Berman (Academic Press, San Diego) Chapt. 3; Phys. Rev., A 49, R2213 (1994); Phys. Rev., A 50, 2430 (1994).
P. Cloetens et al. (1995). J. Phys. D, 133–146.
J. M. Cowley and A. F. Moodie (1970). Proc. Phys. Soc. B 70, 486, 497, 505.
T. J. Davis et al. (1995). Phys. Rev. Lett., 74, 3173–3176.
A. M. Gadzhiev et al. (1989). Nucl. Instrum. and Meth., A282, 502.
D. Gao et al. (1995). Australian J. Phys., 48, 103–111.
C. Gorecki, et al. (1994), in *Interferometry '94: New Techniques and Analysis in Optical Measurements,* M. Kujawi ńska and K. Patorski, eds. Proc. SPIE, 2340, 356–365.
C. Kahn Malek (1991). J. of X-ray Sci. and Tech., 3, 45–67.
W. R. Hendee (1995). Physics Today, 48 (11), 51–56.
J. R. Leger and G. J. Swanson, (1990). Opt. Lett. 15, 288–290.
R. B. Leighton (1959). *Principles of Modern Physics* (McGraw-Hill, New York) Chapt. 12.
B. Loechel et al. (1996), J. Vac. Sci. Technol. B, 14(6), November/December.
A. W. Lohman and D. E. Silva (1971). Opt. Commun., 2, 413.
A. W. Lohman and J. A. Thomas (1990). Appl. Opt., 29, 4337–4340.
M. Mansuripur (1997). Optics and Photonics News, 8 (4), 42–47.
W. J. Meredith and J. B. Massey (1977). *Fundamental Physics of Radiology* (3rd Ed., Year Book Medical Publishers Inc., Chicago).
A. G. Michette and C. J. Buckley, eds. (1993). *X-ray Science and Technology* (Institute of Physics Publishing, Philadelphia).
Momose et al. (1995). Rev. Sci. Instrum., 66(2), 1434–1436.
K. A. Nugent, et al. (1996). Phys. Rev. Lett., 77, 2961–2964.
K. Patorskii (1989). *Progress in Optics XXVII,* ed. by E. Wolf (Elsevier, Amsterdam), 1–108.
K. Patorskii (1993). *Handbook of the Moiré Fringe Technique,* (Elsevier, Amsterdam).
J. C. Slater and N. H. Franck (1947). *Electromagnetism* (McGraw Hill, New York), Chapt. IX.
H. I. Smith et al. (1984), in *X-ray Microscopy,* ed. by G. Schmal and D. Rudolph (Springer-Verlag, Heidelberg) Chapt. 7.
H. I. Smith (1996). J. Vac. Sci. Technol. B, 14(6) November/December, 4318–4322.
A. Snigirev et al. (1995). Rev. Sci. Instrum., 66(12), 5486–5492.
A. Snigirev et al. (1996). Nucl. Instrum. and Meth., A 370, 634–640.
V. A. Somenkov, et al. (1991). Sov. Phys. Tech. Phys., 36 (11), November, 1309–1311.
M. Sonoda et al. (1983). Radiology, 148, 833.

H. Talbot (1836). Philos. Mag., 9, 401.

W. Thomlinson et al. (1992). Rev. Sci. Instrum., 63(1), 625–628.

K. Umetani et al. (1992). Rev. Sci. Instrum., 63(1), 629–631.

K. Wasa and S. Hayakawa (1992). *Handbook of Sputter Deposition Technology* (Noyes Publ., Park Ridge. N.J.).

R. J. Weiss, (1997). OE Reports (ISSN 1048–6879, SPIE—The International Society of Optical Engineering), #158/February p.2.

R. M. White and S. W. Wenzel (1988). Sensors and Actuators, 13, 391–395.

J. T. Winthrop and C. R. Worthington (1965), J. Opt. Soc. Amer., 55, 373–381.

S. Yokozeki and T. Suzuki (1971). Appl. Opt. 10, 1575, 1690.

F. Zernike (1935). Z. Tech. Phys., 16, 454.

Part I. Technical field of the Invention

The Invention relates to the fields of x-ray radiography and radiology and provides practical apparatus and methods for important improvements to practice in these fields. It provides new apparatus and methods for totally eliminating the blurring and contrast reducing effects of x-ray scatter. It does not use a Bucky grid, whereupon the associated increase in effective detector quantum efficiency results in a corresponding decrease in image quantum mottle. Nor does it require a narrow solid-angle source collimator to reduce scatter induced blur, whereupon 3D images are produced via computed tomography (CT) using many simultaneously recorded paths through the examined object at considerably reduced scanning time. It provides new practical apparatus and methods for realizing two fundamentally new radiographic imaging methodologies, wherein previous attempts to do so by other workers have been unsuccessful. Conventional radiography uses the methodology of "absorption-contrast imaging", wherein the image derives from an x-ray shadow of the object's opacity distribution. One new methodology is "refractive-index contrast" imaging, wherein the Invention images an object's refractive-index gradient distribution to give strong edge-enhancement of imaged artifacts, and to image low-Z artifacts (e.g in soft-tissue) that are totally invisible with conventional radiography. In mammography, the contrast of small micro-calcifications is increased typically 4-fold, or more by said edge enhancement. The other new methodology is "element-selective contrast imaging", wherein the Invention resonantly images only artifacts that contain a specific "tracer-element". An image can be obtained during a single brief x-ray exposure with the examined object present. The Invention also can be configured so that with one such exposure it produces simultaneously two independent images, such as one of the object's opacity distribution and one of its refractive-index distribution. By these improvements, the Invention provides radiograms with greatly improved resolution, contrast and versatility. While the Invention has a wide range of application, it is ideally suited for medical imaging of biological soft-tissue, and especially for mammography, angiography and whole-body CT.

The fields of physics whose mastery are required for a full understanding of the Invention's operation are listed in Sect. I.2. Part II, consisting of Sects. II.1–II.3 describe related prior art. Part III, consisting of Sects III.–III.10.3, discloses the basic operational principles for the Invention along with design Formulae for calculating critically important apparatus dimensions. Part IV provides descriptions of the drawings. Examples of preferred embodiments and their associated representative dimensions and fabrication methods are described in Part. V, consisting of Sects. V.–V.7. Part VI then gives a brief overview of the Invention's industrial applicability. The Invention is thus disclosed sufficiently to allow its construction and understanding by one skilled in all of the various arts discussed herein.

I.1 Notation and mathematical definitions

The following abbreviations and symbols are used: $i=(-1)^{1/2}$, 1 m=1 meter, 1 cm=$10^{-2}$ m, 1 mm=$10^{-3}$ m, 1 $\mu$m=$10^{-6}$ m, 1 nm=$10^{-9}$ m, n=refractive-index, Z=an element's atomic number. Italic symbols, e.g. the symbols b, g, j, k, m, $m_*$, n, $n_*$, p, q, r, $r_*$, U, V, V, and x, always represent integers. (Note to compositor: please carefully observe this font distinction.) X-ray energies are always given in keV (kilo-electron-Volts).

A function f(x;a), parameterized by the period a, is defined as 1D-periodic with period a with respect to the independent dummy variable x if it satisfies $$f(x;a)=f(x+ja;a) \tag{I.1}$$

for all applicable values of x, where j is any integer (positive, negative or zero). The function f(x,y;a), parameterized by the period a, is defined as 2D-periodic with period a with respect to the independent dummy variables x and y if it satisfies $$f(x,y;a)=f(x+ja,y+ka;a), \tag{I.2}$$

for all applicable values of x and y, where similarly j and k are any pair of integers. For "practical purposes" the functions f(x;a) and f(x,y;a) are considered as 1D and 2D-periodic functions if respectively Eqs. (I.1) and (I.2) hold for "applicable" x, y, j and k for each within a large positive and negative "applicable" finite range, but wherein said ranges are sufficiently large (i.e. their "ends" are sufficiently far away from the region of interest) that the existence of said finite range limits has negligible effect on the problem at hand. A "separable" 2D-periodic function of x and y with period a is defined via Eq. (I.1) as one that may be written as a product of a 1D-periodic function of x with the same function of y, as per $$f_{sep}(x,y;a)=g \pm f(x;a) f(y;a), \tag{I.3}$$

where f(x;a) satisfies Eq. (I.1), $f_{sep}$(x,y;a) satisfies Eq. (I.2) and g is a constant. A "checkerboard" 2D-periodic function is defined as one that is written as the sum of two separable 2D-periodic functions, each offset by a half-period from the other, as per $$f_{ckbd}(x,y;a) \equiv g \pm \left[ f(x;a)f(y;a) + f\left(x+\frac{a}{2};a\right)f\left(y+\frac{a}{2};a\right) \right], \tag{I.4}$$

where f(x;a) satisfies Eq. (I.1), $f_{ckbd}$(x,y;a) satisfies Eq. (I.2), and g is a constant.

A unit rectangle-function is defined as $$rect(x) \equiv \begin{cases} 1 & \text{for } |x| \leq 1/2, \\ 0 & \text{otherwise.} \end{cases} \tag{I.5}$$

A 1D-periodic rectangle function of the independent variable x, parameterized by its period a and duty-cycle s/a, is defined as a periodic string of rectangle-functions by $$H(x;s,a) \equiv \sum_j rect\left(\frac{x+ja}{s}\right) = \begin{cases} 1 & \text{for } |x+ja| \leq s/2, \\ 0 & \text{otherwise,} \end{cases} \tag{I.6}$$

where j is any integer. The function H assumes only the discrete values 0 and 1.

I.2 General physics background

Discussions of the physics of x-ray generation, absorption, scattering, diffraction, fluorescence, and refraction are given by Leighton [1959] and by Michette and Buckley [1993]. General discussions of the field of x-ray medical imaging are given by Meredith and Massey [1977] and by Hendee [1995]. Light and penetrating (hard) x-rays are both forms of electromagnetic radiation. X-ray wavelength λ in meters is $$\lambda = \frac{hc}{E},\qquad(I.6)$$

where E is the x-ray energy in keV, h is Planck's constant, c is the speed of light, and hc=$1.24 \times 10^{-9}$ m-keV. The principles of physical optics, as given for example by Born and Wolf [1967], apply to both forms. The operation of the Invention relies on applications of physical optics to the wavelength regime of hard x-rays. Given the significantly different photon energies for light and x-rays, then a very different technology is required for each form. Michette and Buckley [1993, Chapts. 7,8] discuss cross-over applications of physical optics principles and techniques that are commonly used with light, and that have been applied to soft x-rays; however, except to x-ray diffraction by atomic microstructure, physical optics principles are rarely considered important for hard x-rays.

The Invention uses the x-ray analog of what is known in the physics of light as the "fractional Talbot effect", and for the first time employs important features of said effect to the domain of hard x-rays. The Talbot effect and the more general fractional Talbot effect have been demonstrated with light [Patorskii, 1989]. Array illuminators, based on the fractional Talbot effect have been demonstrated with light by Lohman and Thomas [1990] and by Leger and Swanson [1990]. Related theoretical treatments of these effects are given by Cowley and Moodie [1970], Winthrop and Worthington [1965], Berry and Klein [1996], M. Mansuripur [1997], and by Clauser and Reinsch [1992]. Demonstrations of applications of the fractional Talbot effect to atom interferometry are given by Clauser and Li [1997].

II.1 Prior art for reducing scatter-induced image blur

X-ray scattering within an examined object displaces x-ray photon detection points on the detector plane from "x-ray-bright" image areas to "x-ray-dark" ones. Thereby, it blurs the resulting radiogram's weak features and severely limits the resolution and contrast. Tight source collimation is used (esp. for CT-scan 3D imaging) to reduce scatter production, and tight detector collimation is used to reduce the detection of scattered x-ray photons. The only implementation of detector collimation for wide-angle planar imaging currently practical and in wide-spread routine use is the Bucky incli-scatter) grid. A Bucky grid is included in an x-ray imaging apparatus between the object and the detector to attenuate scattered x-rays [Meredith and Massey, 1977, pp.250–263]. A Bucky grid is inherently thick. Its structure is similar to that of a louver or a venetian blind, with said louvers made from lead. Its operation is also similar. Its louvers are either all parallel or are "fanned" to match the x-ray incidence-angle. It selectivity attenuates scattered x-rays by vignetting, i.e. it absorbs obliquely incident x-rays and allows passage of x-rays that are incident nearly parallel to its louvers. Ideally, it provides minimal attenuation of the nearly parallel x-rays that are useful for reduced-blur image production. Unfortunately, a typical Bucky grid also significantly attenuates (typically 3 to 4-fold) the parallel x-rays. The resulting loss of transmitted x-ray flux, in turn, raises the detector's photon shot-noise level and its associated image "quantum-mottle".

The ratio of the absorption cross-section to the scattering cross-section increases with increasing x-ray energy. Thus, low energy x-rays provide minimum scatter-induced blur and are generally used for imaging low-contrast soft tissue. However, at low energy, elastic scattering (i.e. x-ray diffraction by the tissue's molecular structure) dominates and produces mostly small-angle (<5°) scattering that is not removed by a Bucky grid. Elastic scattering is further enhanced by the presence of long-chain periodic organic molecules in biological tissue that act as miniature randomly oriented diffraction gratings (i.e. as linear micro-crystals). The average scattering angle is then so small that it requires an impractically large object-to-detector distance for it to be sufficiently widely distributed on the detector to become a uniform background. The scattering angle is still, however, large enough to cause significant image blur. As a result, minimum object-to-detector distance is generally used, and the sharpness and contrast of weak image features smaller than about 4 mm are degraded, especially for soft-tissue imaging.

Three noteworthy inventions [Anno, U.S. Pat. No. 4,651, 002; Barnea, U.S. Pat. No. 4,433,427; and Ema U.S. Pat. Nos. 4,688,242 and 4,837,796], use a method, referred to herein, as the image subtraction method for reducing the blurring effects of scatter. All three inventions use normal absorption imaging. To implement this method, two (or more) independent images are taken via subsequent exposures. One image is produced only by highly-scattered photons, while the other is produced by both highly-scattered and minimally-scattered photons. The two images allow a third image to be produced by digitally subtracting the first image from the second. The third image is then due to minimally-scattered photons alone.

These three inventions use what are herein called "gratings", or more specifically "binary absorption gratings". A binary absorption grating contains a spatially periodic array of x-ray transmitting apertures and is otherwise x-ray absorbing. It acts as a spatially periodic mask. While a grating also may be designed to refract and diffract x-rays, none of the gratings used by prior art is so designed. On the contrary, the gratings used by these three inventions are specified clearly by their inventors to be negligibly diffracting (i.e. to have large periods), and these inventors totally ignore any possible x-ray refraction by the gratings.

To create the two images, all three inventions start with a conventional radiography apparatus configuration, and further include one (and only one) pre-object periodic grating. The pre-object grating is positioned between the x-ray tube's focal spot and the examined object. Then, by using a very small focal spot, it and the pre-object grating create a 1D or 2D-periodic shadow on the detector's surface with x-rays that pass through the object. Anno's fourth embodiment and Barnea's invention further include a second post-object periodic mask (grating). In Barnea's invention the post-object grating is thick and also acts as a Bucky grid. Ema's invention uses no post-object grating but instead uses a continuously recording 2D imaging detector, that is effectively made periodic by a post-exposure recognition of the periodic shadows formed on it. In one exposure, the two gratings and focal spot occult each other, and then only widely-scattered x-ray photons are recorded. The gratings and focal spot are then relatively repositioned for an additional exposure. Said repositioning is accomplished by moving either the gratings or the focal spot between exposures. One (or more) subsequent independent exposure(s) is (are) then made, wherein such occultation does not occur and both widely-scattered and minimally-scattered photons are recorded. The subsequent exposure thus includes the image data, which is extracted by subtraction of the two (or more) images.

The scattering angle of the x-ray photons that are rejected by these inventions depends on the angular change in x-ray propagation that a scattering event must cause to move a photon's final image registration point from an x-ray dark to an x-ray bright grating shadow or vice-versa. Anno's and Ema's pre-object gratings create wide shadows and image details of the object within the widths of these shadows, whereupon this angle is quite large. These inventions thus reject only photons with moderately wide scattering angles, and scatter-induced blur from small-angle scattering persists in the un-shadowed areas. Ema's invention does, however, provide an in-situ method for apparatus alignment, by its post-exposure recognition of the shadow positions. In Barnea's invention each un-shadowed portion of the image is specified to be aligned with an image pixel; however, no method is provided for obtaining said alignment. Barnea's method is superior to that by Anno and Ema since it rejects small-angle scattered photons. However, a critical analysis of Barneas's geometry reveals that the finite width of the focal spot strongly geometrically blurs each of the image spots produced by the pre-object grating unless an unrealistically small focal spot is used. Barnea ignores this crippling deficiency and throughout assumes the focal spot's width to be zero. The multiplicity of exposures and/or the post-object gratings required by these inventions reduce detector quantum efficiency and cause increased patient dosage. The apparatus realignment intervening between exposures, as required by these inventions, prevents a rapid sequence of images to be taken and further allows significant movement blurring (e.g. between exposures) in the subtracted image.

II.2 Prior art for x-ray refractive-index imaging

Structure may be present in the refractive-index distribution of an object that is transparent to light. A transparent object casts no shadow, so that said structure is not revealed by its light absorption. Nonetheless, methods have been developed for use with light to image this structure. Methods for imaging otherwise transparent air-flow patterns include the Mach-Zehnder interferometer, Schlierin, and shadowgraph, as well as less well-known methods that are based on the Talbot and the related Lau effect [Lohman and Silva, 1971; Yokozeki and T. Suzuki, 1971]. Physical-optics principles are used to give the phase-contrast refractive-index imaging method used by the phase-contrast microscope and invented by Zernike [1935; see also Born and Wolf, 1967, pp.424–428]. These methods work for light; however, they all use components such as lenses, lasers, etc. that do not have x-ray analogs, and thus are not adaptable for use with x-rays.

X-ray refraction is due to the fact that x-rays are coherently elastically forward-scattered via zeroth-order diffraction by all of the electrons along their path [Slater and Franck, 1947; Leighton, 1959, pp.454–457; Michette and Buckley, 1993, pp.184–198]. The energy-dependent value for the x-ray refractive index n may be calculated to reasonable precision (away from absorption edges) at x-ray energy E by using the classical Lorentz Formula [Michette and Buckley, 1993, Eqs. 5.84–5.86]. The value of n−1 is negative for x-rays in virtually all materials, and is very small ($\approx 10^{-6}$). However, the wavelengths of hard x-rays are also very short, and only a very thin layer of material is needed to produce significant x-ray phase shift.

There are two important characteristic lengths for any material that may be used to compare the relative importance of x-ray absorption and x-ray refraction by the material. The length $L_I$ is the path length of material needed for 1/e intensity absorption, and the length $L_R$ is the path length of material needed for $-2\pi$ radians phase shift by refraction. The ratio $L_I/L_R$ then gives the comparison. At say about 20 keV for a low-Z low-density material such as water this ratio is about 760 while it is only about 7 for a very high-Z very dense material such as gold. From this viewpoint, all materials, and especially low to medium-Z materials, are seen as much more refractive than they are absorptive for x-rays. At the radiographic energies 17–40 keV a low-Z layer less than 1 $\mu$m thick provides significant x-ray phase shift with negligible absorption, while a layer with typically 10–60 $\mu$m of a very high Z very dense material is needed for significant absorption. Biological soft tissue is dominantly a low-Z material. The high $L_I/L_R$ for soft tissue then implies that its radiographic refractive-index contrast is potentially much higher than its radiographic absorption contrast, and the motivation for an ability to perform refractive-index imaging with x-rays is then evident.

The above considerations have motivated many workers to seek a method for performing refractive-index imaging with x-rays; however, techniques used with light for refractive index imaging are not readily adaptable for use with x-rays, for which quite different techniques are required. Bonse and Hellkötter [1969] measured n for 8 keV (Cu Kα) x-rays using an x-ray interferometer. Using 8 keV x-rays reflected by crystals, Somenkov, et al. [1991], Davis et al. [1995], and Gao et al. [1995] imaged refractive-index gradients of very thin objects. Using x-rays reflected by crystals, but further employing a synchrotron radiation x-ray source, Cloetens et al. [1995], Snigirev et al. [1995, 1996], and Nugent et al. [1996] demonstrated refractive index-imaging for moderate x-ray energies. Using an x-ray interferometer similar to that by Bonse and Hellkötter [1969] and 13.5 keV x-rays produced by a synchrotron and reflected by crystals, Momose et al. [1995] demonstrated x-ray phase-contrast imaging of an object's refractive index distribution. Unfortunately, none of these methods is readily adaptable to routine medical radiography. The thickest sample thusly imaged so far is less than 1 mm thick and the extreme cost of a synchrotron prohibits its clinical use for medical imaging.

Consider the effect of transmission of x-rays through a thin layer of material with thickness $Z_T$ on the propagation of a complex-valued scalar electromagnetic field amplitude, $\exp[i(kz-\omega t)]$, for x-rays propagating in the +z direction, where k≡2 $\pi$E/(hc) and ω≡2 $\pi$E/h. Behind the layer, the field amplitude that would have been present otherwise in vacuum without the layer's presence is now multiplied by the complex phase factor, $$\eta(z_T) = \exp\left[-\left(\frac{i}{L_R} + \frac{1}{2L_I}\right)z_T\right], \qquad (II.1)$$

where, the energy-dependent "refraction length", i.e the thickness needed to give a $-2\pi$ radian phase shift, is given via the Lorentz Formula as $$L_R(E) = \frac{hc}{2\pi[1-n(E)]E} = \frac{4\pi\epsilon_0 m_e c}{n_e e^2 h} E, \qquad (II.2)$$

and where $\epsilon_o$ is the permittivity of vacuum, $m_e$ and e are the mass and charge of an electron, and $n_e$ is the density of electrons in the matter. Since n−1 is negative, the phase shift is negative.

II.3 Prior art for X-ray element-selective imaging

There are various examples of prior art for element-selective x-ray imaging. Commonly, these are identified under the names "dual-energy x-ray angiography" (DEXA) and "digital subtraction angiography" (DSA). Dual-energy x-ray imaging reputedly was invented by L. Alverez at Lawrence Berkeley Laboratory, and works via the fact that at moderate x-ray energy, photo-electric and Compton cross-sections have different energy scalings, along with different scalings with an element's atomic number Z. Two images taken at respectively high and low energies then show different relative opacities for high and low Z image artifacts. Differently weighted linear combinations of these two images are then calculated to enhance, for example, high-Z bone artifacts relative to low-Z soft-tissue artifacts, or vice-versa. Fuji Corporation markets a system for DEXA in which two stimulated luminescense plates are stacked to provide two independent detectors with an energy filter (thin foil) sandwiched between them. Only high energy x-rays pass through the first plate and filter to be recorded on the second plate, while low energy x-rays are preferentially recorded on the first plate. The two associated images are then digitized and computer processed together to yield independent third and fourth (high-Z and low-Z) images.

The best examples of digital subtraction angiography are discussed by Michette and Buckley [1993, p.35], and by Thomlinson et al, [1992], and utilize the high x-ray brightness available from a synchrotron. A DSA system is vaguely similar in concept to a DEXA system, except that the abrupt opacity energy variation for a specific tracer element across that element's K absorption edge provides the different relative opacities for tissue with and without the tracer element. In a DSA system using synchrotron radiation, the x-rays are energy-filtered by a crystal monochromator to produce two beams of narrow bandwidth x-rays with energies above and below the K-absorption edge of the element to be selectively imaged. Umetani et al. [1992] further include an energy-filter comprised of said element. Unfortunately, these latter methods rely on the use of a synchrotron x-ray source, that is impractical for routine clinical usage.

Part III. Disclosure

The Invention may operate in any of three "modes"—"geometric-shadow mode", "amplitude-interferometric mode", and "phase-interferometric mode". The two interferometric modes, in turn, are each a multiplicity of discretely definable modes, and geometric-shadow mode is a limiting case of one amplitude-inteferometric mode. Virtual elimination of image blur by scatter is featured by all three modes. The Invention also may employ any of three methodologies—absorption contrast imaging, refractive-index gradient contrast imaging, or element-selective contrast imaging. The choice of mode depends to some extent on the choice of methodology and/or on the Invention's application. Geometric-shadow mode is used only for absorption contrast. Either of the interferometric modes give refractive-index contrast (see Sect. III.7), and/or element-selective contrast (see Sect. III.8). Additionally, the Invention can employ more than two methodologies simultaneously (see Sect. III.9), and can produce two independent images simultaneously from a single x-ray exposure, e.g. one that shows only refractive-index-gradient contrast and one that shows only absorption contrast.

The fact that the Invention can operate in its various modes and methodologies is due to a quantitative "window" for the Invention's parameter values. The Inventor's discovery and exploitation of said parameter window underlies the inventive concept herein disclosed. Section III.1 summarizes the basic teaching by the Invention, and discloses the components of its inventive concept. The teaching listed in Sect. III.1 then provides the Invention's basic objectives. The Invention is distinguished from a conventional apparatus by its deletion of the Bucky grid, and by its further including important hardware components. The added hardware components are configured with the dimensions specified by Formulae/Equations disclosed herein. Specific examples of the scaling of these dimensions are shown on FIGS. 21a–f. These scaling examples are then used to provide preferred embodiments, as discussed in Part V. It is very important to recognize that the Invention's basic teachings are realized only when dimensions calculated from these Formulae/Equations and scalings are used and applied in the manner disclosed herein.

In a conventional planar-imaging radiography apparatus, x-rays are generated at focal spot S within x-ray tube T, filtered by energy filter F, collimated by collimator C, pass through imaged object BDY, and are detected by imaging detector D. FIG. 1 shows the simplest overall configuration for the Invention, used for planar imaging. It includes the above components of a conventional apparatus (and no Bucky grid) and further includes additional hardware components. The center of focal spot S defines one point on the x-ray axis, $C_L$, while the center of imaging detector D defines a second. Where appropriate, all Figures display coordinates x, y, z, denoted as coordinate system xyz. X-ray axis $C_L$ is oriented in the z-direction. The terms "lateral" and "longitudinal" refer respectively to the x and y directions (both perpendicular to $C_L$) and the z direction (parallel to $C_L$). Pinholes PH1 PH2 and mirror M2, shown in FIG. 1, are positioned within the apparatus (on axis $C_L$) during alignment only. FIG. 2 shows a laterally expanded view of a thin ribbon-shaped slice through the Invention taken along x-ray axis $C_L$. X-rays propagate dominantly along the longitudinal +z-axis, downward in FIGS. 1 and 2, in a divergent beam (limited by collimator C) roughly centered on axis $C_L$. FIGS. 6a–12c show details of apparatus components. The configuration of FIG. 1 uses a single large-area imaging x-ray detector D, whose surface is periodically segmented into image pixels. Inter-pixel gaps are kept minimal to minimize the loss of x-ray flux there-through. FIGS. 3a,b show details of alternative detector arrangements for use with continuous detector media, e.g. film. FIG. 4a shows an alternative overall configuration in which the detector is further segmented to consist of a sparse mosaic of small pixel arrays, and in which the whole apparatus is rotationally scanned about an axis SCN, passing through focal spot S, across object BDY. FIG. 5 shows a configuration used for a CT scan, in which the detector is either a single array, as per FIG. 1, or is segmented, as per FIG. 4a, and in which the whole apparatus is rotationally scanned around object BDY about an axis SCN, passing through object BDY.

Consider FIG. 1. Within x-ray tube T focused electron beam eB is produced by electron gun eG and accelerated to focal spot S on anode A. X-rays are produced at focal spot S. The tube's accelerating high voltage is from a regulated ripple-free DC supply HV. The kinetic energy of the electrons (in keV) is set by the supply's DC high voltage (in kV). This voltage then sets an upper limit to the x-ray energy. The x-rays pass through energy-filter F and collimator C to produce a collimated beam of energy-bandwidth-limited x-rays. The x-ray beam then propagates sequentially through two very thin pre-object spatially-periodic material structures, herein referred to as gratings G1 and G2, and thence through object BDY to imaging detector D. Each of these very-thin spatially-periodic material structures is generally supported by an associated thin substrate SUB (as shown in FIG. 2). The DC high voltage, anode A, and filter F (and additional minor energy filtering by the substrates) are specified by the Invention's teachings to control the x-ray average energy $E_X$ and energy bandwidth $\Delta E$ of x-rays eventually reaching object BDY and/or the detector.

Optionally, a post-object spatially-periodic grating G3 is further included, positioned between object BDY and detector D, as closely as possible to detector D, as shown in FIG. 2. Its inclusion then extends the range of the parameter window, and/or allows the use of a detector with a large pixel period, and/or allows refractive-index contrast to obtain with a continuous media detector, and/or acts as an alignment fiducial. Unfortunately, the presence of grating G3 frequently causes some increased object dosage (for the same degree of quantum mottle). Grating G3 is preferably omitted in dosage-sensitive applications; however, when either detector configuration of FIG. 3a or 3b is used, then grating G3 is always present. In the detector arrangement of FIG. 3b (giving only small increased dosage) grating G3 is present and made from a periodically structured fluor (x-ray converter) material, whereupon it becomes a component of detector D.

Gratings G1, G2 and G3 are longitudinally very thin, i.e their spatially periodic structures each have a typical thickness that is generally less than about 60 μm, in most embodiments is only a few μm thick, and in some cases is even slightly less than 1 μm, depending on the kind of grating used. Within fabrication tolerances the gratings are substantially-planar and substantially-mutually parallel. (It should be noted in passing, however, that it is also possible for the Invention to work with all gratings and the detector very gently curved with such curvature centered on focal spot S, and/or for it to work with all gratings and the detector configured in a piece-wise planar arrangement. Such configurations, however, are not considered to depart from the notion of their being "substantially-planar" and/or "substantially-mutually parallel".) The needed spatially periodic structures for the gratings are fabricated using current-practice microfabrication technology. They are most readily fabricated by laminating the spatially periodic structures onto a supporting substrate SUB, as shown in FIGS. 6a,b for binary absorption gratings. Free-standing (unsupported) thin membrane grating structures or grating structures embedded within a substrate are also possible without departing from the Invention. For supporting gratings G1 and G2, the substrate is typically a thin wafer about 200–300 μm thick that is made from an x-ray and light transmitting dimensionally stable material such as fused silica. When grating G3 is included, it may use a similar substrate; however, as shown in FIG. 2, it is preferably laminated directly to the surface of detector D, during the detector's fabrication.

The thickness $z_T$ of the very thin layer comprising each grating varies spatially as a 1D-periodic (in x) or 2D-periodic (in x and y) step-function profile that usually includes zero-thickness steps. The gratings are unlike Bucky grids, in that the layer is kept as thin as possible while still performing its desired function. Said thinness provides minimal vignetting so that the grating's periodic absorptive, transmissive, and refractive character is minimally affected by the incidence direction of impinging x-rays. A 2D-periodic grating preferably has the same period in both the x and y directions. Together, the gratings are either all 1D-periodic or all 2D-periodic. The grating planes are accurately parallel to each other and in x-y planes. The spatial periods of gratings G1, G2, and G3 are respectively $a_1$, $a_2$, and $a_3$, and are precisely specified. (If they have unequal x and y-directed periods then they are respectively $a_{1x}$ and $a_{1y}$, $a_{2x}$ and $a_{2y}$, and $a_{3x}$ and $a_{3y}$, respectively, with obvious notation.) In FIGS. 1 and 2 imaging detector D (e.g a CCD array with a built-in front-surface fluor) has a substantially planar 2D-periodic pixel array. The detector is sensitive to x-rays (preferably with a high quantum efficiency) and to light (at least weakly). Its plane is also an x-y plane. Usually, it is a square array with a carefully selected pixel period, $a_D$, although a rectangular array (with associated x and y periods $a_{Dx}$ and $a_{Dy}$), or even a hexagonal array also may be used, if desired.

The spatially periodic grating structures of gratings G1, G2, and G3, may be viewed as each being contained within an associated and respective very thin slab-shaped volume, with the three associated slab-volumes denoted as SV1, SV2, and SV3. Portions of slab-volumes SV1, SV2, and SV3 are shown on FIG. 2. Each such slab-volume is bounded between an associated mutually-parallel pair of substantially planar and very closely spaced imaginary surfaces BS, shown on FIG. 2 by dotted lines. (Mutual-parallelism of two thin slab-volumes is then taken to mean mutual parallelism of the associated bounding surfaces BS, wherein these bounding surfaces are the slab faces of the associated slab-volumes.) A spatially periodic structure always occupies each of these slab-volumes, including slab-volume SV3. When grating G3 is present it becomes the spatially-periodic structure within slab-volume SV3, and then detector D may or may not be spatially periodic. When grating G3 is absent, then the spatially-periodic front surface of detector D takes its place and instead occupies slab-volume SV3, whereupon the detector's front surface then must be spatially periodic. For scatter induced blur to be removed by the Invention, not only must the front surface of detector D be spatially periodic, but the individual pixels within its spatially periodic array must also simultaneously and independently record the locally incident flux of x-rays incident on them. However, in a very simple Embodiment of the Invention that use the detector arrangement of FIG. 3a, refractive index imaging is obtained without the subtraction of scatter induced blur, and then only grating G3 is spatially periodic. Furthermore, even when the detector's basic makeup is continuous and not spatially periodic (e.g. a screen-film detector), it may be made spatially periodic by a post-exposure digital scanning of its surface, as per Sect. V.6.

Grating G1 is preferably located longitudinally as close as possible to focal spot S, as allowed by intervening components, and as shown on FIG. 1. The longitudinal positionings of the gratings and of the detector are critical. The longitudinal spacing between grating G1 and grating G2 (i.e. between slab-volume SV1 and SV2) is the carefully controlled length $R_1$, while the longitudinal spacing between grating G2 to the surface of detector D, or to grating G3 instead, if grating G3 is included (i.e. the perpendicular distance between slab-volumes SV2 and SV3). is the carefully controlled length $R_2$. The sum of these two lengths is $$L = R_1 + R_2, \qquad (III.1)$$

as shown by appropriate dimensioning on FIGS. 1 and 2. The total source-to-detector distance is $$L_T = R_S + R_D, \qquad (III.2)$$

also as shown on FIGS. 1 and 2. It is slightly greater than L since the gratings are between focal spot S and detector D. Since the front surface of detector D and grating G3 are interchangeable as the contents of slab-volume SV3, and since the slab-volumes containing these various spatially periodic structures are all very thin, then measurements of $R_1$ and $R_2$ in general may be taken to these slab-shaped volumes, whether or not grating G3 is present.

The Invention's description uses the parameters α and M. The parameter α is defined as the ratio of $R_2$ to $R_1$, $$\alpha = \frac{R_2}{R_1}. \tag{III.3}$$

Relative to a fictitious x-ray point S' located on the plane of grating G1, as shown in FIG. 2, the parameter M is the geometric magnification for a geometric projection from S' of the periodic structure of grating G2 onto the surface of slab-volume SV3. It is given by $$M = \frac{R_1 + R_2}{R_1} = 1 + \alpha. \tag{III.4}$$

Note that $R_1$, $R_2$, L, α, and M are all determined by specifying any one of the lengths $R_1$, $R_2$, or L, and either one of the dimensionless parameters M or α. One may specify $R_1$ and $R_2$, in terms of L and α, by $$R_1 = L\frac{1}{1+\alpha}, R_2 = L\frac{\alpha}{1+\alpha}. \tag{III.5}$$

The length ρ is defined as $$\rho = \frac{R_1 R_2}{R_1 + R_2} = \frac{\alpha L}{(1+\alpha)^2}. \tag{III.6}$$

Once L, α, and $E_X$ are chosen, then the seemingly minor but, in fact, critically important chosen value for $a_2$, along with the structures, shapes, dimensions and material compositions of the periodic layers on gratings G1, G2, and G3, determine the Invention's mode. Operation of the Invention occurs in the interferometric modes only at or near specific discretely allowed values for $a_2$ that, in turn, depend on L, α, and $E_X$, as disclosed in Sects. III.3, III.4, and III.8. For fixed L, $E_X$ and a chosen mode, the associated discretely allowed value for $a_2$ then depends only on α. This a-dependence is shown as the solid-line curve on each of FIGS. 21a–f for various associated Invention modes and chosen L and $E_X$. Operation in geometric-shadow mode occurs only for a specifically allowed range of values for $a_2$. In the interferometric modes and/or at the range limit for geometric-shadow mode, then given L, α, $E_X$ and mode choice, the period $a_2$ is determined by Equations/Formulae given in Sects. III.2–III.2.4, the period al in Sect. III.5, the period $a_3$ in Sect III., and the period $a_D$ in Sects. III.6–III.6.4. A more convenient design starting point and associated apparatus definition is also provided in Sect. III.6.4, where, given choices for L, $E_X$, $a_D$ and mode, then the associated allowed values for α, $a_1$, $a_2$ and $a_3$ are determined in an equivalent manner.

Two kinds of gratings are used by the Invention—binary absorption gratings and phase gratings. Each has a spatially periodic surface layer. The layer XAL on a binary absorption grating is strongly x-ray (and light) absorbing, so that it acts as a spatially periodic mask for x-rays. Its 1D-periodic spatially-dependent transmission (ideally) is proportional to the periodic rectangle function H, as defined by Eq. (I.6). This function assumes only two values 0 and 1, that then correspond to layer thicknesses $Z_T$ and 0. A binary absorption grating defined by function H with period a and with the zero-thickness area width s, has $0 < s/a \leq 1$. The ratio s/a is called the "duty-cycle". The elevation x-z views of cuts through gratings that are shown in FIGS. 2, and 6a,b are drawn with the surface layer profiles of binary absorption gratings. Grating G1 and, when present, grating G3 are both always binary absorption gratings.

In the geometric-shadow and amplitude-interferometric modes grating G2 is a binary absorption grating. In geometric-shadow mode grating G2 simply acts as a periodic x-ray absorbing mask that casts a periodic geometric shadow in the transmitted x-rays. In the interferometric modes, however, given finite x-ray wavelength and small $a_2$, grating G2 acts as a diffraction grating that deflects transmitted x-rays. In phase-interferometric mode grating G2 is a non-absorbing phase grating that casts no shadow and can only act as a diffraction grating. Elevation x-z views of the thickness profile of the surface layer of typical 1D-periodic phase-grating thickness profiles are shown in FIGS. 7a–e. A phase-grating has negligible absorption of x-rays. Instead, its laminated layer is made from a minimally absorbing x-ray refractive material, whose spatially-periodic thickness variation provides a spatially periodic variation of the transmitted x-ray phase-shift. Said thickness varies as a 1D or 2D-periodic step-function that assumes two or more discrete values (including zero) within a period. There are $m_*$ steps per period $a_2$, each of width $a_2/m_*$, where $m_*$ is a chosen integer, as disclosed in Sect. III.4.

For 1D-periodic gratings the x-dependent spatially-periodic profile of the surface layer persists for all y (to the grating's edge), while for 2D-periodic gratings the profile's shape varies periodically in y with the same period. The x-y plan view of a 1D-periodic binary absorption grating is shown in FIG. 8a. Its absorbing areas XAL, shown as shaded (by ///-hatching) on FIG. 8a, form stripes. The zero-thickness x-ray (and light) transmitting areas between these stripes, shown unshaded on FIG. 8a, are called "slits". The width of all slits on grating G1 is $s_1$. When grating G2 is a binary absorption grating, its slit widths are all $s_2$. When grating G2 is a phase grating, its step widths are all $a_2/m_*$, where $m_*$ is an integer defined in Sect. III.4.

Plan x-y views of 2D-periodic binary absorption gratings that may be used for gratings G1 and G2 are shown in FIGS. 8b–d. Plan x-y views of two 2D-periodic phase gratings that may be used for grating G2 are shown in FIGS. 9a,b. When gratings G1 and G2 are 2D-periodic, then either may be independently configured as a separable or as a checkerboard 2D-periodic function of x and y, as per Eqs. (I.3) and (I.4), and as shown respectively in FIGS. 8b–d for binary absorption gratings. Shaded areas (by ///-hatching) on FIGS. 8b–d are the x-ray absorbing layer XAL, and unshaded areas are x-ray (and light) transmitting areas on binary absorption gratings with zero-thickness of the surface layer. The transmitting areas shown on FIGS. 8b,c are squares and the absorbing layer XAL is contiguous throughout the grating. These planforms are generated by the use of the function H as defined by Eq. (I.6), and Eq. (I.3) or (I.4) with the + sign and g=0. Similarly, the planform shown on FIG. 8d uses the function H with g=1 with the − sign, so that the absorbing and transmitting areas are interchanged. The plan views shown on FIGS. 9a,b correspond to separable 2D-periodic functions for phase gratings, where unshaded areas have zero thickness of the refractive surface layer and areas shaded with oppositely inclined (/// and \\\) hatching have different thicknesses of the x-ray refracting phase-shifting layer.

When the detector is a periodic array of detector pixels, each pixel's side has the dimension $$a_D = a_3/u, \tag{III.7}$$

where u is a positive even integer greater than or equal to 2. Additionally, to allow subtraction of scatter induced blur, the detector's individual pixels are all labeled in a 2D-periodic manner by the labels b and d, or by b, c, and d to denote their use by the Invention. The 2D-periodic x-y layout for these labels is provided by "tiling". That is, the layout may be viewed as having been formed by laying square tiles in a square array pattern on top of the pixel array, with all tiles having the same orientation and kind. Each tile has a side equal to $a_3$ and exactly covers $u^2$ pixels, as per Eq. (III.7). The tile is thus a $ua_D \times ua_D$ square, comprised of $u^2$ pixel-sized (i.e. $a_D \times a_D$) labeled areas.

The preferred tiling choice uses $u=2$, whereupon each tile is then divided into quadrants; however, it is also possible to construct $ua_D \times ua_D$ pixel-labeling tiles for use in the Invention, where $u \geq 2$ is an even integer. Five kinds of $u=2$ pixel-labeling tiles are then preferably used by the Invention. These are denoted as PT1–PT5, and shown in FIGS. 10a–e. Each tile includes at least one b and one d-labeled pixel. The tile PT5 also includes two c-labeled pixels. Portions of pixel layouts tiled with PT1, PT3 and PT5 tiles are shown respectively in FIGS. 12a–c. Straight lines are the covered pixel boundaries, with the tiles' butted edges shown as heavy solid straight lines and the labeled area boundaries within a tile shown as medium-breadth straight lines. Each pixel's associated label (b, c, or d) is at the center of the associated pixel. The thin curved lines are constant x-ray intensity contours when object BDY is absent, as disclosed further in Sects. III.5 and III.9.

The 1D or 2D-periodic x-y planform of the absorbing layer XAL on grating G3 also may be viewed as having been formed by tiling, again with tiles all having the same orientation and kind. A structure occupying slab-volume SV3 is then always tiled with the tiling period $a_3$, and via its tiled construction, grating G3 then automatically has the spatial period $a_3$. Note that the period $a_3$ is always defined for the Invention, whether or not detector D consists of a spatially periodic array of pixels. The tiles used for configuring the planform of grating G3 are then all $a_3 \times a_3$ in size.

When grating G3 is present and detector D is also spatially periodic the G3-forming tiles have the same size as that of the pixel-labeling tiles. The grating G3 tiles are then also similarly divided into $u^2$ square pixel-sized (i.e. $a_D \times a_D$) areas, and grating G3 is aligned (by methods discussed in Sects. III.10–III.10.3) so that each G3-forming tile is directly over and covers an associated pixel-labeling tile on detector D, whereupon each of the $u^2$ pixel-sized areas of the G3-forming tile obtains the associated label of the respectively covered pixel.

When present, grating G3 has an associated defining positive integer v. For cases with $v>1$ each of the pixel-sized labeled areas of a G3-forming tile is further subdivided into a square array of $v^2$ small squares, where $v \geq 2$ is an integer, so that each full G3-forming tile now contains $u^2 v^2$ small squares, and the side of each such small square is $a_D/v$. Each small square has either zero or $z_T$ thickness of the grating's x-ray absorbing layer XAL. Cases with grating G3 configured with $v=1$ are used with the detector arrangements of FIGS. 3a,b, and discussed in Sect. V.6. For $v=1$ the grating's x-y planform is similar to that shown in FIGS. 8a–d, whereupon it automatically has a tiled planform, even though detector D is not necessarily periodic in such case. Cases with $v=1$ generally also include a fluor that converts x-rays to light. While grating G3 may be x-ray absorbing and may be positioned ahead of the fluor for these cases, the grating is more easily fabricated and thinner if it is located behind the fluor, whereupon it then only must be light-absorbing.

For each of the 5 kinds of $u=2$ pixel labeling tiles, PT1–PT5, there is an associated set of G3-forming tile kinds, wherein each member of each set contains a multiplicity of possible tiles further identified by the associated value for v. If grating G3 is included in the apparatus, then a given pixel-labeling tile is used only with G3-forming tiles from the associated set. Examples of x-y planforms for G3 forming tiles are shown in FIGS. 11a–d for $u=2$ and various values of v. G3-forming tiles are denoted on FIGS. 11a–d as G3Tgv, where the first index g denotes the associated pixel-forming tile PTg, and the second index v gives the defining integer (divisor). The method by which these layouts are derived and their use by the Invention is disclosed in Sect. III.6.1.

For the Invention to function properly, it is critically important that gratings G1 and G2 (and G3, if present) are all carefully and accurately aligned with each other and with a periodic detector D. FIG. 1 shows further added components that are used for alignment. Typical required alignment accuracy is to within <1 μm laterally and to within <100 μm longitudinally throughout the planes of the slab-volumes and the associated components G1, G2, G3 and D. Sections III.10–III.10.3 disclose methods, components, and principles of operation for an in-situ laser interferometer that is used to align these four components to said required accuracy. Said methods and added apparatus components for alignment are also an important part of the teaching provided by the Invention. Other important components, needed for data processing and apparatus alignment, include digital computer CP (internally including associated image processing electronics and software) and associated monitor TV, as shown on FIG. 1.

A "resolution element" of the final image produced by the Invention corresponds to the $a_R \times a_R$ square area, as measured on the detector surface. Said area then corresponds to the pixel size of the final image produced by the Invention. Unlike other art, in the Invention the size of an image-pixel $a_R$ is not equal to the size of a detector-pixel, $a_D$. The length $a_R$ is generally chosen as greater or equal to two resolution limiting lengths, $a_{RG}$ and $a_{RQ}$, and greater than or equal to the SV3 tiling period (i.e. to u times the detector pixel period) as per $$a_{RG} \leq a_R, \ a_{RQ} \leq a_R, \ u \ a_D = a_3 \leq a_R. \tag{III.8}$$

The length $a_{RG}$ is the resolution length set by "geometric blurring" [Meredith and Massey, 1977, pp.220–221]. It is $$a_{RG} = \frac{W_S R_D}{R_S}, \tag{III.9}$$

where $R_S$ is roughly the distance between object BDY and focal spot S, where focal spot S (viewed longitudinally) has an approximately elliptical profile with a maximum lateral width $W_S$, and where the spacing between object BDY and detector D is roughly $R_D$, as shown on FIGS. 1 and 2. The length $a_{RQ}$ is the resolution limit set by "quantum mottle" [Meredith and Massey, 1977, pp.202–203], i.e. by photon shot-noise at detector D. For a faintly imaged object artifact that produces an image feature with some minimum detectable change (say about 1%) in image gray-scale, and whose projected area on the detector has the area $a_R \times a_R$, then the length $a_R$ sets the minimum area for said image feature to allow the detector to integrate sufficient x-ray flux so that said feature is distinguished at 1-to-1 signal-to-noise ratio from quantum-mottle induced features on the image with the same area. The length $a_{RQ}$ may be reduced only by using an x-ray detector with increased quantum efficiency, and/or by increasing the x-ray flux transmitted by object BDY. (In a conventional radiography apparatus it also may be increased by removal of the Bucky grid.) For medical imaging, however, patient dosage limits restrict improvements via increased flux.

III.1 The Invention's teaching

There are basically six key ingredients to the Invention's inventive concept. Minimally, the first two are required for the Invention to produce new useful effects. (1) The first key ingredient is using a periodic grating G2, configured either as a binary absorption grating or as a phase grating, as disclosed in Sects. III., III.3, III.4, and III.8, and configured so that a (fictitious) point x-ray source S' located on the plane of grating G1, as shown on FIG. 2, forms a generally non-sinusoidal spatially-periodic x-ray intensity interference fringe pattern Q with a very small period, $a_Q$, on slab-volume SV3, wherein detector D or grating G3 resides. This fringe pattern Q is formed by wave interference via the x-ray analog of the fractional Talbot effect. The more commonly discussed but less general non-fractional Talbot effect is then automatically included as a special case of the more-general fractional Talbot effect. While it is less commonly recognized but basically evident upon study, spatially-periodic geometric-shadow formation is then also automatically included as a special case of the more-general Talbot effect. Via wave interference effects the fractional Talbot effect allows point source S' and grating G2 to create an "aliased" pattern Q whose dominant spatial frequency is an integral multiple (harmonic) of the geometric-shadow's dominant spatial frequency, and also to create a spatially-periodic x-ray intensity interference fringe pattern Q when grating G2 is a non-absorbing phase grating.

(2) The second key ingredient, as disclosed in Sect. III.5, is forming a periodic source via the further inclusion of grating G1 positioned near to but spaced from focal spot S, configured with a period $a_1$ so that a high-contrast, high-intensity, G1-averaged spatially-periodic pattern P is formed via registration of the various contributions by each of the grating G1 periods. Pattern P, is thus projected by gratings G1 and G2 acting together, and has the spatial period $a_P$, with $a_{P \leq aQ}$. Simple geometric considerations indicate that grating G1 can create pattern P with a dominant spatial frequency that is a rational fraction of of pattern Q's dominant spatial frequency. It is seen that pattern P, as created by gratings G1 and G2 acting together and projected on slab-volume SV3, is quite different from a pattern created by focal spot S and either grating acting alone (i.e. in the same position but with the other absent) and similarly projected on slab-volume SV3. Acting alone, either grating acts similarly to the single pre-object grating used by Barnea. Given the finite width $W_S$ of focal spot S, however, a single grating produces a pattern that, although spatially periodic, has a much diminished spatial intensity variation (contrast) relative to the pattern projected by gratings G1 and G2 acting together. Furthermore, given the finite spacing between focal spot S and either grating, the single-grating pattern also has a dominant spatial period that is different from pattern P (as projected by gratings G1 and G2 acting together).

(3) The third key ingredient, as disclosed in Sects. III.6 III.6.4 and III.8, is providing a harmonic matching of the actual spatial period and phase of pattern P (with no object present) to the detected spatial period and phase of pattern P. This method is conceptually similar to one introduced by early radar technology (reportedly by R. Dicke) in the temporal-frequency domain, therein called synchronous detection, although here, it is used in the spatial-frequency domain. There are various ways for applying the synchronous-detection method here. Some require no further added hardware components and may be performed during a post-exposure reduction of image data. Thus, in a realizable (but not preferred) configuration for the Invention a spatially continuous detector may occupy slab-volume SV3, whereupon only phase and period-specific attributes of its recorded image are then used to compute the final image. Obtaining accurate phase and period matching with such a configuration, however, is both difficult and not readily adaptable to a clinical environment. Thus, added hardware components are preferred for doing so.

Such components take various configurations and generally occupy slab-volume SV3. A spatially periodic detector in slab-volume SV3 does so, with its periodic pixel array period and phase matched to pattern P. A spatially periodic grating G3 occupying slab-volume SV3 also does so with its spatially-periodic structure then period and phase matched to pattern P. whereupon it then acts as a mask to mask the recorded spatial profile of pattern P. The masked pattern P then may be detected using a spatially-continuous detector, or it also may be period and phase matched to the spatially-periodic pixel array of a spatially-periodic detector.

When the grating periods are sufficiently small so that $a_P$ is appropriately small, as disclosed in Sect. III.7, then the refractive-index contrast methodology can obtain from these three ingredients alone. For scatter-induced image blur to be eliminated by the Invention, however, two more key ingredients (4 and 5) are required. (4) The fourth key ingredient, disclosed in Sects. III., III.6 and III.6.1, is configuring the detector with a pixel array wherein all pixels simultaneously and independently record the x-ray intensity locally incident on them, and wherein a tiling algorithm is used to provide interlaced b and d pixel labels. The periods $a_D$ and $a_P$ must be both smaller than the size $a_R$ of an image resolution element, and the third key ingredient must be performed so that the phase and period of pattern P matches the phase and period of the detector pixel labels. (5) The fifth key ingredient, as disclosed in Sects. III.6.2, III.8 and III.9, is performing an image subtraction for each resolution element using x-ray intensities measured by the b-labeled (and in Sect. III.9, c-labeled) pixels within said resolution element and by d-labeled pixels that are either within said resolution element or are within neighboring resolution elements.

In principle, the above five key ingredients are sufficient for the Invention to function fully, and to include its removal of scatter-induced blur. However, as a critically important practical matter, it is necessary to include additional apparatus components and methods so that the above required phase matching can be achieved conveniently in practice. (6) The sixth key ingredient, as disclosed in Sects. III.–III.10.3, is providing an in-situ laser interferometer (herein a collateral Invention) for apparatus alignment that then allows phase matching to obtain in practice.

Additional inventive features of the Invention all rely on these six key ingredients. The following teachings then underlie the objectives of the Invention:

The Invention first teaches the 6 key ingredients behind its inventive concept, as given above.

Regarding key ingredients 1–5, the Invention teaches that the method of image subtraction for removing the blurring effects of scatter, as taught by the prior art of Anno, Barnea, and Ema (wherein said prior art includes a single pre-object grating), is significantly improved by the further inclusion of a second pre-object grating located near the finite area diffuse source S of x-rays, and that source S with the further added pre-object grating together effectively create a spatially-periodic x-ray source, and that the two gratings together with x-ray illumination from the finite area diffuse source S of x-rays form a high-contrast high-intensity spatially-periodic x-ray intensity pattern P on the surface of slab-volume SV3 when no imaged object BDY is present in the apparatus. In the Invention, the grating nearest the x-ray source S is labeled G1, while the grating next encountered by the propagating x-rays is labeled G2. Regarding key ingredients 1–5, the Invention teaches that the method of image subtraction for removing the blurring effects of scatter, as taught by the prior art of Anno, Barnea, and Ema, wherein said prior art requires a multiplicity of sequential exposures with imaged object BDY present and a relative realignment of apparatus components between these various exposures, is improved significantly by allowing the method to obtain with image data all recorded simultaneously during a single exposure and without concomitant component realignment needed, and wherein said improvement obtains by configuring the image recording detector D with a periodic array of pixels with period $a_D$, by periodically interlacing sparse arrays of b- and d-labeled pixels within the detector's pixel array via a tiling algorithm, wherein each different label indicates a different use of the associated pixel's recorded data, by configuring the period $a_D$ so that the phase and period of the b-labeled pixels matches that of the high-contrast periodic intensity pattern P, and finally by using recorded data from the b- and d-labeled pixels in an image subtraction algorithm.

Regarding key ingredients 1–3, the Invention teaches that for period and phase matching to obtain, then a very precise relationship between the grating G1 period $a_1$, the grating G2 period $a_2$, the SV3 tiling period $a_3$, the period $a_P$ of pattern P, the detector period $a_D$, and the dimensionless parameter $\alpha$, that is the ratio of the distance from slab-volume SV2 to the slab-volume SV3 (grating G3 or detector D) to the distance between gratings slab-volumes SV1 and SV2 (i.e. between gratings G1 and G2), is necessary, and that the slab-volumes must be kept precisely parallel.

Regarding key ingredients 4 and 5, the Invention teaches, in consideration of very small-angle (less than 1°) x-ray scatter by biological tissue, that the improved image subtraction method is further improved by the use of gratings with grating periods that are typically much smaller than those used by prior art, that are smaller than the resolution length $a_R$, as measured on the detector's surface, and that are smaller than the typical lateral displacement of x-ray photon detection points caused by said scatter.

Regarding key ingredient 1 the Invention teaches what is the appropriate lower limit set by physical optics principles, by the apparatus geometry, and by the x-ray energy for the choice of period $a_2$ for the formation of geometric shadows by grating G2, and how to calculate this limit.

Regarding key ingredients 1 and 2, the Invention teaches that the Talbot and/or fractional Talbot effects can be used for the formation of a high-contrast G1-averaged interference pattern P, with values of $a_2$ smaller than those that no-longer give geometric shadows, and that these smaller values are useful for high-resolution radiography.

Regarding key ingredient 1, the Invention teaches that the Talbot and fractional Talbot effects obtain only at very specific choices for grating G2 period $a_2$, that are typically much smaller than and mutually exclusive of the allowed range of values for $a_2$ that provide geometric shadows.

Regarding key ingredients 1 and 2, the Invention teaches that when grating G1 and G2 are used together, then the Talbot and fractional Talbot effects obtain over the whole detector area when precision alignment is maintained, that these effects occur without the presence of one or more lenses, as are commonly used in demonstrations of these effects with light, and that said effects may be applied usefully to radiography practice.

Regarding key ingredients 1 and 2, the Invention teaches that the Talbot and fractional Talbot effects occur with viable microfabricated grating structures, made from realizable materials and used with hard penetrating x-rays with energies useful for radiography, and that the microfabricated spatially-periodic grating surface layers then have thicknesses that provide acceptably low vignetting by their structures.

Regarding key ingredients 1 and 2, the Invention teaches how said microfabricated grating structures are configured either as phase gratings or as a binary absorption gratings, and how such gratings are designed and fabricated.

Regarding key ingredients 1 and 2, the Invention teaches that at specific choices of $a_2$ that depend on x-ray energy and on the apparatus geometry, then periodic x-ray interference pattern P with period $a_P$ is formed on slab-volume SV3 grating by G1 multi-period averaging of pattern Q, and that, in turn, pattern Q is formed with period $a_Q$ via the x-ray analogs of the Talbot and fractional Talbot effects by the Invention's geometry when grating G2 is a binary absorption grating, and further teaches appropriate values for $a_2$, profiles, planforms, structures and materials for said grating, and that these specific choices of period have values at which geometric shadows are not cast by grating G2.

Regarding key ingredients 1 and 2, the Invention teaches that at specific choices of $a_2$ that depend on x-ray energy and on the apparatus geometry, then periodic x-ray patterns Q and P are similarly formed on slab-volume SV3 via the x-ray analogs of the Talbot and fractional Talbot effects by the Invention's geometry when grating G2 is a non-absorbing phase grating, and further teaches appropriate values for $a_2$, profiles, planforms, structures and materials for said grating, and that geometric shadows are not cast by such a grating.

Regarding key ingredient 1, the Invention teaches suitable choices for filter F and anode A materials and for an AC-ripple-free DC high voltage specification for power supply HV for generating x-rays with a conventional x-ray tube T, that then allow the x-ray spectral bandwidth $\Delta E$ there-produced to be sufficiently narrow to allow the x-ray analogs of the Talbot and fractional Talbot effects to obtain.

Regarding key ingredients 1–3, the Invention teaches the needed values of $a_2$ and apparatus geometric parameters whereby the Talbot and fractional Talbot effects obtain in the Invention in a manner wherein image contrast is obtained from refractive-index-gradients of object BDY, and that said refractive-index-gradients produce an edge-enhanced image of artifacts within object BDY.

Regarding key ingredients 1–3, the Invention teaches that images with refractive-index gradient contrast may be obtained with the Invention by using three spatially periodic gratings G1, G2, and G3, appropriately configured and a continuous recording media for the detector, such as a fluor-screen and film.

Regarding key ingredients 1–3, the Invention teaches, that the fractional Talbot effect provides energy-dependent contrast reversals of periodic pattern P. These contrast reversals may be used to provide a dual energy x-ray imaging system. When the energy of such a contrast reversal is appropriately configured in the x-ray analog of this effect to match the energy of the abrupt absorption and/or refractive index change of a given element that occurs at an absorption edge that is characteristic of that element, then such a configuration further allows image contrast to obtain for only said element distributed within object BDY. It further teaches that the refractive-index variation with energy of said element provides added image contrast. It further teaches that higher element-selective contrast is much higher when grating G2 is a phase grating than when it is a binary absorption grating. It further teaches methods for configuring the Invention so that element-selective imaging obtains with the Invention.

Regarding key ingredients 1–5, the Invention teaches how to obtain simultaneously two independent images, such as an image of an examined object's absorption distribution and an image of its refractive-index gradient distribution with the Invention from data recorded during a single x-ray exposure via the additional interlacing of c-labeled pixels within the detector's periodic pixel array via a tiling algorithm, wherein the data from b-, d-, and c-labeled pixels are used in an image subtraction algorithm.

Regarding key ingredient 3, the Invention teaches that the further inclusion of a third grating, G3, that is located immediately in front of or immediately behind a detector's periodic pixel array and is configured as a binary absorption grating and with a periodic planform that is devised via a tiling algorithm, can be used to mask portions of each detector pixel so that phase and period matching then occurs for detectors having pixel periods larger than $a_P/2$, whereby the useful range of apparatus parameter values is extended. The Invention also teaches that use of grating G3 to mask a spatially continuous detector facilitates phase matching and alignment, and also may be used to obtain refractive-index imaging by masking BRIGHT fringes of pattern P (to provide an otherwise DARK field with object BDY absent) without requiring a periodic detector-pixel array and the associated expense.

Regarding key ingredient 6, the Invention teaches suitable methods by which a collateral Invention, consisting of a new form of laser interferometer, is used in-situ for obtaining and maintaining precision alignment of its apparatus, by further exploiting the Inventor's discovery that exactly the same Equations and parameter values that allow the Invention to function with x-rays, then also allow said in-situ optical interferometer to be built, that, in turn, forms with light interference pattern O with the same period a as that of pattern P, and thereby allows pattern O to be used for apparatus alignment with light. The Invention further teaches methods for using this laser interferometer to obtain accurate apparatus alignment and to achieve accurate period and phase matching.

Regarding key ingredients 1–6, the Invention teaches that the Invention's not requiring realignment between exposures allows acquisition of image data via a rapid temporal sequence of x-ray exposures, wherein the apparatus is reoriented relative to the object between exposures, and wherein during each exposure a portion of the final image data is acquired, and wherein these various acquired data sets for the various exposures of the sequence eventually can be synthesized to form the final image. So doing, the Invention can use a sparse array of inexpensive small CCD detectors. Also so doing, the Invention can be used for a CT scan.

Regarding key ingredients 1–6, the Invention teaches that the Invention's reduced scatter-induced blur allows removal of source collimation in a CT scanning apparatus so that the Invention may be used therein, whereby an increased number of paths through object BDY is recorded simultaneously, and whereupon the required total scanning time is then reduced.

Regarding key ingredients 1–6, the Invention teaches apparatus configurations and methods, for realizing the above teachings in practice and with detector arrays with various different sizes, and further teaches associated fabrication details and appropriate materials.

Other teachings and objectives of the Invention also will become apparent as remaining details of the Invention are disclosed.

III.2 Calculation of pattern Q using physical optics principles

To provide details of the operation of the Invention, it is helpful to define two x-ray intensity patterns, Q and Q'. These are idealized intensity profiles of interference patterns that would be formed on the surface of slab-volume SV3 by x-rays emitted by an idealized (fictitious) point source S', shown on FIG. 2, located at lateral position $x_1$, $y_1$ (referenced to $C_L$) on the plane of grating G1. Patterns Q and Q' correspond to situations with object BDY respectively absent and present. With object BDY absent, x-rays emitted by point source S' propagate through grating G2 directly to slab-volume SV3, and pattern Q is then formed on the surface of slab-volume SV3. Pattern Q is spatially periodic, with said periodicity displaying high contrast. When object BDY is present, x-rays are transmitted both by grating G2 and object BDY, whereupon object BDY modulates pattern Q so that pattern Q' is formed instead.

The intensity of pattern Q has a periodic spatial dependence, specified by the function $I_Q(x_3,y_3; x_1,y_1)$, where $x_3$ and $y_3$ are measured laterally on the surface of slab-volume SV3 (e.g. on the surface of periodic detector D). When grating G2 is 1D-periodic, then interference pattern Q is also 1D-periodic and given by the function $I_Q(x_3;x_1)$. When source S' is located on axis $C_L$ (at $x_1,y_1 = 0,0$), $I_Q$ is then specified by the 2D and 1D-periodic functions $$I_Q(x_3,y_3)=I_Q(x_3,y_3;0,0), \tag{III.10}$$

and $$I_Q(x_3)=I_Q(x_3;0). \tag{III.11}$$

In geometric-shadow mode grating G2 is a binary absorption grating. An unscattered x-ray photon's path from source S' to surface D may be viewed as along a negligible-thickness straight-line path through a single transmitting aperture in grating G2. This path is similar to that for a point particle. Indeed, the inventions by Anno, Barnea, and Ema assume such a propagation model. In such case pattern Q is immediately seen to be the binary transmission distribution of grating G2 geometrically projected onto slab-volume SV3. In an interferometric mode, period a has a small numerical value. Since x-rays are a form of electromagnetic radiation, then physical optics principles govern their propagation. X-rays acting as electromagnetic waves (rather than as point particles) coherently propagate simultaneously through adjacent G2 periods, whereupon grating G2 diffract the x-rays. Thus, for small $a_2$ the wave-like nature of x-rays must be considered, and the evaluation of pattern Q then involves solving the physical optics problem for diffraction by grating G2. At typical periods for $a_2$ and typical hard x-ray wavelengths used by the Invention, virtually all Fraunhofer diffraction orders overlap, whereupon under certain additional conditions the (non-fractifractional Talbot effect or fractional Talbot effect then obtains.

The above formulated general physical-optics diffraction problem for scalar waves of any kind was first solved by Cowley and Moodie [1970] for the case wherein G2 is an infinitely-wide planar grating with periodically varying transmission. The Cowley and Moodie solution uses the Huygens-Fresnel-Kirchoff diffraction integral [Born and Wolf, 1967, p.380] from physical optics. It is adapted for use with complex-valued transmission functions by Clauser and Reinsch [1992, Appendix B]. It is expressed as a complex-valued Fourier series expansion for the wave amplitude that impinges on the surface of slab-volume SV3. Clauser and Reinsch [1992] also solved a similar problem for grating G2 having finite number of periods. While their solution has a different appearance from that by Cowley and Moodie, for a very large number of periods, the solutions give asymptotically equivalent results, and either solution may be used. Applied to the above problem, both solutions assume that the electromagnetic waves are monochromatic with some energy, E, wherein the functions $I_Q(x)$ and $I_Q(x, y)$ are then obtained as the squared modulus of the complex amplitude, as calculated via said diffraction integral.

The general form of the physical-optics solutions immediately provides two important features of pattern Q that always obtain, regardless of the Invention's operational mode. The first is referred to as the "seesaw effect". Said effect, for example, explains the operation of a "pinhole camera". The effect is that when source S' is laterally displaced by increasing $x_1$ by a distance $\delta$, then the whole resulting pattern Q is correspondingly laterally displaced in the opposite direction by the distance $\alpha\delta$. Given the seesaw effect one can then write $$I_Q(x_3;x_1)=I_Q(x_3+\alpha x_1), \tag{III.12}$$

and $$I_Q(x_3,y_3;x_1,y_1)=I_Q(x_3+\alpha x_1,y_3+\alpha y). \tag{III.13}$$

The second feature is that since the transmission function of grating G2 is (for practical purposes) spatially periodic with period $a_2$, as per Eq. (I.1), then pattern Q, as formed by a reasonably broad grating G2, is also spatially periodic with some period $a_Q$, and one may neglect any corresponding residual error created by distant ends of grating G2 (as per the aforementioned asymptotic equivalence of the two solutions and caveats of Sect. I.1). Periodicity then implies $$I_Q(x)=I_Q(x\pm k\, a_Q), \tag{III.14}$$

and $$I_Q(x,y)=I_Q(x\pm ka_Q, y\pm k'a_Q), \tag{III.15}$$

where k and k' are integers. Equations (III.12)–(III.15) are fundamental to the operation of the Invention in all modes.

If grating G2 is 1D-periodic, its complex-valued amplitude transmission is denoted by $t_2(x_2)$ as a function of lateral position $x_2$ on G2, with its periodicity implying $$t_2(x_2)=t_2(x_2+a_2). \tag{III.16}$$

The associated intensity transmission function of grating G2 is then just the squared modulus of $t_2(x_2)$, $$T_2(x_2)=T_2(x_2+a_2)=|t_2(x_2)|^2. \tag{III.17}$$

With Eq. (III.16) (and thus with a very broad grating) the physical-optics solutions show quite generally that $I_Q$ is always periodic with the period $Ma_2$. Notwithstanding, $I_Q$ also may or may not be periodic at a higher harmonic of this period. Thus, its period is, quite generally, $$a_Q = \frac{Ma_2}{p}, \tag{III.18}$$

where p is an integer that depends on the value of a fundamental scaling parameter $\beta$, introduced below. If the amplitude transmission function of grating G2 is 2D-periodic and separable as per Eqs. (I.2) and (I.3), it may be shown via reference to the form of the diffraction integral that $I_Q(x_3,y_3)$ is then also 2D-periodic and separable, also satisfying Eqs. (I.2) and (I.3), as per $$I_{Q\text{-}sep}(x,y)=I_Q(x)I_Q(y). \tag{III.19}$$

With $t_2$ a periodic checkerboard function satisfying Eqs. (I.2) and (I.4), then under suitable (no overlap) conditions $I_Q(x_3,y_3)$ is also given as a checkerboard function satisfying Eqs. (I.2) and (I.4), as per $$I_{Q\text{-}ckbd}(x,y) = I_{Q\text{-}sep}(x,y) + I_{Q\text{-}sep}\left(x+\frac{a_Q}{2}, y+\frac{a_Q}{2}\right) \tag{III.20}$$

The solutions show that for small a the shape of pattern Q depends in a complicated manner on the detailed shape of the grating's periodic transmission function. However, for illumination by quasi-monochromatic x-rays with wavelength $\lambda=hc/E$, where E is the associated photon energy, then the solutions' basic scaling properties and resulting value for p are comparatively simple and hold for all $a_2$ and E, including values of $a_2$ and E for which geometric shadows obtain. With respect to variations of $a_2$, $\alpha$, L, and $\lambda=hc/E$, the scaling is determined by the single parameter, $\beta$, defined as $$\beta = \frac{\lambda\rho}{a_2^2} = \frac{hc\rho}{Ea_2^2} = \frac{hc\alpha L}{Ea_2^2(1+\alpha)^2}, \tag{III.21}$$

where the definition of $\rho$ from Eq. (III.6) and of $\alpha$ from Eqs. (III.3)–(III.5) are incorporated. The relative shape of pattern Q, the value of p, and the period $a_Q$ for Eq. (III.18) depend only on the value of $\beta$. To use Eq. (III.21) under independent variations of either $a_2$ or E while the other is held fixed, it is helpful to define two functions $$\tilde{a}_2(E) = \frac{1}{1+\alpha}\left(\frac{hc\alpha L}{E}\right)^{1/2}, \tag{III.22}$$

and $$\tilde{E}(a_2) = \frac{hc\alpha L}{a_2^2(1+\alpha)^2}. \tag{III.23}$$

For L=1 m, $\alpha=1$, and E=17.4 kev, Eq. (III.22) gives $\tilde{a}_2(E)=4.2\ \mu$m. A variation of $a_2$ with E held fixed provides an associated variation of $\beta$ given by $$\beta = \left(\frac{\tilde{a}_2(E)}{a_2}\right)^2, \tag{III.24}$$

Similarly, a variation of E with $a_2$ held fixed provides an associated variation of $\beta$ given by $$\beta = \frac{\tilde{E}(a_2)}{E}. \tag{III.25}$$

The physical optics solutions show that for -quasi-monochromatic illumination, then pattern Q displays quite remarkable periodic features that occur via superposition of the Fraunhofer diffraction orders formed by grating G2, for values of $\beta$ with $$\beta = \frac{n}{m} \pm \epsilon, \tag{III.26}$$

where n and m are both integers, and where $\epsilon$ is a small real number. These features are examples of the "fractional Talbot effect". A special case of the more general but subsequently discovered fractional Talbot effect, is a truly remarkable effect that is known in light-optics as the "Talbot effect". The (non-fractional) Talbot effect occurs when Eq. (III.26) obtains for integers $n \geq 0$ and m=1, and for $\epsilon=0$. At the corresponding values of $\beta$, pattern Q then has the form of a nearly exact self-image of the grating's periodic transmission function, magnified by M, whereupon the image has the period $Ma_2$. Geometric shadows correspond to a special case of the Talbot effect with the integers m=1 and n=0 and small $\epsilon$. Perhaps even more remarkable than the non-fractional Talbot effect is the more general fractional Talbot-effect, that obtains for $\beta$ having a value such that Eq. (III.26) obtains with small $\epsilon$ and with integers m>1 and n≧1, where the fraction n/m is reduced to lowest terms, i.e. where the integers n and m have no common integer divisor. Such a pair of integers are said to be "coprime" or "relatively prime". In such cases pattern Q consists of a coherent sum of m side-by-side amplitude self-images per period, all magnified by M, each having the period $Ma_2$, and with each such self-image laterally displaced from the next by the distance $Ma_2/m$. This feature is commonly referred to as m-fold "aliasing". Each component self-image is thus an "alias", and the integer m is the "alias multiplicity". There are m such coherent aliases that occur per period.

To observe aliased self imaging in practice in amplitude interferometric mode, the integer m must be kept sufficiently small so that only a modest number of aliases are formed. When the self-images do not overlap, they form a periodic pattern with the period $Ma_2/m$. When they do overlap, they interfere and produce a variety of interference effects. Noteworthy among these effects is the formation of a binary intensity pattern (i.e. one with either zero intensity of a constant finite intensity) by a carefully designed step-function shaped periodic phase grating. When the illumination is highly monochromatic and the grating contains a very large number of periods so that Fraunhofer orders still overlap, then the integer n may be quite large and the Talbot effect still obtains.

III.3 Action of grating G2 when configured as a binary absorption grating

When grating G2 is a binary absorption grating, the Invention then operates either in geometric-shadow or in amplitude-interferometric mode. Neglecting the effects of its ends and of the finite "leakage" of its x-ray absorbing layer XAL, the grating's binary amplitude transmission as a function of lateral position $x_2$ on grating G2, is given (ideally) by Eq. (I.6) as $$t_2(x_2) = H(x_2; s_2; a_2). \tag{III.27}$$

Since the function H is always 0 or 1, then via Eq. (III.17) the associated intensity transmission function is given by $$T_2(x_2) = [H(x_2; s_2, a_2)]^2 = H(x_2; s_2, a_2). \tag{III.28}$$

If the grating duty-cycle satisfies the "1D no-overlap" restriction $$\frac{s_2}{a_2} < \frac{1}{m}, \tag{III.29}$$

then when Eq. (III.26) is satisfied for quasi-monochromatic illumination with m and n integers and with $\epsilon \approx 0$, then, via aliased self imaging, the intensity spatial distribution of pattern Q is given by $$I_Q(x_3) = \frac{1}{m} H\left(x_3 - \frac{mn}{2} Ma_2; Ms_2, \frac{Ma_2}{m}\right). \tag{III.30}$$

In such case pattern Q is spatially periodic with period $a_Q$. The period is given by Eq. (III.18) with $$p = m. \tag{III.31}$$

Equation (III.30) is plotted in FIG. 13a versus $x_3$ for p=1. High intensity stripe-shaped 1D fringes labeled BRIGHT have the width $S_Q = Ms_2$, and alternate with zero-intensity stripe-shaped fringes labeled DARK. The binary intensity pattern's duty-cycle is $$\frac{s_Q}{a_Q} = m \frac{s_2}{a_2}. \tag{III.32}$$

For m=1 the pattern's duty-cycle is the same as that of the geometric shadow pattern. Additionally, a lateral half-period pattern shift $Ma_2/2$ occurs via Eq. (III.30) when the integer product mn is odd. While this shift is totally negligible if it remains constant, it has important consequences used by the Invention (and discussed below) when it does not.

Geometric-shadow mode in the Invention consists of the special limiting case associated with large $a_2$ (and/or for large E). It corresponds to the case with m=1, n=0 and small $\epsilon$, whereupon pattern Q then consists of the geometrically projected and thereby magnified periodic geometric shadow of the grating. Pattern Q is then spatially periodic with the period $a_Q = Ma_2$ Thus, for geometric-shadow mode the period $a_Q$ is given by Eq. (III.18) with $$p = 1, \tag{III.33}$$

and the binary-intensity pattern's duty-cycle is $s_Q/a_Q = s_2/a_2$. Since geometric shadow mode obtains in the large E limit, it thus also obtains for broad-band illumination in this limit.

When grating G2 is 2D-periodic via Eqs. (I.1)–(I.3) with $f(x;a_2)=t_2(x)$, and with the "2D no-overlap" restriction, $$\frac{s_2}{a_2} \leq \frac{1}{2m}, \tag{III.34}$$

used in place of Ineq. (III.29), then the 2D functional form of $I_Q$ is given by Eqs. (III.19), (III.20) and (III.30). For configurations with $\beta \approx n/m$, pattern Q has the typical resulting 1D and 2D-periodic profiles shown respectively on FIGS. 13a and 14a–c with x-ray-bright and dark fringes indicated as BRIGHT and DARK. The displayed patterns are shown for negligible "leakage" transmissions of the x-ray absorbing areas of grating G2. Finite leakage gives non-zero DARK intensity fringes and slightly reduced intensity BRIGHT fringes. If the grating G2 planform is that of FIG. 8d, then the associated 2D-periodic intensity distribution $I_Q(x_3,y_3)$ shown on FIG. 14c is found by similarly setting $f(x;a_Q)=I_Q(x)$ in Eq. (I.3) with g=1 and the minus sign. This latter grating choice produces a higher net transmission for grating G2.

For fixed $a_2$ Eqs. (III.25) and (III.26) with $\epsilon \approx 0$ imply that m-fold aliased self-imaging occurs via the fractional Talbot effect for x-rays with energy E at the specific x-ray energies $$E_{n,m}(a_2) \equiv \frac{m}{n} \tilde{E}(a_2) = \frac{m}{n} \frac{hcL\alpha}{(1+\alpha)^2 a_2^2}, \tag{III.35}$$

whereupon pattern Q then obtains with period $a_Q$ given by Eqs. (III.18) and (III.31). The special case m=1 gives (un-aliased) self-imaging and the (non-fractional) Talbot effect. To obtain either form of self-imaging and thereby to produce a binary intensity pattern Q in the Invention, grating G2 is configured as a binary absorption grating for operation in the n,m amplitude-interferometric mode. For such operation in an apparatus of length L with x-rays whose average energy is $E_X$, the values for $\alpha$, $a_2$, n and m are correspondingly chosen so that the associated value of $E_{n,m}(a_2)$ occurs at the average x-ray energy $E_X$, as per $$E_X \approx E_{n,m}(a_2), \tag{III.36}$$

with $\beta$ then correspondingly at or near the design's operating point value $$\beta_x \equiv \frac{n}{m}. \tag{III.37}$$

So doing, $\epsilon=0$ obtains for x-rays whose energy E is approximately equal to the average energy $E_X$. In turn, Eq. (III.36) obtains by selecting the value for the grating G2 period $a_2$ from an associated set of discretely allowed values, given by $$a_2 = \left(\frac{m}{n}\right)^{1/2} a_2(E_x) = \left(\frac{m}{n}\right)^{1/2} \left(\frac{R_1 R_2}{R_1 + R_2}\right)^{1/2} \left(\frac{hc}{E_x}\right)^{1/2}, \tag{III.38}$$

where n and m are coprime integers, and where the second half of Eq. (III.38) follows from Eqs. (III.1), (III.3) and (III.22).

Exact self-imaging wherein pattern Q correspondingly has exactly a periodic rectangular functional form, occurs only for x-rays whose energy exactly satisfies Eq. (III.36), and thus only for values of $\beta$ satisfying Eq. (III.26) with c=0, and with infinite-width gratings and monochromatic illumination. Importantly for the operation of the Invention, however, nearly exact self-imaging also occurs for values of $\beta$ giving modestly small but finite $\epsilon \neq 0$, and with wide gratings and narrow bandwidth illumination, wherein pattern Q is then slightly rounded but deviates only a little from the form of the periodic rectangular functions given above. For large $\epsilon$ and x-rays with energy E far from $E_X$, however, said deviation becomes large and the contrast of pattern Q (at period $a_Q$) then deteriorates or vanishes entirely, or even reverses.

The effective contrast (at period $a_Q$) of pattern Q for any $\beta$ may be determined by expanding $I_Q$ as Fourier series, and then by examining the $\beta$, $a_2$, and/or E-dependence of the spatial-frequency component of $I_Q$ with period $a_Q$ [Clauser and Reinsch, 1992, FIGS. 5a–e]. For a grating that is symmetrical with respect to $C_L$, the Fourier-series expansion is $$I_Q(x) = \sum_{j=0}^{\infty} Q_j(\beta) \cos\left(2\pi j \frac{x}{Ma_2}\right), \tag{III.39}$$

where the various (real-valued) Fourier coefficients $Q_j(\beta)$ are given by $$Q_j(\beta) = \frac{1}{Ma_2} \int_{-Ma_2/2}^{Ma_2/2} I_Q(x) \cos\left(2\pi j \frac{x}{Ma_2}\right) dx. \tag{III.40}$$

The various coefficients $Q_j(\beta)$ then specify the magnitudes of the associated spatial-frequency components of $I_Q$. The lowest spatial frequency has the period $Ma_2$, i.e. that of the geometric shadow pattern formed on the surface of slab-volume SV3 at large $a_2$. The Fourier coefficient $Q_0$ is independent of $\beta$ and $a_2$ but does depend on the grating's structure. To remove its bias, it is useful to normalize by $Q_0$ all of the $Q_j$ for j>1. The contrast of pattern Q is proportional to the amplitude of the spatial variation of its intensity fringes. Said contrast (i.e. the non-sinusoidal generalization of the fringe visibility of sinusoidal fringes) at the period $Ma_2/m$, is determined by examining the $\beta$-dependence of $Q_m(\beta)/Q_0$. The contrast of the pattern Q at the geometric shadow period $Ma_2$, for example, is determined by examining the $\beta$-dependence of $Q_1(\beta)/Q_0$. Aliased (m-fold) self-imaging is then evident as a strong "resonance" of the associated $Q_m/Q_0$ at values of $\beta$ given by Eq. (III.26) with $\epsilon \approx 0$.

FIG. 15 shows a numerical evaluation of $Q_1(\beta)/Q_0$ as a function of $\beta$ for a binary absorption grating, with each curve on FIG. 15 corresponding to a different choice for the grating G2 duty-cycle $s_2/a_2$. Via the equivalent Eqs. (III.21), (III.25) and (III.26), FIG. 15 is plotted with three equivalent horizontal axes. The lowest of these gives the controlling value of $\beta$, with $\beta$ increasing to the left. FIG. 15 shows isolated sharp peaks in $Q_1/Q_0$ for $\beta$ centered on the values $\beta=n$, where n is an integer. These are the m=1 resonances that occur when a m=p=1 self-image is formed via the (non-fractional) Talbot effect. For integers m>1 similar resonances occur in the dependence of a similar plot of the Fourier coefficient $Q_m/Q_0$, respectively centered on the values $\beta=n/m$. Similarly, these are the m>1 resonances that occur whenever a m-fold "aliased" p=m grating self-image is formed via the fractional-Talbot effect. These finite-width resonances were first discovered and explained by Clauser and Reinsch [1992]. For fixed $a_2$ such resonances correspondingly occur for x-rays with energies given by Eq. (III.35). As shown by Clauser and Reinsch [1992, see Sect. 1.3, Eq. (65)] the full width of a resonance at $\beta=\beta_x$ for any integers n and m in Eq. (III.37) is given by $$\frac{\Delta \beta}{\beta_x} = \frac{2s_2}{na_2}. \tag{III.41}$$

In an apparatus configured via Eq. (III.38) a binary intensity pattern Q forms for x-rays with energy $E \approx E_X$. However, in operation the Invention's x-ray energy spectrum is not monochromatic, but instead has a finite spread of x-ray energies E of bandwidth $\Delta E$ centered on the average energy $E_X$. Once the values for the parameters L, $\alpha$, $E_X$, and $a_2$ are chosen, and thus may be viewed as fixed quantities, then by reference to the upper horizontal axis, drawn via Eq. (III.25), FIG. 15 may be used to determine the effective contrast for pattern Q formed with p=1 for x-rays with energy $E \neq E_X \approx E_{n,m}(a_2)$, and that have an associated value of $\beta$ for which $\epsilon \neq 0$. Similar plots of $Q_m/Q_0$ versus $\beta$ [e.g. [Clauser and Reinsch, 1992, FIGS. 5a–e] may be used to determine the effective contrast for pattern Q formed with p=m. In turn, such plots may be used for defining a maximally allowed energy spread $\Delta E_{max}$, such that if the bandwidth $\Delta E$ of the illuminating x-rays is maintained at less than $\Delta E_{max}$, then the energy distribution is sufficiently close to monochromatic that energy E is always within the finite resonance width, and for practical purposes then, all x-rays at energies within $\Delta E$, in turn, provide acceptably high contrast to pattern Q. Via Eq. (III.41), said acceptably high pattern contrast occurs in the n,m amplitude-interferometric mode when the x-ray energy bandwidth is limited by $$\Delta E_{max} = \frac{2s_2 E_{n,m}}{na_2} = \frac{2s_2 E_x}{na_2}, \tag{III.42}$$

whereupon $\beta$ is within the resonance width, $$\beta_x - \Delta\beta/2 \leq \beta \leq \beta_x + \Delta\beta/2. \tag{III.43}$$

Resonances with n=1 have the largest $\Delta E_{max}$. The desired bandwidth limitation for the Invention is then $$\Delta E \leq \Delta E_{max}. \tag{III.44}$$

It is noteworthy that $\Delta E_{max}$ limits the x-ray spectral bandwidth to values somewhat narrower than those commonly used in radiography. Nonetheless, Sections III.8, V.1 and V.3 teach how in the Invention the materials comprising anode A and filter F are chosen and how the energy of electron beam eB is set by the ripple-free constant DC high-voltage from supply HV to provide a spectral bandwidth $\Delta E$ satisfying Ineq. (III.44).

Allowed limits for $a_2$ for operation of the Invention in geometric-shadow mode also may be found from FIG. 15. If the values of L, $\alpha$, and $E_X$ are held fixed and the energy bandwidth ΔE is small, then a variation of $a_2$ gives a corresponding variation of β and an associated variation of the shape of pattern Q. The associated variation of β via Eq. (III.24) provides the middle horizontal axis for FIG. 15. The geometric-shadow limit occurs for large $a_2$, and thus occurs for β→0 via Eqs. (III.21). Via Eq. (III.26) this limit occurs for β=ε as the wing of the m=1, n=0 resonance that, in turn, is centered at β=0. Geometric-shadow formation thus occurs at one specific resonance, among a set of many such resonances, and in the large $a_2$ limit the function $I_Q$ then asymptotically becomes the grating's magnified geometric-shadow pattern, with pattern Q periodic as per Eqs. (III.18) and (III.33). The ratio $Q_1/Q_0$ gives the contrast of pattern Q at the Fourier component in Eqs. (III.3) and (III.40) at spatial period $Ma_2$, which for the geometric-shadow pattern is the dominant component.

Consider a variation of apparatus design, with grating G2 configured as a binary absorption grating, that varies $a_2$ but holds L, α, and E constant. Observe from FIG. 15 the associated variation of $Q_1(\beta)/Q_0$ by reference to the middle horizontal axis. It indicates for which $a_2$ values the geometric-shadow pattern does or does not obtain. As expected, it does obtain for large $a_2$ and small β. A limiting value of a below which it no longer forms depends on the grating duty-cycle $s_2/a_2$. Indeed, it is possible to show that geometric shadows never form for any of the discrete values specified by Eq. (III.38) with n≧1 and m≧1 and any duty cycle $s_2/a_2 \leq 1$. Thus, the geometric-shadow and amplitude-interferometric modes obtain for mutually exclusive values of $a_2$. For a typical duty-cycle the geometric-shadow limit is crudely given from FIG. 15 at β≈16. In terms of L, α, and $E_X$, $$a_2(\text{shad-limit}) \approx 4\, \tilde{a}_2(E_X), \qquad (\text{III.45})$$

is then the approximate value of $a_2$ for which $Q_1/Q_0$ assumes a reasonable fraction of its ultimate value for very large $a_2$. This value then may be taken as a rough limiting value for $a_2$ for operation in geometric-shadow mode, while small $s_2/a_2$ requires somewhat larger $a_2$ for the mode to obtain. Thus, the Invention may operate in geometric-shadow mode only for choices of $a_2$ larger than $a_2$(shad-limit). For L=1 m, α=1, and $E_X$=17.4 kev Eq. (III.45) gives $a_2$(shad-limit)=17 μm.

III.4 Action of grating G2 when configured as a phase grating

A binary absorption grating is not the only grating structure that produces a 1D or 2D-periodic rectangular-function binary intensity pattern at a Talbot-effect or fractional Talbot-effect resonance. Pattern Q with such a form is also produced via the fractional Talbot effect by a non-absorbing step-function shaped 1D or 2D-periodic phase grating, as was demonstrated with plane-wave illumination by light by Lohman and Thomas [1990] and by Leger and Swanson [1990]. This disclosure, however, is the first effort to propose x-ray phase gratings with similar properties.

Consider an x-ray grating that is structurally similar to a binary absorption grating grating, as shown in FIG. 6a, in that it has a thin spatially-periodic layer on the surface of a negligibly absorbing substrate SUB. Instead of the layer being made from an x-ray absorbing material, however, for a phase grating it is made from a negligibly-absorbing low-Z material that is highly-refracting for x-rays. The layer's thickness varies spatially in a step-function fashion, and further may assume not only two values including zero, but in some cases it may assume 3 or more locally stationary values on locally flat steps, as shown in FIGS. 7a–e and 9a,b. Within a step, the layer's thickness is locally constant (to within suitable fabrication tolerances). The layer's thickness profile variation, in turn, provides a spatially periodic variation of the phase of the transmitted x-rays. As per the discussion of Sect. II.2, a very thin layer of said low-Z material is sufficient to give substantial x-ray phase shift.

Consider a family of 1D-periodic phase gratings, wherein all gratings in the family have the same period $a_2$. Each grating in the family has a different profile shape that is identified by the symbol $PG(n_*, m_*, r_*)$, and is thus specified by three integers, $n_* \geq 1$, $m_* \geq 2$, $r_* \neq 1$, wherein the integers $n_*$ and $m_*$ are further specified to be relatively prime (coprime), i.e. they have a greatest common integer divisor of 1. Each period of a $PG(n_*, m_*, r_*)$ profile is divided into $m_*$ constant-thickness, equal-width locally flat steps to give it a step-function shape. Each step's width is then $a_2/m_*$. The complex transmission function of a 1D-periodic phase grating with the profile $PG(n_*, m_*, r_*)$ is specified to be the unit-modulus complex step function given by $$t_2(x_2) = \sum_{k=0}^{m_*-1} \eta_k H\left( x_2 - \delta_k(n_*, m_*)a_2; \frac{a_2}{m_*}, a_2 \right). \qquad (\text{III.46})$$

where the unit-modulus phase factor $\eta_k$ is $$\eta_k \equiv \exp[i\, \phi_k(n_*, m_*, r_*)]. \qquad (\text{III.47})$$

The offset for the k'th step, $\delta_k(n_*, m_*)a_2$, within a period is defined as $$\delta_k(n_*, m_*) \equiv \frac{[(n_* k)\ \text{modulo}\ m_*]}{m_*}, \qquad (\text{III.48})$$

Since the numerator in the right-hand side of Eq. (III.48) is an integer, one may set it equal to some integer $j = m_* \delta_k(n_*, m_*)$ that now represents the sequential ordering of steps within a period, and since there are $m_*$ steps per period, and via Eq. (III.46) $\delta_k$ is the fraction of a period that each step is laterally offset.

It can be shown that Eq. (III.48) specifies lateral offsets of the steps within a period that may (or may not) give a simple periodic permutation of a simple sequential ordering of the steps, i.e. the ordering of values in associated sequences of j and k values used in the summation of Eq. (III.46). The choice $n_*=1$ does not permute the step order. For example, for $n_*=1$ and $m_*=5$, Eq. (III.48) gives a one-to-one mapping between the integer sequences j=0, 1, 2, 3, 4 and k=0, 1, 2, 3, 4. However, a different choice of $n_*$ may (or may not) cause a permutation of the step order. For example, for $n_*=2$ and $m_*=5$, Eq. (III.48) gives a one-to-one mapping between the integer sequences j=0, 1, 2, 3, 4 and k=0, 3, 1, 4, 2. Nonetheless, whether or not the step order is permuted, Eq. (III.47) provides the fact that each value of k occurs once and only once per period. Inclusion of the offsets via Eq. (III.48) provides a further generalization of the design Formulae used by Leger and Swanson [1990] that also includes the results of their Formulae.

Equations (III.17), (III.46) and (III.47) imply that the grating's intensity transmission function, $T_2(x_2)$, is defined and equals one for all $x_2$. The phase shift $\phi_k(n_*, m_*, r_*)$ in Eq. (III.47) for x-rays with energy $E=E_*$, passing through the k'th step of this grating is specified in radians for a $PG(n_*, m_*, r_*)$ grating profile to be given by $$\phi_k(n_*, m_*, r_*) = \pi n_* r_* \left( k - \frac{k^2}{m_*} \right) - \phi_*(n_*, m_*, r_*). \qquad (\text{III.49})$$

The spatially constant term $\phi_*(n_*, m_*, r_*)$ in Eq. (III.49) is independent of k, and given by $$\phi_*(n_*, m_*, r_*) = \begin{cases} \pi n_* r_* m_*/4 & \text{for } m_* \text{ even,} \\ \pi n_* r_* (m_*^2 - 1)/(4m_*) & \text{for } m_* \text{ odd.} \end{cases} \quad \text{(III.50)}$$

It is included to keep all $\phi_k(n_*,m_*,r_*)$ less than or equal to zero. The step-function shaped surface layer on the phase grating generates the desired transmission function specified by Eqs. (III.46)–(III.49) for x-rays with energy $E_*$ if the thickness of the layer's k-th step is $$z_{Tk} = -\frac{\phi_k(n_*, m_*, r_*)}{2\pi} L_R(E_*), \quad \text{(III.51)}$$

where $L_R(E_*)$ is the thickness of said low-Z material that gives a $-2\pi$ phase shift at energy $E_*$, as may be calculated via Eq. (II.2). The energy $E_*$, is specified by $$E_* = \frac{m_*}{n_*} \tilde{E}(a_2) = \frac{m_*}{n_*} \frac{hcR_1R_2}{(R_1+R_2)a_2}, \quad \text{(III.52)}$$

where the second half of Eq. (III.52) follows from Eqs. (III.1), (III.3) and (III.23). The overall thickness scale of grating G2 is determined also by specifying the integer $r_*$. Note that the phase shift produced by such a periodic layer depends on energy via Eq. (II.2), so that the grating's transmission function is given by Eqs. (III.46)–(III.49) only for x-rays with energy $E_*$; however, the profile is fully specified by Eqs. (III.46)–(III.52), so that its complex transmission function may be calculated for x-rays with any energy E via Eqs. (II.2), (III.46)–(III.48), (III.51) and (III.52), since Eq. (II.2) implies that the phase shift by any step for x-rays at energy E is $E/E_*$ times the phase shift by that step at energy $E_*$.

Given the grating's period $a_2$, then it and the choices for the three integers $n_*$, $m_*$, and $r_*$, via Eqs. (III.46)–(III.52), completely define the associated PG($n_*,m_*,r_*$) step-function thickness spatial profile, $z_T(x_2)$, for the low-Z surface layer on a 1D-periodic phase grating. FIGS. 7a–e plot the normalized thickness profile $z_T(x_2) \times [2\pi/L_R(E_*)]$ versus $x_2$, as specified by Eqs. (III.46)–(III.52) for $r_*=1$ and for various choices of $n_*$ and $m_*$. The coefficient in square brackets rescales the thickness to display in radians the (negative) magnitude of the associated negative phase shift produced by the profile at energy $E_*$. (A positive phase shift would appear below the abscissa.) The profiles' steps in FIGS. 7a–e are labeled by associated values of j and k, where $j=m_*\delta_k(n_*,m_*)$ via Eq. (III.48) is an integer. FIG. 7e shows the above-mentioned possible permutation for $n_*>1$.

Next, consider a 2D-periodic phase grating whose complex transmission function is given via Eqs. (III.46)–(III.52) by the separable function $$t_{2\text{-}sep}(x_2,y_2) = t_2(x_2) t_2(y_2), \quad \text{(III.53)}$$

where $t_2(x_2)$ satisfies Eq. (I.1) and $t_{2\text{-}sep}(x_2,y_2)$ satisfies Eq. (I.2). It is then $$t_2(x_2,y_2) = \sum_{k_x=0}^{m_*-1} \eta_{k_x} H\left(x_2 - \delta_{k_x}(n_*, m_*)a_2; \frac{a_2}{m_*}, a_2\right) \times \sum_{k_y=0}^{m_*-1} \eta_{k_y} H\left(y_2 - \delta_{k_y}(n_*, m_*)a_2; \frac{a_2}{m_*}, a_2\right), \quad \text{(III.54)}$$

where the function H is defined by Eq. (I.6). A similar definition via Eq. (I.4) (with g=0 and the + sign) may be used to give the analogous 2D-periodic checkerboard amplitude transmission function. FIGS. 9a and 9b respectively show for PG(1,2,1) and PG(1,3,1) profiles the x-y plan views of their associated 2D-periodic step-function thickness distributions, where, as with FIGS. 7a–e, the step thicknesses are again normalized and multiplied by $[2\pi/L_R(E_*)]$. By Eq. (III.54) the 2D-periodic surface layer's steps all have square or rectangular x-y planforms, as shown on FIGS. 9a,b. Since the function $t_2(x_2,y_2)$ on any such 2D step is the product of the two 1D-periodic phase factors $\eta_{k_x}$ and $\eta_{k_y}$ given by Eqs. (III.49) and (III.54), then the associated phase shifts add, as do the steps' thicknesses. That is, the thickness of such a 2D square or rectangular step is just the sum of the thicknesses associated with each of the phase factors $\eta_{k_x}$ and $\eta_{k_y}$.

Although the phase shift by any step of the above-defined phase grating profiles is energy dependent, the profiles are still spatially periodic with period $a_2$. Consider pattern Q produced by illumination of phase grating G2 by point source S' with quasi-monochromatic x-rays with energy E. Via the physical optics solutions for this problem outlined in Sect. III.2 the pattern exhibits the Talbot and fractional Talbot effects at values of β with ε≈0 in Eq. (III.26). The values of E and $a_2$ that give β=n with ε≈0, give the (non-fractional) Talbot effect whereupon pattern Q is an un-aliased magnified amplitude self-image of the grating's complex transmission function. However, while this self image now has a spatially periodic step-function phase shift, it has constant unit intensity throughout. Thus, the intensity distribution for pattern Q is just that of the magnified geometric shadow amplitude, which is constant (since $T_2(x_2)=1$ for all $x_2$), whereby said phase grating casts no intensity geometric shadow. At β=n the intensity of pattern Q thus exhibits no spatial variation and its contrast is zero.

For other values of β given by the rational fraction of Eq. (III.26) with ε≈0 and the integer m>1, however, the intensity contrast is not zero. Then, m-fold aliased self-imaging occurs via the fractional Talbot effect. The grating's geometrically-magnified amplitude-shadow pattern is added (aliased) m times per period, with each successively added amplitude pattern phase shifted and laterally displaced from the next. All m of these patterns overlap each other and interfere. On some steps there is constructive interference, and on others, destructive interference. The 1D and 2D-periodic PG($n_*,m_*,r_*$) grating profiles are specified by Eqs. (III.46)–(III.53) in such a manner that upon illumination of a grating G2 having such a profile by x-rays from point source S' at energy $E=E_*$, the interference of the superposed amplitudes produces pattern Q with a binary intensity distribution, i.e. destructive interference occurs in all image steps within each period except one. The 1D-periodic PG($n_*,m_*,r_*$) profile for grating G2 gives pattern Q with the binary periodic rectangular-function shaped intensity distribution $$I_Q\left[x_3 - \left(\frac{n_*}{2} + \frac{1}{2}\right)a_Q\right] = m_*H\left(x_3; \frac{Ma_2}{m_*}, Ma_2\right), \quad \text{(III.55)}$$

where the constant offset in the argument of $I_Q$ is inconsequential. (The profiles in FIGS. 7a–e have been laterally shifted by $[(n_*/2)+(\frac{1}{2})]a_Q$ to remove the effects of this offset.) Pattern Q now has the period $a_Q=Ma_2$, a BRIGHT stripe-shaped fringe width $s_Q$ with the duty-cycle $$\frac{s_Q}{a_Q} = \frac{1}{m_*}, \quad \text{(III.56)}$$

and has its period a given by Eq. (III.18) with p=1. (III.57)

The 1D-periodic pattern Q is similar to that produced by a 1D-periodic binary absorption grating, as shown on FIG.

13a. The corresponding 2D-periodic intensity pattern Q produced by grating G2 configured with a 2D-periodic PG(n*,m*,r*) profile via Eq. (III.53) is similarly given by Eq. (III.19), or by Eq. (III.20) for a checkerboard configuration. A typical 2D-periodic pattern Q thus produced has a form similar to that produced by a 2D-periodic binary absorption grating, as shown in FIG. 14a.

A phase grating so configured is used in the Invention for grating G2 as an alternative to a binary absorption grating, whereupon the Invention then operates in phase-interferometric mode via the fractional Talbot effect. For very large m* a PG(1,m*,1) profile asymptotically approaches the shape of a co-phased periodic array of parabolic lenses. A 2D-periodic phase grating G2 is far more efficient than is a binary absorption grating that produces the same pattern Q, in that the phase grating effectively focuses x-rays onto square spots (in 2D) or onto stripes (in 1D), with negligible absorption of x-rays by grating G2. Given that a phase grating produces a binary pattern Q with a small duty-cycle, it allows a large duty-cycle to be used for grating G1 without an associated loss of contrast of pattern P. Since the required thickness for a phase grating is generally much smaller than that of a binary absorption grating, it also features significantly reduced vignetting. Thus, when 2D-periodic gratings are used in the Invention, then configuring grating G2 as a phase grating, rather than as a binary absorption grating provides a more efficient and practical apparatus with a higher net x-ray transmission by gratings G1 and G2.

Following the discussion of Sect. III.3, the contrast of pattern Q with p=1 is indicated by the ratio of coefficients $Q_1/Q_0$ in the Fourier series expansion of $I_Q$ via Eqs. (III.39), and (III.40). The $\beta$-dependence of $Q_1/Q_0$ for the various respective phase grating profiles of FIGS. 7a–e is shown in FIGS. 16a–e, by reference to the lower horizontal axis, with $\beta$ increasing to the left, that is obtained via Eqs. (III.25) and (II.2). As with FIG. 15, the associated energy dependence is given by reference to the upper horizontal axis, while the associated $a_2$-dependence is given by reference to the middle horizontal axis. As on FIG. 15, resonances are also evident on FIGS. 16a–e. Strong resonance peaks indicate the formation of pattern Q with a binary intensity distribution (rectangular functional form) and with p=1, as may be verified by directly evaluating the pattern's shape at the resonance, via the Cowley Moodie Formulae. The formation of a binary intensity pattern described by Eqs. (III.55)–(III.57) at E=E* corresponds to the strong resonance peak on each of FIGS. 16a–e (all for r*=1) at $\beta$=n*/m*, indicated as E*. Resonances with $Q_1/Q_0$ positive, give the intensity distribution of Eq. (III.55), while those with $Q_1/Q_0$ negative give the same distribution shifted laterally by $Ma_2/2$, in a similar manner to the behavior of Eq. (III.30). Points of vanishing $Q_1/Q_0$ that occur at the values $\beta$=n and marked by diamonds on FIGS. 16a–e are a vanishing of the contrast via the non-fractional Talbot effect, as mentioned above. Contrast reversals (sign changes of $Q_1/Q_0$) occur for r*=1 for profiles with m*-odd on FIGS. 16b,d,e, and are marked by + signs. Said reversals occur at the values $\beta$=n/2 with n-odd. These are discussed in greater detail in Sect. V.8 and are used to obtain element-selective contrast. A periodic binary intensity pattern also generally forms for values of $\beta$=n/m* with coprime n and m*. In general, patterns used by the Invention in phase-interferometric mode all have p=1, even for m>1 and $\epsilon \approx 0$ in Eq. (III.26). However, patterns with p>1 also sometimes occur, and these may be used also, if desired. Profiles with r*>1 have additional resonances, narrower resonances, and additional sharper contrast reversals.

To obtain operation of the Invention in the n,m phase-interferometric mode, grating G2 is configured as a phase grating with a PG(n*,m*,r*) profile and r*-odd. Its period $a_2$ is selected as per Eq. (III.36) in the same manner as that of Sect. III.3. The desired coprime integers n and m are chosen, as per Eq. (III.36) and (III.37) to give the associated value of $\beta_x$=$E_x$/E=n/m, to provide the desired operating point, as shown, for example, by reference to FIGS. 16a–e. The period $a_2$ is then one of the discretely allowed values, given by Eq. (III.38). For example, to obtain a binary intensity pattern Q with the Invention, as per Eq. (III.55)–(III.57), the resonance at E* is centered (by the appropriate choice of $a_2$) to occur at $$E_* \approx E_X, \qquad \text{(III.58)}$$

thus placing the design's operating point at $\beta_x \approx$ n*/m*. The associated value for period $a_2$ is $$a_2 = \left(\frac{m_*}{n_*}\right)^{1/2} \tilde{a}_2(E_x) = \left(\frac{m_*}{n_*}\right)^{1/2} \left(\frac{R_1 R_2}{R_1 + R_2}\right)^{1/2} \left(\frac{hc}{E_x}\right)^{1/2}, \qquad \text{(III.59)}$$

where the second half of Eq. (III.59) follows from Eqs. (III.1), (III.3) and (III.22). Alternatively, to obtain the same binary intensity pattern Q that occurs at $\beta_x \approx$ n/m* with values of n>1, i.e. at $E_x$=m*E/n, the corresponding choice for $a_2$ is $$a_2 = \left(\frac{m_*}{n}\right)^{1/2} \tilde{a}_2(E_x) = \left(\frac{m_*}{n}\right)^{1/2} \left(\frac{R_1 R_2}{R_1 + R_2}\right)^{1/2} \left(\frac{hc}{E_x}\right)^{1/2}. \qquad \text{(III.60)}$$

If one desires to center $E_X$ with $\beta_x \approx$ n/2 (with n-odd) on a contrast reversal, as is needed for obtaining element-selective contrast (see Sect. III.8), then the grating period $a_2$ is chosen to be $$a_2 = \left(\frac{2}{n}\right)^{1/2} \tilde{a}_2(E_x) = \left(\frac{2}{n}\right)^{1/2} \left(\frac{R_1 R_2}{R_1 + R_2}\right)^{1/2} \left(\frac{hc}{E_x}\right)^{1/2}. \qquad \text{(III.61)}$$

Typically, a binary intensity pattern forms at resonances whose energy-widths are comparable to but slightly wider than those typical of amplitude-interferometric mode, so that if Eq. (III.34) and Ineq. (III.44) hold, then moderately high contrast obtains for pattern Q with finite $\Delta E$, as may be produced by x-ray tube T and filter F via methods given in Sect. V.3. Following the discussion of Sect. III.3, a more precise value for $\Delta E_{max}$ may be determined by consulting the curves shown on FIGS. 16a–e, or those calculated similarly for other chosen grating profiles and/or operating points. Application of phase-interferometric mode to the imaging of refractive-index gradients, as discussed below in Sect. III.7, is done via Eq. (III.59) and either Eq. (III.60) or (III.61), with Eq. (III.60) providing a grating that is more easily built.

III.5 Action of grating G1

Consider two actual x-ray intensity patterns that are formed by the Invention on the surface of slab-volume SV3—pattern P formed when object BDY is absent, and pattern P' formed when object BDY is present. As with idealized pattern Q, actual pattern P is spatially periodic and exhibits high contrast. Patterns P and P' are formed by averaging respectively patterns Q and Q' over the multi-period x-ray emission by grating G1. Patterns P and P' are conceptually similar to those of a dot-matrix television raster (assuming dark areas interlaced between the raster dots), respectively with and without an image present. Pattern P' is approximately spatially periodic, but modulated in a manner that provides an image. As with the television dot-matrix raster, the period of these patterns is at or below the visual resolution limit of the viewed image, and is not visually evident within the image.

Periodic pattern P is formed on detector D only when all three of the Invention's components—focal spot S and grating G1 and grating G2—are all present and are all properly aligned, configured and acting together. Unlike prior art, in the Invention no components are moved (or removed) for the final image to be obtained. On the contrary, once these components are precisely positioned relative to slab-volume SV3 via the alignment system, as disclosed in Sects. III.10–III.10.3, their positions thereafter remain fixed, unless an unavoidable apparatus drift necessitates their realignment.

Grating G1 is always a binary absorption grating. It may be 1D or 2D-periodic. In the latter case it is described by either a separable or a checkerboard function, as per Eq. (I.3) or (I.4). In order for pattern P to exhibit high contrast, however, there are two important requirements regarding its period, $a_1$. The first is that $a_1$ must be carefully chosen to satisfy $$a_1 = \frac{b}{q} \frac{a_Q}{\alpha} = \frac{b}{q} \frac{Ma_2}{\alpha p} = \frac{b}{qp} \frac{(1+\alpha)}{\alpha} a_2 = \frac{b}{qp}\left(\frac{R_1 + R_2}{R_2}\right) a_2, \quad \text{(III.62)}$$

where b and q are positive coprime integers, so that their greatest common integer divisor is 1, and where Eqs. (III.3), (III.4) and (III.18) are used in forming the various forms of Eqs. (III.62). Equations (III.62) give a set of allowed choices for $a_1$, that depend on the associated choices of b and q. The choices b=q=1 are preferred, since these yield the highest grating G1 net transmission and give minimum vignetting. These choices give $$a_1 = \frac{a_Q}{\alpha} = \frac{Ma_2}{\alpha p} = \frac{(1+\alpha)a_2}{\alpha p} = \frac{1}{p}\left(\frac{R_1 + R_2}{R_2}\right) a_2. \quad \text{(III.63)}$$

The effect of Eqs. (III.63) is to guarantee that each successive G1 slit or square aperture of G1 is positioned so that it individually illuminates G2 from such a position that the associated contribution to pattern P is the same high-contrast periodic pattern with the same period, but shifted by exactly one whole period of pattern Q from the previous contribution, whereupon such shift is inconsequential. For the choices b≠1 and q=1, the effect of Eqs. (III.62) is to guarantee that it is shifted by b full periods, and for b≠1 and q≠1, that it is shifted by 1/q times the period. The choice q≠1 is consequential, since it reduces the period of pattern P relative to that of pattern Q by the factor q. Thus, in general the period $a_P$ of pattern P for all coprime b and q is given by $$a_P = \frac{a_Q}{q}. \quad \text{(III.64)}$$

When Eq. (III.63) holds (i.e. for b=q=1), then all of the individual contributions to pattern P by individual G1 slits are exactly aligned with each other, whereupon pattern P, itself, is periodic with period $a_Q$ and has the same high contrast as that of each such contribution. Equations (III.62)–(III.64) are called the "pattern registration conditions". They provide a mathematical formulation for key ingredients (1) and (2) of the inventive concept, as disclosed in Sect. III.1.

The second important requirement for the period $a_1$ is that a plurality of G1 periods spans the set of straight-line paths from all points on the finite-width of focal spot S to any one point on the surface of slab-volume SV3, as per $$a_1 \ll \frac{LW_S}{L_T}. \quad \text{(III.65)}$$

For slab-volume SV1 near focal spot S, $L \approx L_T$ holds and Ineq. (III.65) is then $$a_1 \ll W_S. \quad \text{(III.66)}$$

Fortunately, Ineqs.(III.65) or (III.66) are readily satisfied, given Eqs.(III.62) and typical apparatus parameter values, as discussed in Sect. V.1. Given Ineq. (III.65), then the x-ray pattern produced on the surface of slab-volume SV3 by focal spot S, and gratings G1 and G2, all acting together, is quite different from the pattern produced when either one of the gratings is removed. Given the constraint by Ineq. (III.65), given the associated finite area of focal spot S (along with its proximity to grating G1), and given well known principles of radiometry, then binary absorption grating G1 and focal spot S together effectively create a "spatially periodic source" at the plane of G1. Said spatially periodic source is an essential feature of the Invention that allows the high contrast periodic pattern P to be produced when focal spot S and gratings G1 and G2 are all present. Given that Ineq. (III.65) holds, it has a spatially periodic x-ray brightness distribution functionally described by $B_{G1}(x_1, y_1)$, which, throughout the finite width of focal spot S approximately satisfies Eqs. (I.1)–(I.2) and is proportional to $f_{sep}(x_1, y_1; a_1)$ or $f_{ckbd}(x_1, y_1; a_1)$, of Eqs. (I.3) and (I.4).

On the other hand, if Ineq. (III.65) is not satisfied, so that instead $W_S$ spans only a small number of grating G1 periods, and given a finite spacing between focal spot S and grating G1, then these two components by themselves create a long-period blurred periodic shadow with very low contrast, on and through object BDY and onto slab-volume SV3. Thus, when object BDY is absent and both gratings are present, but Ineq. (III.65) is not satisfied, then said blurred shadow gives pattern P an associated spatial modulation (periodic envelope variation) of its intensity and/or an occultation by the edges of grating G1, whose presence is undesirable. Although said modulation and/or occultation can in some cases be renormalized by image processing, this modulation also provides non-uniform object dosage and non-uniform quantum mottle. However, when $W_S$ is much larger than $a_1$ so as to satisfy Ineq. (III.65), then this variation disappears, and focal spot S and grating G1 acting together without the added presence of grating G2 produce a uniform x-ray illumination of object BDY and slab-volume SV3, and when grating G2 is also present then no such intensity modulation occurs. Given the results of Sects. III.3 and III.4, the period $a_2$ of G2 is generally even smaller than $a_1$, and is similarly small with respect to $W_S$ so that focal spot S and grating G2 without the added presence of grating G1, similarly provides uniform x-ray illumination of object BDY and slab-volume SV3.

The intensity distributions of patterns P and P' are denoted respectively by $I_P(x_3, y_3)$ and $I_{P'}(x_3, y_3)$, where $x_3, y_3$ are lateral coordinates measured relative to axis $C_L$ of points on the surface of slab-volume SV3. The presence of object BDY modulates intensity distribution $I_Q$ to become intensity distribution $I_{Q'}$. The various mechanisms by which said modulation occurs are discussed in Sects. III.6.2, III.7, and III.8. The functions $I_Q$ and $I_{Q'}$ may be viewed as intensity Green's functions. The functions $I_P$ and $I_{P'}$ are calculated respectively in terms of $I_Q$ and $I_{Q'}$ for all modes by using Lambert's law and well known principles of radiometry [Born and Wolf, 1967, Chapt. 4.8], by integrating (averaging) $I_Q$ and $I_{Q'}$ over the spatial profile $B_{G1}(x_1,y_1)$, whose finite envelope is the lateral intensity profile of focal spot S. The integration is then over the back-illuminated x-ray transmitting areas of grating G1, viewing each differential area on the G1 plane as an independent, incoherently-emitting, elementary radiator of x-rays, i.e. as fictitious point source S'. Lambert's law then gives $$I_P(x_3, y_3) = \int\int_{G1} I_Q(x_3, y_3; x_1, y_1) B_{G1}(x_1, y_1) dx_1 dy_1, \qquad (III.67)$$

and $$I_{P'}(x_3, y_3) = \int\int_{G1} I_{Q'}(x_3, y_3; x_1, y_1) B_{G1}(x_1, y_1) dx_1 dy_1, \qquad (III.68)$$

where the integration limits are set by the finite number of back-illuminated G1 periods.

Given Ineq. (III.65) and Lambert's law, the small but finite spacing between G1 and S has negligible effect on the shape of pattern P, since via Lambert's law the illumination by a spatially incoherent diffuse source of any point on G2 or on SV3 does not depend on the longitudinal spacing between said point and said diffuse source, but instead only depends on the surface brightness of the diffuse source and on the associated solid-angle subtended by it from the point. Said solid-angle now is constrained by Ineq. (III.65), and/or by the periodic structure of grating G2. In such case the plane of G1 then may be regarded as the effective source of illumination (rather than S) and components G1 and S then together create a spatially-periodic, but otherwise spatially-incoherent source.

Given $I_Q$ and $B_{G1}$, given the periodicity and see-saw conditions as disclosed in Sect. III.2, and for q=1, then Eq. (III.67) may be evaluated approximately for 2D-periodic gratings to give $$I_P(x_3, y_3) = C \int_{-\alpha s_1/2}^{\alpha s_1/2} \int_{-\alpha s_1/2}^{\alpha s_1/2} I_Q(x_3 + x, y_3 + y) dx dy, \qquad (III.69)$$

where C is a constant. (For 1D-periodic gratings the integration is only over x.) For q>1 the function $I_P(x_3,y_3)$ is given by a sum of q such integrals, each with the form of Eq. (III.69) but with $x_3$ and $y_3$ each shifted within the arguments of $I_Q$ by $a_P$ so that for all q pattern P has period $a_P$, as per Eq. (III.64). For $\alpha s_1/a_P = s_1/a_1 \leq 1$ not too large, then Eq. (III.69) implies that $I_P$ will maintain reasonably high contrast, despite the averaging of $I_Q$ over the finite width, $s_1$ of a transmitting square (or slit) on grating G1. Choices of q>1, however, require reduced $s_1$ (and associated increased vignetting) for such reasonably high contrast to obtain.

A typical 1D-periodic intensity profile of pattern P is shown on FIG. 13b, assuming negligible "leakage" transmissions of the x-ray absorbing areas of gratings G1 and G2. To use 2D-periodic gratings, the Invention may be configured with grating G1 (and/or G2 if it is a binary absorption grating) described either by Eq. (I.3) or Eq. (I.4). The resulting pattern P then has the form of a 2D-periodic separable or checkerboard periodic lattice of spaced truncated square pyramids (with rounded corners at mid-height), as shown in FIGS. 14d–f. The flat-topped region of each BRIGHT fringe is referred to as the "umbra", and the slopping sides as the "penumbra". Corresponding to FIGS. 14d and 14e, FIGS. 12a,c and 12b respectively show constant-intensity closed contours for 2D-periodic checkerboard and separable patterns P, that surround the umbra. The width (relative to the pattern's period) and shape of a BRIGHT fringe, is determined by $s_1/a_1$, and on $s_2/a_2$ or $1/m_*$. The base width of the pyramid is $s_Q + \alpha a_1$. For $s_1/a_1 = s_2/a_2$ (or $s_1/a_1 = 1/m_*$) and p=1 the pyramid tops are pointed and the umbra disappears (c.f. FIGS. 12b and 14e).

While the variously described absorption and phase grating structures specify ideal periodic step or rectangle functions for their profiles, practically fabricated gratings provide only approximations to these ideal profiles. However, the Invention operates as described herein, even when gratings with moderate departures from these profiles are used. Said departures include profiles that are trapezoidal or rounded (in some cases rounded sufficiently to become nearly sinusoidal), and only diminish the contrast of periodic pattern P. While high-contrast for periodic patterns Q and P is highly desirable, it is not essential, and moderate contrast is acceptable. Indeed, grating "leakage", averaging via Eq. (III.69), and averaging over the x-ray finite energy bandwidth $\Delta E$ already provide moderate rounding of patterns Q and P and associated contrast diminution.

Also, it should be noted that the Invention may be configured with periods $a_1$, $a_2$, $a_3$, $a_P$ etc. that differ in the x and y directions, wherein $a_Q$ then is replaced by the two values, $a_{Qx}$ and $a_{Qy}$, $a_P$ is replaced by two values, $a_{Px}$ and $a_{Py}$, and $a_R$ is replaced by two values, $a_{Rx}$ and $a_{Ry}$, etc. The directions for coordinates x and y need not be exactly perpendicular to each other, but must be the same for all gratings and the detector. Indeed, it is even possible, if so desired, to configure the 2D-periodic grating G2 with a hexagonally tiled form to give pattern Q a similar hexagonal symmetry (Winthrop and Worthington, 1965). In such case detector D, grating G1, and pattern P then all have hexagonally tiled forms. However, neither the hexagonal nor the unequal-period configuration appears to serve any particularly useful purpose beyond that of square arrays. For such gratings the periodicity direction is generally perpendicular to straight-line edges of the grating's periodic structure, and thus gives a minimum measured period for an infinitesimal rotation of the grating (relative to the measurement direction) about a grating's surface-normal as a rotation axis.

III.6 Harmonically matching the phase and period of pattern P to the detector pixel array All of the pixels within a periodic detector D pixel array are physically the same as each other; however, they are not all used in the same way by the Invention. Key ingredient (4) of the inventive concept disclosed in Sect. III.1 involves configuring the detector pixel array with interlaced b and d-labeled pixels, and with $a_D$ and $a_P$ both smaller than the final image-pixel size $a_R$. As per Sect. III and FIGS. 10a–e and 12a–c, individual detector-pixels are each labeled b, c, or d to identify the pixel's use. The tiling algorithm therein disclosed provides the interlace. Pattern P provides periodically alternating BRIGHT and DARK fringes, as shown on FIGS. 14d–f, illuminating slab-volume SV3 with x-rays. Key ingredients (3) and (4) of the inventive concept provide a harmonic matching of the phase and period of pattern P (with no object present) to the detector pixels with associated labels. The desired effect of said matching depends on the imaging methodology used. Under methodologies that obtain absorption contrast or refractive-index contrast, then period and phase harmonic matching causes the BRIGHT fringes of pattern P to illuminate only b-labeled pixels, while DARK fringes of pattern P (very dimly) illuminate only d-labeled pixels, as shown on FIGS. 12a–c for situations with grating G3 absent. The respectively illuminated pixels record simultaneously the associated locally incident x-ray intensities. FIGS. 12a–c show the period $a_P$ of pattern P equal to the tiling pixel-label period $2a_D$ for u=2 tiling. When $a_P$ is smaller than $2a_D$ then grating G3 is included to mask appropriate areas of each pixel so that BRIGHT fringes of pattern P still illuminate only b-labeled pixels, and DARK fringes illuminate only d-labeled pixels.

Achieving harmonic matching requires using a pixel-labeling tile that is appropriate to the form of 2D-periodic pattern P. When both gratings G1 and G2 are 1D-periodic, then pattern P is also 1D-periodic, as shown in FIG. 13b, and tile PT2 is used to configure the array of pixel labels. To obtain a 2D-periodic separable intensity pattern P, as shown in FIGS. 12a, 12c, and 14d, then both gratings G1 and G2 are configured via 2D-periodic separable functions, and either pixel-labeling tile PT1 or PT5 is used. Tile PT5 is used, as in FIG. 12c, when it is desired to obtain two simultaneous images from one exposure, as per Sect. III.9, and tile PT4 is used when grating G3 is also present and formed by the associated set of tiles G3T4v. If either or both gratings are configured via 2D-periodic checkerboard functions, then a 2D-periodic checkerboard intensity pattern results, as shown in FIGS. 12b and 14e, and tile PT3 is used (whether or not grating G3 is present). The inverted pattern P shown in FIG. 14f is produced when grating G1 is configured as per FIG. 8b, and grating G2 is configured as per FIG. 8d, whereupon tile PT4 is used.

To achieve phase matching, it is first necessary to have period matching, so that without grating G3 present the b-pixel period is the same as the pixel-label tiling period, u $a_D$. Period matching is obtained in the Invention by designing the apparatus so that this period is harmonically matched to the period $a_Q$ of pattern P, as per Sects. III.6.1, III.6.3 and III.6.4. The associated grating and detector period fabrication accuracies required to achieve period matching are disclosed in Sect. III.10. Given period matching, then to achieve phase matching it is also necessary to align the apparatus so that the phases of pattern P and of the pixel layout are matched. Said alignment is accomplished using key ingredient (6) of the inventive concept, via an in-situ laser interferometer, as disclosed in Sects. III.10–III.10.3.

Given phase and period matching, then key ingredient (5) of the inventive concept can obtain. It consists of performing an image subtraction for each resolution element by using x-ray intensities measured by the b-labeled pixels within said resolution element, and by also using x-ray intensities measured by d-labeled pixels that are either within said resolution element or are within neighboring resolution elements. Simultaneous recording of intensities by all pixels then allows image data recorded during a single exposure to be used in image subtraction algorithms. The algorithm for image subtraction used for the absorption-contrast and refractive-index-contrast imaging methodologies is disclosed in Sect. III.6.2. Pixels labeled c are used to obtain two simultaneous independent images during a single exposure with object BDY present. That use is disclosed in Sect. III.9, along with an associated image subtraction algorithm. Section III.8, discloses that to obtain element-selective contrast, harmonic period and phase matching have a similar but slightly modified effect to that given above (used for obtaining absorption and/or refractive-index contrast), and it discloses an associated image subtraction algorithm.

III.6.1 Detector pixel, grating G3, and resolution-element layouts

Note that the lengths $a_Q$, $a_P$, $a_R$, and $a_D$ all derive from quite unrelated concerns. Given the apparatus geometry, x-ray energy $E_X$ and operational mode, allowed values for $a_Q$ and $a_P$ derive from physical optics principles. The resolution length (image-pixel size), $a_R$, is the pixel size of the final output image (or images), and its value is lower-limited by a number of factors that depend on the x-ray brightness of tube T, allowed object dosage, the size of $W_s$, etc., as discussed in Sect. III. The detector period $a_D$ is set dominantly by available detector technology. Despite the disparate origins of these various lengths, the lengths should have the size ordering, $$a_R \geq u\ a_D \geq a_P. \tag{III.70}$$

consistently with Ineqs. (III.8). Via Ineq. (III.70) the smallest possible value for $a_R$ allowed by Ineq. (III.70) is $a_R = 2a_D = a_Q$, for the preferred choice q=1. This value may occur with grating G3 absent, and only when $a_R$ does not have further lower limitations set by Ineqs. (III.8). Situations (with q=1) may arise, however, that require $a_Q \neq 2a_D$, for example, when a detector with sufficiently small period $a_D$ is unavailable to meet the physical optics requirements for the needed value of $a_Q$, or when a configuration with $a_Q = 2a_D$ causes excessive vignetting by the gratings. Inclusion of grating G3 then allows an extension of the Invention's allowed parameter range that, in turn, allows both a larger detector period, and reduced vignetting by the gratings. Larger $a_0$ also reduces the size of the data volume that must be handled by computer CP. Detector period harmonic matching is obtained by setting $$ua_D = a_3 = va_P = \frac{v}{q}\ a_Q = \frac{v}{qp}\ Ma_2 = \frac{v}{qp}\left(\frac{R_1+R_2}{R_1}\right)a_2, \tag{III.71}$$

where v is an integer, and where Eqs. (III.4), (III.7) (III.18) and (III.64) are used. The integer v is 1 if grating G3 is absent, or in the situation discussed in Sect. V.6, and it is greater than 1 if grating G3 is present. From Eq. (III.71), the detector period $a_D$ is then deduced as $a_D = (v/u)\ a_P$.

The presence of grating G3 allows the pixel period to be matched to a sub-harmonic of pattern P. Grating G3 is a 1D or 2D-periodic binary absorption grating, with period $a_3$ as per Eq. (III.7). The overall x-y planform form for grating G3 is constructed via the tiling algorithm disclosed in Sect. III. For v>1, Eqs. (III.71) implies that v/u periods of pattern P are incident on grating G3 per pixel period $a_D$. Grating G3, when present, is positioned as closely as possible to the x-ray detecting front surface of detector D, whereupon grating G3 acts as a periodic mask that selectively absorbs x-ray photons incident on various areas of detector D. By such action it then prevents x-ray photons incident in BRIGHT fringes of pattern P from being detected by d-labeled pixels, and similarly prevents photons incident in DARK fringes of pattern P from being detected by b-labeled pixels. The tile patterns shown in FIGS. 11a–d are derived by superimposing the associated pattern P atop the labeled pixel pattern, and then drawing a pattern of $(a_D/v) \times (a_D/v)$ occulting squares XAL atop each unwanted BRIGHT or DARK fringe of the superimposed pattern P. (As a convention, the patterns shown in FIGS. 11a–d start with a BRIGHT fringe and b-labeled pixel in the upper left hand corner, except for the pattern P of FIG. 14f, which uses the opposite convention.) Unfortunately, grating G3 is present at the cost of absorbing instead of detecting, (i.e. effectively throwing away) x-ray photons that are otherwise useful for imaging, and thereby increasing dosage and/or $a_{RQ}$. Thus, its inclusion should be avoided where possible in dosage-limited applications.

Recall that resolution element dimension $a_R$ is the associated image-pixel size. The lower limit for $a_R$ set by Ineqs. (III.8) also may require $a_R > 2a_D$. In such case one may set $$a_R = w \; a_3 = w \; u \; a_D = w \; v \; a_P, \quad \text{(III.72)}$$

where w is an integer, and the data from $u^2 w^2$ pixels are then combined (within computer CP) to form one image pixel. The size of a resolution element $a_R$, then is adjustable under software control in computer CP through the choice of the integer w. Each such image resolution element (image-pixel) is defined on said tiled array of detector-pixel labels so that it contains a number $w^2$ of said tiles on a square, where w is an integer. An $a_R \times a_R$ resolution element then has an area equal to $u^2 w^2 a_D^2$ and covers $u^2 w^2$ pixels. For the preferred u=2 tiling choice, it contains 4 $w^2$ pixels. The resolution elements so defined form an array that covers the array of pixels, and via said tiling each resolution element within the covering array of resolution elements contains the same number of b, c, and d-labeled detector-pixels.

III.6.2 Pattern P' and image subtraction under the absorption-contrast methodology X-rays interact dominantly with electrons within matter and negligibly with nuclei [Leighton, 1959]. The dominant interaction processes for low-energy (<20 keV) x-rays and with dominantly low-Z biological soft-tissue are photoelectric absorption and elastic scattering. These two processes cause patterns P and P' to differ. Photoelectric absorption by object artifacts is the most important process for obtaining absorption contrast in pattern P', since it provides sharp shadows that are then imprinted on pattern P'. Scattering, however, blurs the image imprinted on pattern P'. Other differences between patterns P and P' and the associated use of phase matching by the methodologies to obtain refractive-index contrast and element-selective contrast are discussed respectively in Sects. III.7 and III.8.

In geometric-shadow mode the absorption contrast (intensity opacity) of object BDY locally multiplies the intensity $I_Q$ for x-rays that propagate along a negligible width straight-line trajectory. It thus becomes $I_{Q'}$. In either interferometric mode the amplitude for all such possible paths is similarly multiplied by the object's amplitude opacity. In the interferometric modes with a modestly large bandwidth x-ray spectrum and finite $a_2$, then only a few adjacent grating G2 periods and associated paths give coherent x-ray illumination of any given point on slab-volume SV3, and the net effect for these methodologies on the associated intensity at said point by said multiplication is similar to the effect for geometric mode. Thus, for all modes under the absorption-contrast methodology said modulation by the object's opacity simply multiplies the associated intensity locally incident on b-labeled pixels. Via Eq. (III.68) modulated pattern Q' becomes modulated pattern P' and said multiplication is directly transferred (with added geometric blurring) to pattern P'.

Were x-ray absorption the only important physical process occurring, then its modulation of pattern Q would provide the only significant difference between pattern Q and pattern Q', and thence, between patterns P and P'. In such case the d-labeled pixels would remain darkly (or dimly) illuminated, even with object BDY present. However, a second difference between patterns P and P' results from the fact that x-rays are scattered by object BDY. X-ray scatter displaces the propagation of some x-ray photons from b-labeled pixels onto otherwise dark d-labeled pixels, whereupon said d-labeled pixels receive increased x-ray illumination. Scattering also displaces photons from one b-labeled pixel to another b-labeled pixel, whereupon an image made from data from only b-labeled pixels is blurred and loses contrast.

Given harmonic phase matching, however, an image subtraction algorithm is used to remove the blurring effects of scatter. Consider a resolution element identified by the index x, within the array of resolution elements that covers the surface of slab-volume SV3. (Index x is used as a shorthand notation for $x_3, y_3$ of a pixel's center.) The detector-pixels within resolution element x each record simultaneously the associated locally incident intensity. Following an x-ray exposure, computer CP first calculates the average intensities $I_b(X)$ and $I_d(X)$, respectively incident on b and d-labeled detector-pixels within resolution element x, by summing the x-ray associated intensity measured by all b and d-labeled pixels covered or partially covered by the resolution element, by appropriately weighting said measurements in the sum by the pixel's contributed fraction of the resolution element area. Computer CP then calculates a "subtracted image", whose gray-scale for each resolution element x is $$I_{sub}(x) = I_b(x) - I_d(x). \quad \text{(III.73)}$$

Note that within each resolution element d-labeled detector-pixels are interlaced with the b-labeled detector-pixels. The above-described algorithm uses the fact that the scattered photons are more uniformly distributed on slab-volume SV3 than are the absorption-image-carrying unscattered x-ray photons. Indeed, if they are distributed similarly, then there is no associated image blur. As a result, the photon flux that is scattered onto a given b-labeled pixel is approximately the same as that scattered onto nearby or adjacent surrounding d-labeled pixels. As a result $I_b(x)$ and $I_d(x)$ each contain roughly equal amounts of scattered x-ray intensity. Said equal amounts then cancel in Eq. (III.73), and the subtracted image made from the dot-matrix array of intensities $I_{sub}(x)$ then represents the net unscattered flux incident on the associated array of resolution elements. If the dominant scattering process displaces x-ray photon detections by several resolution element periods (as may be determined by trial and error), then the algorithm may be improved by including, as part of the above-described weighted average that gives $I_d(x)$, the intensities measured by d-labeled pixels in nearby resolution elements, rather than just those of d-labeled pixels within (or partly within) resolution element x. The weighting also may be chosen to decrease with increasing distance of these additionally included d-labeled pixels from the center of resolution element x. In such case the statistical fluctuation (from quantum mottle) of $I_d(x)$ is reduced, and the quality of the subtracted image is further improved.

III.6.3 Design requirements for period and phase harmonic matching

Once period matching is achieved, then phase-matching is readily accomplished via a slight lateral adjustment of the position of either grating G1 or G2. A more basic question is, what are the requirements for the apparatus so that period matching obtains? It is worthwhile to summarize the above-disclosed relations between the periods $a_1, a_2, a_D, a_Q$ and $a_P$. Given that the period $a_2$ is set by physical optics considerations and mode choice, periods $a_1, a_Q, a_P$ and $a_D$ may be expressed in terms of $a_2$. First, for all modes there are the relations Eqs. (III.4), (III.18) and (III.64) from physical optics for the period of pattern P $$a_P = \frac{a_Q}{q} = \frac{(1 + \alpha) a_2}{qp}, \quad \text{(III.74)}$$

where p is given via Eqs. (III.31), (III.33) and (III.57) as $$p = \begin{cases} 1 \text{ for geo. -shad. mode,} \\ m \text{ for } n, m \text{ ampl. -int. mode,} \\ 1 \text{ for } p = 1, r_* = 1 \text{ phase-int. modes,} \\ 1 \text{ for elem. -sel. contrast } @ \beta = \frac{n}{2} \text{ .} \end{cases} \quad (III.75)$$

Next, the pattern registration condition of Eqs. (III.64) gives $$a_1 = \frac{b}{q} \frac{a_Q}{\alpha}, \quad (III.76)$$

where b and q are coprime integers. Equation (III.76) then guarantees that the various periods of grating G1 each project G1-period averaged pattern Q in register, thereby to form pattern P with high contrast. Harmonic period matching then adds a third requirement from Eqs. (III.7) and (III.71), $$a_D = \frac{a_3}{u} = \frac{v a_P}{u}, \quad (III.77)$$

where v is an integer, and where u=2 tiling is preferred.

Equations (III.74)–(III.77), are then the basic design requirements that must be met by the apparatus for both phase matching and pattern registration to occur. Given $\alpha$, v, $a_2$ and p, these quantities uniquely determine $a_Q$, $a_P$ and $a_D$. Once the design is complete, the integers b, q, p, u and v assume fixed values, and once gratings G1 and G2 have been fabricated, then the values of $a_1$ and $a_2$ also become fixed. Irrespective of L, Eqs. (III.74) and (III.76) may be combined, as per Eqs. (III.62) to give $$a_1 = \frac{b}{q} \frac{a_Q}{\alpha} = \frac{b}{q} \frac{Ma_2}{\alpha p} = \frac{b}{qp} \frac{(1+\alpha)}{\alpha} a_2 = \quad (III.78)$$

$$\frac{b}{qp} \left( \frac{R_1 + R_2}{R_2} \right) a_2,$$

that must hold independently of the value of $a_Q$ and tiling parameter u. Equations (III.78) (or (III.62)) may be rewritten to show that the now-fixed values of $a_1$, $a_2$ and p together automatically define a specific also now-fixed and now-required value for $\alpha$, as per $$\alpha_* = \frac{ba_2}{qpa_1 - ba_2} . \quad (III.79)$$

Equations (III.76), (III.77) and (III.79) give an associated also now-fixed and now-required value for $a_3$ as $$a_3 = \frac{v a_1 a_2}{qpa_1 - ba_2}, \quad (III.80)$$

wherein the preferred choices for the integer b and q in Eqs. (III.76) and (III.78)–(III.80) are both 1. Note that Eqs. (III.78)–(III.80) hold irrespectively of both $\alpha$ and L, so that a small error in $a_1$, $a_2$ or $a_D = a_3/u$ (e.g. that results from a fabrication error) may not be compensated by an adjustment of $\alpha$ (=$R_2/R_1$), as one might naively assume. If $a_D$ is selected from a catalog, then the gratings must be fabricated so that $a_1$ and $a_2$ are related precisely to $a_D$ by Eqs. (III.7) and (III.80). The apparatus also must be assembled so that $\alpha$ is precisely equal to $\alpha_*$. The required precision is addressed quantitatively in Sect. III.10.

Period matching is accomplished in two steps. First, the gratings are designed and fabricated as accurately as possible so that Eq. (III.80) is accurately satisfied. Second, precise equality and phase matching are obtained by careful apparatus alignment, wherein the longitudinal positions of the gratings and of the detector D and/or grating G3 are adjusted so that the actual value of $\alpha$ is accurately equal to the design value $\alpha_*$. Note that L and $E_X$ also must be such that a given resonance obtains if an interferometric mode is to be used. However, given the broad resonances shown in FIGS. 15, and 16a–e, and given that p is constant and Ex (e.g. ch such resonance, then small errors in L and $E_X$ (e.g. introduced during apparatus assembly) are easily tolerated.

III.6.4 Catalog selection of $a_D$

The Formulae given in Sect. III.6.3 use the period $a_2$ as a starting point for the apparatus design. It is frequently more convenient, however, to start with the detector pixel period $a_D$ instead, as may be chosen, for example from a detector catalog. Thus, given the chosen mode and the associated value for the integer p, and given $E_X$ and L, then the design value for $\alpha_*$ may be calculated so that $a_D$ then equals the desired value from the catalog. Said calculation also determines whether or not there is a need for grating G3, and if so, what value(s) of v is (are) appropriate. Gratings G1 and G2 then may be fabricated accordingly. With geometric shadow mode (implying p=1) and grating G3 absent (implying v=1), if a value for $a_2$ is desired that is much larger than $a_2$(shad-limit), then (for b=q=1, and u=2) given this choice for $a_2$, the associated value for $\alpha_*$ is simply $$\alpha_* = \frac{2 a_D}{a_2} - 1. \quad (III.81)$$

More generally, however, if operation in geometric shadow mode at the limiting value $a_2=a_2$(shad-limit) is desired, or if operation in the n,m amplitude-interferometric mode at the resonance $E_X=E_{n,m}$ is desired, or if p=1 operation in phase-interferometric mode using a PG(n$_*$,m$_*$,1) phase-grating profile with $E_X$ centered on the energy resonance at $E_*$ or at $m_*\tilde{E}(a_2)/n$ is desired, then a different procedure is called for. In these four cases the associated values for $a_2$ required by physical optics considerations as per Eqs. (III.40), (III.45) and (III.59) are given by $$a_2 = \tilde{a}_2(E_X) \times \begin{cases} 4 \text{ for geo.-shad. mode } @ a_2 = a_2(\text{shad.lim.}), \\ \left(\frac{m}{n}\right)^{1/2} \text{ for } n, m \text{ ampl.-int. mode,} \\ \left(\frac{m_*}{n_*}\right)^{1/2} \text{ for } p = 1, r_* = 1 \text{ phase-int. modes,} \\ \left(\frac{2}{n}\right)^{1/2} \text{ for elem.-sel. contrast } @ \beta = \frac{n}{2} \text{ .} \end{cases} \quad (III.82)$$

Equations (III.74), (III.77) and (III.82), may be solved simultaneously to give the now-required value for $\alpha_*$ as $$\alpha_* = \frac{u^2 q^2}{v^2} \frac{a_D^2}{L} \frac{E_X}{hc} \times \quad (III.83)$$

$$\begin{cases} \frac{1}{16} \text{ for geo.-shad. mode } @ a_2 = a_2(\text{shad.lim.}), \\ mn \text{ for } n, m \text{ ampl.-int. mode,} \\ \frac{n_*}{m_*} \text{ for } p = 1, r_* = 1 \text{ phase-int. modes,} \\ \frac{n}{2} \text{ for elem.-sel. contrast } @ \beta = \frac{n}{2} \text{ .} \end{cases}$$

A need for grating G3 is indicated when Eq. (III.83) yields an unacceptably large value for $\alpha_*$, with the chosen detector period $a_D$ and v=1. Too large a value for $\alpha_*$, in turn, typically provides excessive vignetting by grating G1. Then, knowing $\alpha_*$, the associated value for $a_2$(for q=1) is $$a_2 = \frac{uqp}{v} \frac{a_D}{1+\alpha_*} = \frac{uqp}{v} \frac{R_1}{R_1+R_2} a_D = \frac{qp}{v} \frac{R_1}{R_1+R_2} a_3, \quad \text{(III.84)}$$

where p is given by Eq. (III.75), the value of a (for q=1) is given via Eq. (III.77) as $$a_1 = \frac{bu}{v} \frac{a_D}{\alpha_*}, \quad \text{(III.85)}$$

and the values of $a_Q$ and $a_P$ are then evaluated at $\alpha = \alpha_*$ via Eq. (III.72) as $$a_P = \frac{a_Q}{q} = \frac{(1+\alpha_*)a_2}{qp}. \quad \text{(III.86)}$$

Note that in the above, the preferred tiling is with u=2, the preferred values for b and q are both 1, and that Eqs. (III.82)–(III.86) are derived for the restricted set phase gratings with cases with $r_*=1$ and p=1, but are readily generalized to include other usable cases as well.

III.7 Refractive-index-gradient contrast methodology

Consider the propagation of x-rays through a cylinder whose electron density is greater than that of the surrounding medium. Just as the curved surfaces of a refracting glass cylinder deflect light rays in the manner of a convex cylindrical lens, here the cylinder acts like a very weak convex lens for x-rays. However, the x-ray refractive index of all materials is very close to one and is negative, so that the convex lens has a very long negative focal length for x-rays. Thus, the resulting ray deflections by the cylinder are diverging, and the deflection angles are only a few microradians ($\mu$rad).

A ray path for this propagation is shown in FIG. 17. The deflection angle is highly exaggerated on the Figure to allow it to be drawn. Suppose that the cylinder has an index of refraction n' and is embedded in a medium with an index of refraction n. Both 1−n, and 1−n' are positive and very small with respect to 1. The refractive-index change at the cylinder's surface is $$\delta n = n - n', \quad \text{(III.84)}$$

with $|\delta n| \ll 1$. The ray enters the cylinder with an incidence angle $\theta$, relative to the surface-normal. The net deflection angle (in radians) of an x-ray path passing through the cylinder is given by geometrical optics as $$(\Delta\theta)_{cyl} \approx 2 \, \delta n \, \tan\theta. \quad \text{(III.88)}$$

Suppose that the x-ray energy is 17.4 keV and that the cylinder is $CaCO_3$ (1−n'=1.8×10$^{-6}$) embedded in water (1−n=7.6×10$^{-7}$). The cylinder then has parameters similar to those of a cancer-indicating micro-calcification in breast tissue. For a ray incident with $\theta=45°$, the deflection angle is $|(\Delta\theta)_{cyl}| \approx 2.2\,\mu$rad. If the cylinder (in water) is object BDY in the Invention, the ray is then displaced at the surface of slab-volume SV3 by roughly $$\Delta x_3 \approx R_D (\Delta\theta)_{cyl} = 2 R_D \, \delta n \, \tan\theta. \quad \text{(III.89)}$$

For $R_D \approx 25$ cm the net deflection is $|\Delta x_3| \approx 0.5\,\mu$m. A ray passing closer to the edge of the cylinder with $\theta=80°$ has a larger lateral deflection, providing the displacement $|\Delta x_3| \approx 1.5\,\mu$m for the ray at the surface of slab-volume SV3. This displacement, while not large, is a significant fraction of a typical value for $a_P$ for the Invention operating in an interferometric mode, and produces contrast enhancement of images produced by the Invention.

The contrast enhancement appears as an edge-enhancement of imaged artifacts. Rays passing near the edge of the cylinder (i.e. rays with large $\theta$ in FIG. 17) are deflected outward, toward (or even slightly beyond) the terminator of the cylinder's geometric shadow. An outward deflection of rays, similar to that shown on FIG. 17, is produced by any refractive-index gradient within object BDY, and especially by the high gradients associated with an artifact's edges. The deflection then causes artifacts with round or sharp boundaries to appear edge-enhanced in an image produced by the Invention whenever the artifact's gradients span both several periods of SV3 and of grating G2. Edge-enhancement is desirable, in that weakly imaged artifacts then become much more evident under a visual inspection of the image. Small artifacts have proportionately stronger gradients, and thus the contrast of small artifacts is strongly enhanced.

Images displaying refractive-index-gradient contrast, as due to such ray deflections, are produced using any of six methods and associated apparatus configurations for the Invention. In all such configurations, pattern P is period and phase matched to the spatially periodic structure within slab-volume SV3 (i.e to the pixel array on detector D and/or to grating G3), as per Sects. III.6–III.6.4. Such refraction-induced deflections distort pattern P and laterally displace the BRIGHT fringes of pattern P, i.e. those of FIGS. 12a–c, 13b, and 14d,e. Such distortions then act like a spatial phase modulation of pattern P, whereupon refractive gradients in object BDY provide a third difference (in addition to absorption and scatter) between patterns P and P'.

The first configuration (and associated method) is that disclosed above in Sect. III.6.2. This configuration automatically produces an edge-enhanced image in a dot-matrix image made from $I_{sub}$, given small $a_P$. With object BDY absent b-labeled pixels (or b-labeled areas on SV3) are illuminated by x-rays in BRIGHT fringes of pattern P, while d-labeled pixels receive only weak illumination from DARK fringes. When object BDY is present, then BRIGHT fringes are laterally displaced by said ray deflection, thereby diminishing the x-ray illumination of b-labeled pixels and increasing that of d-labeled pixels. A decrease in the intensity on b-labeled pixels and a simultaneous increase in the intensity of d-labeled pixels decreases $I_{sub}$, as per Eq. (III.73). A refractive-index gradient within object BDY then becomes apparent in the subtracted image. Since gradients may occur in either of the x and y directions, then 2D-periodic gratings are needed to sense both possible gradients. Thus, on FIGS. 12a–c, a displacement of a BRIGHT fringe of pattern P in any lateral direction causes a decrease of the net x-ray flux recorded by b-labeled pixels and a simultaneous increase of it respectively on d, or on c-labeled pixels. The edge-enhanced image from the configuration of Sect. III.6.2 still also shows absorption, which also gives a decrease in $I_{sub}$, and thus the effects of absorption and refraction reinforce to enhance the contrast. If desired, it is also possible to obtain independent refraction and absorption images via a second method and configuration, disclosed in Sect. III.9, that use the intensity recorded on c-labeled pixels. The third through sixth methods and configurations that obtain refractive-index contrast use the detector configurations of FIGS. 3a,b or variants thereof, and are discussed in Sect. V.6. In these latter configurations the detector media CRM has no pixels, and the phase matched b- and d-labeled pixels become phase matched b-areas and d-areas on slab-volume SV3, that then contains grating G3.

The contrast and edge enhancement in the Invention by refractive-index gradients is proportional to the ratio of $\Delta x_3$ to $a_P$, and it may be controlled via proper selection of the associated apparatus parameters. Via physical optics, as applied to x-rays herein, the Invention's interferometric modes automatically give inherently small values for $a_P$, comparable in magnitude to $\Delta x_3$. These modes then provide an excellent means for providing strong refractive-index contrast. If extremely high sensitivity to refractive-index gradients is desired, then very small $a_P$ may be obtained via an amplitude-interferometric mode with large p=m, or via phase-interferometric mode with operation at $E_X=E_*/n$ with large n. Small $a_P$ also may be obtained via a configuration with small $\alpha$, or with much large $a_D$ but with a grating G3 with large v. The deflection $\Delta x_3$ is increased proportionately via increased $R_D$, via Eq. (III.89).

While deflection angles estimated via geometrical optics are useful for giving a conceptual view of how refractive-index contrast obtains in the Invention, a more accurate calculation of the shape of the phase-modulated pattern P directly uses the methods of physical optics. The intensities $I_Q$ and $I_{Q'}$ produced by propagation of x-rays from point source S' through grating G2 through object BDY to a point $x_3$ on slab-volume SV3 may be calculated numerically by using the Huygens-Fresnel-Kirchoff diffraction integral. Given very small $|1-n|$ and $\Delta\theta$, the effect of object BDY on the propagation along a ray path is calculated with excellent accuracy by calculating the path-integral for the amplitude along the undeflected path to give the phase shift along this path, and then calculating the integrated amplitude at any point $x_3$ on slab-volume SV3 by summing (i.e. by numerically integrating) the amplitudes for all paths through a set of very closely spaced points on the full span of grating G2 to the point at $x_3$. In turn, $I_P(x_3)$ and $I_{P'}(x_3)$ are calculated from $I_Q(x_3)$ and $I_{Q'}(x_3)$ via Eqs. (III.69) and (III.68), where the latter intensities are just the squared moduli of the associated integrated (summed) amplitudes.

To illustrate refractive-index gradient contrast formation in 1D and the associated edge-enhancement of an artifact's x-ray geometric shadow, the results of such a numerical calculation are presented in FIGS. 18a–c. FIG. 18a shows as a function of $x_3$ the resulting intensity profiles of $I_{Q'}(x_3)$ (solid line) and $I_Q(x_3)$ (dotted line), while FIG. 18b shows the associated profiles of $I_P(x_3)$ (solid line) and $I_{P'}(x_3)$ (dotted line). The calculation simulates operation in phase-interferometric mode at $E_*=E_X$ using a 1D-periodic PG(1, 2,1) phase grating profile, with $a_2=4.22$ $\mu$m, $a_1=a_P=8.4$ $\mu$m, and $s_1=1.3$ $\mu$m. It assumes L=1 m, and $E_X=17.4$ keV, and that object BDY is a $CaCO_3$ cylinder, imbedded in water, with a diameter of 150 $\mu$m. The cylinder's axis is oriented parallel to the y-axis and is located at $x_3=0$ and $R_D=25$ cm. FIGS. 18a–c all correspond to half of the cylinder's projected image (symmetric about $x_3=0$). The cylinder's axis projects to $x_3=0$, and its shadow terminator projects to $x_3=100$ $\mu$m. The calculation ignores the effect of scattering for FIGS. 18a,b, but that contribution would disappear from $I_{sub}(x_3)$ (FIG. 18c) in any case. FIGS. 18a,b show weak absorption by the cylinder, as indicated by a slightly diminished height of $I_{Q'}(x_3)$ in the cylinder's shadow, $0 \leq x_3=100$ $\mu$m. Also evident, especially near the shadow's terminator at $x_3=100$ $\mu$m, is a lateral displacement (phase-shift) and distortion of the BRIGHT fringes.

FIG. 18c shows as a solid-line curve the subtracted image profile, $I_{sub}(x_3)$, calculated via Eq. (III.73), from pattern P' of FIG. 18b, with resolution elements x located at associated values of $x_3$. The calculation is simplified by assuming that grating G1 has only one uniformly illuminated slit, whereby geometric blurring by finite $W_S$ is ignored. The solid curve on FIG. 18c shows the combined effects of refraction and absorption by the cylinder. To provide a base-line, the dotted line shows $I_{sub}$ calculated from $I_P$ for object BDY absent. To show the effects of absorption and refraction independently, the dash-dot line shows $I_{sub}$ calculated for a geometrically identical cylinder, with normal absorption but with its refraction artificially set to zero. It then displays the profile obtained by a normal absorption-contrast radiogram. The dashed line similarly shows $I_{sub}$ for said cylinder with normal refraction but with its absorption artificially set to zero. A comparison of these curves indicates that the effects of absorption and refraction are roughly additive.

Note that the parameters used in this calculation are appropriate for mammography. The calculation indicates that the average image contrast of a 150 $\mu$m dia. spherical micro-calcification in breast tissue is more than quadrupled by the contribution from (2D) refractive-index gradient contrast, relative to the corresponding average image contrast obtained with conventional absorption-contrast. Consider an image wherein the detection of weak artifacts is limited by quantum mottle. A conventional apparatus with a Bucky grid (say with 3× attenuation) would provide about $3 \times 4^2 = 48$ times the patient-dosage as the Invention's apparatus (with the above parameters in 2D) for both apparatuses to detect the same micro-calcification with the same quantum-mottle limited signal-to-noise ratio. Use of large $R_D$, small $a_P$, and phase-interferometric mode with higher n all increase the improvement. For example, operation of the above-described apparatus at n=3 increases the refractive-index contrast by a factor of $3^{1/2}=1.73$. Also note that the dashed curve on FIG. 18c shows that refractive-index contrast obtains for an object with no absorption at all, but with only a spatial density gradient. Thus, the Invention provides a radiogram of an object that is otherwise totally transparent to x-rays. Further note the ratio $L_I/L_R$ is about 600 for water, while it is about 200 for $CaCO_3$. The contrast enhancement by refractive-index gradients is then about 3 times stronger for density gradients of comparable magnitude produced instead by low-Z hydrocarbons relative to $CaCO_3$. Thus, the otherwise weak contrast evident in the absorption contrast of a cancer-indicating low-Z breast-tissue "mass" is expected to be improved dramatically by the Invention. Finally note, that since hair-line fractures and osteoporosis in bone tissue provide particularly strong refractive-index gradients, such artifacts will be strongly imaged under this methodology.

III.8 Element-selective contrast methodology

An important medical-imaging application of the Invention is its use under a new imaging methodology, wherein images are obtained via element-selective contrast. It may be used either as a DEXA or a DSA imaging system (see Sect. II.3) I the latter usage, this methodology then selectively images a very small concentration of a specific tracer-element whose K absorption edge is resonant with the Invention. When the Invention is configured to obtain element-selective contrast, it then images only that element, and does not image other artifacts (e.g. bone) that do not contain the element, and whose presence may obscure details being sought in the image. The resonant selection can be configured to match elements with Z typically in the range 35–56. Significant contrast enhancement also occurs by the element's abrupt refractive-index change across the absorption edge, whereupon very small concentrations of the element with low absorption contrast may be imaged. As with all other configurations for the Invention, the blurring effects of scatter are also eliminated by configurations that image with element-selective contrast.

For medical imaging the element is chosen and administered to the patient in a manner that allows desired artifacts to be highlighted. The element may be in any form, and may be a component of a non-toxic and non-radioactive compound. Suitable elements are As, Se, Br, Kr, Rb, Sr, Y, Zr, Nb, Mo, Ru, Rh, Pd, Ag, Cd, In, Sn, Sb, Te, I, Xe, Cs, Ba. In phase-interferometric mode, element-selective imaging can operate at moderately high energy to include iodine and even barium. When used for angiography very small amounts of iodine (Z=53) may be administered. (See preferred Embodiment 5 in Sect. V.1.) Alternatively, the tracer-element may be one that is selectively absorbed by cancerous tissue, or by nerve tissue (for myography), etc.

So far, disclosure of the Invention's operation in the interferometric modes has concentrated on operation with an $E_{n,m}$ energy resonance centered on the average energy $E_X$, e.g. in phase-interferometric mode at the wide resonance with $E_X \approx E_* = E_{n,m_*}$. Element-selective imaging, on the other hand, is done with $E_X$ located between resonances. That is, the apparatus is "tuned" by adjusting $a_2$ (and/or L) so that two resonances with opposite-sign contrast instead straddle the energy $E_X \approx E_K$. As discussed in Sects. III.3 and III.4, the effective contrast of a p=1 pattern Q is measured by the ratio of Fourier coefficients $Q_1/Q_0$. FIG. 15 shows the associated β-dependence of $Q_1/Q_0$ with grating G2 configured as a binary absorption grating for various duty-cycles, and FIGS. 16a–e show it with grating G2 configured as a phase grating for various profiles. Note that $Q_1/Q_0$ passes through zero at various values of β, as indicated on FIGS. 16a–e by diamonds and plus signs.

Zeros located by a diamond are contrast nulls, that occur via the non-fractional Talbot effect, and are not useful here. Zeros located by a plus sign on FIGS. 15, 16b and 16e are contrast-reversing, i.e they occur at a sign reversal of $Q_1/Q_0$. That is, x-rays with energies on either side of the reversal have interchanged BRIGHT and DARK fringes in patterns Q and P. Equivalently, the relative intensities recorded by b and d-labeled phase-matched pixels are interchanged. Said interchange results (essentially) from an otherwise negligible half-period shift of pattern P, seen, for example, in Eq. (III.30). Contrast-reversals occur for amplitude gratings configured with odd values of m=p, and for phase gratings (with p=1) whose profiles have odd-$m_*$. A binary absorption grating with the duty-cycle $s_2/a_2 \geq \frac{1}{2}$ (dotted curve) has continuous contrast-reversals, similar to those of a phase grating. A duty-cycle $s_2/a_2 < \frac{1}{2}$ (solid, and dashed curves), on the other-hand, gives a discontinuous reversal, as indicated on FIG. 15 by the abrupt vanishing of $Q_1/Q_0$ at $\beta = s_2/a_2$.

Contrast reversals are used by the Invention to obtain element-selective contrast. For a phase grating with odd $m_*$ or for a binary absorption grating with p=1, contrast reversals occur at half-integer values of β, i.e. at values of β given by $$\beta = \frac{n}{2}, \qquad (\text{III.91})$$

where n is an odd integer. These reversals then occur at the corresponding energies $$E_{n,2}(a_2) = \frac{2}{n} \tilde{E}(a_2), \qquad (\text{III.92})$$

as given by Eq. (III.35). To obtain element-selective contrast, grating G2 may be either a phase grating or a binary absorption grating; however, the resulting contrast is much lower when a binary absorption grating is used. Phase gratings with PG(1,3,1) and PG(2,5,1) provide convenient strong contrast reversals at the operating point $\beta_x = \frac{1}{2}$, i.e. at m=2, n=1 in Eq. (III.37). The energy of a contrast reversal is then configured (for example) with m=2, n=1 via Eq. (III.91) by the appropriate choice of $a_2$ via Eq. (III.82) with n=1 (i.e. via Eq. (III.38)), $$a_2 = 2^{1/2} \tilde{a}_2(E_X), \qquad (\text{III.92})$$

to lie at the average x-ray energy $E_X$. In turn, $E_X$ is chosen to lie at the energy $E_K$ of the element's K-edge, as per $$E_X \approx E_K \approx 2/n\tilde{E}(a_2), \qquad (\text{III.93})$$

so that the finite x-ray bandwidth ΔE of the illuminating x-rays straddles the contrast-reversal, and provides x-rays with energies above and below the contrast reversal. The values for α, L, and $E_K$ of the element to be imaged then fix the value of $\tilde{a}_2(E_X)$, whereupon Eq. (III.82) provides a specific set of allowed choices (indexed by the integer n) for the G2 grating period $a_2$, as per Eqs. (III.82), that may be used to obtain element-selective contrast.

The mechanism by which element-selective contrast obtains may be understood by considering FIGS. 19a–e, all plotted using the same linear energy scale. The example illustrated by FIGS. 19a–e is for iodine ($E_K$=33.17 keV) with an apparatus configured with its m=2, n=1 contrast reversal centered at $E_K$, via Eqs. (III.92) and (III.93). A suitable x-ray illumination spectrum is shown in FIG. 19b. It is produced by x-ray tube T and filter F, configured via methods presented in Sect. V.3. This continuous spectrum covers both the energy range where the iodine's absorption and refractive index are rapidly varying, as well as the energy range where the contrast reverses.

FIG. 19a shows the x-ray energy dependence of the contrast of the p=1 spatial-frequency component of pattern Q, as indicated by the ratio $Q_1/Q_0$, when grating G2 is a phase grating with a PG(1,3,1) profile (solid line), with a PG(2,5,1) profile (dashed line), and when grating G2 is a binary absorption grating with $s_2/a_2 = \frac{1}{2}$ (dotted line). These three curves are just the solid curves on FIGS. 16b, 16e, and 15, replotted on a linear energy scale. The spectrum may be viewed as containing x-rays of two types—$E_{low}$ x-rays are those with energies below $E_K$, and $E_{high}$ x-rays are those with energies above $E_K$. Given the contrast reversal now centered at $E_K$, the two types of x-rays give opposite contrast from each other, i.e. $E_{low}$ x-rays give negative contrast, while $E_{high}$ x-rays give positive contrast.

Period and phase harmonic matching under the element-selective imaging methodology are accomplished via Eq. (III.77) and with the same hardware configuration and conditions disclosed in Sects. III.6.–III.6.4, but with the numerical values of the apparatus parameters slightly different. However, given the contrast reversal, the effect of said matching is now different from that for the absorption or refractive-index imaging methodologies. Indeed, it has opposite effects for $E_{high}$ and $E_{low}$ x-rays. When object BDY is absent the effect causes positive-contrast $E_{high}$ photons to have BRIGHT fringes of pattern P illuminate b-labeled pixels, and to have DARK fringes of pattern P illuminate d-labeled pixels. For negative-contrast $E_{low}$ photons, however, the effect causes just the reverse to happen, i.e. BRIGHT fringes then illuminate d-labeled pixels, while DARK fringes illuminate b-labeled pixels.

Consider the use for angiography of the Invention configured for element-selective imaging with iodine as the tracer element. The most common components present in object BDY that contain no iodine are water and bone. FIGS. 19c, 19d, and 19e show respectively the linear absorption (i.e. $1/L_f$(cm)) of iodine, water and CaCO$_3$ (bone). Water and bone both have an absorption (and refraction) that varies slowly across $E_K$ and is not significantly different for $E_{low}$ and $E_{high}$ photons. The ratio of the intensities of $E_{low}$ to $E_{high}$ x-rays, determines the weighting of these intensities in a full-spectrum average of $Q_1/Q_0$, that, in turn, determines the net contrast produced by water and CaCO$_3$. This ratio may be adjusted, by adjusting the x-ray tube's DC high voltage, or by adjusting the relative thickness of filter F. If a thin cell that contains a liquid solution with a very weak concentration of iodine is included as part of filter F, then this ratio also may be adjusted by varying the cell's iodine concentration. Then, by carefully controlling this ratio, the net contrasts for both water and $CaCO_3$ can be made to cancel approximately in an image that is calculated from $I_{sub}$, as per Eq. (III.73). (If said control instead enhances the differences between water and $CaCO_3$, the Invention then functions as a DEXA system, rather than as a DSA system, when no iodine is present.) Once canceled, then both bone and water-dominated tissue artifacts that contain no iodine almost completely disappear from the final image. Further, if instead of using Eq. (III.73) to calculate $I_{sub}$ in the image subtraction algorithm, $I_{sub}$ is instead calculated for the x'th pixel via $$I_{sub}(x) = \frac{I_b(x) - I_d(x)}{I_b(x) + I_d(x)}, \quad (III.94)$$

then the appearance in the image of absorption by these uninteresting but strongly absorbing artifacts (like bone) is more completely erased from the image. Note that Eq. (III.94) also eliminates scatter-induced blur from the resulting image, similarly to its elimination by Eq. (III.73).

Unlike water and $CaCO_3$, however, iodine has both a large abrupt change in its absorption and a similar abrupt change in its refractive index [see Michette and Buckley, 1993, Sect.5.5] at energy $E_K$. Its absorption spectrum is shown in FIG. 19c. Via Moseley's law (Leighton, 1959, pp. 422–426), the energy $E_K$ of an absorption K-edge is associated with a unique element, so that when the Invention is configured as per Eqs. (III.92) and (III.93), then only the selected element is imaged. For artifacts containing iodine the positive and negative contrast contributions to the image by $E_{high}$ and $E_{low}$ x-rays do not cancel, since iodine, and only iodine, has a very different opacity and refractive index above and below $E_K$=33.17 keV. These artifacts then appear strongly imaged in a dot-matrix image of $I_{sub}$, as calculated via Eq. (III.73) or (III.94). Their contrast is further edge-enhanced by the abrupt change in the refractive index of iodine that also occurs at $E_K$. The slope of a curve on FIG. 19a at the contrast reversal then determines the element-selective contrast. A higher value of $m_+$ gives higher contrast to a phase grating. Thus, on FIG. 19a notice the greater slope at $E_K$ of the dashed line for a PG(2,5,1) profile relative to that of the solid line for a PG(1,3,1) profile. A binary absorption grating (dotted line) is seen to provide the least contrast. In a further refinement of the Invention, the tracer element, itself, is used in the G2 phase grating' spatially-periodic structure, so that its associated abrupt change in refractive-index and absorption at $E_K$ further enhance the contrast reversal's sharpness.

III.9 Obtaining two independent images from one exposure

The above methods provide one image per exposure, made from a dot-matrix array of the intensities $I_{sub}(x)$, as calculated via Eq. (III.72) or Eq. (III.94). Moreover, the methods disclosed in Sects. III.7 and III.8 provide an edge-enhanced image that is a combination of the object's absorption and refractive-index gradient distribution (or that of the tracer element), i.e. contrast results from a combination of methodologies. However, from only a single x-ray exposure made with object BDY present it is also possible, if desired, to get more than one image from this exposure's data, with each such image deriving from a different "pure" methodology. For example, from such a single exposure the Invention can produce an image giving the object's pure absorption distribution, and simultaneously can produce a second independent image providing the object's pure refractive-index gradient distribution, with both of these images having the blurring effects of scatter removed from them.

To obtain the two images, the pixel layout and phase-matching shown on FIG. 12c are used. Grating G1 is configured as shown on FIG. 8b via a separable function, so as to produce a 2D-periodic separable pattern P as shown in FIGS. 14d and 12c. The pixel layout shown on FIG. 12c includes pixels labeled c, in addition to its b and d-labeled pixels. FIG. 12c indicates correct alignment, since BRIGHT fringe umbras of pattern P illuminate b-labeled pixels and their penumbras and the DARK fringes minimally illuminate the d-labeled pixels. Note that the penumbras also partially illuminate c-labeled pixels, but negligibly illuminate d-labeled pixels.

Before the apparatus is used for x-ray imaging, it must be calibrated (with object BDY absent). To do so, a "calibration" x-ray exposure is taken, wherein the x-ray intensity is measured (for pattern P) by the detector-pixels within each resolution element x. Three calibration constants for each resolution element x are recorded. These are $I_{b0}(x)$, $I_{c0}(x)$, and $I_{d0}(x)$, where each constant is the average intensity recorded respectively by the b, c, and d-labeled pixels within resolution element x with object BDY absent. To verify apparatus stability, if desired, these calibrations may be rechecked after an x-ray exposure is made with object BDY present. Assuming reproducible operation of the apparatus, then recalibration is needed only when the x-ray tube's brightness is changed. (In addition to their use for obtaining two independent images, these and/or similar calibrations may be used with all methodologies to rescale $I_{sub}$ to give a flatter intensity field, if grating errors leave it slightly non-uniform following alignment.)

During the single exposure with object BDY present, the Invention records for each resolution element x three intensities for pattern P'. These values are $I_b(x)$, $I_c(x)$, and $I_d(x)$, as the average intensity recorded respectively by the b, c, and d-labeled pixels within resolution element x with object BDY present. With object BDY now present, the intensities recorded by the b and c-labeled pixels are correspondingly attenuated by the object's absorption. Refraction by the object also laterally displaces the positions of BRIGHT fringes of pattern P, as per the lateral phase modulation of pattern P seen on FIG. 18b. Said displacement decreases the associated b-labeled pixel intensity and increases the intensity on an adjacent c-labeled pixel. Scattered x-rays add intensity roughly uniformly to all neighboring pixels. In terms of these three dominant processes, the relationship between these various intensities with and without the presence of object BDY for resolution element x may be written as $$I_b(x) \approx [I_{b0}(x) - I_R(x)]A(x) + I_S(x), \quad (III.95)$$

$$I_c(x) \approx [I_{c0}(x) + I_R(x)]A(x) + I_S(x), \quad (III.96)$$

and $$I_d(x) \approx I_{d0}(x) + I_S(x), \quad (III.97)$$

where, for the x'th resolution element, $A(x)$ is the object's associated absorption, $I_R(x)$ is the intensity that has been shifted from the b to the c-labeled pixels as a result of the object's refractive-index gradient, and $I_S(x)$ is the local intensity of scattered x-rays. Knowing the calibration constants, $I_{b0}(x)$, $I_{c0}(x)$, and $I_{d0}(x)$, then Eqs. (III.95)–(III.97) can be solved for each resolution element x for the values of $A(x)$ and $I_R(x)$, in terms of th measured intensities $I_b(x)$, $I_c(x)$, and $I_d(x)$. The result is $$A(x) = \frac{I_b(x) + I_c(x) - 2I_d(x) + 2I_{d0}(x)}{I_{b0}(x) + I_{c0}(x)} \quad . \tag{III.98}$$

and $$I_R(x) = \frac{[I_c(x) - I_b(x)][I_{b0}(x) + I_{c0}(x)]}{2I_b(x) + 2I_c(x) - 4I_d(x) + 4I_{d0}(x)} + \frac{I_{b0}(x) - I_{c0}(x)}{2} \quad . \tag{III.99}$$

For each resolution element x the computer CP (and/or its internal image processor) thus calculates via Eqs. (III.98) and (III.99) the associated $A(x)$ and $I_R(x)$. A dot-matrix image made from the $A(x)$ values provides the desired pure absorption image, while one made from the $I_R(x)$ values gives the pure refractive-index gradient image. Scrutiny of Eqs. (III.98) and (III.99) indicates that the images produced by these Formulae also have scatter-induced blur eliminated by subtraction.

Each of these two independent images gives different information about the internal structure of object BDY. These images may be regarded separately, or, if desired, they may be synthesized to form a doubly-descriptive "false-color" image of object BDY. For example, the colored image's red intensity may be made proportional to $I_R(x)$ and the image's green intensity may be proportional to $A(x)$. In such an image, large image artifacts appear as green with yellow to reddish colored outlines. If preferred, a different color combination may be used. A similar procedure may be followed using the element-selective imaging methodology. In angiography, for example, small coronary arteries, having a large refractive-index gradients are then displayed as one color, while larger arteries and heart chambers show with a different color.

III.10 Apparatus alignment system

Gratings G1, G2, G3 and detector D require careful relative alignment, in order to achieve period and phase harmonic matching. Alignment operations are performed with object BDY absent. The Invention provides additional components and methods specifically included for performing said alignment. These components are disclosed in Sect. III.10.1. The components together form an in-situ laser-light optical interferometer, that is a collateral Invention herein disclosed. Detailed principles of operation of said optical interferometer are disclosed in Sect. III.10.2. Following careful apparatus assembly the optical interferometer is used for exact alignment, as disclosed in Sect. III.10.3.

The alignment system obtains period and phase matching throughout the whole area of detector D. To do so, the allowed fractional error in Eqs.(III.7) and (III.76)–(III.80) must be somewhat less than 1 one part in $N_Q$, where $N_Q$ is the number of periods of pattern P that span the detector. For example, a detector 2.5 cm wide and pattern period $a_P \approx 18$ $\mu$m give $N_Q \approx 1400$ periods spanning detector D, whereupon the cumulative error in $a_P$ relative to $a_D$ then must be somewhat less that 0.07%, say about 0.01%. The relative positioning accuracy of gratings G1, G2, G3 and detector D also must be to within better than $a_P$. Not only must such accuracy be achieved, it also must be maintained for reasonable durations, so that realignment is not needed too often. Thermal stability is thus important, as discussed in Sect. V.2. Unavoidable residual drifts of the alignment may be corrected as needed via brief x-ray exposures with object BDY absent, and/or via briefly rechecking and readjusting the alignment with the optical interferometer, say immediately prior to an exposure with object BDY present. Additionally, said brief x-ray exposure with object BDY absent also may serve for apparatus calibration (or recalibration), as disclosed in Sect. III.9.

As per Sect. III.6.3, the gratings and detector must be fabricated so that the resulting "as-built" values of $a_1$, $a_2$, $a_3$ and $a_D$ satisfy Eqs.(III.7) and (III.80) with a required accuracy for each of them that is somewhat better than 1 part in $N_Q$. Fortunately, the current state-of-the-art for microfabrication technology readily works to tolerances much tighter than 0.01%, so that achieving the needed fabrication accuracy is not a problem. Via Eq. (III.79) the "as-built" values for $a_1$ and $a_2$ define the value $\alpha_*$ as the now-required value for $\alpha$. At any given state of the alignment operation, the value $\alpha_!$ of $\alpha$ that obtains in practice is defined as $$\alpha_! = \frac{R_{2!}}{R_{1!}} \quad , \tag{III.100}$$

where $R_{1!}$ and $R_{2!}$ are the actual values of $R_1$ and $R_2$ at any particular state during the alignment process. In general, $\alpha_!$ is slightly different from the desired value $\alpha_*$. One goal of alignment is to achieve and maintain $\alpha_! \approx \alpha_*$ with the relative error, $1-(\alpha_!/\alpha_*)$, kept somewhat smaller than $1/N_Q$. For $R_{1!}$ and $R_{2!}$ both about 0.5 m, either grating then must be longitudinally positioned to an accuracy of typically better than 360 $\mu$m.

Lack of parallelism of the grating and detector periodicity directions caused by rotation of the gratings about the z direction relative to each other and relative to the detector also must be eliminated. Achieving said parallelism is called "rotational alignment", and "rotation" of a grating refers to rotations about the z-direction (i.e around an axis parallel to $C_L$), unless otherwise specified. Thus, when the "rotational alignment" is not correct, then phase matching can occur approximately only in a small localized area of the grating, but cannot occur simultaneously throughout the detector's whole surface area. In turn, the required rotational alignment accuracy prohibits rotational errors from displacing the periphery of pattern P laterally by more than a small fraction of $a_P$ relative to detector D.

The rotation of the plane of a grating about the x or y directions is called "tilt". The plane of a "tilted" grating is then not perpendicular to $C_L$, nor is it parallel to the planes of the other gratings and/or of the detector. Note that the required longitudinal positioning accuracy for $R_{1!}$ and $R_{2!}$ must be maintained throughout the planes of the gratings and the detector. When these planes are not accurately parallel via grating tilt, then different values of $\alpha_!$ hold for different propagation paths of the x-rays, and phase matching fails at some locations on detector D.

When grating rotation, tilt, and longitudinal positioning are all correctly aligned, then for accurate phase matching to obtain, the relative lateral positioning errors of gratings G1, G2 and detector D still must be controlled to well within a single grating period width (typically<<3–60 $\mu$m). Fortunately, alignment is highly simplified by the fact that the gratings are spatially periodic, so that alignment to any one period of a grating is equivalent to alignment to any other.

III.10.1 Alignment system components

The components of the Invention that are used for its alignment are shown on FIG. 1. Laser LS produces narrow bandwidth light with wavelength $\lambda_L$. Laser LS is a temperature stabilized single-mode diode laser, including an associated collimating lens and beam circularizing optics that gives it a parallel diffraction-limited output beam. Its wavelength $\lambda_L$ is adjustable over a narrow range via adjustment of its temperature and/or injection current. Reflections are prevented from reentering the laser by Faraday optical isolator FOI and by spatial filter SF. Spatial filter SF is comprised of two lenses with a Newtonian focus and a pinhole positioned at this focus. Light from laser LS, after passing through FOI and SF has optic axis LCL. It then passes through adjustable-focus telescope AFT, comprised of two lenses. The focal lengths of its lenses are chosen so that the laser beam exiting the telescope has a typical diameter of about 3 mm–1 cm. Telescope AFT is aligned to laser optic axis LCL. Its focus is adjusted in a manner that does not perturb axis LCL, but allows the laser beam to be brought to a focus at various distances from it including infinity. Optionally, it may be desirable to include within telescope AFT orthogonally mounted and independently translatable cylindrical lenses to thereby allow the telescope's single focus to be turned into a pair of orthogonal line foci whose longitudinal positions are independently adjustable.

X-ray axis $C_L$ passes through the center of focal spot S and through the center of detector D. X-ray transmitting mirror XTM is very thin, partially reflecting of light, and negligibly absorbing of x-rays (e.g. a microscope coverslide). It negligibly laterally displaces transmitted light. Positionally-adjustable mirrors M1 and XTM reflect the laser beam so that the reflection of laser optic axis LCL and x-ray axis $C_L$ coincide. Said coincidence is obtained by using removable pinholes PH1 and PH2 as fiducials. These pinholes are made from a high-Z material that transmits neither light nor the x-rays. They are positioned during alignment within the apparatus on kinematic mountings, so that following their removal they may be repositioned at exactly the same position. Their lateral positions are set using x-y translation micropositioning means, included as part of each of their mountings. The holes are only a few $\mu$m in diameter, and comparable in size to that of a diffraction-limited beam-waist formed by focusing the laser beam on them.

Laser LS, along with its associated beam forming (AFT, SF, FOI, etc.) and beam steering components (M1, XTM, etc.), gratings G1 and G2 and detector D, together form an in-situ optical interferometer that is used to obtain accurate alignment of the apparatus. The substrate material SUB for the gratings G1 and G2 is further specified to transmit the laser's light. The periodic structure on these gratings either absorbs and/or refracts the light, so that gratings G1 and G2 then act as diffraction gratings for the laser light. Said action is crucial to the operation of the laser interferometer. X-ray transmitting cover XTC (e.g. black paper or plastic) is opaque to visible light. It is removed during alignment. Laser light reflected by mirror XTM then passes through the gratings to impinge on slab-volume SV3. An in-situ optical interferometer is thereby created that forms spatially periodic interference pattern O in the intensity distribution of the laser light incident on the surface of detector D, and/or incident on grating G3, if it is included. Pattern O has a dominant lowest spatial frequency component with the spatial period $a_P$. Detector D is sensitive to both light and x-rays, and detects said light. When the apparatus is in correct alignment, pattern O is then also period and phase matched to detector D, similarly to the desired phase matching between period P and detector D. The Invention uses an important discovery by the Inventor that pattern O mimics pattern P, and does so independently of the focusing of telescope AFT, directly via the defining Equations (III.7) and (III.74)–(III.80) for the apparatus. That it does so even though the x-ray and laser photon energies (and their associated wavelengths) differ by a factor of about $10^4$, is somewhat remarkable.

When alignment is incorrect, pattern O forms a moiré pattern [see Patorski,1993] with the periodic pixel layout of detector D. Color monitor TV displays via computer CP the optical image detected by the b-labeled pixels as one color (e.g. red) and that by the d-labeled pixels as a second color (e.g. green). The moiré pattern is then displayed as a 2D-periodic color variation on monitor TV. Its fringe period is the spatial frequency difference between that of pattern O and of the b-labeled pixels' sparse array, so that the moiré's displayed appearance is a very sensitive indicator of any misalignment of pattern O and of any corresponding lack of phase matching. Computer CP further provides "zoom" and "pan" options to allow observation of fine details of said moiré image. Alignment is then guided by the varying appearance of the displayed moiré, in response to manipulations of the relative alignment of gratings G1, G2, G3 and detector D.

Precision position-defining mountings are used for positioning gratings G1 and G2 and detector D. Such mountings are available commercially, for example, from the Newport Corporation (Irvine, Calif.). Each grating is laterally and rotationally finely positioned by piezoelectric translators. The extension capability of these translators is through more than one associated grating period. If all alignment positioners, including those used for adjusting the focus of telescope AFT, are controlled by computer CP, then the alignment methods may be reduced to simple algorithms that may be executed automatically by computer CP. So doing, alignment of the apparatus may be fully automated.

During apparatus assembly, laser LS also operates as a laser range-finder. Removable mirror M2 is on a kinematic mounting that allows it to be accurately repositioned. Mirrors M2 and M direct light reflected by the gratings and/or by the detector's surface to superpose with light from laser LS on photodiode PD. When operating as a range-finder, laser LS has its wavelength $\lambda_L$ swept via applying a low-frequency triangular or sawtooth-waveform ramp voltage to the laser diode's injection current. Then, using a technique demonstrated by Gorecki et al. [1994], the heterodyne frequency measured on photodiode PD is used in a manner similar to that of FM radar as a laser range finder to determine the initial relative longitudinal positioning of gratings G1 and G2, and grating G3 or detector D. While it is possible to assemble the apparatus accurately without use of this laser range finder, by instead using very careful manual measurements, its inclusion expedites assembly and alignment.

To simplify alignment, the laser system, gratings and detector are assembled as accurately as possible to be "pre-aligned". Laser LS, Faraday isolator FOI, spatial filter SF, and telescope AFT are first aligned to a common optic axis LCL, using standard techniques in optics. X-ray tube T, and detector D are then installed, thereby defining x-ray axis $C_L$. The reflection of the laser's optic axis LCL by mirror XTM is made coincident with $C_L$. Accurately repositionable pin-holes PH1 and PH2 act as fiducials that define points on axis $C_L$ for both light and x-rays. They are placed, one at a time, on axis $C_L$, as shown in FIG. 1. Their positions are each adjusted to be on $C_L$, via a sequence of x-ray exposures, so that each casts a small x-ray spot on the center of detector D. The reflection by mirror XTM of laser optic axis $LC_L$ is aligned to coincide with x-ray axis $C_L$ by adjusting mirrors M1 and XTM and the optic axis of telescope AFT so that the laser LS can be focused either on pinhole PH2 or on the center of detector D. Focus on pinhole PH2 is indicated by its transmitted light being detected by detector D. Next, the tilt of the plane of detector D is adjusted. Pinhole PH2 is removed and pinhole PH1 is repositioned on axis $C_L$ between x-ray tube T and mirror XTM. The flat surface of detector D reflects laser light, which then passes back through mirror XTM to strike pinhole PH1. The telescope is then adjusted to focus on pinhole PH1. Tilt of detector D is adjusted so that the focused laser light reflected by its surface then passes through pinhole PH1 and is detected by photodiode PD.

If grating G3 is to be included in the apparatus, and if it is fabricated accurately as part of detector D, as shown on FIG. 2, then no alignment of grating G3 is needed. If grating G3 is independently fabricated, however, parallelism of its plane to that of detector D is obtained by contacting its periodic surface layer with the front surface of detector D, and/or by inserting very thin shims between these two components. Parallelism is determined by the same method used for tilt-alignment of detector D, with light reflected by the surface of grating G3 brought to a focus on pinhole PH1. Lateral positioning and rotation adjustment of grating G3 is done with light from telescope AFT and laser LS fully illuminating grating G3. The optical shadow cast by grating G3 creates a moiré pattern with the pixel array of detector D, and grating G3 is rotated and translated to remove this moiré and to create uniform illumination of all b and d-labeled pixels of detector D, indicated on monitor TV by a uniform yellow color. Once detector D (and grating G3) has (have) been installed and aligned, it (they) may be used as a reference plane for alignment of gratings G1 and G2, and not be moved thereafter.

Next, a reference range is measured to the front-surface of detector D, (or to grating G3, as appropriate) using the laser range finder. Mirror M2 is installed and positioned, along with mirrors M, so that parallel light passing through mirror XTM, and parallel light reflected by detector D (or grating G3) superposes on photodiode PD. The heterodyne frequency produced at photodiode PD is recorded. Grating G2 is installed next. Its tilt is aligned to position its focused reflection near pinhole PH1. Its reflected light is sampled by the range finder, and its distance $R_{2!}$ from detector D is adjusted so that its associated heterodyne frequency indicates the correct design distance, $R_{2!} \cong R_2$. Finally, the above installation procedure is repeated for grating G1 to give $R_{1!} \cong R_1$.

III.10.2 Operational principles of the optical interferometer

Understanding the operation of the optical interferometer is simplified by initially assuming that the Invention operates with p=1, q=1, u=2, m=1, v=1, grating G3 is absent, and that both tilt and rotation are in correct alignment, but that α is not. Configurations with p>1 are considered at the end of this Section, and the effects of misalignment are considered in Sect. III.10.3. For p=q=1, Eq. (III.79) reduces to $$\alpha_* = \frac{a_2}{a_1 - a_2}, \quad \text{(III.101)}$$

For added simplicity assume that gratings G1 and G2 are both 1D-periodic, and that the telescope provides light rays incident on grating G1 that are parallel to and centered on $C_L$, as shown in FIG. 20. The gratings act as diffraction gratings for the laser light, whereupon Fraunhofer diffraction orders are produced at grating G1, as shown in FIG. 20. On FIG. 20 parallel line pairs represent the envelope of the laser beams, as incident and as created by the various diffraction orders. Each order then propagates independently and is coherent with the other orders. The zeroth order beam $FD_0$ experiences no net deflection at grating G1, but the first order beams $FD_{\pm 1}$ are deflected through the small angles $$\theta_{G1} \approx \sin \theta_{G1} = \pm \frac{\lambda_L}{a_1} = \pm \frac{\lambda_L}{a_2} \frac{\alpha_*}{1 + \alpha_*}, \quad \text{(III.102)}$$

(shown on FIG. 20 for $FD_1$) where Eq. (III.101) is used. Upon arriving at grating G2, orders $FD_{\pm 1}$ have experienced the lateral displacement from order $FD_0$ $$W_{2L} = R_{1!} \theta_{G1}. \quad \text{(III.103)}$$

All other orders are more widely deflected. Typical numerical values for $W_{2L}$ for the preferred embodiments described in Sect. V.1 range from 0.9 cm to 5 cm. For simplicity, assume that the width of grating G2 accommodates only the transmission of the three orders, $FD_0$ and $FD_{\pm 1}$. These three orders have the dominant intensities, while higher orders, $FD_{\pm 2}$, $FD_{\pm 3}$, etc. are much weaker. As indicated below, the interferometer also works with the passage of these additional (weaker) orders.

The $FD_0$ and $FD_{\pm 1}$ orders are then each diffracted by grating G2, to create more Fraunhofer diffraction orders, as shown on FIG. 20. These are labeled by FD with two subscripts, where the first subscript indicates the diffraction order at grating G1, and the second indicates the order at grating G2. The order $FD_{0,0}$ is undeflected by grating G2 and hits the detector's center exactly on $C_L$. Among the orders produced by order $FD_1$, order $FD_{1,-1}$ is the only one that hits the detector anywhere near $C_L$, while the others arrive at detector D with a sufficiently wide separation from $C_L$ that they generally escape detection. For the preferred embodiment parameters used in Sect. V.1, typically they arrive at the detector plane about 2 cm or more from $C_L$. By symmetry, order $FD_{-1,1}$ also hits the detector near $C_L$. Thus, among the orders produced at grating G2, only $FD_{0,0}$, $FD_{1,-1}$ and $FD_{-1,1}$ finally arrive at the detector plane near $C_L$. The angle between order $FD_1$ and order $FD_{1,-1}$ is $$\theta_{G2} \approx \sin \theta_{G2} = \frac{\lambda_L}{a_2}, \quad \text{(III.104)}$$

shown on FIG. 20 between orders $FD_{1,-1}$ and $FD_{-1,0}$ (the 0'th order extension of $FD_1$). The angle $\theta_0$ between beam $FD_{0,0}$ and symmetrically incident beams $FD_{1,-1}$ and $FD_{-1,1}$ is then $$\pm \theta_0 = \theta_{G2} - \theta_{G1} = \frac{\lambda_L}{a_2} - \frac{\lambda_L}{a_1} = \lambda_L \left( \frac{1}{a_2} - \frac{1}{a_1} \right) = \quad \text{(III.105)}$$

$$\frac{\lambda_L}{a_1} \frac{1}{\alpha_*} = \frac{\lambda_L}{a_P}.$$

Beam $FD_{0,0}$ has a scalar field amplitude that is given as a function of longitudinal position z by $$\psi_0 = A_0 \exp\left( \frac{i2\pi}{\lambda_L} z \right), \quad \text{(III.106)}$$

while beams $FD_{1,\pm 1}$ have field amplitudes given by $$\psi_{\pm 1} = A_1 \exp\left( \frac{i2\pi}{\lambda_L} z\cos\theta \right) \exp\left( \pm \frac{i2\pi}{\lambda_L} x_D \sin\theta \right) \exp(i\phi), \quad \text{(III.107)}$$

where φ is the phase shift accumulated by these latter two beams via their transit of a longer path (longer by several hundred $\lambda_L$), and where the symmetry of their geometry gives their two amplitudes the same moduli $A_1$.

Since the beams $FD_{0,0}$, $FD_{1,-1}$, and $FD_{-1,1}$ are coherent with each other, then if and when they positionally overlap, they interfere. Where they overlap on the detector's surface, the resulting superposed amplitudes produce interference pattern O. If the detector surface is located at $z=Z_D$ then the intensity distribution at this surface is functionally described by $I_0(x_D; z_D)$, where $X_D = x_3$ is the lateral position on the surface of detector D. Using Eqs. (III.106), (III.107) and $\theta \approx \sin \theta$, it is given by $$I_0(x_D; z_D) = |\psi_0 + \psi_1 + \psi_{-1}|^2 = A_0^2 + A_1^2 \cos^2\left(\frac{2\pi x_D}{a_P}\right) + \quad \text{(III.108)}$$

$$2A_0 A_1 \cos\left(\frac{2\pi x_D}{a_P}\right) \cos\left[\frac{2\pi z_D}{\lambda_L}(1-\cos\theta) - \phi\right].$$

The first term in Eq. (III.108) is constant. The second is very small and is periodic with period $a_P/2$. These two terms then provide equal illumination to b and d-labeled pixels, and thus no spatial variation to the display's color. If desired, monitor TV may be color re-balanced to eliminate the background yellow hue created by these first two terms to give a uniform white screen, except for the remaining effect by the third term. The third term is much larger than the second and gives a spatial intensity variation at period $a_P$. If periodic pattern O is aligned with (phase-matched to) the periodic pixel array of detector D, and if its maxima are centered on b-labeled pixels (i.e. phase-matched with them) then monitor TV shows a uniformly red tint, while if the maxima are centered on the d-labeled pixels, it shows a uniformly green tint. The whole TV display may be shifted from red to green via laterally repositioning grating G2, via its associated piezoelectric translators by the distance $a_2/2$. Misalignment is indicated by a red-green skewed moiré pattern, as disclosed in Sect. III.2.

Note that interference pattern O forms only when and where the orders overlap. Consider under what conditions overlap occurs. Combining Eqs. (III.100)–(III.105) gives the displacement $\Delta X_D$ between orders $FD_{1,\pm 1}$ and $FD_{0,0}$ on detector D as $$\pm \Delta x_D = \Delta x_2 - R_{2!}(\theta_{G2} - \theta_{G1}) = R_{1!}\frac{\lambda_L}{a_1}\left(1 - \frac{\alpha_!}{\alpha_*}\right). \quad \text{(III.109)}$$

The relative displacement between these three beams is then zero if and only if $\alpha_! = \alpha_*$ holds, and thus, if and only if the apparatus is longitudinally in correct alignment. Furthermore, phase matching between pattern O also occurs throughout all of the area of detector D if and only if the apparatus is laterally and rotationally in correct alignment. In apparatus configurations with p=m>1, the orders $FD_{1,-1}$, $FD_{-1,1}$, and $FD_{0,0}$ do not overlap at the center of detector D. Instead, the orders $FD_{1,-m}$, $FD_{-1,m}$, and $FD_{0,0}$ are found to overlap at said center, whereupon the interferometer operates similarly with $\alpha_*$ given by Eq. (III.79). An apparatus configured with 2D-periodic gratings produces orders diverging and converging in both the x and y directions. Five orders rather than three are then superposed on detector D. Nonetheless, the analysis of 2D-periodic cases gives the same effect as those found for 1D-periodic gratings. Thus, it provides alignment for all p and for both 1D and 2D-periodic configurations.

Note that whenever there is overlap of orders at the detector's center, then for parallel light illumination the spatial period of the third term of Eq. (III.108) is always $a_P$, independently of the actual values of $R_{1!}$ and $R_{2!}$. Also note that this third term is a product of two cosine factors, wherein the second of these factors determines the magnitude of this term's contribution to pattern O. For fixed $R_{1!}$, then as a function $Z_D$ this second factor provides a periodic reversal of the pattern's contrast. This periodic contrast reversal is the simplest example of the (non-fractional) Talbot effect for light. For L≈1m, $\alpha=1$, and $\lambda_L=780$ nm the contrast reverses for a change of $Z_D$ (i.e for a change of $R_{2!}$) equal to about 415 $\mu$m for $a_P=18$ $\mu$m, about 3.2 mm for $a_P=50$ $\mu$m. Phase reversal also may be brought about by a very small change of $\lambda_L$ (about 0.05 nm) via the offset phase $\phi$. Note that for some values of $R_{1!}$, $R_{2!}$, and $\lambda_L$, the resulting value of $\phi$ may cause the contrast to vanish as it reverses sign. (Said contrast reversal is similar to that for x-rays discussed in Sect. III.8.) However, when the moiré pattern shows such diminished contrast during alignment, contrast may be restored via a slight readjustment of the laser's wavelength $\lambda_L$.

Consider next what happens when the telescope is refocused so that the incident light is no longer parallel, but instead forms a focus somewhere on $C_L$. When telescope AFT is not focused on infinity, the size of the spots formed by various diffraction orders on the plane of detector D may increase. Indeed, orders lost off the side of detector D can become sufficiently wide that they overlap the orders superposed on the detector's center. Where they overlap, they interfere and thereby modify the shape of pattern O. The result is again a similarly periodic pattern, but with a different Talbot fringe structure. If the Talbot fringes formed by the associated third term of Eq. (III.108) have an equivalent associated resonance index $n_L = \lambda_L \rho / a_2^2$ that is an even integer, then these fringes are laterally in phase with those of the overlapped central orders, and all overlapping orders again form the same pattern O (if the apparatus is in correct alignment). On the other hand, if $n_L$ is odd, then Talbot fringes formed in the areas of additional overlapping outside orders have opposite phase. (This half-period phase shift is similar to that seen in Eq. (III.30).) In-phase overlapping orders are readily identified by a change in image brightness across the overlap junction, while out-of-phase overlapping orders provide diminished fringe contrast within the overlapped area. A minor readjustment of wavelength $\lambda_L$ then readily switches $n_L$ from odd to even. Then, if the apparatus is in correct alignment and $n_L$ is even, a uniform phase matching persists through regions of said overlap via the Talbot effect for light, no matter how many orders overlap, and interference pattern O is similar to pattern P. It is then formed independently of the telescope's focusing when the apparatus is in correct alignment. A single-mode (narrow bandwidth) laser is needed here to give high fringe contrast, especially when Talbot-effect optical fringes are formed.

III.10.3 Alignment methods

Once the gratings are installed and pre-aligned within the apparatus, the optical interferometer is used to obtain final accurate alignment in an iterative fashion, wherein adjustments of grating rotation, longitudinal positioning (i.e. $\alpha$-adjustment for locating the condition $\alpha_! = \alpha_*$), $\lambda_L$, and tilt are performed sequentially. Rotation and $\alpha$-adjustment tend to dominate the effort. Tilt and $\lambda_L$ adjustment are queued into the iterative sequence as they appear to be needed by the appearance of the moiré. Note that tilt alignment following pre-alignment is generally quite good and usually does not require major readjustment. Moreover, tilt adjustment is probably the least critical among the various needed adjustments, with rotational alignment perhaps being the most critical. Rotational alignment is best attempted first. The $\alpha$-adjustment methods work best when the gratings are nearly parallel under grating rotation. After several iterations, the sequence of adjustments converges yielding asymptotically correct alignment.

When the apparatus is misaligned, then the periods of pattern O and the detector do not match exactly, and a spatially periodic moiré pattern is observed. Upon reaching ideal alignment interference pattern O undergoes negligible change if telescope AFT is focused anywhere, and the period of the moiré pattern becomes infinite. To aid alignment, the position of grating G2 optionally is swept laterally through a few grating periods in the x, y, and/or rotational directions by using the associated piezoelectric translators, and by applying a slow ≈1 Hz sawtooth sweep voltage waveform to them. With said temporal grating sweep, then when correct alignment is obtained, it is indicated by a spatially uniform temporally alternating red-green color on the whole monitor screen. Said spatially uniform temporal red-green alternating color then occurs no matter where telescope AFT is focused, although change of focus does change the area illuminated by the detector. When the apparatus is misaligned, the moiré pattern is observed to walk during each sweep. The direction of walk is an indicator of the needed adjustment direction, while the spatial period of the moiré is an indicator of how far out of alignment the apparatus is. As proper adjustment is approached and reached, the moiré period approaches and becomes infinite, whereupon the uniform temporally oscillating color appears. If correct alignment is overshot, then the moiré reforms with an oppositely directed walking motion. When the apparatus is misaligned, then refocusing telescope AFT has a variety of significant, useful and indicative effects on interference pattern O, and thus on the displayed moiré.

The most accurate adjustment of $\alpha$ is done once rotational grating alignment is nearly at hand. However, when gratings G1 and G2, or grating G2 and detector D have nearly parallel rotational orientations, then $\alpha$ may be adjusted so that $\alpha_1 > \alpha_*$ holds quite accurately via either of two methods. The first $\alpha$-adjustment method is most effective when the periods of gratings G1 and G2 are nearly parallel. Via this method $\alpha$ is adjusted for the condition $\Delta x_D = 0$, as per Eq. (III.109). To use this method, telescope AFT is focused to form a small spot on detector D. The detailed shape of this spot is magnified and displayed via the zoom option of computer CP. With the above-specified laser beam diameter exiting telescope AFT, then when the telescope is focused on detector D, for $L_T \approx 1.1$ m and $\lambda_L = 780$ nm the laser's diffraction limited focus has a width of about 50 $\mu$m. The three orders $FD_{1,-1}$, $FD_{-1,1}$, and $FD_{0,0}$ produce three foci. When these foci coincide (i.e. at $\Delta x_D = 0$), then for $a_P = 18$ $\mu$m the common focus contains about 2–3 (colored) fringes. When there is no overlap (i.e. for $\alpha_1 \neq \alpha_*$), then the three foci are separated and display no interference fringes. The appearance of the display then allows $R_{1!}$ and/or $R_{2!}$ to be adjusted quite accurately to obtain $\alpha_1 = \alpha_*$.

The second $\alpha$-adjustment method is very effective when the periods of grating G2 and detector D are nearly parallel. Telescope AFT is focused on or near grating G1, whereupon the laser's focus forms a diffraction limited spot with a width of about 23 $\mu$m on grating G1, and typically only one grating G1 period is then illuminated by this spot. That period is then centered on the spot (adjusted for maximum light transmission) by laterally positioning grating G1. With this focusing, orders $FD_0$ and $FD_{\pm 1}$ are highly broadened, and $\theta_{G1}$ is no longer definable. Nonetheless, order overlap on detector D results from the Talbot effect for light, as per Sect. III.10.2, and a broad interference pattern with the period $(1+\alpha_1)a_2$ is formed on detector D. As the distance $R_{2!}$ is adjusted, the moiré pattern's period becomes infinite (or maximizes) when $\alpha_1 = \alpha_*$ is obtained. To obtain a Talbot-effect interference pattern with high contrast, however, it may be necessary to adjust $\lambda_L$ slightly to give a Talbot-effect resonance, as per Sect. III.10.2.

Rotational misalignment is indicated by the formation of highly skewed diagonal moiré fringes. With grating sweep these appear as diagonal walking stripes with a very short period. The skew angle and walk direction are indicators of the rotational misalignment magnitude and direction. For rotational alignment of gratings G1 and G2, detector D may be used as a reference with gratings G1 and G2 both rotated relative to it. To obtain correct rotational alignment, telescope AFT is alternately focused near either grating G1 or G2. When focused near grating G1, this grating's rotational misalignment is nearly inconsequential, and the rotation of grating G2 is then brought closer to correct alignment by its rotational adjustment to remove the moiré's skew. Telescope AFT is then refocused near grating G2 and the rotation of grating G1 is similarly adjusted. A few iterations between the adjustments of grating G1 and G2 rotations brings both gratings rapidly into correct rotational alignment. As correct rotational adjustment is approached the skew angle diminishes, and the moiré pattern's period increases. The skew disappears, i.e. remaining moiré fringes become vertical or horizontal, and the fringe period maximizes. Iterative readjustment of $\alpha$ further increases the moiré fringe period, until the period becomes infinite at $\alpha_1 = \alpha_*$.

Tilt misalignment is indicated by the optical Talbot fringes forming a rectilinear moiré that has a fringe period that is uneven from top to bottom or from left to right. It is also indicated via the second $\alpha$-adjustment method by overlap of only two of the three laser's foci. Said misalignment is corrected by fine adjustment of grating tilt. Optical talbot fringes formed by order overlap when telescope AFT is focused near grating G1 are made laterally uniform by adjusting the tilt of grating G2, and vice-versa.

Once a spatially uniform temporally red to green color oscillation is obtained for all telescope focal positions thereby indicating correct alignment, the sawtooth grating sweep is disconnected and the lateral relative position of the gratings is adjusted for maximum redness by applying adjustable DC voltages to the grating G2 x and y piezoelectric translators. The lateral grating positioning is then checked with x-ray illumination and readjusted, also using monitor TV to obtain maximum x-ray illumination of all b-labeled pixels and minimum x-ray illumination of all d-labeled pixels. Should x-ray illumination yield a moiré, then residual misalignment is indicated. The alignment then may be rechecked with laser illumination, and/or tweaked using x-ray illumination.

Part IV

BRIEF DESCRIPTION OF THE DRAWINGS

In FIG. 3a detector screen DS is comprised of fluor FL, grating G3, and light reflector RFL, all mounted on substrate SUB. Continuous recording media CRM is placed in direct contact with grating G3, and then removed for retrieval of the x-ray image imprinted on it, or, its latent image is read-out in-situ from below whereupon its removal is unnecessary.

FIG. 6a shows the most easily built configuration. FIG. 6b shows a variant of FIG. 6a with a "sandwich" construction that reduces vignetting by the grating, as discussed in Sect. V.1.

FIG. 7a shows the PG(1,2,1) profile; FIG. 7b shows the PG(1,3,1) profile; FIG. 7c shows the PG(1,4,1) profile; and FIG. 7d shows the PG(1,5,1) profile. FIG. 7e shows the PG(2,5,1) profile, further revealing its rescaled thickness (by $n_*$) via Eq. (III.49) and a permutation of the step order is via Eq. (III.48), relative to the PG(1,5,1) profile of FIG. 7d, i.e. the set of k values for FIG. 7d within a period have a permuted order relative to the j values within that period. (Associated plan x-y views of 2D-periodic gratings corresponding to 2D-periodic forms of the profiles of FIGS. 7a and 7b are shown respectively in FIGS. 9a and 9b.) Profile thicknesses are rescaled, and shown multiplied by $2\pi/L_R$ ($E_*$) so that the vertical axis displays the associated negative phase shift in radians at x-ray energy $E_*$, where $L_R$ is the thickness of the low-Z material that gives $-2\pi$ phase shift for x-rays at energy $E_*$ as given in Sect. II.2, and where $E_*$ is defined in Sect. III.4. (A positive phase shift would appear below the abscissa.) $PG(n_*, m_* m, r_*)$ profiles are proportionately thicker than the $PG(n_*, m_*, 1)$ profiles shown by the factor $r_*$.

FIG. 8a shows a 1D-periodic grating. FIG. 8b shows a 2D-periodic grating wherein the transmission is described by a "separable" function, as per Eq. (I.3) with g=0 and the plus sign. FIG. 8c shows a 2D-periodic grating wherein the transmission is described by a "checkerboard" function, as per Eq. (I.4) with g=0 and the plus sign. FIG. 8d shows an "inverted" 2D-periodic grating, wherein the transmission is described by a "separable" function, as per Eq. (I.3) with g=1 and the minus sign.

In FIGS. 9a and 9b these indicies label the associated columns and rows formed by the various square portions, and are shown at the sides and bottoms of the Figures. Periodically-sequential integer index $j_x$ is associated with index $k_x$ via Eq. (III.48), and thus defined as $j_x = m_* \delta_{k_x}(n_*, m_*)$. It is also shown on these Figures. Index $j_x$ steps through a simple sequential order (starting with 0) within a single period, as on x-directed imaginary line ILX, and repeats this sequence for each x-directed period. Similarly, periodically-sequential integer index $j_y$ is associated with index $k_y$ via Eq. (III.48), and thus defined as $j_y \equiv m_* \delta_{k_y}(n_*, m_*)$. Similarly, index $j_y$ steps through a simple sequential order (starting with 0) within a single period, as on y-directed imaginary line ILY, and repeats this sequence for each y-directed period. Unshaded portions on FIG. 9a have zero thickness of the low-Z layer, and have associated indices $k_x = k_y = 1$. On FIG. 9a, ///-shaded portions have associated indices $k_x \neq k_y$, and have a constant thickness giving $-\pi/2$ radians phase shift at $E_X = E_*$, while \\\-shaded portions have associated indices $k_x = k_y = 0$, and have a constant thickness that gives $-\pi$ radians phase shift at $E_X = E_*$. Unshaded portions on FIG. 9b have zero thickness of the low-Z layer, and have associated indices $k_x \neq 0$ and $k_y \neq 0$. On FIG. 9b, ///-shaded portions have associated indices $k_x = 0$ and $k_y \neq 0$ or have associated indices $k_x \neq 0$ and $k_y = 0$, and have a constant thickness giving $-2\pi/3$ radians phase shift at $E_X = E_*$, while \\\-shaded portions have associated indices $k_x = k_y = 0$ and give $-4\pi/3$ radians phase shift at $E_X = E_*$.

FIG. 11a shows G3T22, G3T23, and G3T24 tiles that are used with a detector pixel layout formed by PT1 pixel-labeling tiles. FIG. 1b shows G3T42, G3T43, and G3T44 tiles that are used with a detector pixel layout formed by PT4 tiles. By flipping over G3T4v tiles about a 45° axis passing through their lower-left and upper-right corners, they may be used with PT2 tiles. FIG. 11c shows G3T32, G3T33, and G3T34 tiles that are used with PT3 tiles. FIG. 11d shows G3T52, G3T53, and G3T24, used with PT5 tiles.

FIG. 12b shows contours at 20, 40, 60, and 80% of the peak intensity, and FIGS. 12a,c additionally show contours at 0.0001%., and 99.99% of the peak (umbra's) intensity. The closed contour sets constitute the BRIGHT fringes of the intensity patterns. The positioning of these BRIGHT fringes relative to the b-labeled pixels is for an apparatus that is correctly aligned and has object BDY absent. These positionings are examples of period and phase harmonic matching, as disclosed in Sects. III.6 and III.9. Refractive-index gradient contrast is obtained by the fact that a displacement of a BRIGHT fringe of pattern P in any lateral direction causes a decrease of the net x-ray flux recorded by b-labeled pixels and a simultaneous increase of it respectively on d, or on c-labeled pixels. For a detector with no pixels (e.g. the continuous recording media CRM of FIGS. 3a,b), b and d-labeled pixels become b-areas and d-areas on slab-volume SV3.

FIGS. 14a and 14b are respectively described by separable and checkerboard functions. FIG. 14c shows the intensity of an "inverted" separable pattern Q formed by grating G2 with the planform shown in FIG. 8d. FIGS. 14d–f are respectively associated with FIGS. 14a–c when grating G1 has a 2D-periodic separable form. The pointed tops in FIG. 14e occur for $s_1/a_1=s_2/a_2$ or $s_1/a_1=1/m_*$. Plan (x-y) views of associated constant intensity contours for the patterns on FIGS. 14d and 14e are shown respectively on FIGS. 12a,c and 12b.

FIG. 16a is for a PG(1,2,1) profile. FIG. 16b is for a PG(1,3,1) profile. (The spectral response of a PG(1,2,2) grating is similar to that of a PG(1,3,1) grating.) FIG. 16c is for a PG(1,4,1) profile. FIG. 16d is for a PG(1,5,1) profile. FIG. 16e is for PG(2,5,1) profile. The strong contrast reversals at Γ=½ on FIGS. 16b,e are used in Sects. III.8 and V.1 for obtaining element-selective contrast. Low-Z surface layer profile shapes associated with FIGS. 16a–e are shown respectively on FIGS. 7a–e.

FIG. 18a shows the intensity distribution of patterns Q' (solid) and Q (dotted) on slab-volume SV3. FIG. 18b shows the intensity distribution of patterns P' (solid) and P (dotted) on slab-volume SV3. The solid-line curve on FIG. 18c is the subtracted image profile $I_{sub}$ calculated via Eq. (III.73) versus resolution element x position $x_3$ on slab-volume SV3. The dotted line is the base-line profile calculated for object BDY absent. The dash-dot line profile is calculated for a similar cylinder with finite absorption but with its refraction arbitrarily set to zero. The dashed line is for a cylinder with finite refraction but with its absorption arbitrarily set to zero. FIGS. 18a–c all have a common horizontal axis giving the lateral position $x_3$ on the surface of slab-volume SV3. The cylinder's center correspond's to $x_3$=0, so that the graphs show half of the cylinder's symmetrical image. The vertical axis on FIG. 18c has a depressed zero. The dashed line shows that the Invention can obtain an image of an object that is otherwise totally transparent to x-rays. The (reduced contrast) dash-dot line is the profile obtained via conventional absorption-contrast radiography.

FIGS. 19a–e all use the same linear energy scale with x-ray energy in keV. FIGS. 19b–e are computed using the x-ray cross-section data of Biggs and Lighthill (1971).

FIG. 20 shows a schematic diagram of Fraunhofer diffraction orders formed by an in-situ laser interferometer used for apparatus alignment, whose principles of operation are disclosed in Sects. III.10–III.10.3. The diagram is for correct alignment with $W_D$=0. Parallel line pairs are the envelope of the laser beams, as incident and as created by the various diffraction orders at gratings G1 and G2. The labeling of the various Fraunhofer diffraction orders is described in Sect. III.10.2.

FIGS. 21a–f are all plotted on log-log scales and use the preferred choices u=2, q=1 and b=1.

Part V

PREFERRED EMBODIMENTS

Figure 1:
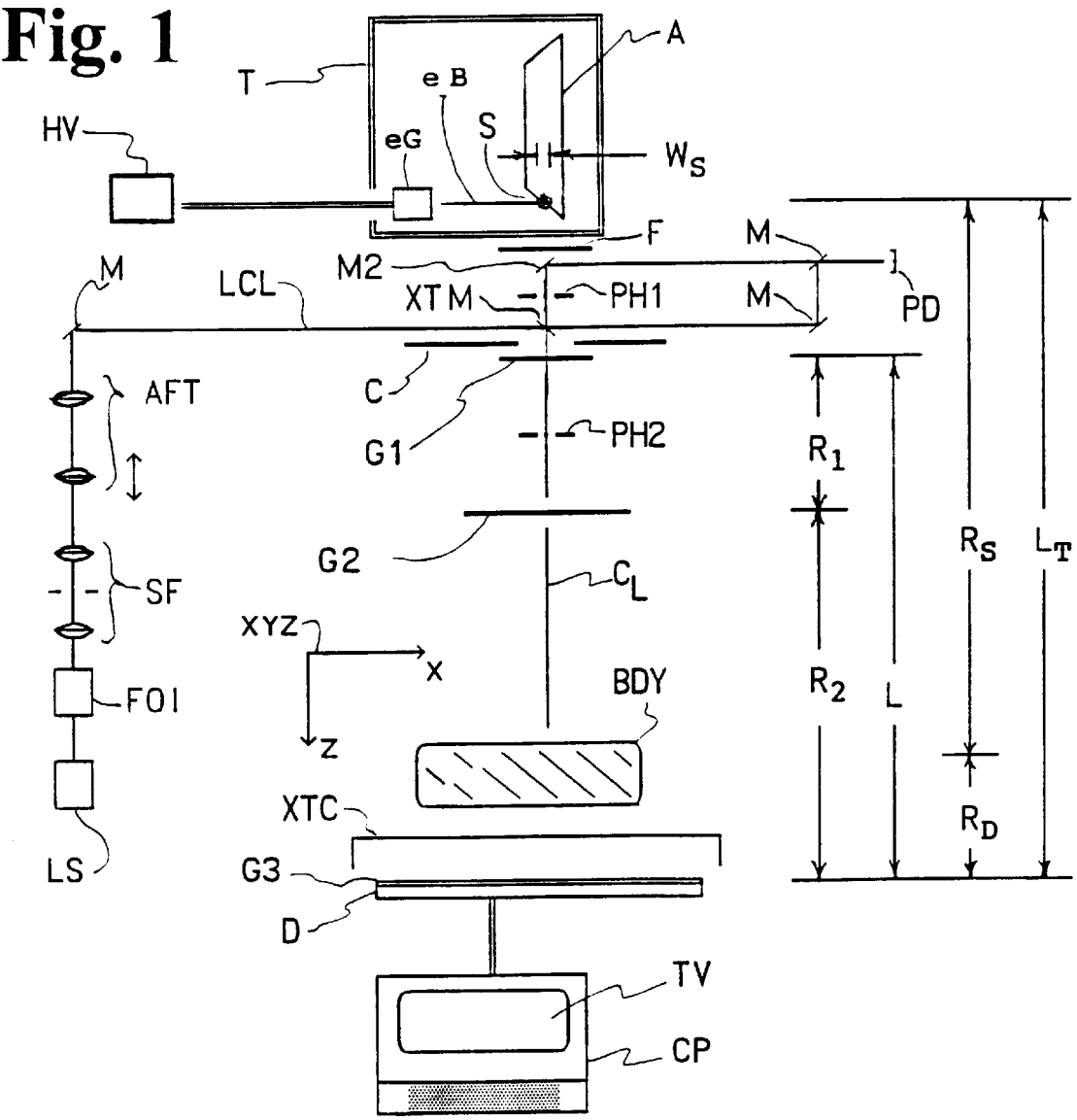
FIG. 1 shows an elevation (x-z) view of the preferred configuration for the Invention for use in planar imaging, showing important components added to a conventional radiography apparatus. Pinholes PH1 PH2 and mirror M2 are positioned within the apparatus (on axis $C_L$) during alignment only.
Figure 4A:
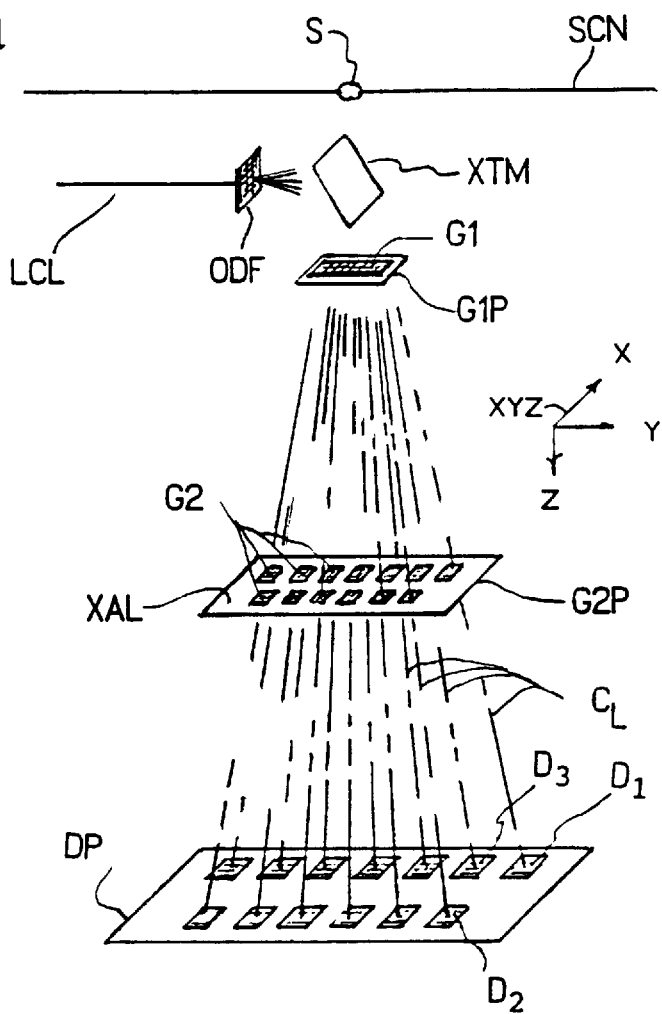
FIG. 4a shows an alternative overall configuration to that of FIG. 1, discussed in Sect. V.7, that may be used when a single detector array with the desired size is unavailable. It uses either of the detector array layouts of FIGS. 4b and 4d, wherein detector D is further comprised of a sparse mosaic of small digital imaging x-ray detector arrays, $D_1$, $D_2$, . . . . Rotationally scanning the apparatus of FIG. 4a about axis SCN across object BDY (not shown), which then passes between grating G2 plane G2P and detector plane DP, produces the image mosaics shown in FIGS. 4c and 4e, respectively for the layouts of FIGS. 4b and 4d, as discussed in Sect. V.7.
Figure 5:
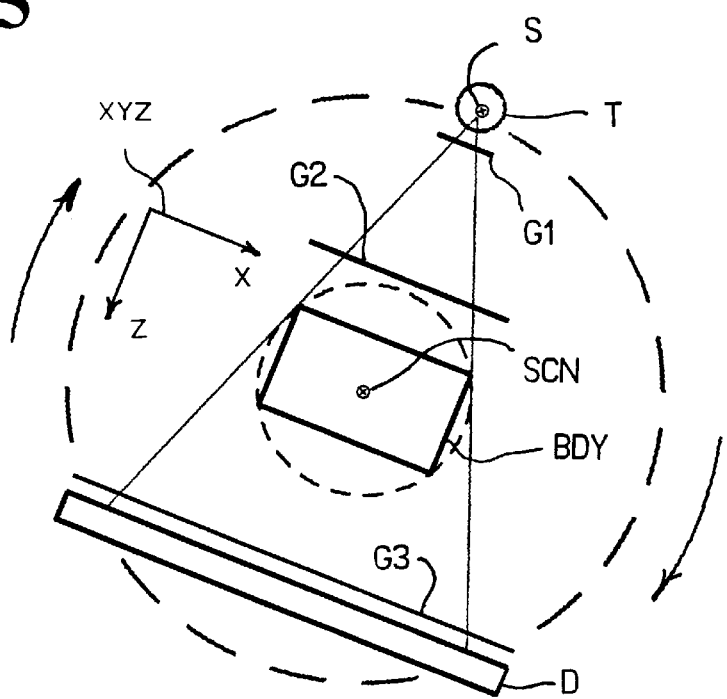
FIG. 5 shows a configuration for the Invention used in obtaining a 3D image via a CT scan. The whole apparatus of FIG. 1 (excluding object BDY, display TV and computer CP) is rotationally scanned about rotation axis SCN (perpendicular to the plane of FIG. 5), and about object BDY, and additionally scanned axially along axis SCN.

Following the teachings and Equations/Formulae disclosed in Parts I–III, Sect. V.1 describes apparatus designs whose parameters fit quantitatively into a "parameter window" allowed by these teachings and specified by these Equations/Formulae. It gives the actual dimensions, suitable material choices, and other associated parameters that result from these Equations/Formulae and teachings, as appropriate examples for realizing the various modes and methodologies disclosed for the Invention. To this end, Sect. V.1 provides Embodiments 1–7 that, at present, are considered examples of preferred embodiments for the Invention. The preferred overall configuration for the Invention for use in planar imaging is shown in FIG. 1, and an alternative overall configuration is shown in FIG. 4a that uses small-area detector arrays. An overall configuration useful for CT scans is shown in FIG. 5. Additional details of the Invention's component parts, along with methods for fabricating components that are not commonly available, are described in Sects. V.2–V.6. Given the teaching by the Invention, however, it will become obvious to one skilled in the art that various changes, interchanges, substitutions, modifications, refinements and optimizations may be made without departing from the Invention. Thus, the Inventor believes that the teachings are sufficiently disclosed herein, and the embodiments are sufficiently described herein, that by following said teachings and descriptions, and by appropriately applying the Equations/Formulae disclosed herein, that embodiments, fully operational in any and all of the Invention's various modes and methodologies can be made by one skilled in the art.

V.1 The Invention's parameter window

Given the above Equations/Formulae for each mode and methodology, it is not immediately obvious, in a quantitative sense, that their solution yields realizable apparatus. This Section shows that these Equations/Formulae do indeed provide useful designs that function as disclosed at radiographically useful x-ray energies, and that can be built using real materials and existing technology. To clarify in a quantitative manner the Invention's description, this Section exhibits parameters within an allowed (but modestly narrow) parameter "window" for each of the above-described operational modes and/or methodologies, wherein said parameters provide realizable apparatus for L and Ex consistent with modern radiography practice. Thus, for various choices of methodology and the associated mode or modes, FIGS. 21a–f, show the $\alpha$-dependencies of the important apparatus parameters that result from the simultaneous solution of Eqs. (III.7), (III.74)–(III.80) and (III.82) for the preferred choices b=q=1 and u=2. On FIGS. 21a–f the resulting value of $a_1$ (in $\mu$m) is shown as a dashed curve, the value of $a_2$ (in $\mu$m) is shown as a solid curve, the value of $a_Q=a_P$ (in $\mu$m) is shown as a dash-dot curve, the value of $R_2$ (in cm) is shown as a dash-dot-dot, curve, and the value needed for $a_D=a_3/2$ (in $\mu$m) with G3 absent is shown as a dash-dot-dot-dot curve.

The curves on each FIG. display a continuum of possible embodiments for the associated methodology and/or mode. For each Figure, one (or more) specific examples of an embodiment is chosen by making a realistic (but somewhat arbitrary) "catalog" choice for the detector period $a_D$, as disclosed in Sect. III.6.4. Each such choice then corresponds to a vertical line shown on the corresponding Figure at the associated value for $\alpha=\alpha_*$. The Embodiments associated with these vertical lines are denoted as 1–7, and the vertical lines so labeled. Note that the parameters for each Embodiment may be obtained directly by evaluating Eqs. (III.82)–(III.86), as appropriate to the chosen mode. Clearly, the set of all possible embodiments for the Invention within the parameter window is not limited by the handful of examples offered in this Section. Thus, similar curves and embodiments for the Invention may be generated for other choices of L, $E_X$, mode, and $a_D$, via the Invention's design Formulae to provide additional useful embodiments of the Invention. It should be noted also that FIGS. 21a–f do not exhaustively show the parameter window's boundaries, as said boundaries are to some extent mobile, and are determined by available detector and microfabrication technology, and by physically acceptable values for L. Other realizable embodiments for the Invention, however, have similar orders of magnitude for their various parameters, within the bounds of said technology.

The x-ray energies $E_X$ used for FIGS. 21a–f cover much of the range commonly used for medical imaging. (For comparison with usual practice, note that an x-ray energy specified in KVP, as is commonly done in radiographic industry jargon, provides a much lower value for $E_X$, since KVP refers to the peak high voltage of an unfiltered rectified-AC supply, and with such a supply, typically, $E_X \approx$ KVP/2.) The curves on FIGS. 21a–f indicate that for these energies the required grating periods and thicknesses are achievable using standard microfabrication techniques, as reviewed in Section V.4. Detectors with the specified periods $a_D$ are readily available, and the values specified for $R_2$ allow ample access room for a patient's body parts within the Invention. For $W_s \approx 100~\mu$m–300 $\mu$m one obtains excellent geometric resolution with these embodiments, with Ineq. (III.65) satisfied for all cases. As discussed in Sect. V.3, the energy bandwidth limit $\Delta E_{max}$ required by the physical optics associated with these various embodiments are readily produced by using a standard x-ray tube T with a carefully selected anode A material, a carefully selected value for the regulated ripple-free DC high-voltage to accelerate electron beam eB, and a carefully selected x-ray energy filter F. As per FIGS. 21b–f and Sect. III.10, the interferometric modes are seen to provide values that are ideally suited for operation under the refractive-index gradient imaging methodology. As per Sect. III.11 and FIG. 21d, phase-interferometric mode is seen to give parameters that are ideally suited for element-selective imaging. Since the Invention does not suffer from the attenuation associated with a Bucky grid, then relative to a conventional apparatus all embodiments feature a simultaneous improvement (reduction) of the resolution limit $a_{RQ}$ set by quantum mottle.

To allow evaluation of the various embodiments, it is useful to provide a quantitative figure-of-merit for a grating's vignetting character. To do so, it is useful to define the aspect-ratio of a grating's periodic structure as $Z_{T1}/S_1$ and $z_{T2}/s_2^5$ for gratings G1 and G2, respectively, where $Z_{T1}$ and $ZT_2$ are the thicknesses of the associated grating's absorbing or refracting periodic structure, and where $s_2$ is taken as $a_2/m_*$ for a phase grating. Experience with Bucky grids indicates that a grating has an acceptably low vignetting character if this ratio is less than or about equal to say 10 to 15.

Use of traditional absorption-contrast methodology (only) is best done with the Invention operating in geometric-shadow mode with 1D-periodic gratings. Consider the $\alpha$-dependence of typical design parameters for preferred embodiments that do so, as depicted on FIG. 21a. The curves on this FIG. correspond to solutions of the above-disclosed design Equations for geometric-shadow mode f or a L=1 m apparatus designed to operate at $E_X$=17.4 keV. The curves depict operation at the small $a_2$ limit, i.e. at $a_2=a_2$(shad-limit), as per Sect. III.3. The vertical line at $\alpha=2.19$ identifies parameters for Embodiment 1 with the detector period chosen as $a_D=25~\mu$m. Associated parameters are then $R_2=0.69$ m, $a_1=22.8~\mu$m, $a_2=15.7~\mu$m, and $a_P=50.0~\mu$m. Embodiment 1 preferably uses 1D-periodic gratings with grating G3 absent. The x-ray spectrum bandwidth $\Delta E$ for Embodiment 1 is not particularly critical and may be essentially the same as that of a conventional radiography apparatus, although cutting off the low energy end of the x-ray energy spectrum further improves contrast of pattern P. Embodiment 1 has parameters useful for mammography.

For a binary absorption grating to be effective, its absorbing layer XAL thickness should be sufficient to limit its transmission to no more than about $1/(2e)=0.14$. Since Embodiment 1 operates in geometric-shadow mode, it uses binary absorption gratings for both G1 and G2. At 17.4 keV Embodiment 1 then may use gratings with gold absorbing layers XAL with $Z_{T1} \approx Z_{T2} \approx 10$ μm. Acceptably high pattern P contrast occurs for Embodiment 1 with $s_1/a_1 = s_2/a_2 = \frac{3}{8}$ (for maximum net transmission), giving $s_1 = 8.6$ μm and $s_2 = 5.9$ μm and a net transmission by gratings G1 and G2 together of about 14%. Negligible vignetting then occurs, since the grating aspect-ratios are then only $z_{T1}/s_1 = 1.2$ and $Z_{T2}/s_2 = 1.7$. Slightly thicker absorbing layers XAL then may be used in this Embodiment, if desired.

The 14% net transmission for Embodiment 1 determines the required x-ray flux emitted by x-ray tube T, as compared, say to that required by a conventional apparatus that uses a Bucky grid. A Bucky grid's transmission is typically only about 33%. To obtain an x-ray flux density at the detector's surface with Embodiment 1 that is comparable to that of a conventional apparatus with a Bucky grid, an x-ray tube T that is about twice as intense is needed by Embodiment 1. Note that in such case examined object BDY (e.g. a patient) receives an x-ray dosage in Embodiment 1 that is only about ⅓ of that received in the conventional apparatus. This reduction is because in the Invention all of the x-ray flux passing through object BDY reaches the detector, while appreciable flux is absorbed by a Bucky grid without its detection. The additional flux emitted via said increased brightness (and then some more) is all absorbed by the gratings and not by the patient (object BDY). Indeed, if the x-ray brightness of tube T is increased to about six-fold over that of the conventional apparatus, then the patient receives comparable dosage in either apparatus, but the Invention's quantum mottle-limited resolution for weakly absorbing (say 1%) features is diminished significantly, indeed, almost to the geometric resolution limit. The needed increased x-ray brightness to do so is available with currently marketed x-ray tubes.

Figure 12A:
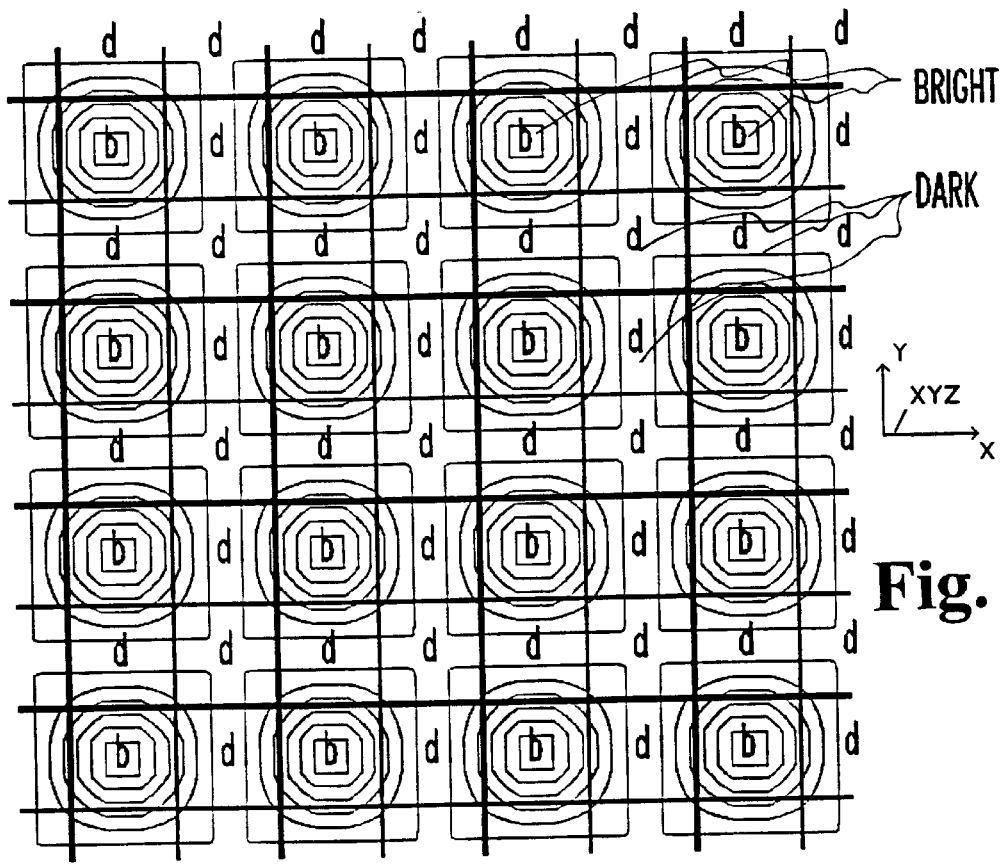
FIGS. 12a, 12b, and 12c show portions of labeled pixel layouts that have been tiled with PT1, PT3, and PT5 tiles, respectively, using u=2 tiling. Pixel boundaries coincide with tile boundaries and tile-quadrant divisions. The tiles' butted edge boundaries are shown as heavy straight lines and the tile-quadrant boundaries within a tile are medium-breadth straight lines. Each pixel's label (b, c, or d) is shown at its center. The overlaid curved light lines on FIGS. 12a,c and 12b are constant intensity contours for pattern P with grating G3 absent, respectively corresponding to the intensity distributions shown in perspective views in FIGS. 14d and 14e, and respectively corresponding to a 2D-periodic separable and checkerboard intensity pattern P.
Figure 12B:
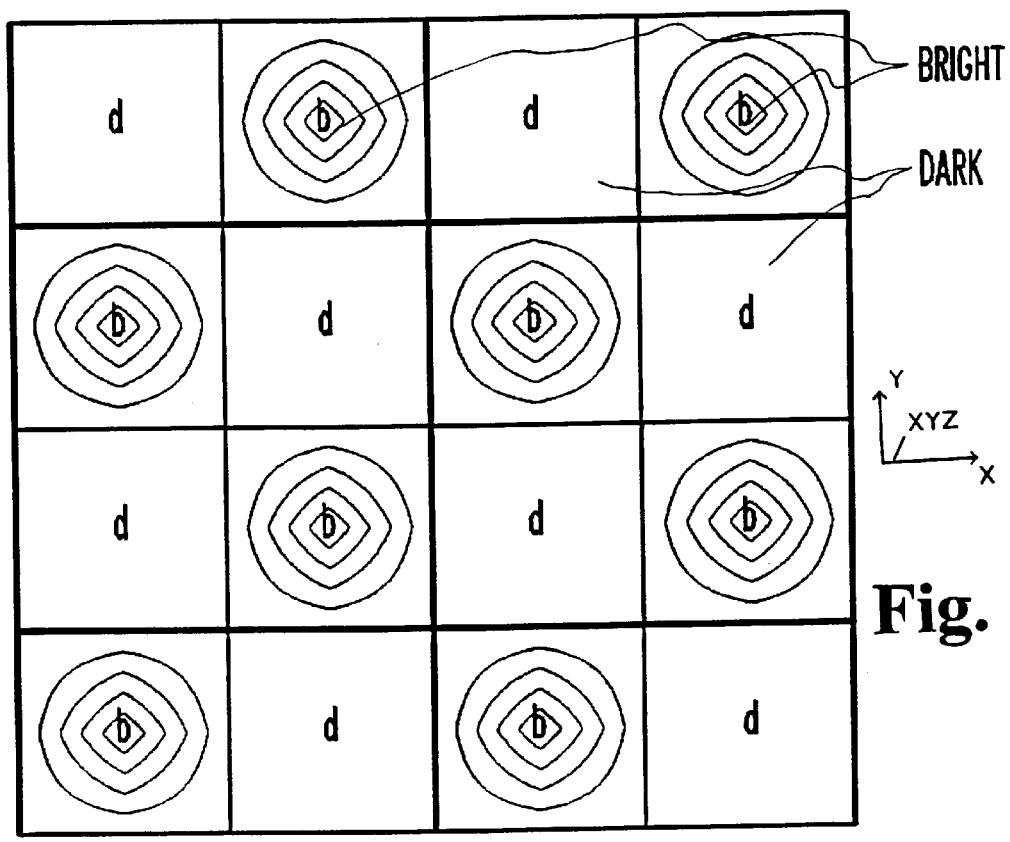
Figure 12C:
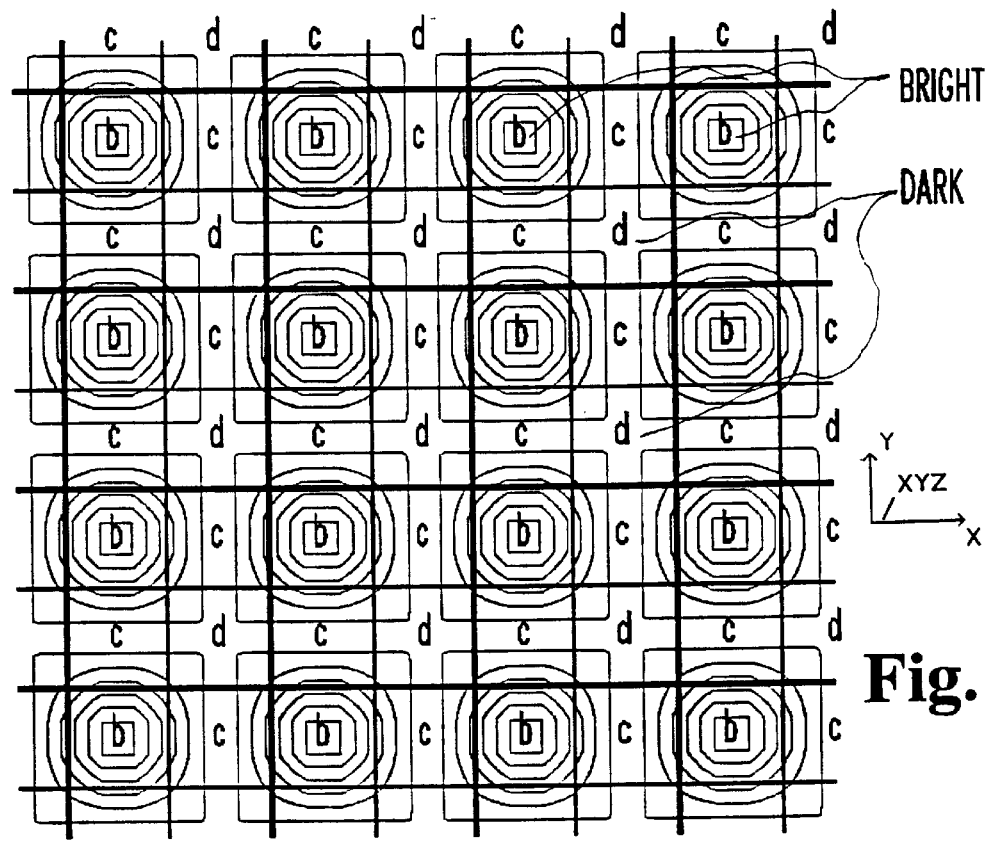
Figure 13B:
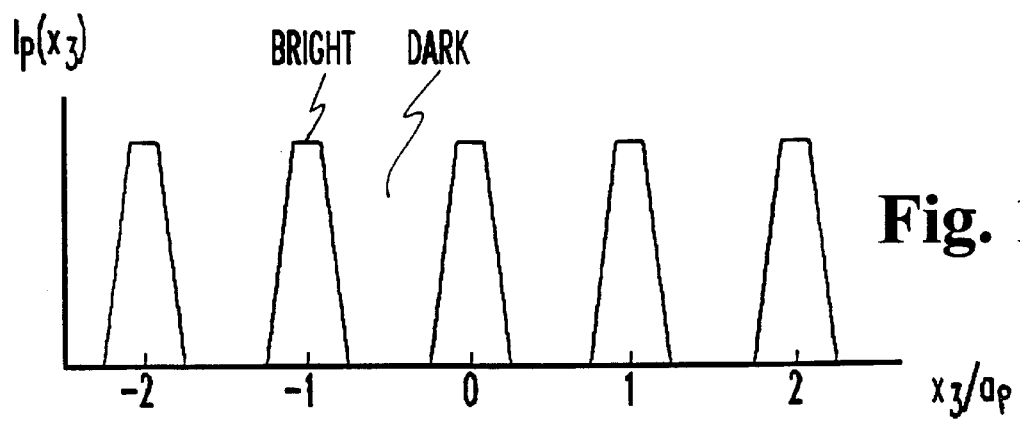
FIGS. 13a,b show typical 1D-periodic intensity profiles, $I_Q(x_3)$ and $I_P(x_3)$ of respective patterns Q and P as a function of respective positions $x_3/a_Q$ and $x_3/a_P$ on the surface of slab-volume SV3. These profiles assume negligible "leakage" for x-ray absorbing layer(s) XAL. The patterns may be produced with grating G2 configured either as a binary absorption grating or as a phase grating. High intensity fringe areas are labeled BRIGHT, and low intensity fringe areas are labeled DARK.
Figure 13A:
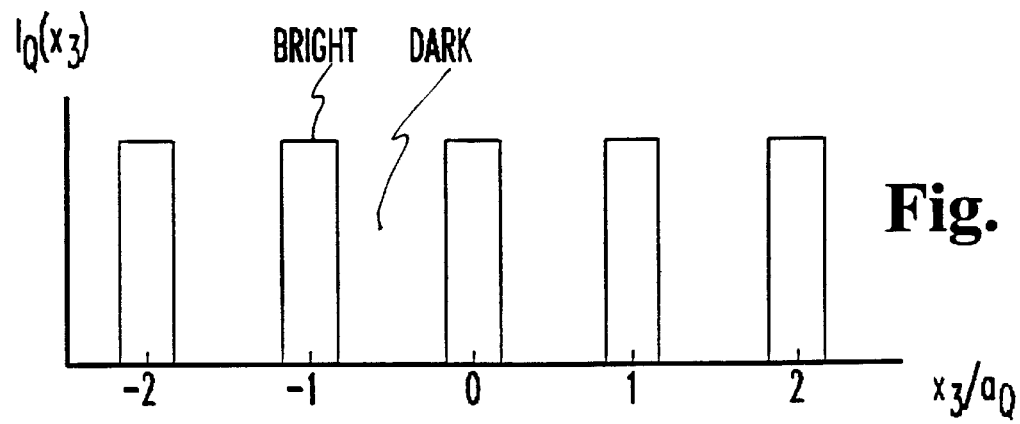

Producing an image whose absorption features are strongly edge-enhanced via refractive-index gradients, or simultaneously producing independent pure absorption-contrast and refractive-index gradient contrast images, as per Sects. III.7 and III.9, is most efficiently done by the Invention using phase-interferometric mode. Consider the α-dependencies of parameters for L=1 m phase-interferometric mode embodiments specified by the curves on FIGS. 21b and 21c. The vertical line at α=2.64 on FIG. 21b denotes parameters for Embodiment 2. The two vertical lines on FIG. 21c at =60 =0.87 and 3.48 denote parameters for Embodiments 3 and 4. Embodiments 2–4 all use the detector period choice $a_D = 9$ μm. Gratings G1 and G2 are both 2D-periodic for these embodiments; grating G1 is a binary absorption grating, and grating G2 is a phase grating. If these embodiments are configured with the pixel layout of FIG. 12c and with gratings G1 and G2 both 2D-periodic via separable functions, then they provide simultaneous refractive-index-gradient-only and absorption-contrast-only images, as per the discussion of Sect. III.9.

Figure 9A:
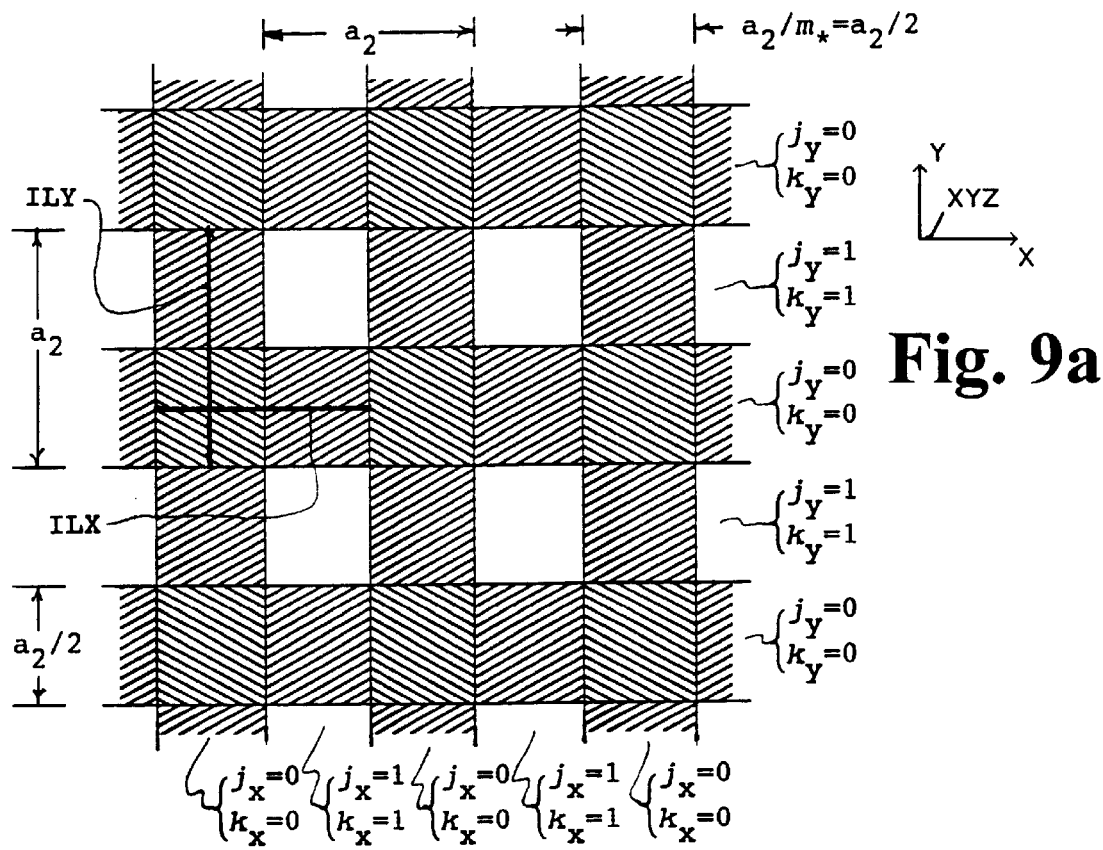
FIG. 9a (associated with FIGS. 7a and 16a) shows the x-y plan view of the low-Z x-ray refractive surface layer on a 2D-periodic phase grating with a 2D-periodic PG(1,2,1) profile, and FIG. 9b (associated with FIGS. 7b and 16b) similarly shows the x-y plan view for a 2D-periodic PG(1,3,1) profile. The mathematical formulation of these profiles is disclosed in Sect. III.4, along with their operation in the Invention. The locally-constant thickness steps of the thin low-Z refracting material surface layer on a phase grating divide this layer into constant-thickness portions. For a 2D-periodic $PG(n_*, m_*, r_*)$ profile, each constant-thickness portion then has an $(a_2/m_*) \times (a_2/m_*)$ square area. Portion boundaries are shown as thin solid lines. The profiles' square locally constant-thickness portions are labeled via Eq. (III.54) by index values, $k_x$ and $k_y$.
Figure 21A:
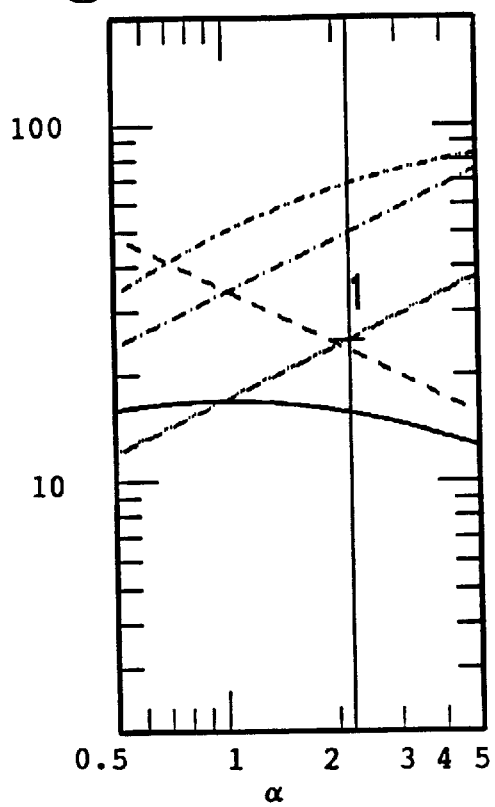
FIGS. 21a–f show detailed comparisons of the α-dependencies of $a_1$ (dashed line), $a_2$ (solid line), $a_Q=a_P$ (dash-dot line), and $R_2$ (dash-dot-dot line) for (a) geometric shadow mode at $a_2=a_2$(shad-lim) at $E_X$=17.4 keV, for (b) phase-interferometric mode at $E_X=E_*$=20.2 keV using a PG(1,2,1) grating profile, for (c) phase-interferometric mode using a PG(1,3,1) grating profile at $E_X=E_*$=40 keV, for (d) element-selective imaging using phase-interferometric mode at $E_X=E_K$=33.17 keV at various (β½ contrast reversals, for (e) n=1, m=2 amplitude-interferometric mode at $E_X$=17.4 keV, and for (f) phase-interferometric mode at $E_X=E_*$=40 keV using a PG(1,3,1) grating profile. Details of associated preferred embodiments are described in Sect. V.1. Parameters for specific Embodiments with a catalog selected $a_D$, as per Sect. III.6.4, have associated values of α depicted by labeled vertical lines on these Figures.
Figure 21B:
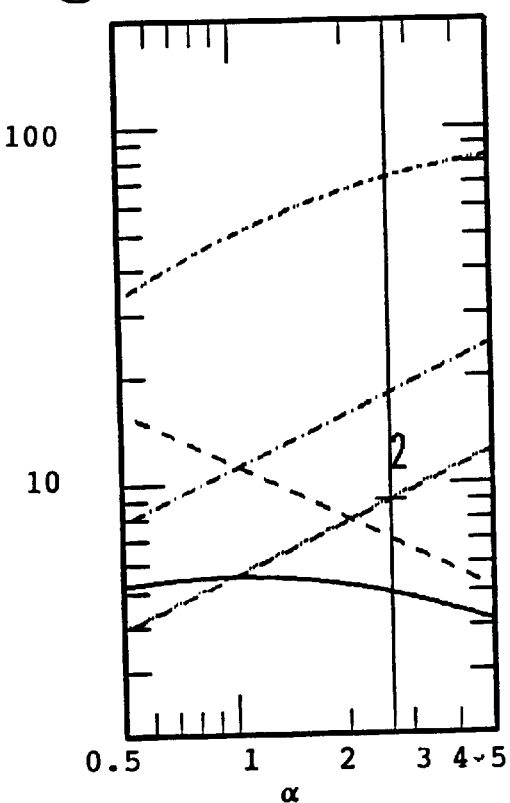

FIG. 21b corresponds to phase-interferometric mode operation at $E_*E_X = 20.2$ keV. It uses a G2 phase grating with a PG(1,2,1) profile. The parameters for Embodiment 2 on FIG. 21b are α=2.64, $a_D = 9$ μm, $R_2 = 0.73$ m, $a_1 = 6.8$ μm, $a_2 = 4.9$ μm, and $a_P = 18.0$ m. At 20.2 keV binary absorption grating G1 now requires a $1/(2e)$ thickness of about $Z_{T1} \approx 14$ μm of either gold or depleted uranium for its absorbing layer XAL. Acceptably high contrast of pattern P is obtained with $s_1/a_1 \approx 0.3$, giving $s_1 \approx 2.0$ μm, and a net (G1 and G2) grating transmission of about 18%, (9% with the pixel configuration of FIG. 12c). The resulting ratio $z_{T1}/s_1 = 7$ indicates acceptable vignetting character for grating G1. Phase grating G2 has the 2D-periodic structure shown in FIG. 9a, with $-\pi/2$ and $-\pi$ phase-shifting thicknesses of $z_{T2}(-\pi/2) = 0.8$ μm and $Z_{T2}(-\pi) = 1.6$ μm of chromium, giving $Z_{T2}(-\pi/2)/s_2 = 0.3$ and $z_{T2}(-\pi)/s_2 = 0.6$, respectively, indicating very low vignetting by grating G2. A suitable x-ray spectrum with a sufficiently narrow bandwidth ΔE is produced for this embodiment by an x-ray tube T using a rhodium anode A operating at 26.9 kV-DC and a 1.3 mm thick aluminum filter F. These parameters provide a symmetrical continuum x-ray spectrum with $E_X \approx 20.2$ keV, and a full width ΔE of about 13.4 keV, that comfortably fits within the resonance spectrum for the mode. The bandwidth is further narrowed by the presence of the anode's rhodium Kα lines at 20.2 keV.

Figure 21C:
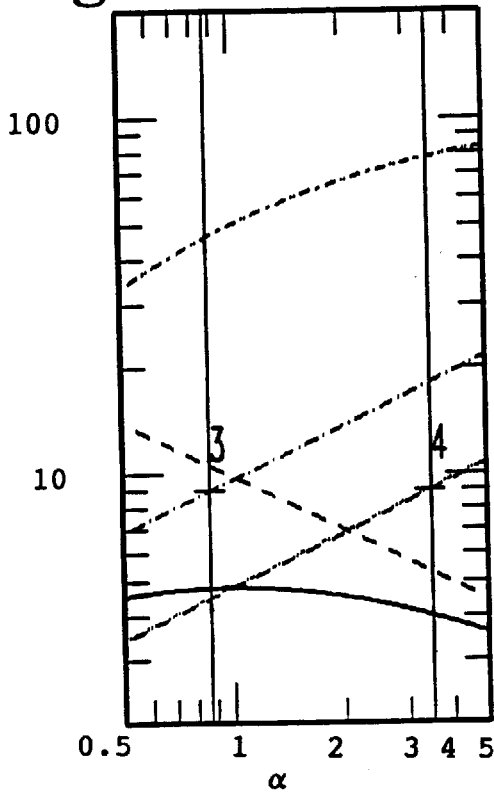

By using Equations disclosed in Part III, embodiments may be designed for a wide range of choices for $E_X$, as needed for various imaging applications. FIG. 21c, for example, shows the α-dependence of parameters for phase-interferometric mode embodiments that operate at the high energy, $E_* = E_X 40$ keV. The curves are for a phase grating G2 configured with a PG(1,3,1) profile and the 2D-periodic planform shown in FIG. 9b. The grating's low-Z refracting material is chromium, with $-2\pi/3$ and $-4\pi/3$ phase-shifting thicknesses of $z_{T2}(-2\pi/3) = 2.0$ μm and $z_{T2}(-4\pi/3) = 4.0$ μm. The resulting duty-cycle $s_Q/a_Q = \frac{1}{3}$ for pattern Q produced by this grating allows a high contrast pattern P to be formed using a comparatively large grating G1 duty-cycle, $s_1/a_1 = \frac{1}{2}$, which then gives a net G1 and G2 grating transmission of about 50% (25% with the pixel configuration of FIG. 12c). The high $E_X$ requires a comparatively thick grating G1 absorbing layer XAL to obtain $1/(2e)$ attenuation. It is thus a $z_{T1} = 59$ μm layer of depleted uranium. A suitably narrow bandwidth x-ray spectrum at $E_X \approx 39.9$ keV for these embodiments is produced using an x-ray tube T with a samarium plated or solid tungsten anode operating at 53.3 kV-DC and 286 μm thick copper filter F. These embodiments are sensitive to refractive-index gradients, and, given the high energy, can image through a very great thickness of soft tissue.

Embodiment 3 on FIG. 21c is configured with grating G3 present. Its parameters are then v=2, α=0.87, $a_D = 9$ μm, $R_2 = 0.47$ m, $a_1 = 10.3$ μm, $s_1 = 5.2$ μm, $a_P = 4.8$ μm, and $a_P = 18.0$ μm. Grating G1 has a moderately high but still acceptable vignetting character with $z_{T1}/s_1 = 11.5$, while grating G2 has low vignetting with $z_{T2}(-2\pi/3)/s_2 = 1.2$ and $z_{T2}(-4\pi/3)/s_2 = 2.4$. Embodiment 4 is configured with grating G3 absent. Its parameters are α=3.48, $a_D = 9$ μm, $R_2 = 0.78$ m, $a_1 = 5.2$ μm, $s_1 = 2.6$ μm, $a_2 = 4.0$ μm, and $a_P = 18.0$ μm, $z_{T2}(-2\pi/3)/s_2 = 1.5$ and $z_{T2}(-4\pi/3)/s_2 = 3.0$. Embodiment 4, unfortunately gives very high vignetting by grating G1, with $z_{T1}/s_1 = 23$. Thus, if a large-area detector D is to be used, Embodiment 3 is preferred for its smaller vignetting. On the other hand, the absence of grating G3 in Embodiment 4 means that it provides about half of the dosage of that of Embodiment 3 and Embodiment 4 is preferred for this latter reason.

Figure 6A:
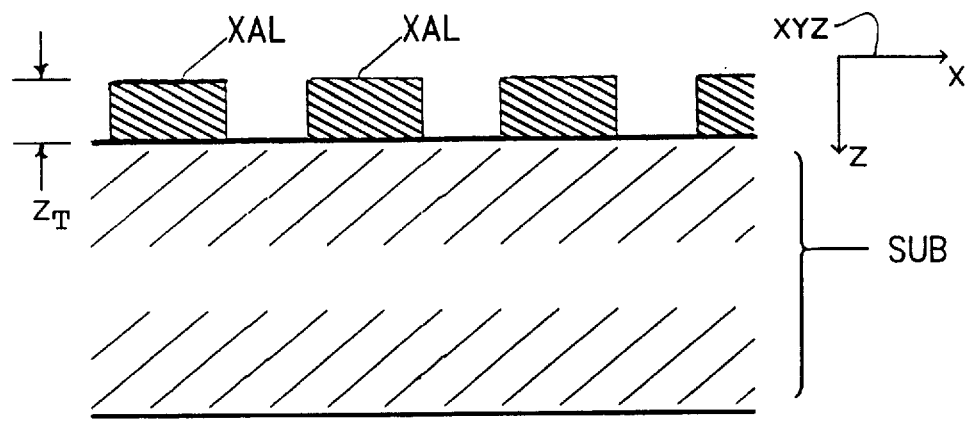
FIGS. 6a and 6b each show x-z elevation views of typical cuts through a binary absorption grating, and also show the spatially periodic thickness profile of x-ray absorbing layer XAL, laminated to x-ray and light transmitting thin substrate SUB. Such gratings are used for grating G1. Configured as shown as a binary absorption grating these structures are also used for grating G2 in geometric-shadow and amplitude-interferometric modes. Although such a structure may also be used for grating G3, the spatially periodic structure of grating G3 preferably is laminated directly to the face of detector D, as shown in FIG. 2.
Figure 6B:
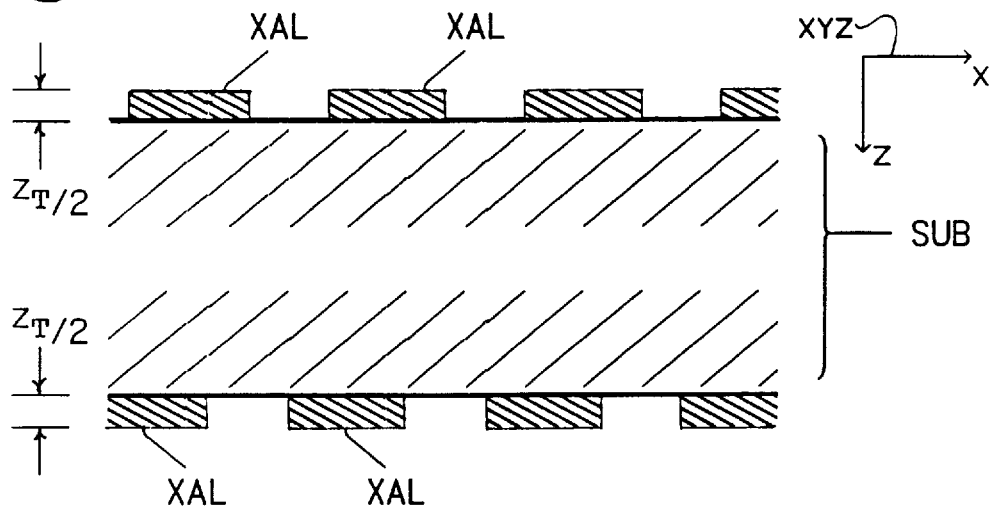
Figure 7E:
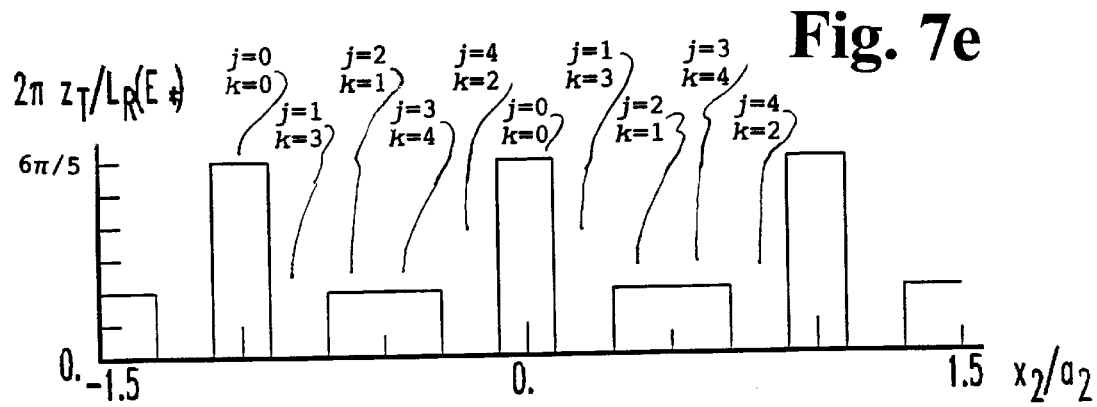
FIGS. 7a–e show various periodically varying step-function shaped 1D-periodic $PG(n_*, m_*, r_*)$ thickness profiles of the low-Z x-ray phase-shifting surface layer on a 1D-periodic phase-grating. Each rescaled profile, $z_T(x_2)$, is shown as a function of lateral position $x_2$ on grating G2. The mathematical formulation of these profiles is disclosed in Sect. III.4, along with their operation in the Invention. The locally-constant thickness steps of the thin low-Z refracting material surface layer on a phase grating divide this layer into constant-thickness portions. On FIGS. 7a–e the profiles' constant-thickness portions are labeled by an associated pair of integer index values, j and k. The periodically-sequential integer index, j, is defined via Eq. (III.48) as $j = = m_* \delta_k(n_*, m_*) = [(n_* k) \mod m_*]$, and steps through a simple sequential order (starting with 0) within a single period, and repeats this finite sequence in each period. The value of k associated with index j is via the mapping of Eq. (III.48).
Figure 7D:
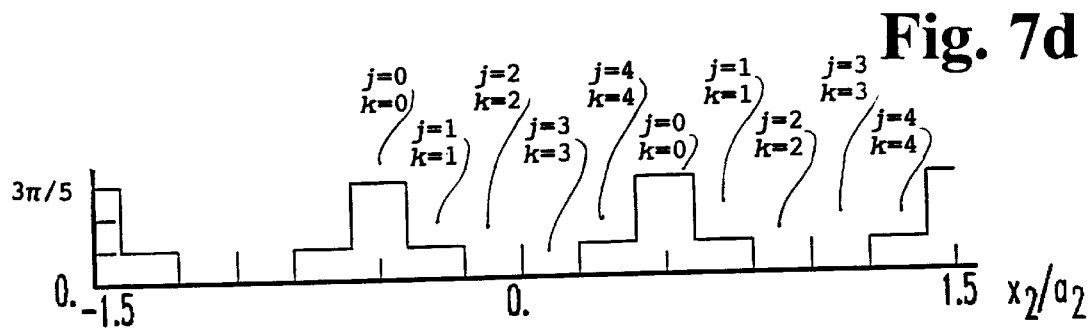
Figure 7C:
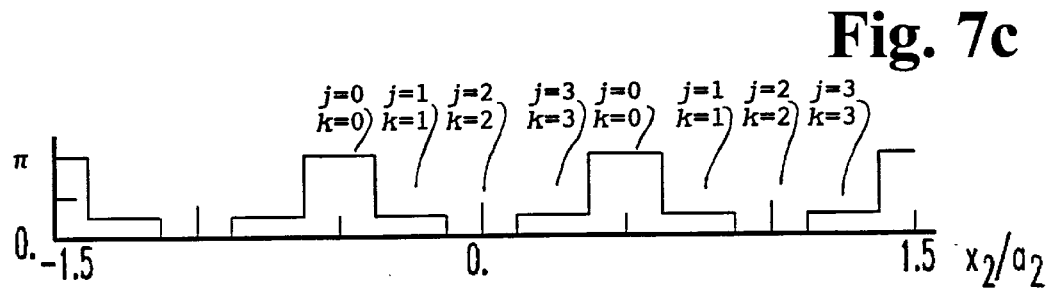
Figure 7B:
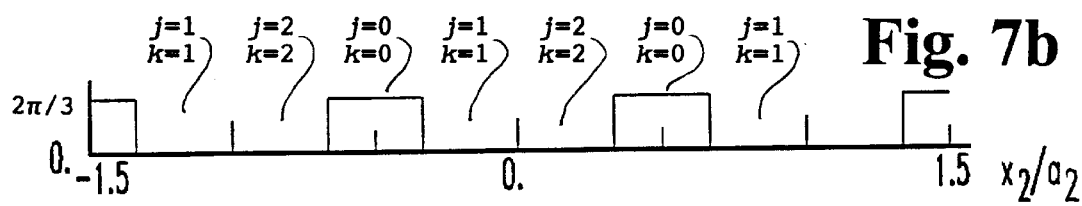
Figure 7A:
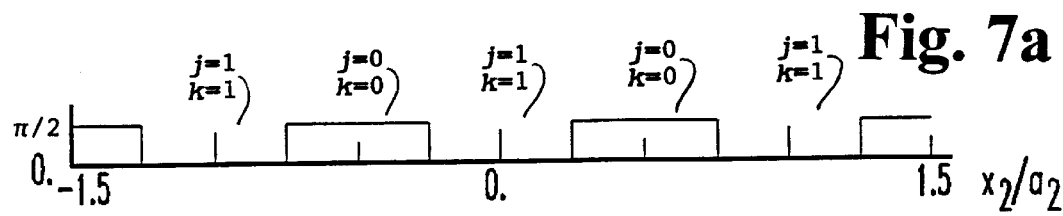

The preferred features of both Embodiments 3 and 4, however, may be obtained together by using Embodiment 3, and by further using a grating G1 that is configured with the "sandwich" structure, shown in FIG. 6b. This structure reduces the aspect-ratio of the grating G1 periodic structure two-fold. As shown on FIG. 6b the absorbing layer XAL is now distributed on both faces of the grating substrate. The periodic structure on the lower face has a period that is very slightly larger than that on the upper face, so that a line passing though each pair of associated opposite-faced periods also passes through focal spot S. So configured, the value of $Z_T$ on each face may be halved. Each of the two periodic structures then has its aspect-ratio halved, and thus the whole grating then exhibits acceptable vignetting, with the "effective" aspect-ratio now only 11.5. Alternatively, a "fanned grating structure", whose fabrication is discussed in Sect. V.4, may be used to reduce vignetting.

An embodiment using parameters near those of Embodiment 2, or with parameters perhaps chosen at a higher value of $E_X$ is ideally suited for use in mammography. Indeed, Embodiments 3 and 4 indicate that the parameter window allows operation at a wide range of radiographic energies. Mammography at increased $E_X$ is desirable in that it allows examination of thicker, and/or more dense breasts. Usually, however, the use of higher energy in a conventional mammography apparatus leads to unacceptably increased scatter-induced blurring of the image [Meredith and Massey, Chapt. XX]. This fact is due to an associated increase of the ratio of scattering cross-section to the photo-electric absorption cross-section with increasing $E_X$ [Michette and Buckley, 1993, p. 11]. To limit scatter-induced blur, mammography is conventionally performed at the lowest possible $E_X$ that still allows adequate x-ray transmission by the thickness of the examined breast. However, the Invention effectively removes said increased blurring, and its edge-enhanced images significantly improve its capability for detecting malignancies. Operation at increased $E_X$ then simultaneously allows improved image resolution with increased penetration for the examination of thick and/or dense breasts. (An optimal value for $E_X$ for mammography with the Invention may be determined from experience.) Importantly, the use of higher $E_X$ significantly reduces the required compressive force that is conventionally applied to an examined breast. The pain and discomfort resulting from this compressive force is an important deterrent that prevents many women from seeking a mammographic examination. Millions of women will thus rejoice upon hearing of this Invention's approval for general clinical use and of its reduced associated pain!

Figure 9B:
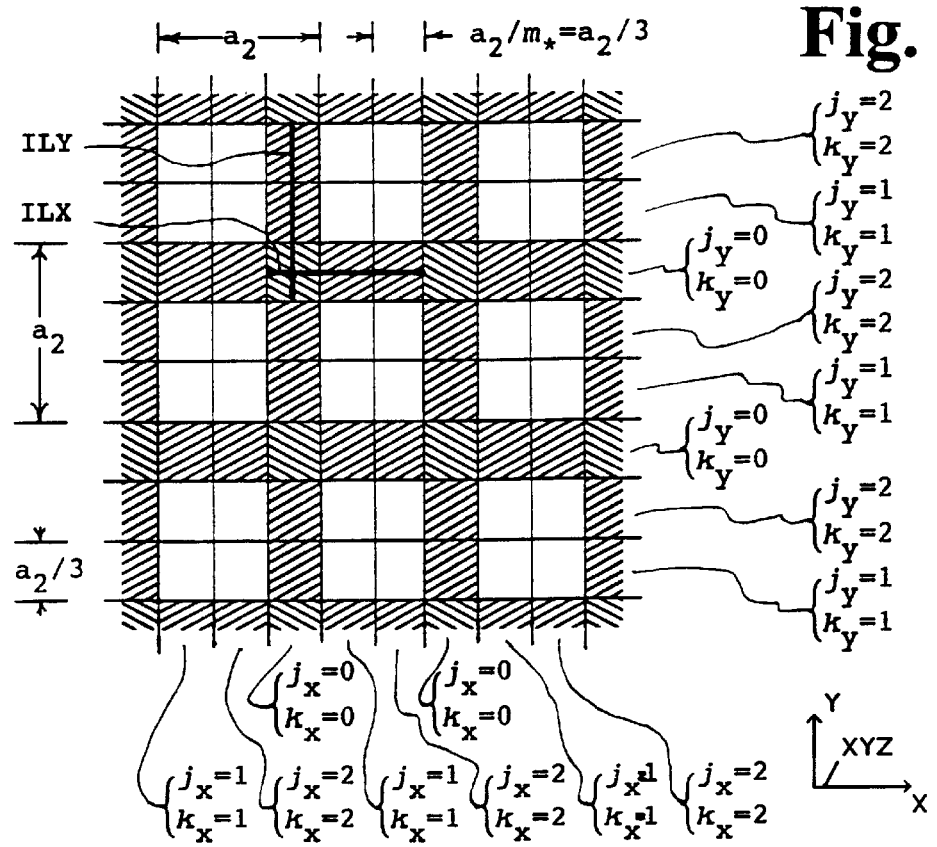
Figure 10A:
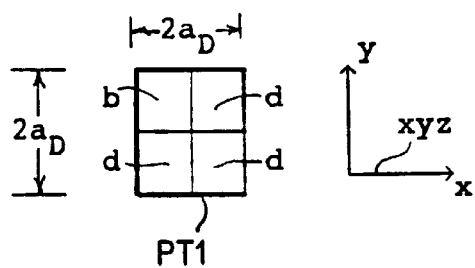
FIGS. 10a–e respectively show the five pixel-labeling (or SV3 area labeling) tiles, PT1–PT5, used by the Invention to construct the detector-covering array of pixel (or area) labels via u=2 tiling. Each tile is $_2a_D \times 2a_D$ and is divided into four $a_{D \times aD}$ quadrants, with each quadrant bearing a pixel label. Tiles PT1 and PT5 are used when pattern P is 2D-periodic and has a separable form. Tile PT5 is used when it is desired to obtain two simultaneous images from one exposure, as per Sect. III.9. Tile PT2 is used when pattern P is 1D-periodic. Tile PT3 is used when pattern P is 2D-periodic and has a checkerboard form. Tile PT4 is used when pattern P is 2D-periodic with a separable form and when grating G3 is also present and formed by the associated set of tiles G3T4v. Tile PT4 is also used when pattern P has the inverted form shown in Fig. 14f.
Figure 10B:
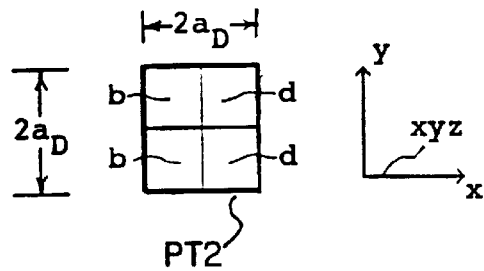
Figure 10C:
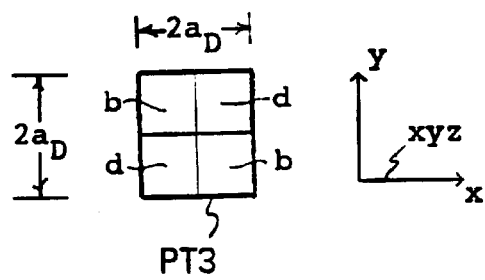
Figure 10D:
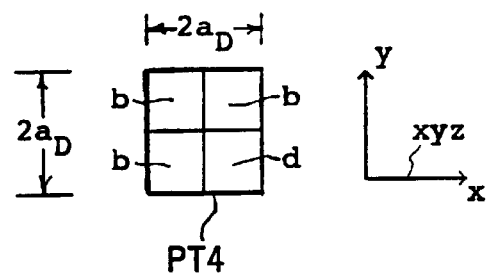
Figure 10E:
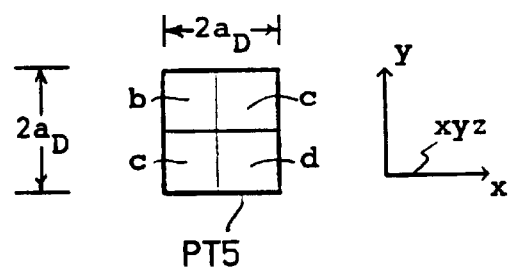
Figure 11A:
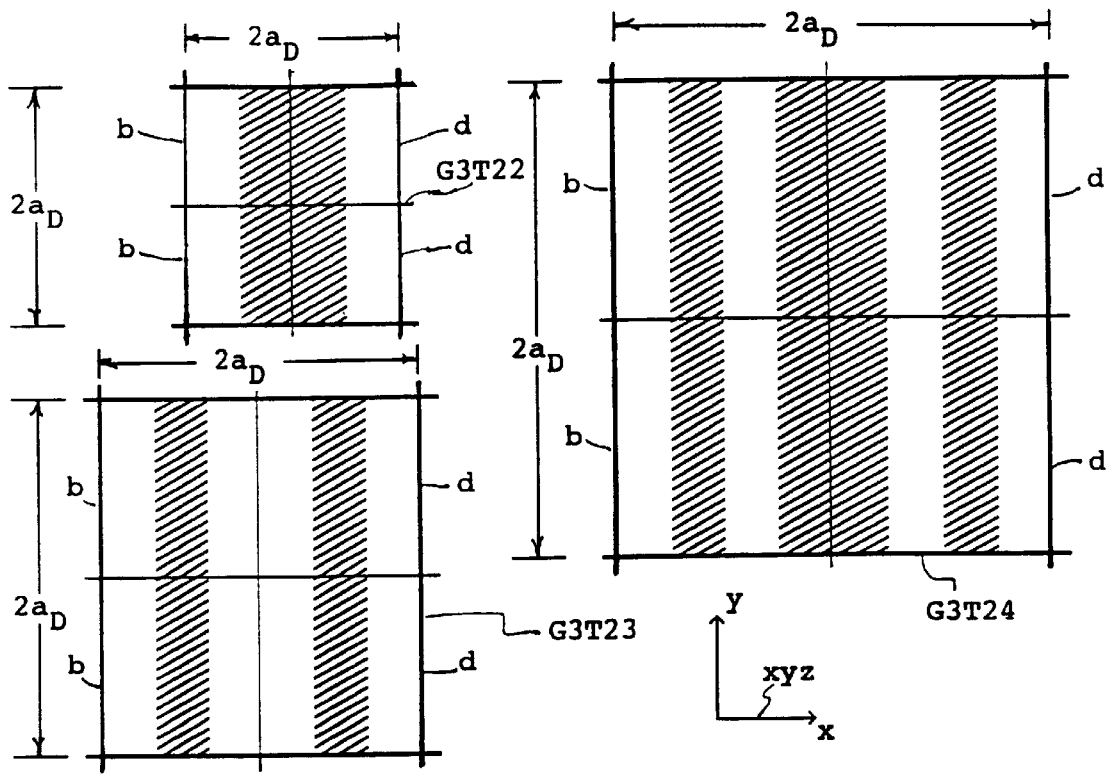
FIGS. 11a–d show x-y planforms for various v>1 G3-forming tiles, as disclosed in Sects. III. and III.6.1, for use in u=2 tiling along with associated pixel-labeling tiles PT1–PT5. Areas shaded by /// hatching are x-ray and light absorbing, while unshaded areas are x-ray and light transmitting. Heavy solid lines are tile boundaries, while thin lines are covered pixel boundaries. A grating constructed from these tiles is used only with a detector configured with an associated pixel labeling tile. (Associated pixel-labeling tiles are shown in FIGS. 10a–e.) Despite the differing shown apparent sizes, all tiles have the same $2a_D \times 2a_D$ edge dimension. The tile kind is denoted as G3Tgv, where the first index, g, here denotes the associated pixel-labeling tile PTg, and the second index gives the integer divisor v, as per Sect. III. Small squares forming the tile are $a_D/v$ on a side.
Figure 11B:
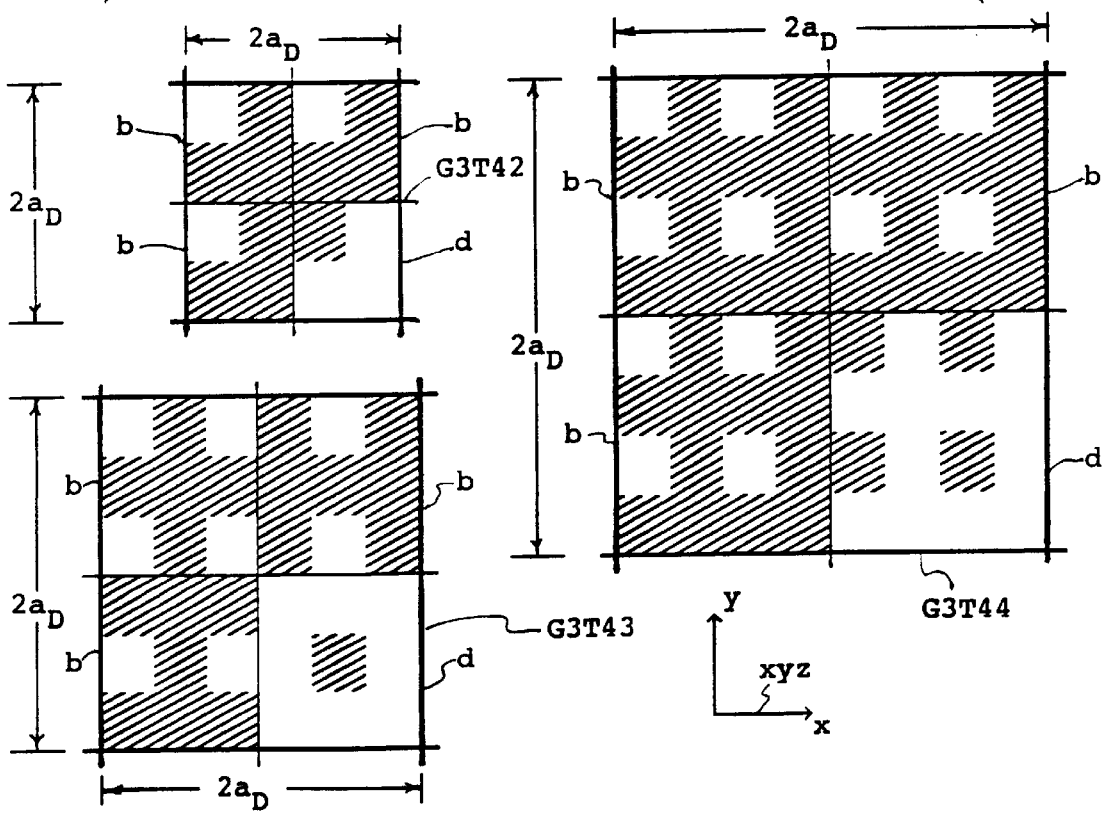
Figure 11:
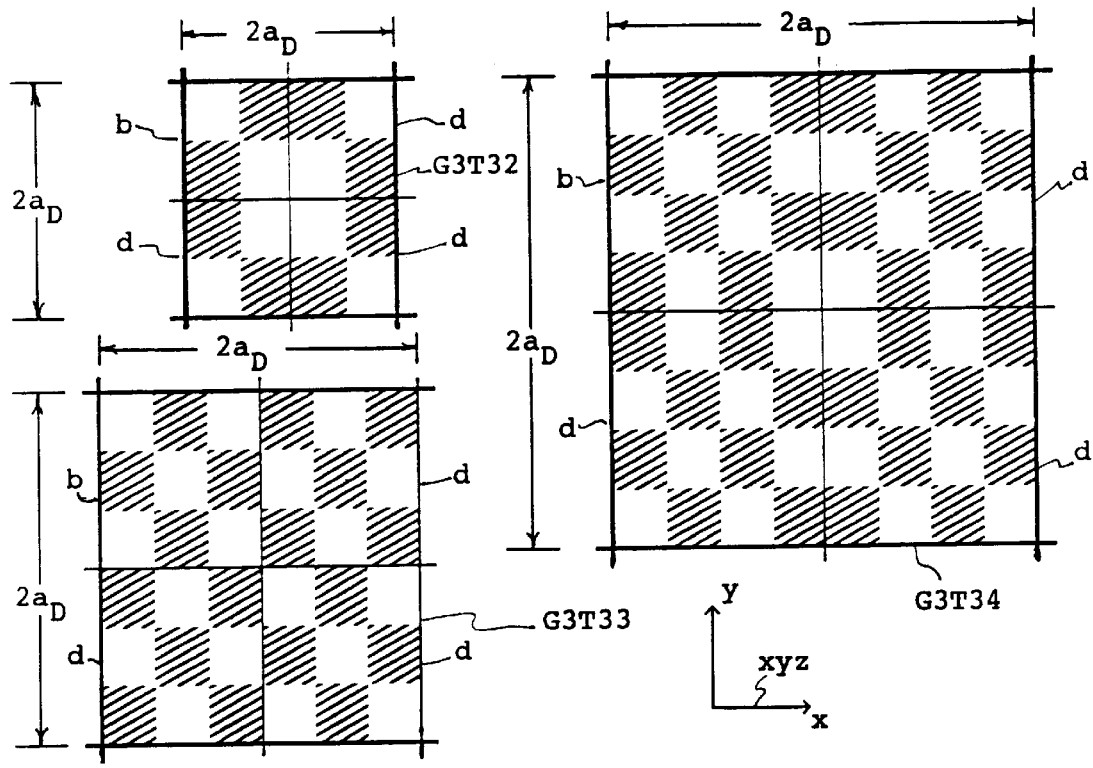
Figure 11D:
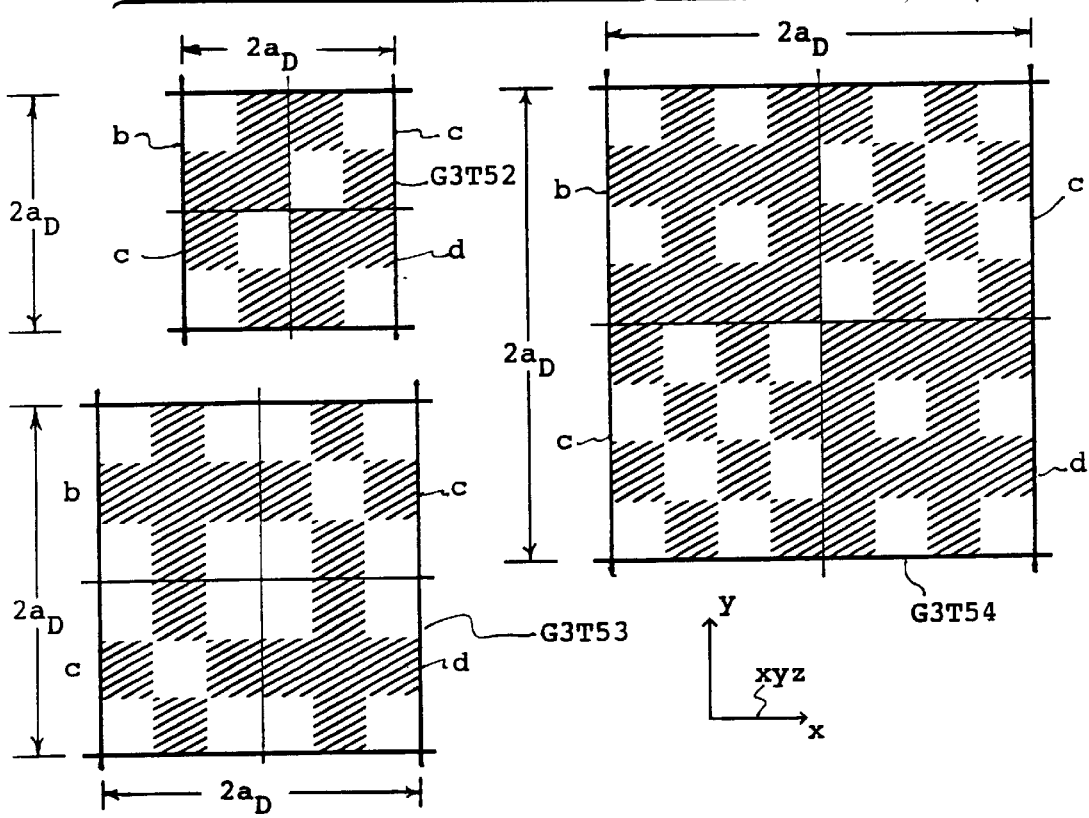
Figure 19E:
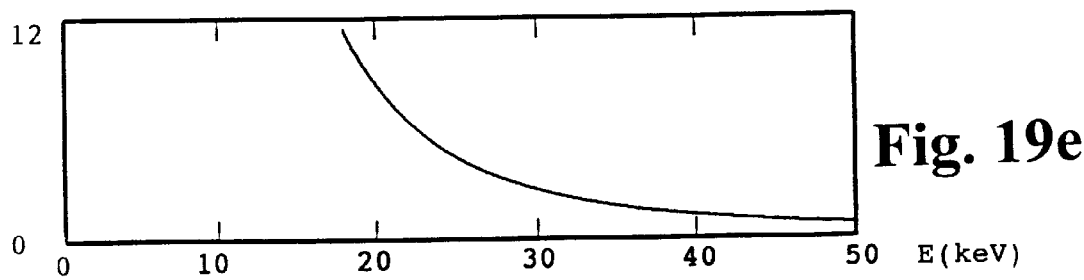
FIGS. 19c–e show the energy dependencies of the absorption ($cm^{-1}$) for (c) iodine, (d) water and (e) $CaCO_3$. The absorption is $1/L_f$.
Figure 19D:
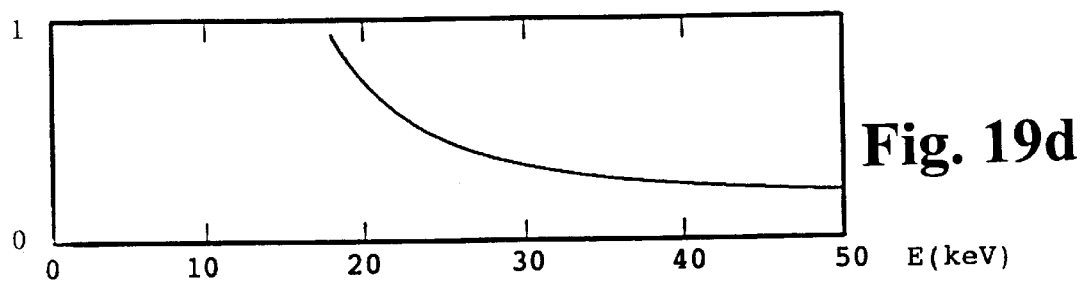
Figure 19C:
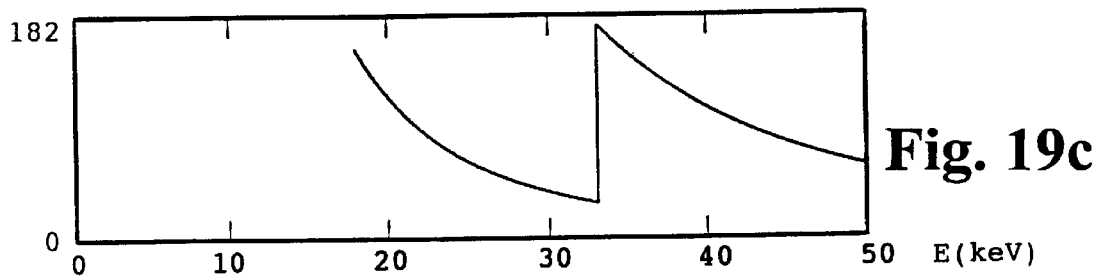
Figure 19B:
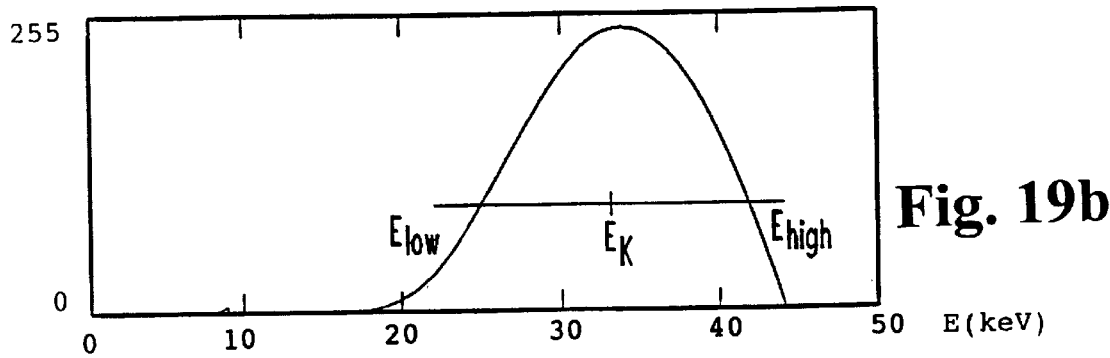
FIG. 19b shows the X-ray spectrum with $E_X \approx E_K$=33.17 keV produced using x-ray tube T with a tungsten anode A operating with electron beam eB accelerated at 44.2 kV-DC after passing a $1/73$ μm thick copper filter F and grating substrates at 600 μm of $SiO_2$. The energy $E_K$ is that of the iodine K-edge.
Figure 19A:
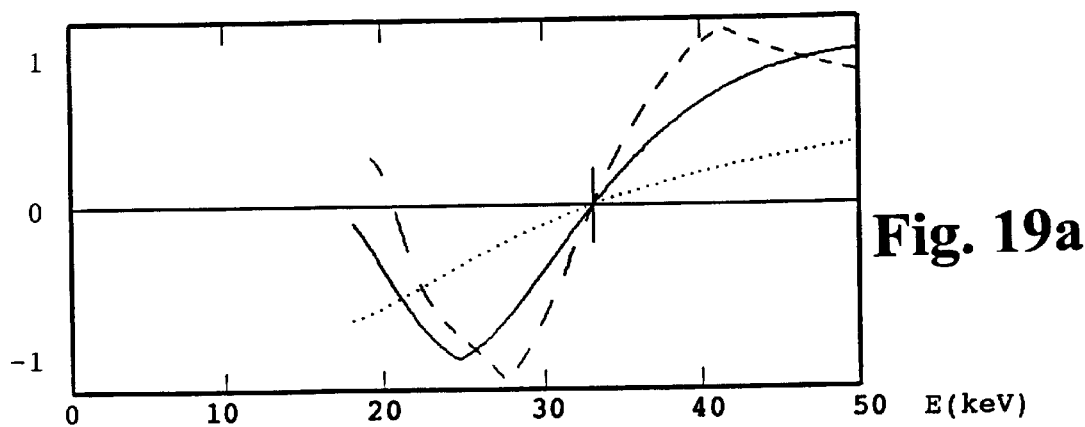
FIG. 19a shows the x-ray energy dependence of pattern Q contrast, as indicated by $Q_1/Q_0$, for a phase grating with a PG(1,3,1) profile (solid line), a phase grating with a PG(2,5,1) profile (dashed line), and a binary absorption grating with $s_2/a_2$=½ (dotted line). These curves are respectively the solid-line curves of FIGS. 16b, 16e and 15 replotted on a parameter-specific linear energy scale.
Figure 21D:
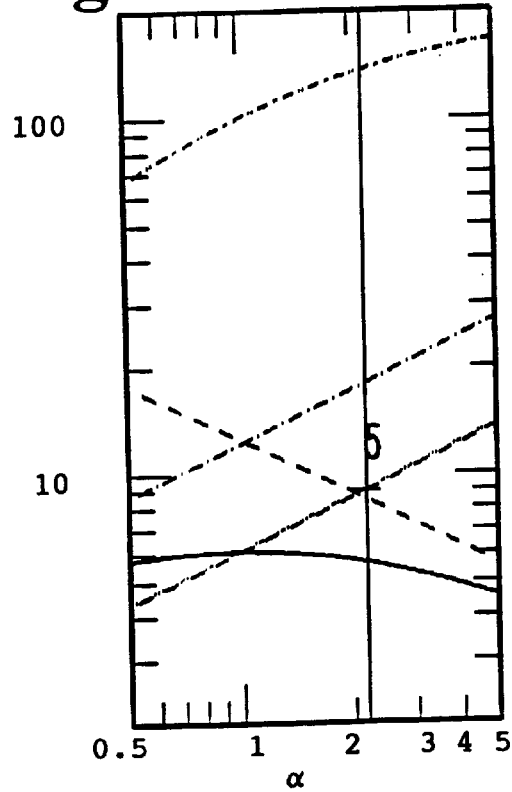

Consider next preferred embodiments that are useful for element-selective imaging, as disclosed in Sect. III.8. FIG. 21d corresponds to a L=2 m apparatus designed to perform element-selective imaging using iodine as its resonant tracer-element at $E_X=E_K=33.17$ keV$\neq E_*$. Gratings G1 and G2 are both 2D-periodic; grating G1 is a binary absorption grating, and grating G2 is preferably a phase grating with its $\beta=\frac{1}{2}$ contrast reversal centered on $E_K$. The x-ray spectral properties of the gratings and of the x-ray illumination are shown on FIG. 19b and discussed in Sect. III.8. The x-ray spectrum shown in FIG. 19b with $E_X \approx 33.17$ keV for these embodiments is produced using an x-ray tube T with a tungsten anode A operating at 44.2 kV-DC with a 173 $\mu$m thick copper filter F. Embodiment 5 is specified by the catalog choice $a_D=9$ $\mu$m, and is denoted by the parameter values on the vertical line on FIG. 21d at $\alpha=2.17$, giving $R_2=1.37$ m, $a_1=8.3$ $\mu$m, $a_2=5.7$ $\mu$m, and $a_P=18.0$ $\mu$m. The absorbing layer XAL on grating G1 is depleted uranium with $z_{T1}=36$ $\mu$m. Grating G2 may be configured as a phase grating with a PG(1,3,1), PG(2,5,1) or other suitable profile and, for example, may use a chromium refracting layer. In such case one may use $s_1=4.2$ $\mu$m, giving $z_{T1}/s_1=8.6$. The 2D-periodic plan view for a PG(1,3,1) profile is shown in FIG. 9b. It then requires $-2\pi/3$ and $-4\pi/3$ phase-shift thicknesses of $z_{T2}(-2\pi/3)=2.5$ and $z_{T2}(-4\pi/3)=5$ $\mu$m of chromium, and $z_{T2}(-2\pi/3)/s_2=1.3$ and $z_{T2}(-4\pi/3)/s_2=2.6$, respectively, thus indicating low vignetting by grating G2 and only moderate vignetting by grating G1. A PG(2,5,1) profile provides higher sensitivity, but it is more complicated to fabricate and has higher vignetting, with $z_{T2}(-12\pi/5)/s_2=13$. Use of a binary absorption grating at $s_2/a_2=\frac{1}{2}$ for grating G2 in Embodiment 5 is also possible. However, it provides considerably reduced sensitivity, requires reduced $s_1/a_1$, and has noticeably higher vignetting by grating G1. It also has a much lower net transmission by the gratings, and given its deficiencies, a phase grating is clearly the preferred choice for grating G2 in Embodiment 5. Additional realizable embodiments may be made that use a PG(1,3,1) profile at the $\beta=\frac{3}{2}$ contrast reversal; however, these embodiments exhibit very high vignetting by grating G1 unless grating G3 is included at v=3. Embodiment 5 (with a phase grating) is suitable for use in angiography. The above parameters may be rescaled to other values of $E_K$, if desired. For example, by rescaling to $E_X=E_K=37.44$ keV, then embodiments may be made that use barium as the tracer element.

Figure 14A:
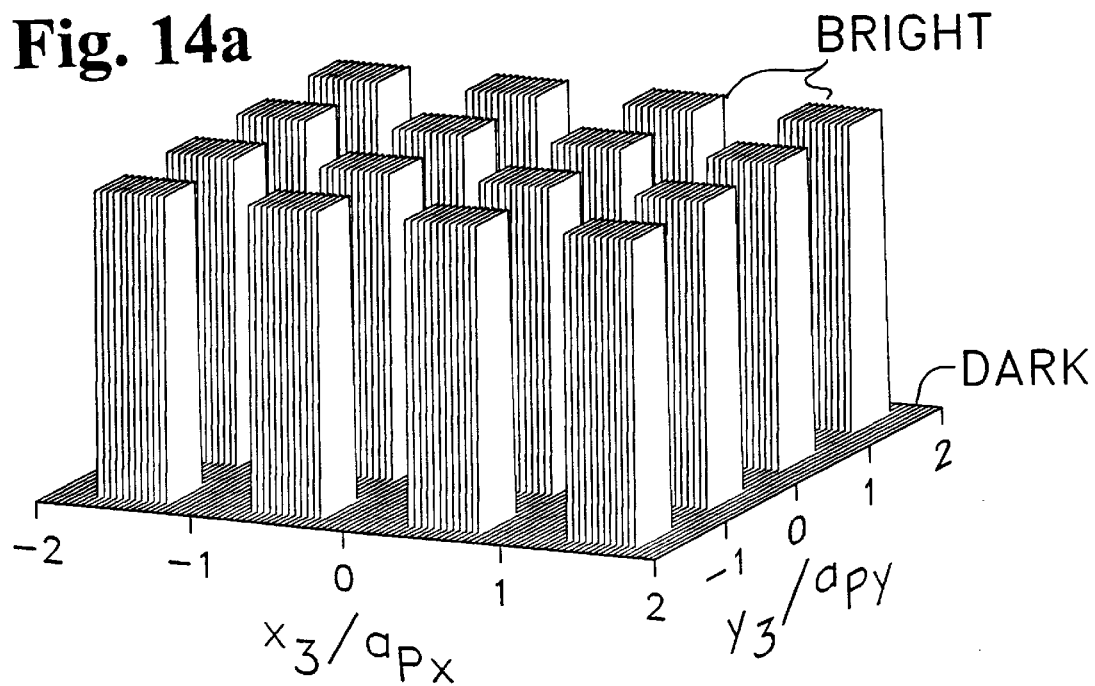
FIGS. 14a–c show perspective views of the intensity spatial distribution $I_Q(x_3,y_3)$ of pattern Q plotted as a function of $x_3/a_{Qx}$ and $y_3/a_{Qy}$.
Figure 14B:
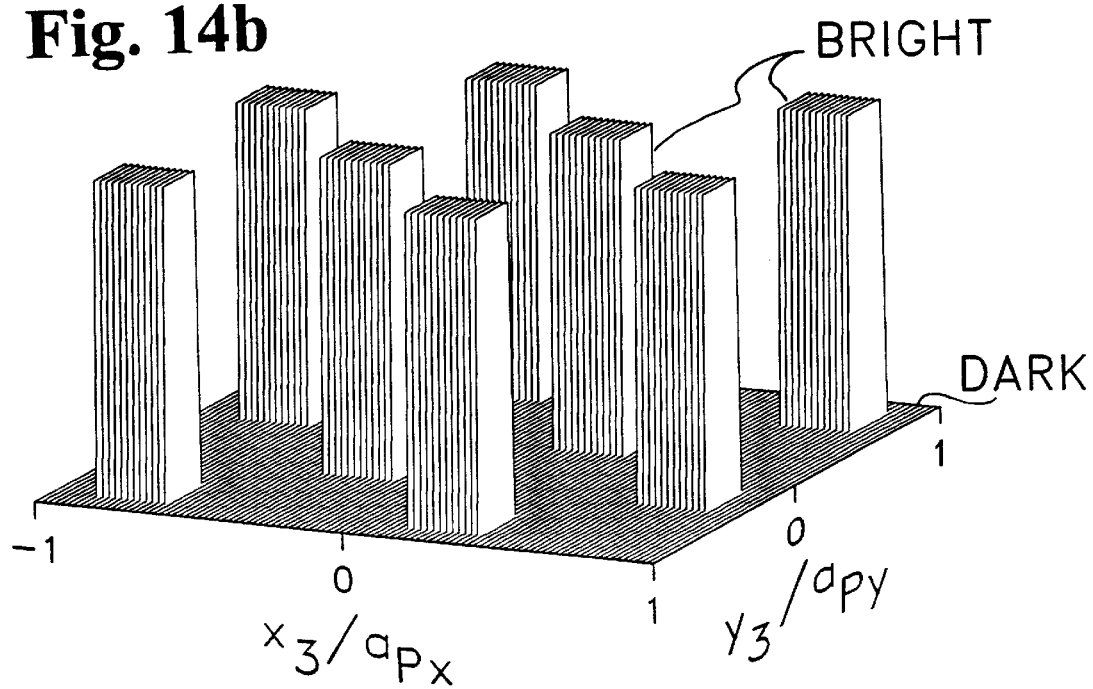
Figure 14C:
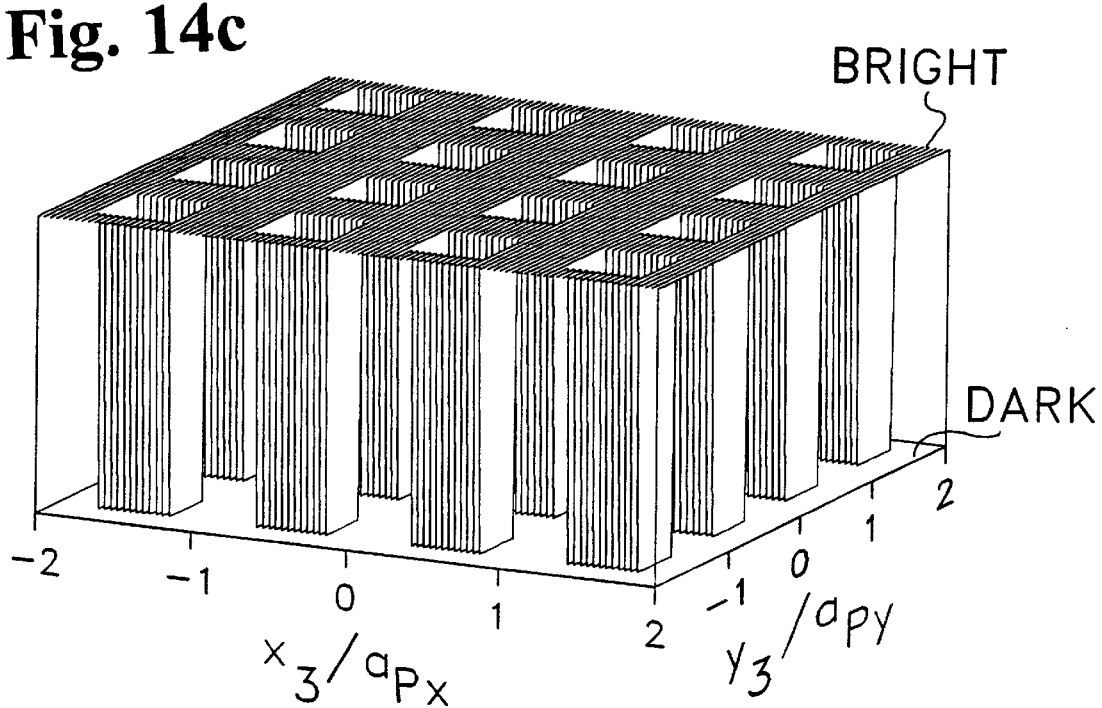
Figure 14D:
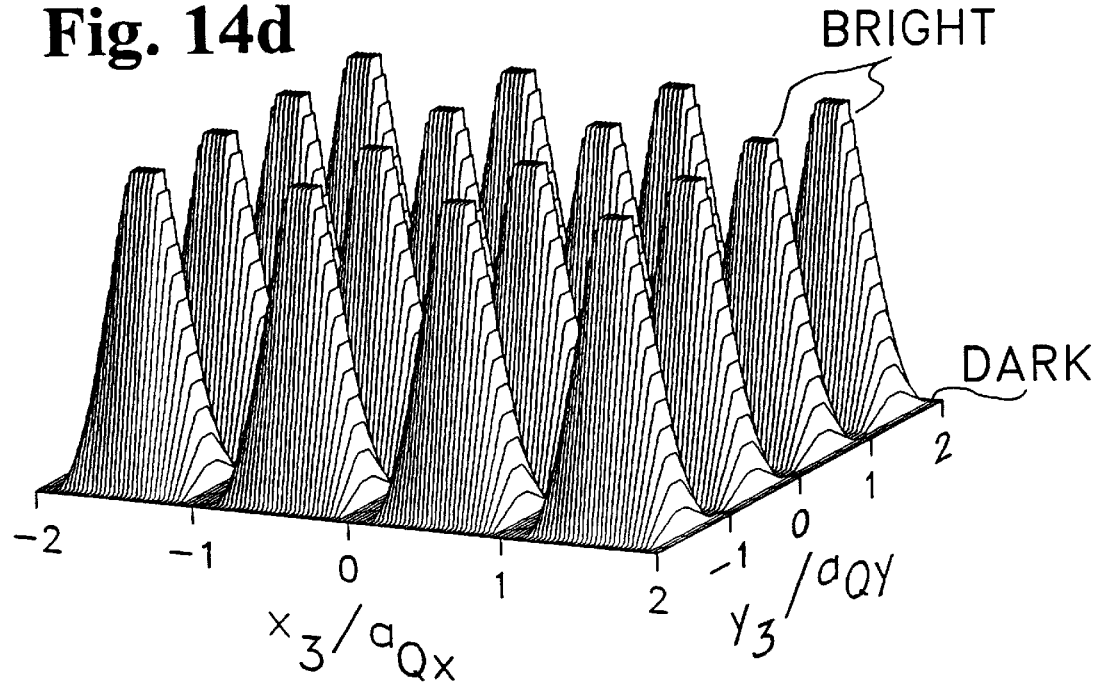
FIGS. 14d–f show the intensity spatial distribution $I_P(x_3,y_3)$ of patterns P, plotted as a function of $x_3/a_{Px}$ and $y_3/a_{Py}$. For equal x and y periods $a_{Qx}=a_{Qy}=a_Q$ and $a_{Px}=a_{Py}=a_P$ hold. The intensities $I_Q$ and $I_P$ are plotted upward.
Figure 14E:
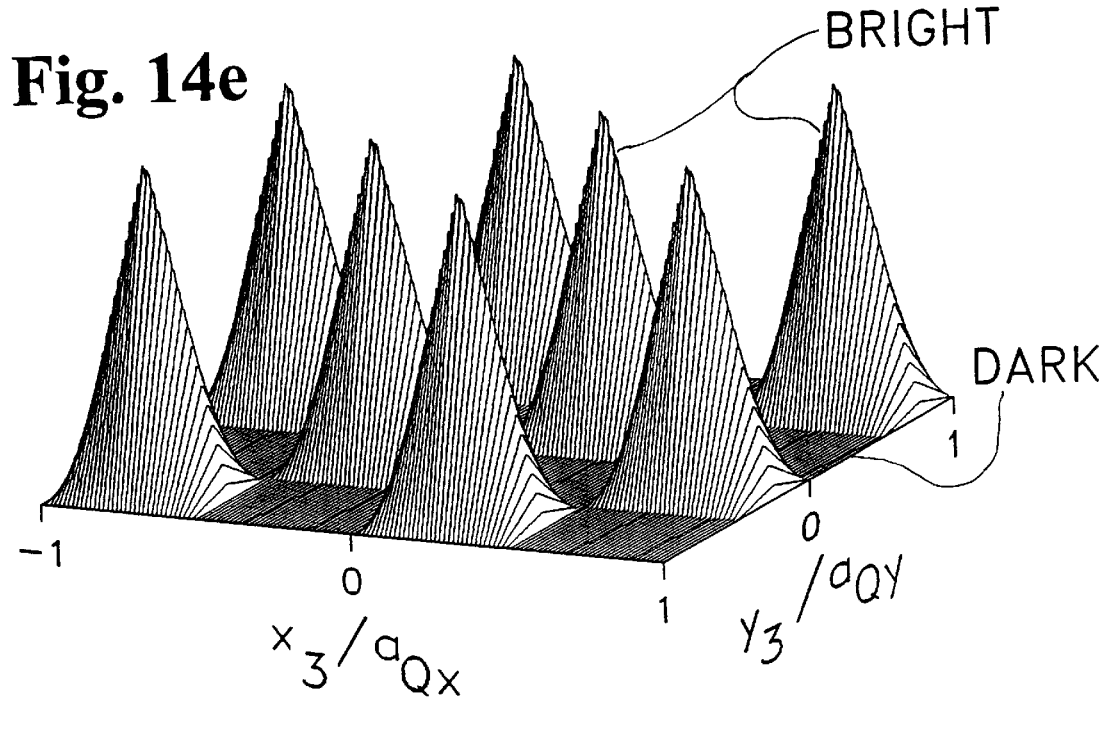
Figure 14F:
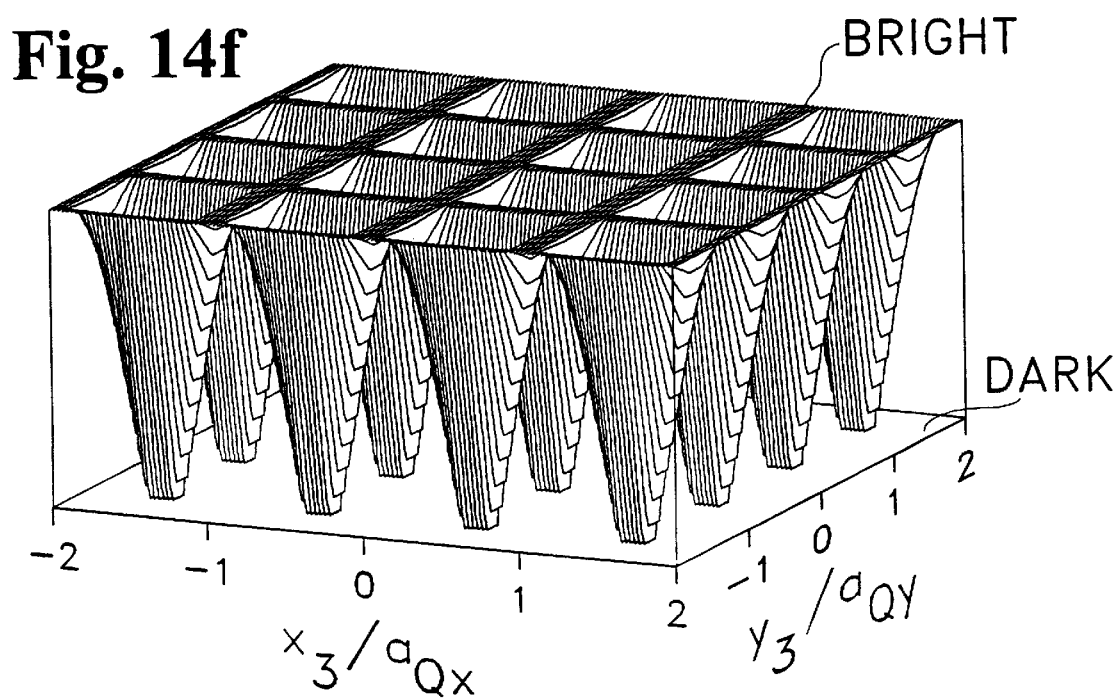
Figure 15:
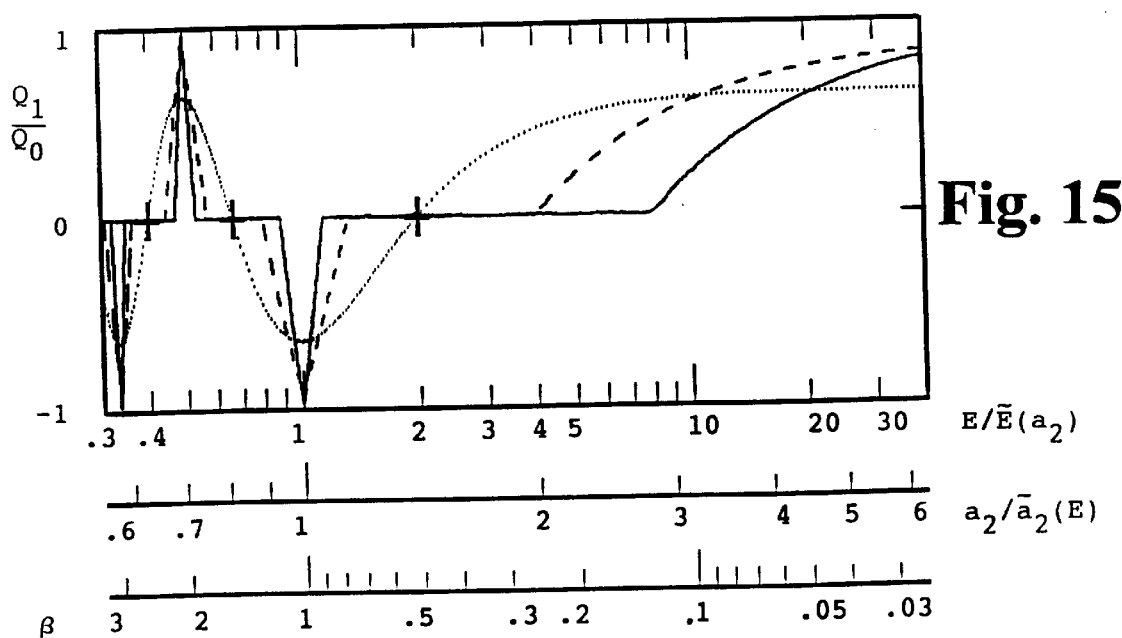
FIG. 15 shows the results of a numerical evaluation of the pattern Q contrast at period $Ma_2$, as indicated by the Fourier coefficient $Q_1(\beta)/Q_0$ in the Fourier expansion of $I_Q$ by Eqs. (III.39) and (III.40) for a binary absorption grating. Three equivalent horizontal axes are provided via Eqs. (III.24) and (III.25). The lower axis defines $\beta$ (increasing to the left); the middle axis gives $a_2/\tilde{a}_2(E)$ (increasing to the right) for a variation of $a_2$ with k-ray energy E held constant, and the upper axis gives $E/\tilde{E}(a_2)$ for an x-ray energy E variation with $a_2$ held constant. All three horizontal axes are on logarithmic scales. Resonance widths on the upper scale set the maximum energy bandwidth $\Delta E_{max}$ allowed for the x-ray spectrum. Different curves correspond to different grating duty-cycles. The solid-line curve is for $s_2/a_2=\frac{1}{8}$, the dashed curve is for $s_2/a_2=\frac{1}{4}$, and the dotted curve is for $s_2/a_2=\frac{1}{2}$. Plus symbols at values of $\beta=n/2$ with odd integer n denote contrast reversals.
Figure 16C:
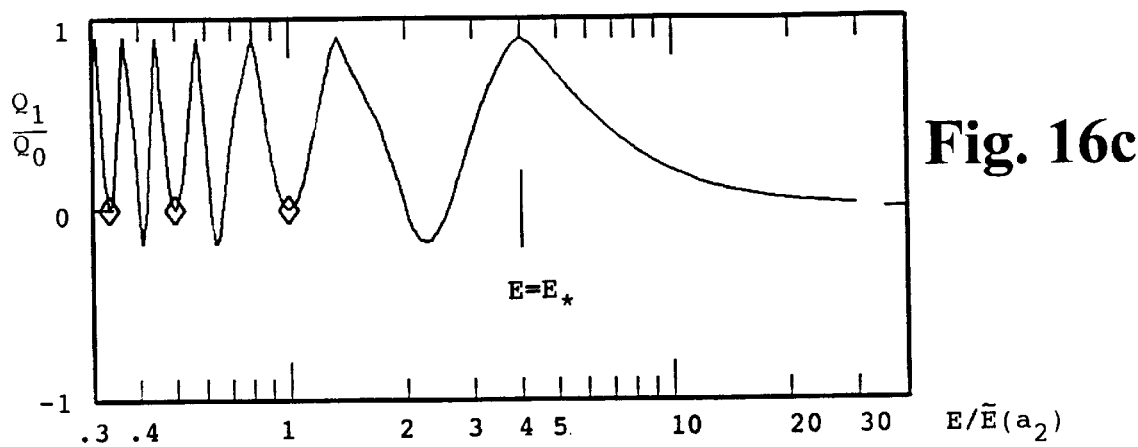
FIGS. 16a–e show the results of a numerical evaluation of $Q_1/Q_0$, as a function of $\beta$, $a_2/\tilde{a}(E)$ and $E/\tilde{E}(a_2)$ for phase gratings with various profiles, PG($n_*,m_*,1$), where $\tilde{a}_2(E)$ is given by Eq. (III.22), and $\tilde{E}(a_2)$ is given by Eq. (III.23). The quantity $Q_1/Q_0$ is a direct measure of the contrast (equivalent of visibility, but for a non-sinusoidal fringe pattern) of the p=1 spatial frequency component of pattern Q. All three equivalent horizontal axes (similar to those of FIG. 15) apply to all of FIGS. 16a–e, and all are on logarithmic scales. Resonance widths on the energy scale set the maximum energy bandwidth $\Delta E_{max}$ allowed for the illuminating x-ray spectrum. Diamond symbols at integer values of 62 indicate contrast nulls where (non-fractional) Talbot-effect self imaging of the grating's geometric-shadow pattern occurs. Contrast reversals occur at half-integer values of β for $m_*$-odd. They are marked by plus symbols, discussed in Sect. III.8, and are used to obtain element-selective contrast. The energy $E_*=\tilde{E}(a_2)m_*/n_*$, defined by Eq. (III.52) is also marked. The gratings form a p=1 binary intensity pattern at $E=E_*$ via the fractional Talbot effect.
Figure 16B:
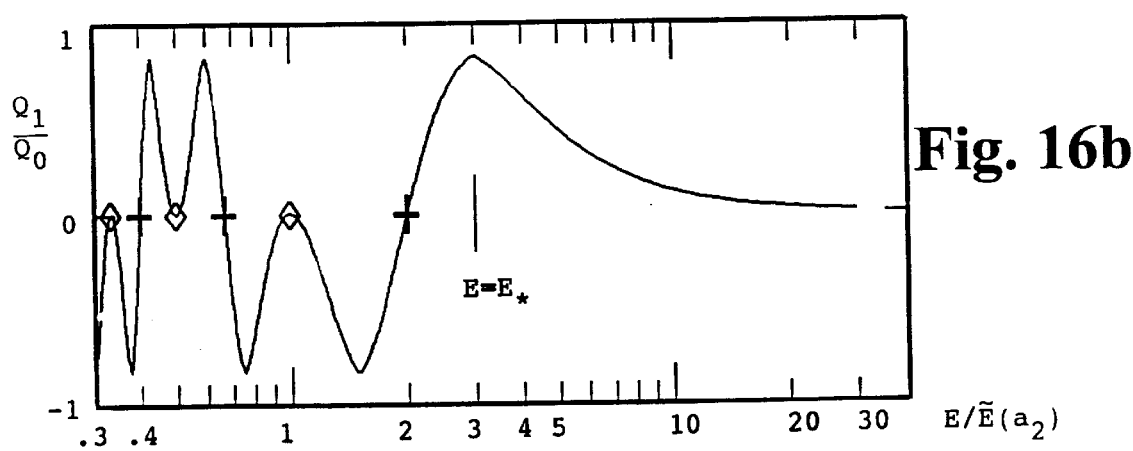
Figure 16A:
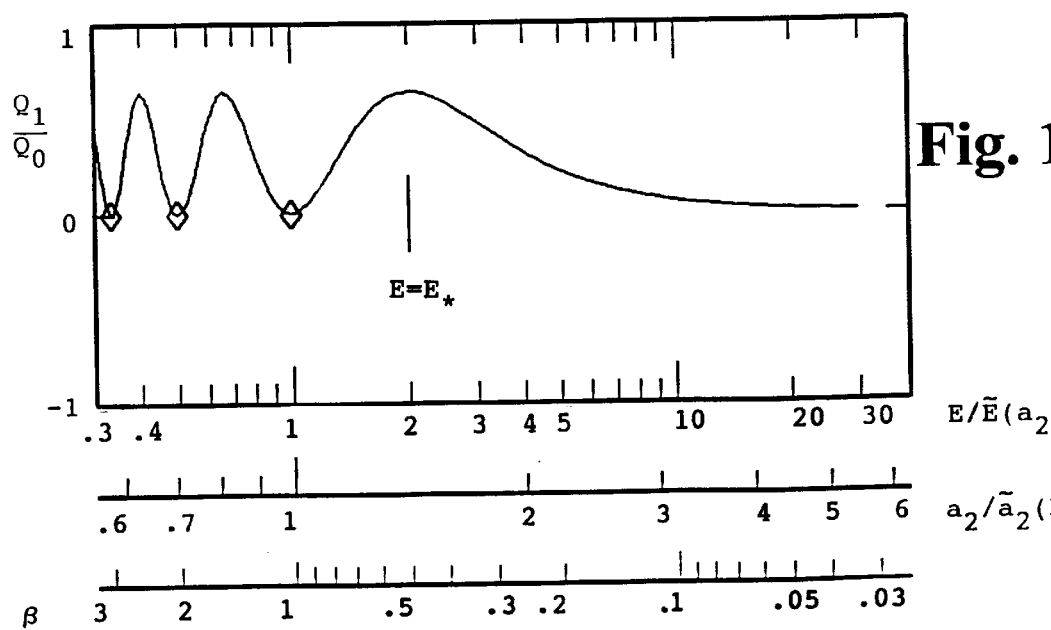
Figure 16E:
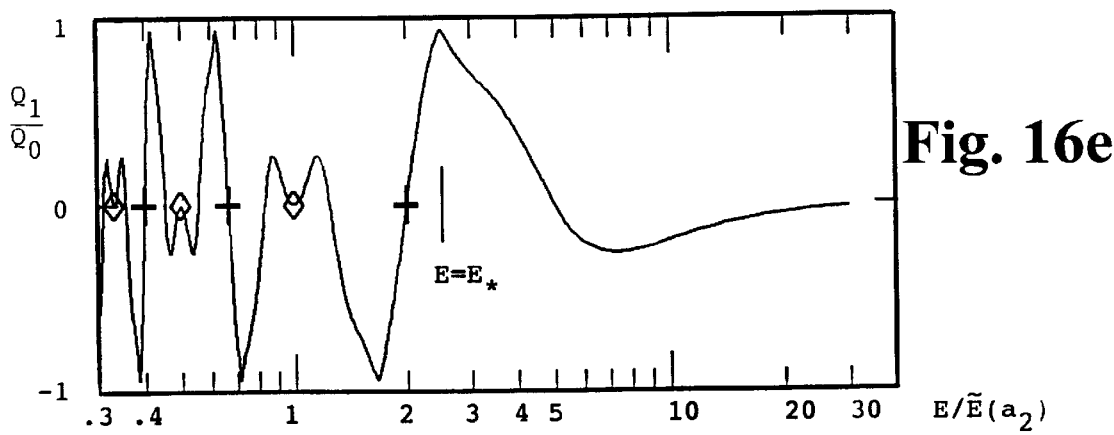
Figure 16D:
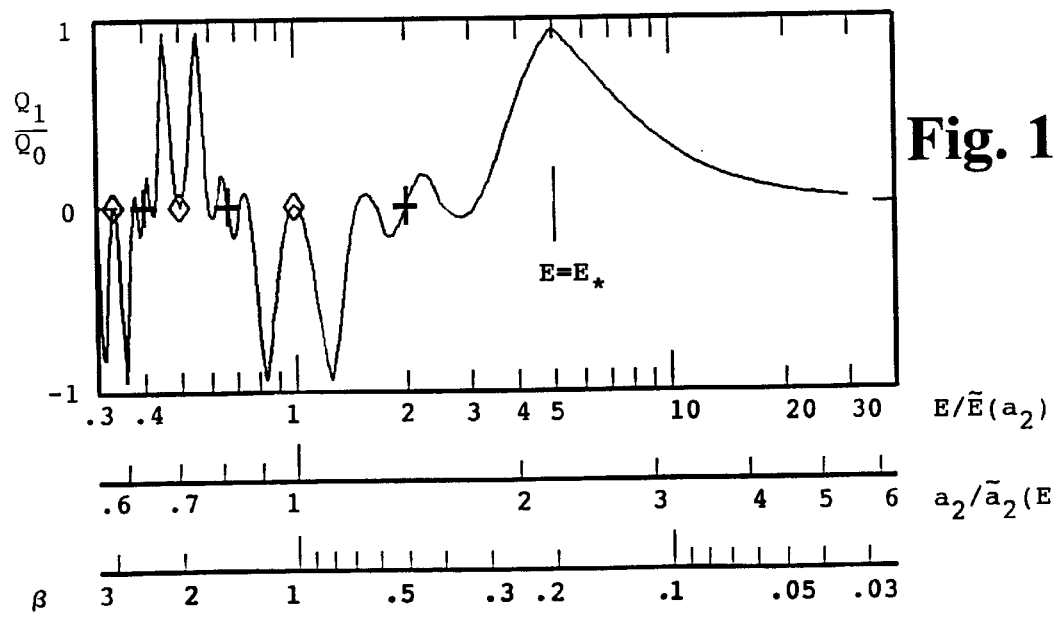
Figure 17:
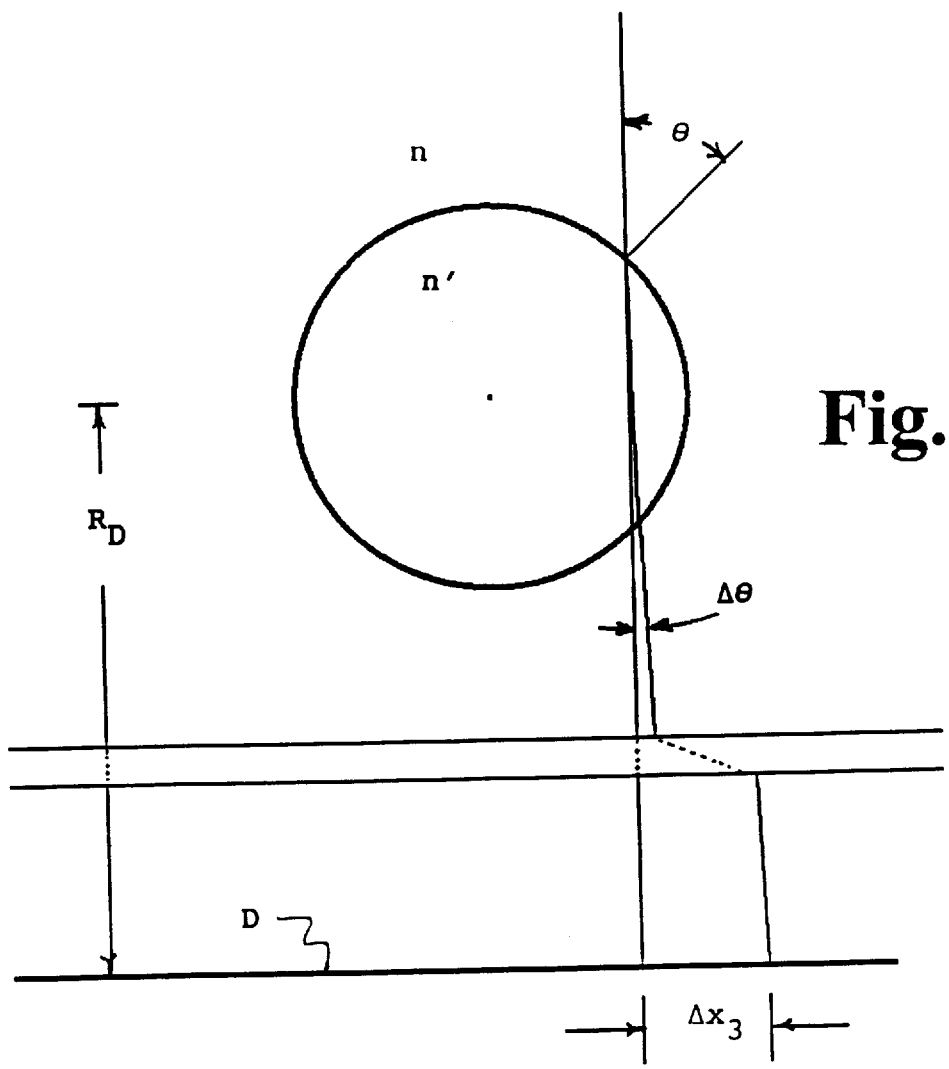
FIG. 17 shows a ray path for x-ray propagation through a cylindrical object with x-ray refractive index n', embedded in a medium with index n. The cylinder's electron density is greater than that of the surrounding medium, whereby the cylinder's refraction gives a diverging ray deflection. The deflection is drawn highly exaggerated to allow it to be apparent. The ray is incident with angle θ with respect to the cylinder's surface normal, and experiences a deflection Δθ, as discussed in Sect. III.7. The refracted ray is shown to the right of the straight-through path that would have been followed in the cylinder's absence. A gap is shown in the propagation (and in the associated dimension labeling for $R_D$) to show the ray's eventual displacement $\Delta x_3$ upon its arrival at slab-volume SV3. Propagation in the gap is shown as dotted.
Figure 18C:
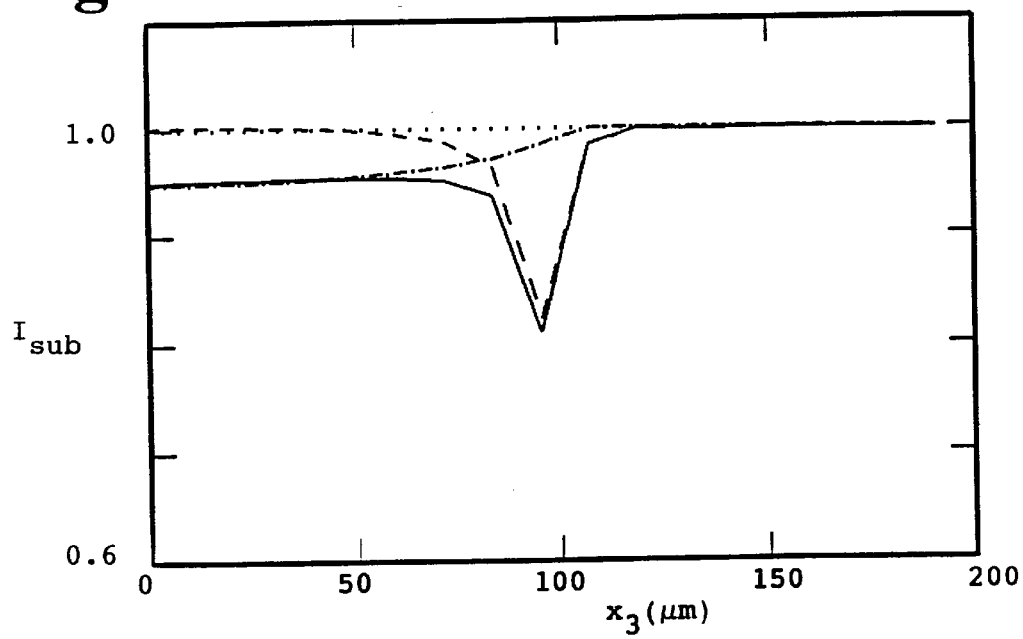
FIGS. 18a–c show the results of a numerical calculation described in Sect. III. 7 that simulates the contrast improvement and edge-enhancement of an image that obtains in the Invention from refractive-index gradient contrast. Object BDY is a 150 μm dia. $CaCO_3$ cylinder in water at $R_D$=25 cm, whose axis is oriented parallel to the 1D-periodic grating periods. The Invention operates here in phase-interferometric mode at $E_*=E_X$=17.4 kev with L=1 m and α=1 using a 1D-periodic PG(1,2,1) phase grating profile. Similar results are obtained in simulations of amplitude-interferometric mode. The simulation's parameters are appropriate for mammography.
Figure 18B:
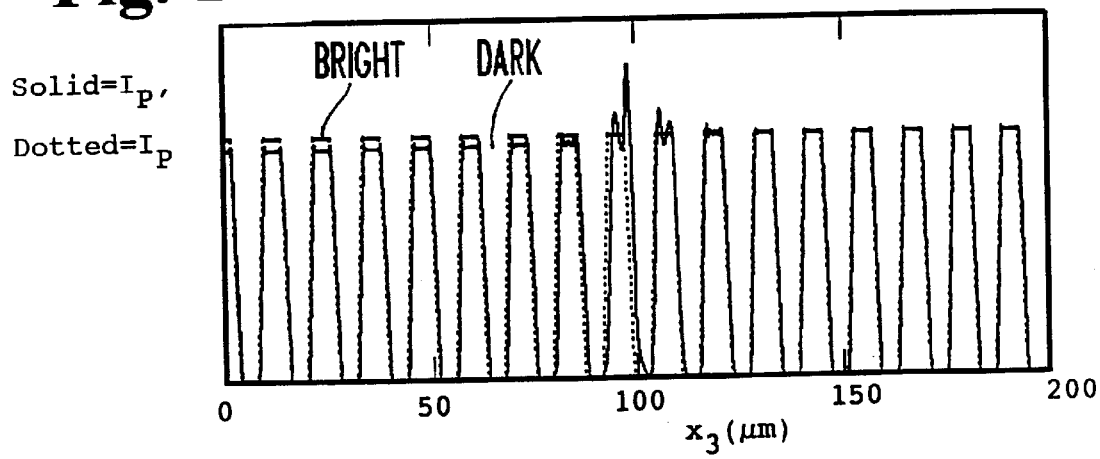
Figure 18A:
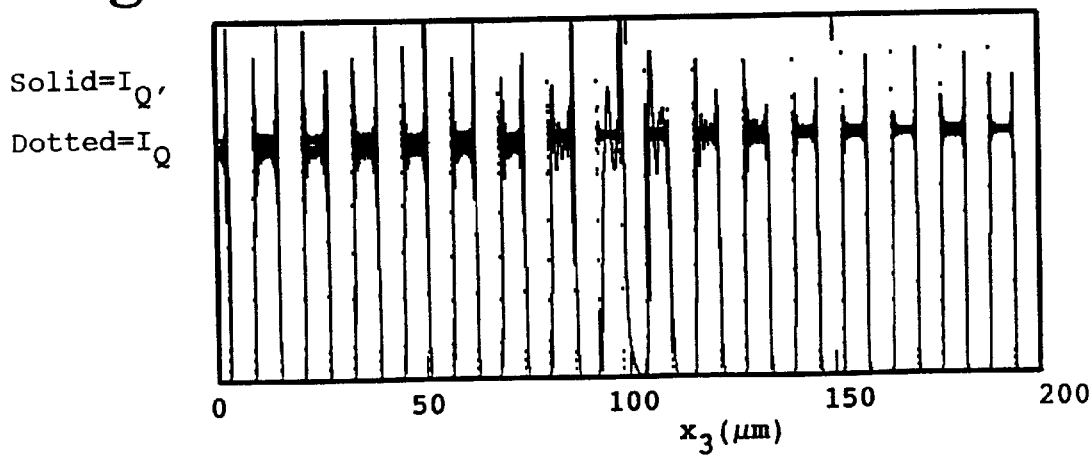
Figure 21E:
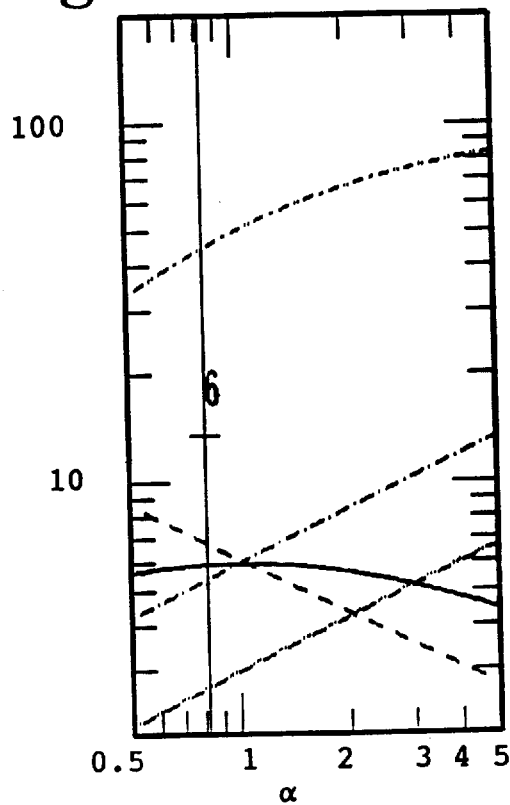

Consider next, amplitude-interferometric mode embodiments that are configured for a high sensitivity to refractive-index gradients. FIG. 21e corresponds a L=1 m apparatus that operates in the m=2, n=1 amplitude-interferometric mode at $E_X=17.4$ keV. Gratings G1 and G2 are both 2D-periodic binary absorption gratings with $z_{T1}=z_{T2}=10$ $\mu$m gold or depleted uranium absorbing layers XAL. The vertical line at $\alpha=0.82$ depicts parameters for Embodiment 6, and corresponds to the catalog choice $a_D=13.5$ $\mu$m. To provide small $a_P$ and yet to allow use of a detector with large $a_D$, grating G3 is included at v=5. The associated parameters are then $R_2=0.45$ m, $a_1=6.6$ $\mu$m, $a_2=5.9$ $\mu$m, and $a_P=6.75$ $\mu$m. Vignetting is minimized by choosing $s_1=s_2=2.3$ $\mu$m, and grating vignetting is then modest with $z_{T1}/s_1=z_{T2}/s_2=4.3$. X-rays with a suitably narrow bandwidth spectrum for this embodiment are produced using an x-ray tube T with a molybdenum anode A operating at about 23.2 kV-DC and a 800 $\mu$m thick aluminum filter F. Considerably improved grating throughput is achieved if this embodiment uses the inverted pattern P of FIG. 14f or has both gratings G1 and G2 configured with checkerboard patterns and uses pattern P of FIG. 14e.

Figure 21F:
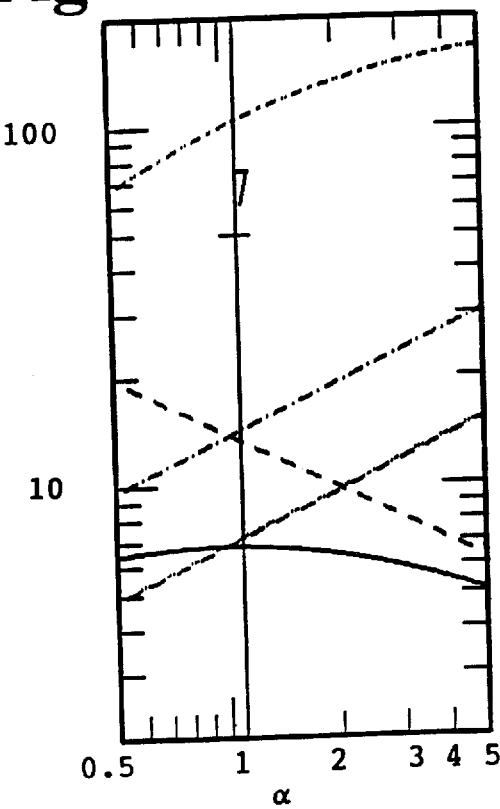

Finally, consider high energy preferred embodiments that are useful in a CT scanning apparatus (in addition to Embodiment 5), as described in Sect. V.7. FIG. 21f corresponds to a L=2 m apparatus designed to perform imaging at $E_X=40$ keV. Gratings G1 and G2 are both 2D-periodic; grating G1 is a binary absorption grating, and grating G2 is a phase grating with a PG(1,3,1) profile. The x-ray source and grating thickness parameters are similar to those used with Embodiments 3 and 4. A comparison of FIGS. 21c and 21f shows the effect on parameter scaling from increasing L from 1 m to 2 m. Embodiment 7 on FIG. 21f is configured with grating G3 present. Its parameters are then v=7, $\alpha=1.10$, $a_D=50$ $\mu$m, $R_2=1.05$ m, $a_1=13.0$ $\mu$m, $s_1=6.51$ $\mu$m, $a_2=6.8$ $\mu$m, $s_3=7.1$ $\mu$m, and $a_P=14.3$ $\mu$m. Gratings G1 and G3 have acceptable vignetting character with $z_{T1}/s_1=9.1$ and $z_{T3}/s_3=8.3$, while grating G2 has low vignetting with $z_{T2}(-2\pi/3)/s_2=0.9$ and $z_{T2}(-4\pi/3)/s_2=1.8$. If a larger value of $R_2$ is required to accommodate large patients, the configurations with v=5 and v=6 still have acceptable vignetting character, and respectively give $R_2=1.37$ and $R_2=1.20$.

V.2 Apparatus dimensional and temperature stability

Maintaining accurate alignment of the apparatus so that only infrequent realignment is needed requires good dimensional stability of the apparatus. Said stability depends on the temperature and vibrational environment of the gratings and detector D, and on the associated thermal expansion coefficients and rigidity of these components and of their mountings. Vibrations induced by anode rotation and/or by object BDY, if the latter is a live patient are potential causes of misalignment. A stainless steel or invar supporting structure that is both thermally and vibrationally isolated from the positioning means for object BDY and x-ray tube T is worthy of incorporation into the apparatus structural design. The gratings, themselves, must be dimensionally stable and have low thermal expansion. Improved dimensional stability for the apparatus as a whole is provided, if necessary, by actively stabilizing the temperature and vibrational environments of the Invention's components, supporting structures and mountings.

V.3 X-ray tubes and filters

Standard x-ray tubes with values for $W_S$ in the range of 100–2000 $\mu$m may be used in the Invention, with the smaller values providing the least geometric blurring. An x-ray tube T with high x-ray brightness and small $W_s$, consistent with Ineq. (III.65), is preferred to minimize $a_{RO}$ and $a_{RG}$. Suitable tubes T with a variety of anode A materials are available, for example, from Varian X-ray Tube Products (Salt Lake City, Utah) and other vendors. The x-ray spectrum emitted by anode A of tube T is described by Leighton [1959, pp.405–421] and by Michette and Buckley [1993, pp.13–17 and Chapt. 2]. It includes a Bremstrahlung continuum. Depending on electron beam eB energy and anode A material, it also includes one (or more) clusters of closely spaced narrow emission lines that are characteristic of the anode's composing material. If one uses a medium-Z anode A material, such as molybdenum or rhodium, that is excited by an electron beam eB whose energy is 120–150% of its K-line's energy $E_{K\alpha}$, then typically half of the emitted x-ray power appears in the K-line emission.

The x-ray spectral bandwidth limit $\Delta E_{max}$ set by the Talbot and fractional Talbot effects is not difficult to achieve. In amplitude-interferometric mode the allowed bandwidth $\Delta E_{max}$ scales with $s_2/a_2$ via Eq. (III.42), and moderately wide $s_2/a_2$ ($\approx$0.3–0.5) is desirable in any case to give reasonable x-ray transmission by grating G2. For phase-interferometric mode $\Delta E_{max}$ is already quite broad, typically comparable to that of amplitude interferometric mode, and the x-ray transmission by grating G2 is then $\approx$100%. A suitable x-ray profile that is symmetrical about $E_X$ and has $\Delta E \leq \Delta E_{max}$ is produced by a suitably filtered voltage-limited thick-target Bremstrahlung spectrum, with or without added emission lines. Additional narrowing of this spectrum with improved pattern P contrast is achieved by choosing the anode A material with $E_{K\alpha} \approx E_X$ to add emission K-lines.

A characteristically broad thick-target Bremstrahlung continuum radiation bandwidth is produced by impact at focal spot S of the mono-energetic electron beam eB from electron gun eG, accelerated by AC-ripple-free DC high voltage from supply HV. This spectrum is readily narrowed to fit within the $\Delta E_{max}$ limitation by the use of filter F. A conventional rectified AC high-voltage supply is described by Meredith and Massey [1977, FIG. 205, Chapt. XXIII]. Power supply HV provides a narrower $\Delta E$ by removing the AC ripple left in the high voltage output of such a supply. It is readily built by adding to that supply a capacitor filter (e.g. typically about 0.2 $\mu$f for a 60 Hz supply), a series resistor, and a gas-discharge voltage regulator (e.g. a long series string of Ne2H neon bulbs @ 90V ea.). The spectral upper limit (in keV) of a thick target Bremstrahlung spectrum is set by the DC voltage of this supply (in kV).

Further narrowing of this spectrum may be done by chopping off its high-energy edge with the K edge of the material in filter F; however, doing so then produces an asymmetric spectrum, and the filter F may then fluoresce and thereby increase $W_S$ (and $a_{RG}$). A suitable symmetrical spectrum is produced by using a low-Z material for filter F whose K-edge and K-line energies are very much less than the high voltage value. The filter F material is chosen so that it neither fluoresces at high energy nor leaks x-rays below its K-edge. Aluminum ($E_K$=1.56 keV, $E_{K\alpha}$=1.5 keV) is a good choice for a filter F material for use with the low-$E_X$ Embodiments 2 and 6. Copper ($E_K$=8.04 keV, $E_{K\alpha}$=8.98 keV) is a good choice for the high-$E_X$ Embodiments 3–5 and 7. (Copper tends to leak x-rays near its L edge if embodiments with low-$E_X$ embodiments, and such leakage is weakly visible on FIG. 19$b$.) Low energy emission-lines (e.g. L$\alpha$) from the anode A are also cut by the filter F. An approximate rule-of-thumb for estimating the x-ray source parameters is to set the DC high voltage at about ($\frac{4}{3}$)$E_X$, and then to choose a filter F thickness with about 1/e absorption at $E_X$. Sightly increased filter F thickness then raises (hardens) $E_X$ and reduces $\Delta E$, and vice-versa. Numerical simulations can be made to define the desired thickness more precisely. Note that the grating substrates also provide additional spectral filtering. The filter F and x-ray tube T parameters given in Sect. V.1 assume additional spectral filtration by the grating substrates from about 600 $\mu$m of $SiO_2$. A peaked spectrum of the filtered continuum, such as that shown on FIG. 19$b$, then results. The high voltage and parameters for filter F given in Sect.V.1 all give continuum spectra with an appearance and $\Delta E/E_X$ similar to the spectrum shown on FIG. 19$b$.

V.4 Grating structures and their fabrication

The absorbing layer XAL on a binary absorption grating need not be fully opaque to x-rays. However, this layer preferably should provide at least about 1/(2e) absorption, yet it still should be physically thin enough to not provide excessive vignetting. The material from which it is made thus requires a high absorption per unit path length for x-rays at energy $E_X$. The material should then have a high-Z and a high density. Gold and depleted uranium are both excellent choices. Since the resulting transmission of the absorbing material for XAL is small, its x-ray refractive index, in general, may be ignored. upon illumination with x-rays whose energy is well above that of the material's K or L-lines, the absorbing material may weakly reemit x-rays at the energy of these lines. For gold absorbing layers on the x-ray tube's side of the grating substrates, most of this reemission is absorbed by the substrates. When uranium is used for grating G2 at high energy, however, then an additional thin layer ($\approx$3–5 $\mu$m) of gold directly beneath the uranium may be included as part of layer XAL to absorb the uranium L-lines at 13.6, 16.4, and 17.2 keV.

The substrate SUB for grating G2 should have a relatively uniform thickness. It should also be as thin as possible (e.g. $\approx$200–500 $\mu$m) to limit its x-ray absorption, especially when low $E_X$ is used. If its thickness varies with position, it should do so slowly so that the overall relative phase shifts of the x-rays transmitted by neighboring periods are all about the same, whereupon said variation then has negligible effect on the shape of pattern P. The substrates for all gratings should transmit light, as this property is needed by the alignment system disclosed in Sects. III.10–III.10.3. A typical substrate SUB is shown on FIGS. 6$a,b$ for binary absorption gratings. An excellent substrate material is clear fused silica ($SiO_2$). It has a low coefficient of thermal expansion, low x-ray absorption, transmits light, and is available for use in microfabrication in the form of wafers with an acceptably uniform thickness. Sapphire ($Al_2O_3$) is also an excellent material with similar features. If laser LS produces infra-red light rather than visible light, then silicon may be used for the substrate material.

While the structure of the periodic surface-layer on a phase grating has many similarities to the layer on a binary absorption grating, it is instead made from a low to medium-Z material that is minimally absorbing of x-rays and also may have more than two thicknesses. Use of a dense material is preferred since it then has a small thickness that reduces vignetting, although vignetting by a phase grating is usually quite mild. Phase gratings may be made by either of two methods, or by a combination of the methods when 3 (or more) level gratings are used. As with an absorption grating the periodic structure may be laminated onto the substrate. Alternatively, since the substrate material is also refracting but negligibly absorbing, the periodic structure and substrate may be the same material, and the periodic profile may be etched into the substrate's surface. The needed thickness of $SiO_2$ for $-\pi/2$, and $-7$ radian phase shifts is about 1.4 μm and 2.8 μm, respectively at $E_x$=17.4 keV. Elements such as aluminum, silicon, titanium, chromium, and vanadium, and moderately high density compounds that incorporate only low and medium-Z elements are usable. Photoresist that does not contain silver halide is also usable.

Figure 3A:
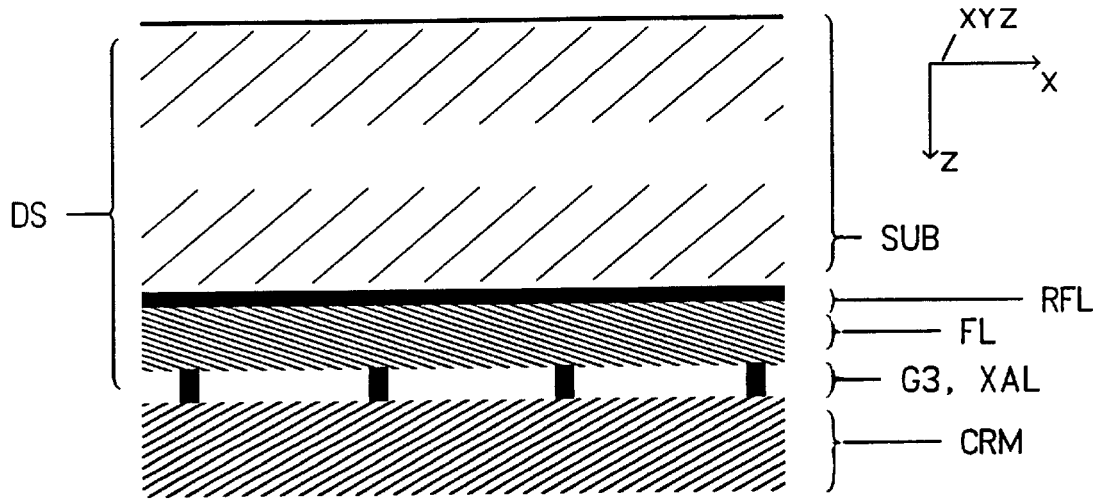
FIGS. 3a,b show elevation (x-z) views of the structure of detector screen DS that is used with continuous recording media CRM, as described in Sect. V.6.
Figure 3B:
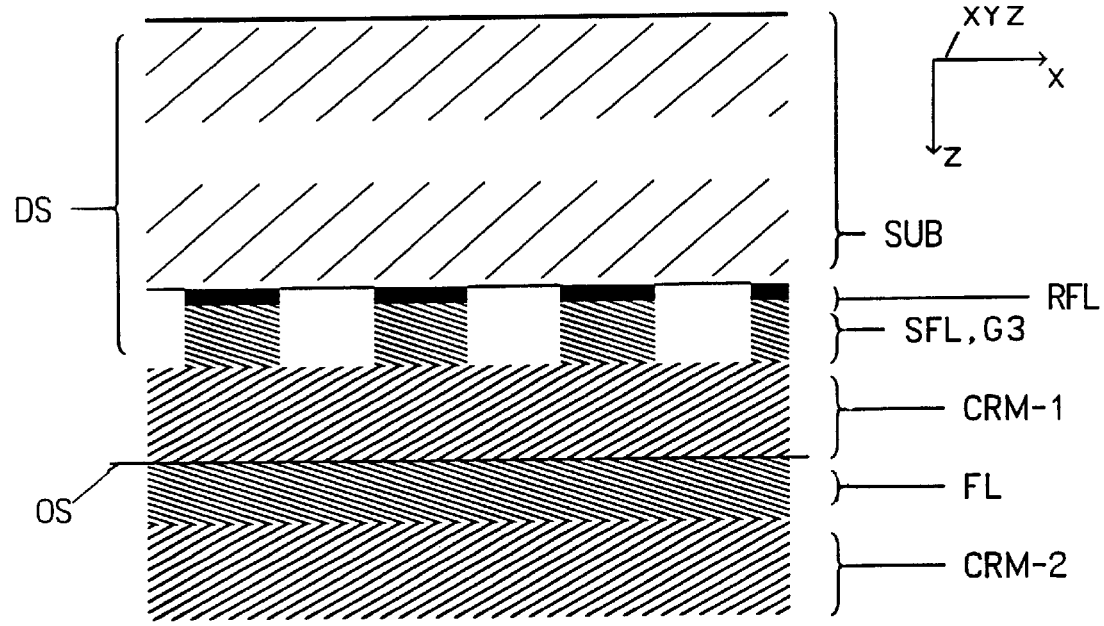
FIG. 3b shows detector screen DS comprised of structured fluor SFL, and light reflector RFL, both mounted on substrate SUB. The configuration of FIG. 3b uses two separate independent continuous recording media, CRM-1 and CRM-2, that are separated by a thin opaque sheet, OS and a second fluor FL. In the configuration of FIG. 3b, structured fluor SFL is spatially periodic and absorbs x-rays. This light is recorded by media CRM-1. It also acts as grating G3, for x-rays recorded by media CRM-2. The detector arrangement of FIG. 3b thus has two parts, with each part yielding a separate image. The first part consists of structured fluor SFL and media CRM-1, while the second part consists on fluor FL and media CRM-2. The second part may be omitted, if subtraction of scatter-induced blur is not needed.

Microfabrication of the gratings may be performed using methods commonly used by the microfabrication industry. The gratings used by the Invention, if they have metallic layers such as gold or chromium, are very similar to "reticules", as are commonly used in optics. Thus, there is a ready supply of vendors from which these gratings may be custom ordered. Similarly, phase gratings with the periodic surface layer etched into the surface are very similar to "diffractive optics" as are now commonly available by custom order. To make a grating, the pattern for its periodic structure is generally transferred to the substrate by photolithography with a photoresist. The material comprising the periodic structure on the substrate may be the photoresist itself. The material may be deposited onto the substrate prior to the photolithography and then etched away; it may be etched from the substrate's surface itself; or it may be electro-deposited onto the surface before or after photolithography. If the material is to be deposited prior to etching, such deposition may be done by sputter deposition, for almost any material (including uranium) as described by Wasa and Hayakawa [1992]. Very thick gold layers may be electro-deposited onto a thin chromium and gold sputter deposited "seed" layer. Also, for very thick gold layers, thin gold leaf may be carefully glued to the substrate. A review of some of the needed techniques, already used successfully by other applications, is given by Kahn Malek [1991]. Fabrication methods via micromachining with an eximer laser for a structured fluor that acts a light-emitting grating G3 in the detector arrangement of FIG. 3b are under development by Resonetics, Inc. (Nashua N.H.).

The x and y period directions of 2D-periodic gratings and of detector D are preferably accurately perpendicular. When they are not thusly perpendicular, then the x and y periodicity directions will not be respectively mutually parallel to each other among the gratings, and phase matching can be made to occur in one direction but not simultaneously in both of the x and y directions. If the lithography process used for fabricating the gratings does not provide sufficiently accurate perpendicularity, however, said lithography process still may be used for grating fabrication. In such case each 2D-periodic grating may consist of a pair of 1D-periodic gratings, each on its own substrate, combined with their periodic surface layers in face-to-face contact with each other. Each grating of each face-to-face pair is then rotationally aligned within the apparatus, independently of the other in its face-to-face pair. The addition of phase shifts for 2D-periodic phase gratings, as discussed in Sec. III.4, allows 2D periodic phase gratings to be made and aligned via this method.

To perform photolithography, the substrate is first coated with a layer of photoresist. The desired pattern for the structure is exposed onto the photoresist. Short wavelength UV light may be used for the photoresist exposure for periodic structures with periods greater than about 0.25 μm . Smaller structures may be fabricated using e-beam lithography, if needed. Photolithography may be done either using a projected image or via a contact-print from a mask. Masks with almost any computer generated pattern are readily made using industry-standard pattern-generating machines. Upon developing the photoresist the desired pattern is dissolved away from the residual photoresist, thereby uncovering the base surface. The remaining photoresist is hardened by baking it. Very thick and/or high aspect-ratio photoresist structures may be made using methods described by Loechel et al. [1996]. For single thickness phase gratings that use photoresist as the refracting structure the grating is complete at the end of photolithography. A phase grating that requires multiple step heights may be made by repeated lithography, etching and/or deposition steps, as needed. Alignment of opposite faces of a two-sided "sandwich" grating, as shown in FIG. 6b, may be done using methods described by White and Wenzel [1988].

The electro-deposition method has been used very effectively to fabricate gold gratings for various other applications [Smith et al., 1984]. It should be also very effective for making gold binary absorption gratings for the Invention, although it is doubtful that it will work with uranium layers. In this method a very thin conducting layer (e.g. 0.1 μm ) of some metal (e.g. chromium) is first deposited onto the substrate prior to photolithography, (e.g. by sputter deposition or evaporation). Following photolithography the substrate is immersed in a gold electroplating solution. The exposed areas of the now conducting substrate are electrodeposited with gold, with said deposition conforming to the vertical-walls of the patterned photoresist which now acts as a mold. Next, the photoresist is removed by etching in a reactive-ion oxygen plasma. Finally, the thin conducting layer remaining in the zero-thickness areas of the periodic structure is removed by a wet etch.

Gratings with high aspect-ratio structures also can be made via dry etching with an anisotropic plasma. This technique, known as sputter etching, is discussed by Wasa and Hayakawa [1992, Chapt.6], who indicate that both uranium and gold may be sputter etched by 500 eV argon ion beams, at rates respectively three and seven times faster than that of a masking photoresist, to yield high aspect-ratio vertical-walled periodic structures. They also present tables of sputter etching rates for a wide variety of other materials including chromium and gold. Smith [1996] indicates that since $UF_6$ is a gas, then uranium may be reactively etched with high resolution and high aspect-ratio by a fluorocarbon plasma. Bazylenko and Gross [1996] demonstrated that a reactive-ion $CHF_3$-Ar mixture plasma rapidly etches thick fused silica patterns to form very high aspect-ratio vertical-walled structures at rates 10 times faster than the masking photoresist is etched. Sputter etching generally uses a carefully controlled parallel ion beam from a large area planar source to provide the vertical walled structures. However, if a focused-beam ion source area is used instead, and if the ions are allowed to converge and then diverge in a controlled fashion, then "fanned" periodic grating structures also may be fabricated in the divergent portion of the ion beam, wherein high aspect-ratio periodic structure members are produced that are then inclined toward focal spot S. The resulting fanned structures then provide reduced vignetting over large detector area, in the same fashion as that of a "focused Bucky grid" [see Meredith and Massey, p.257].

Depending on the material forming the periodic layer structure on a grating, said structure may be made using wet etching techniques. For example, if a silicon wafer with a <110> crystal orientation is used for the grating substrate (and an infra-red laser correspondingly is used in the alignment system) then a step-function shaped G2 phase grating structure with vertical walls may be wet etched into the silicon by first coating the wafers with a thin 0.1–1 μm layer of silicon nitride and then plasma etching the pattern (via photoresist) into the silicon nitride overcoat. After removal of the photoresist, the substrate is then immersed in a hot KOH solution to etch away exposed silicon. The silicon nitride acts as a secondary mask during the KOH etch, since it is insoluble in KOH. Grating structures with low aspect-ratios also may be made using other materials via wet etching techniques, since the characteristic undercutting of side walls via wet-etching does not distort the walls of a low aspect-ratio structure in a harmful way. Thus, a low aspect-ratio chromium phase grating structure may be made using standard chromium wet-etching techniques.

V.5 Available detector sizes

One of the more important considerations for design of the overall apparatus configuration is the size of available detectors. The simplest and generally preferred configuration for the Invention uses a single large-area detector, as shown on FIGS. 1 and 5. Whether or not this simple configuration may be used, however, depends on the desired size of the image field and, in turn, on the availability of a digital x-ray detector array with that size. (See also Sect. V.6) The detector preferably also has a high effective x-ray quantum efficiency. More or less any CCD array is readily converted into a high quantum efficiency digital x-ray detector by coating or contacting its surface with a fluor (also referred to as a "converter", "phosphor" or "scintillator"). Suitable fluor materials are described by Michette and Buckley [1993, pp.240–248] that efficiently convert each incident x-ray photon into many optical photons. To improve such a detector's effective quantum efficiency for x-rays, the fluor may also have a thin partially reflective coating (e.g. 0.1 μm of aluminum or low-Z white paint) on its front face that transmits x-rays and reflects most of the optical photons that are emitted by it towards the CCD (e.g as per light reflector RFL in FIGS. 3a,b, see Sect. V.6). Note, however, that the fluor and reflective layer together must weakly transmit some light from laser LS, as needed for alignment. Said light transmission, however, may be quite weak, since an enormous brightness of light is available, from laser LS, even at very low power output. Indeed, care must be exercised with all embodiments during alignment when telescope AFT focuses light on the surfaces of detector D and/or of the gratings, to prevent high intensity focused laser light from damaging these surfaces. Most CCD detectors typically feature rapid digital readout of image data. However, a simplification to the required CCD technology is allowed by the Invention, since charge may be accumulated during the x-ray exposure and read-out may proceed at a leisurely pace afterwards, whereupon use of a "slow-scan" CCD device is acceptable. Very high quantum efficiency for the optical photons generated by the fluor may be achieved by the use of a "back-illuminated" CCD array. A silicon CCD array with an integrated fluor or a SiPD array that directly detects incident x-rays without an added fluor also may be used. Cooling the CCD also may be helpful to reduce its dark current.

Figure 4B:
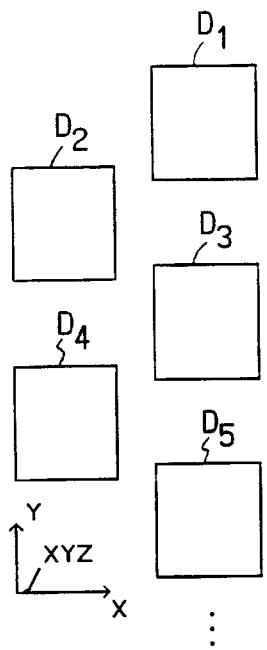
Figure 4C:
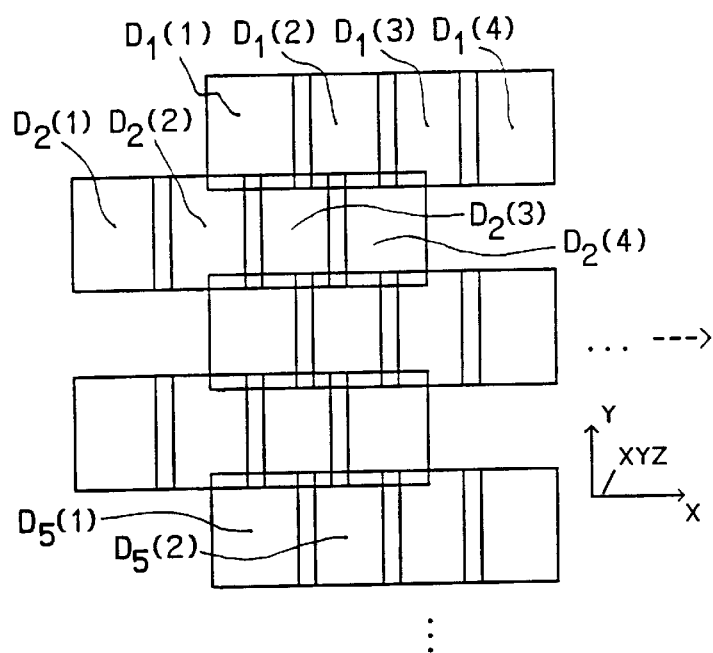
Figure 4D:
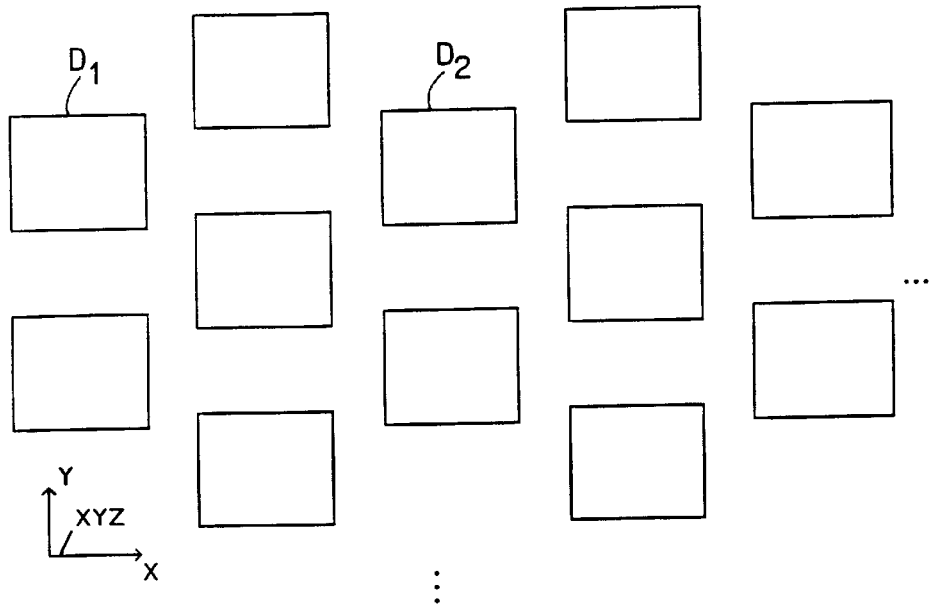
Figure 4E:
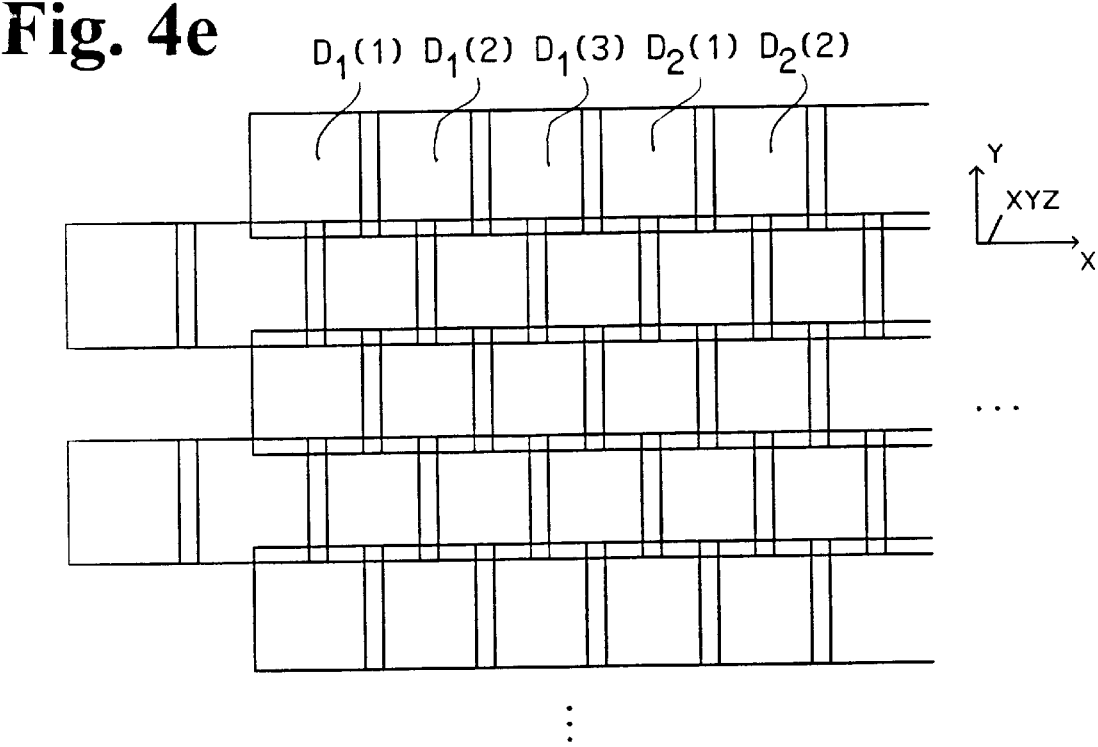

A wide variety of small CCD arrays is commonly available with $a_D \approx 3$–50 μm for use as a "retina" in a miniature digital television camera, and in other applications. Section V.7 describes the overall configuration of FIG. 4a for the Invention, as a variant of that of FIG. 1, that uses a sparse array of small CCD arrays, with the layout shown on FIGS. 4b and 4d. Its final image consists of a "tiled" array of (very slightly overlapped) small image segments, as shown in FIGS. 4c and 4e, that are "stitched" together to form a large final image using computer CP. The final image is then a mosaic of the image segments recorded by the individual tiles within the mosaic. Use of such a mosaic in the Invention requires maintaining phase continuity of the pixel periods (at both $a_D$ and $a_R$), and parallelism of these periods across each tiling butt-joint. Use of said sparse arrays of CCD arrays requires scanning the whole apparatus's orientation, as discussed in Sect. V.7.

Creation of a very-large-area tiled mosaic that is not sparse and does not require scanning may be done by assembling a mosaic array of small CCD arrays that is not sparse on the image plane of detector D. To do so, however, the small CCD arrays must be closely and precisely butted together at their edges, preferably in a seamless fashion, with negligible-width gaps at the butt-joints. "Three edge buttable" CCD arrays are available that may be butt-joined on three sides with only a few pixels missing at each seam [Blouke, 1995]. Doing so with all four edges butted together is complicated by the necessity of making electrical connections at the CCD edges. However, Molecular Structures Corp. (Houston, Tex.), Schott Fiber Optics, Inc. (Southbridge, Mass.) and Princeton Instruments, Inc. (Trenton, N.J.) make large area detectors and/or associated tapered fiber-optic bundles [Blouke, 1995; Weiss, 1997]. The small end of each fiber-optic bundle is coupled to a CCD array, wherein the CCD is smaller than the large end of the tapered bundle to provide clearance for edge connections to be made to the CCD. As many bundles as needed are then assembled into a tiled mosaic with an x-ray fluor material coating the large ends of the bundles. The assembled mosaic then forms an arbitrarily large detector array, with the plane of the fluor material forming the surface of detector D.

Figure 8A:
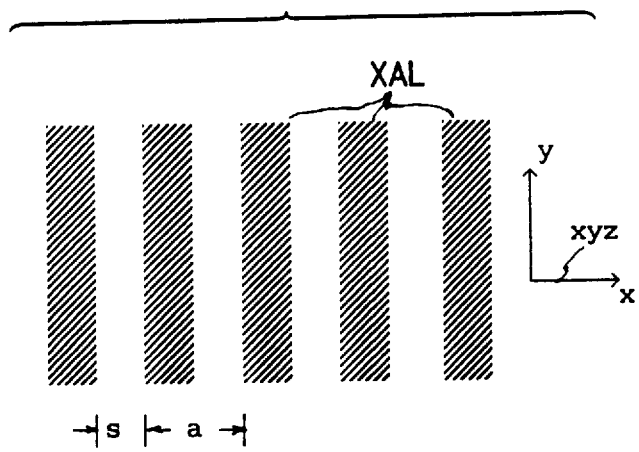
FIGS. 8a–d show various planforms for binary absorption gratings. The planforms are shown with equal x and y-periods a, and with slit or transmitting-square widths s. (On the inverted profile of FIG. 8d, however, s is the width of an absorbing square.) One of these patterns is selected for the layout of grating G1 in all modes, setting $s=s_1$ and $a=a_1$. In geometric-shadow and amplitude-interferometric modes, one is also selected for grating G2, setting $s=s_2$ and $a=a_2$. These planforms also may be used for a v=1 configuration of grating G3. Unshaded areas are x-ray (and light) transmitting. Shaded areas (by /// hatching) are x-ray (and light) absorbing (and/or opaque) surface layer XAL.
Figure 8B:
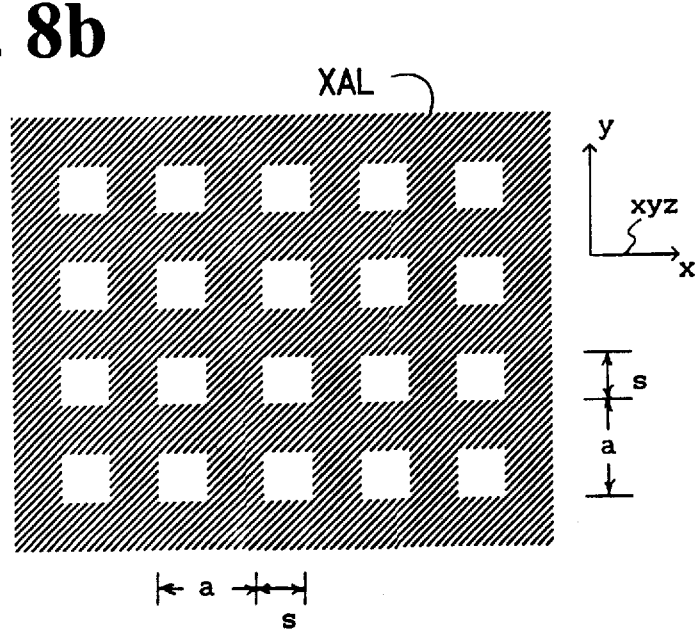
Figure 8C:
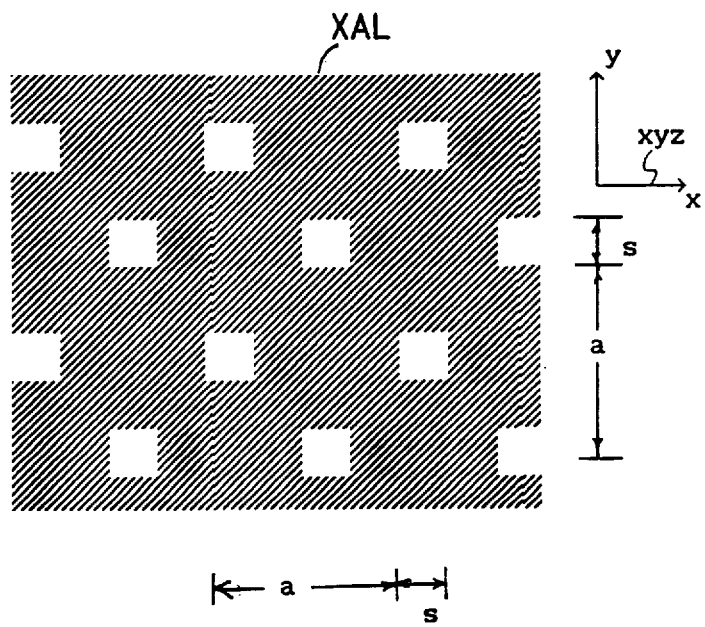
Figure 8D:
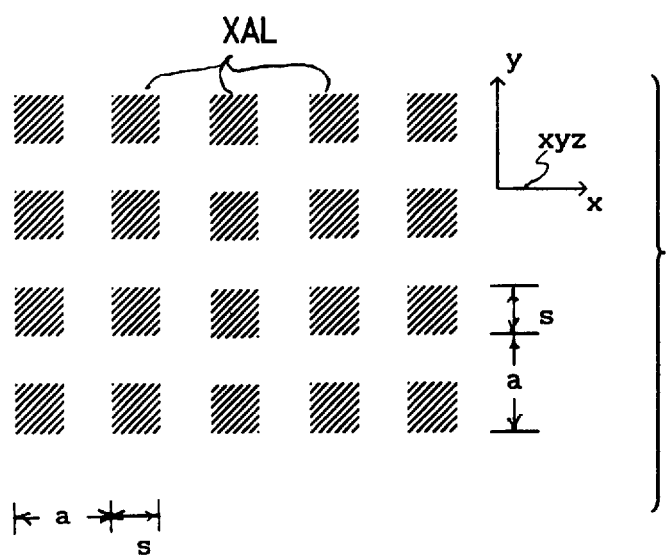

Assembly of such a detector array into a mosaic (sparse or not) with the needed period parallelism and pixel phase continuity may be done with the final surface of the detector in contact with a 2D-periodic optical Ronchi ruling. The period of the Ronchi ruling is $a_D$, and its planform is similar to that of FIG. 8b. It is illuminated with diffuse light. Assembly is done with each CCD array active by observing and eliminating any resultant moiré formed on the CCD as it is added to the mosaic, whereby phase continuity across butt joints is obtained.

A limited variety of medium-area and large-area CCD arrays is also available, with availability now increasing rapidly. Blouke [1995] reviews the state-of-the-art for medium and large-area CCD arrays and their use as x-ray detectors. Currently, 1" square CCD arrays with a 9 μm period are commercially available from the Eastman Kodak Corp. (Rochester, N.Y.). EEV Ltd. (Chelmsford, UK) currently markets 2.7 cm×5.4 cm arrays with 13.5 μm pixels. (Note that Embodiments 2–5 use $a_D = 9$ μm , and Embodiment 6 uses $a_D = 13.5$ μm .) Arrays of 3 μm pixels with 3 cm×3 cm areas have been built and used for astronomy. In limited-production custom made CCD's with much larger areas also have been demonstrated. Phillips Imaging Technology (Eindhoven, Netherlands) has produced 8.6 cm×11 cm arrays with 12 μm pixels. Arrays of 8.7 μm pixels with 8 cm×8 cm areas are under development by Loral Fairchild Imaging Sensors (Tustin, Calif.).

A variety of other large-area digital x-ray detector arrays are also under development that use similar or very different technology. These also may be used in the Invention. Large-area moderate-cost amorphous silicon x-ray detectors are currently being developed for medical imaging by Varian Assoc. (Palo Alto, Calif.). A fluor coupled either directly or by a fiber-optic faceplate to an image intensifier tube and vidicon, is also usable as a digital x-ray imaging detector, given appropriate raster scan accuracy. Vidicon-style electron-tube based x-ray detectors with areas of up to 40 cm×40 cm have been built. Dimensionally stable continuous image recording media also may be used for detector D, as per Sect. V.6.

V.6 Variant detector configuration using continuous detector media

A very large area detector may be built by using a continuous recording media CRM. Such media include dimensionally stable film and the stimulated luminescence plate [Fuji Corp. Japan; see also Sonoda et al., 1983]. Two configurations for doing so are depicted in FIGS. 3a and 3b. Another case of such media, that of a TV video camera whose photosensitive pixels are not necessarily phase and period matched to pattern P nor to grating G3 (not shown on the drawings) also falls into this category and is included in the discussion that follows. Some of the configurations discussed in this Section allow phase and period harmonic matching, and some do not. Those that do may be used to achieve subtraction of scatter-induced blur, as per Sect. III.6.2, and/or element selective contrast, as per Sect. III.8. Those that do not still may be used to obtain images that give refractive-index gradient contrast. As noted in Sect. III.1, the presence of grating G3 in these configurations,. while not essential for the minimal functioning of the Invention, is strongly preferred for a practical device.

First consider the configuration of FIG. 3a. It shows an elevation x-z view of detector screen DS to be used at the position of detector D in FIG. 1, with grating G3 located longitudinally at the end of the $R_2$ measurement. Detector screen DS is comprised of fluor FL, grating G3, and light reflector RFL, all mounted together on substrate SUB. Continuous recording media CRM is placed in direct contact with grating G3, and then removed for retrieval of the x-ray image imprinted on it. Alternatively, its latent image is read-out in-situ from below whereupon its removal is unnecessary and media CRM is then permanently positioned as shown in FIG. 3a.

Grating G3 may be located either above fluor FL or below it. The latter case is the one shown in FIG. 3a. When located above fluor FL, grating G3 is comprised of an x-ray absorbing layer XAL. When located below fluor FL, it needs to be (at least partially) opaque only to the light, and then may be very thin, since it does not need to be opaque to x-rays. In either location it has the same net effect, and its opaque areas mask x-ray detection by media CRM in a spatially periodic fashion. In the lower location it masks x-ray detection by blocking (shadowing) light from reaching media CRM, wherein such light is emitted from portions of fluor FL located directly above the opaque areas of grating G3. In both locations it also masks the laser light in pattern O, as needed for apparatus alignment. Light reflector RFL reflects (partially) light downward toward continuous recording media CRM to minimize loss of light. To act as a light mask, grating G3 opaque areas may consist of a very thin thickness (about 0.05 μm) of aluminum or other light-opaque material. Grating G3 also may be embedded in fluor material FL to provide additional light reflection and to prevent lateral migration of light within fluor FL.

During an x-ray exposure, the continuous imaging media CRM is in direct contact with the surface of grating G3. Supporting substrate SUB and its mountings are sufficiently rigid that such contact does not disturb the alignment of grating G3. Fluor-emitted light is then proximity focused directly onto continuous media CRM as a contact-print. It is also possible to intervene a large-area fiberoptic faceplate between the continuous recording media CRM and grating G3 (i.e. between grating G3 and media CRM in FIG. 3a) to increase the stiffness of substrate SUB, whereupon substrate SUB then may be eliminated. In such case the media CRM instead contacts the fiber-optic faceplate. Following x-ray exposure, the continuous media may be removed from contact with grating G3 (or the faceplate) and transferred to a container in darkness for transport to a developer and/or a laser read-out apparatus, if desired.

The third method for producing images from refractive-index-gradient contrast uses the detector configuration of FIG. 3a to provide a very simple and inexpensive apparatus. Since no pixels are present in continuous recording media CRM, b-labeled and d-labeled pixels are then instead similarly labeled b-areas and d-areas on grating G3 (within slab-volume SV3). Under this method, grating G3 is configured at $v \geq 1$. At v=1 it has a planform similar to one shown in FIGS. 8a–d. Phase matching is obtained between pattern P and grating G3 with grating G3 now configured and aligned, so that with object BDY absent, then all BRIGHT fringes (incident on b-areas) are masked by the grating G3 periodic structure, and so that then only light emitted by fluor FL excited by x-rays incident in DARK fringes is not masked by grating G3 d-areas. This light is then contact-imaged onto media CRM. The portion of the image that passes grating G3 d-areas is effectively an image of the refractive-index gradient distribution in object BDY. With $s_O/a_P$ of pattern P smaller than $s_3/a_3$ of grating G3, then the image detector (e.g. film media CRM) receives negligible illumination with object BDY absent. When object BDY is present, however, its refractive-index gradients then cause deflections of BRIGHT fringes onto d-areas, that, in turn, create illumination of d-areas, and give an image of the object's refractive-index gradient distribution on the d-areas. This method does not provide a means for image subtraction and the associated removal of scatter-induced blur. Nonetheless, for a modest scattered intensity contribution to d-areas, the fractional intensity increase on these d-areas is large, and a useful sharp image is still produced, despite the presence of scattered x-ray intensity.

Advantages of this third method include its simplicity and associated low cost, the fact that image subtraction along with the associated complicated digital imaging system and computer are not required, and the fact that various continuous recording media CRM (e.g. film) are readily available with very large detector areas. Its disadvantages include a slightly higher object dosage (for comparable quantum mottle), the use of a low quantum efficiency detector (e.g. film), and the lack of removal of residual scatter-induced image blur. Alignment of the third configuration is performed with continuous recording media CRM absent, by using a possibly movable zoom-focus TV camera (not shown) located some distance below grating G3 to examine the lower side of the fluor by viewing grating G3 from below and imaging its transmitted light, thereby imaging the moiré pattern formed by pattern O and grating G3.

The fourth method and configuration for obtaining refractive-index-gradient contrast is by a modification to the arrangement of FIG. 3a, in which media CRM is deleted altogether. Instead, this method then images the light emitted by fluor FL through grating G3 from the lower side of G3 with a zoom-focus TV camera, similar to that used by the third method for alignment. This fourth method and configuration may operate with or without the camera's detector pixels phase matched by the camera's focusing optics to grating G3, and correspondingly to pattern P. When the camera's pixels are not phase matched, this fourth method obtains the same image as that of the third method, and thus provides no subtraction of scatter-induced blur. Without phase matching, the TV camera acts similarly to media CRM. To further obtain phase matching of the camera's pixels (to allow element-selective imaging and/or scatter-induced blur subtraction), however, the TV camera must be carefully aligned (and focused) so that its internal retina pixels are effectively aligned as with the configuration of FIG. 1. Doing so, however, generally limits the camera's field of view to image only a small area. A larger image may be obtained by positionally scanning the camera step-wise and stitching together a final large image. However, use of such a scheme is probably impractical for medical imaging, since realignment of the video camera must be accomplished between each step of the scan, during which operation object BDY should be removed and then accurately repositioned within the apparatus for the next x-ray exposure step.

In a fifth method for obtaining refractive-index-gradient contrast, the continuous recording media CRM used in the configuration of FIG. 3a is effectively given a pixel structure (and period) by a post-exposure scanning of media CRM, whereby also scatter-induced blur may be subtracted, and/or element-selective imaging performed. For a v>1 configuration, grating G3 has a planform layout similar to one shown in FIGS. 11a–d. For operation at v=1 with scatter-induced blur subtraction, grating G3 is configured with the 2D-periodic x-y planform similar to that of a wide-mesh square woven screen, similar to the configuration shown on FIG. 8b, but with a very large duty-cycle $s/a=s_3/a_3$ (0.9–0.95). It then acts both as an intermediate reference grid that provides an observable moiré pattern for alignment of and to gratings G1 and G2, and thus to patterns P and O, as well as a tracking guide for scanning media CRM. Alignment is via the same method (via below mounted TV camera with CRM absent) used with the third and fourth methods. After an x-ray exposure, a readout scan of media CRM is performed by placing media CRM within a read-out apparatus wherein it is then raster-scanned (with a raster period equal to $a_D$) by a laser. The film's light transmission or the stimulated luminescence plate's luminescence is recorded as a function of laser position within the raster. Phase-lock tracking of the scanning laser's raster to the media's imprinted pixel array is obtained by following the grating G3 shadows on media CRM via a feedback system to control the scanning motion of the read-out laser, thereby to follow the imprinted pixel rows (or columns) on the media, in a manner similar to that used in a CD player or computer disk drive. It is also feasible that a stimulated luminescence plate can be made at least partially transparent, so that the laser read-out apparatus then may be incorporated as part of the whole detector, whereupon laser-scanning may be done in-situ from the lower side of CRM, and removal of media CRM from contact with grating G3 (with possible misalignment resulting therefrom) is then no-longer needed.

The sixth method for obtaining refractive-index-gradient contrast, uses the detector configuration of FIG. 3b and provides a means (slightly crudely) for subtraction of scatter-induced blur and/or for performing element-selective imaging. FIG. 3b shows an elevation x-z view of detector screen DS to be used under this method at the position of detector D in FIG. 1. Here, detector screen DS is comprised of structured fluor SFL, and light reflector RFL, both mounted on substrate SUB. The configuration of FIG. 3b uses two separate independent continuous recording media, CRM-1 and CRM-2, that are separated by a thin opaque sheet, OS and a second fluor FL. In the configuration of FIG. 3b, structured fluor SFL is spatially periodic, absorbs x-rays, is partly opaque to light (at least on its upper side via the additional periodic structure provided by RFL), and also acts as grating G3. If desired, very thin vertical extensions of the light reflecting material of light reflector RFL may be added to the vertical side walls of the finite thickness portions of structured fluor SFL to prevent lateral migration of light emitted by structured fluor SFL. Structured fluor SFL, light reflector RFL and substrate SUB remain fixed within the apparatus. These fixed components are aligned via the use of a below-mounted upward-pointing TV camera, in a manner similar to that used for the detector configuration of FIG. 3a.

Media CRM-1 and CRM-2, along with fluor FL and opaque sheet OS are removable from the apparatus. During alignment, they are absent. During an x-ray exposure, they are in direct contact with structured fluor SFL (also grating G3), as shown in FIG. 3b. Structured fluor SFL creates light by absorption of x-rays, which, in turn produce a contact image on media CRM-1, in a manner similar to that of the third method. The finite thickness portions of structured fluor SFL act as b-labeled pixels. Structured fluor SFL is thus aligned within the apparatus so that its finite-thickness portions are phase matched with BRIGHT fringes. Since structured fluor SFL must absorb x-rays in order to produce light, it casts a periodic shadow in the x-rays that arrive at the upper face of media CRM-1. These x-rays incident between the fluor portions are negligibly absorbed by media CRM-1 and opaque sheet OS, and thus propagate downward to fluor FL, wherein they are absorbed and produce light. Given the spatially periodic shadow structure of the x-ray, the light generation in fluor FL also has a spatially periodic structure. This periodically structured light emitted by fluor FL is contact imaged onto media CRM-2, that then records a d-area contact-image, in a manner similar to that of the third method. Media CRM-1 and CRM-2 are thus imprinted respectively with an equivalent of a b-pixel image and a d-pixel image. (Alternatively, if desired, the alignment of structured fluor SFL may be to DARK fringes, whereupon the roles of CRM-1 and CRM-2 are then simply interchanged.) Following, exposure media CRM-1 and CRM-2 are removed from the apparatus and opaque sheet OS and fluor FL are discarded.

Given the two analog images recorded on media CRM-1 and CRM-2, a subtraction now may be performed. One method for doing so is to transfer both media, one at a time, to a read-out apparatus, as is used with the fifth method, and perform the subtraction digitally. Alternatively, an analog subtraction may be performed without scanning, if the media is semi-transparent film. To do so, one of the two films (CRM-1 or CRM-2) is developed as a negative image and one as a positive image (e.g. by making a secondary contact print from one of them). The resulting positive and negative film images are then contacted and registered with each other. (Corner reference fiducials also may be imprinted on the film via the x-ray exposure to aid registration, if desired.) Under back-illumination, the registered pair of films then displays the desired subtracted image.

V.7 Positionally scanned configurations

The ability of the Invention to obtain an image with only one x-ray exposure is given above as one of its important features. However, the use of a step-wise sequence of exposures provides additional design flexibility and applications for the Invention. The Invention allows such a sequence to be made rapidly without apparatus realignment being required between steps of the sequence. FIGS. 4a and 5 show overall configurations for the Invention wherein the apparatus of FIG. 1 is positionally scanned rotationally in a step-wise fashion. (Positionally scanned embodiments with a linear translational scan of the apparatus are also possible.) During said scan the whole apparatus, including focal spot S, gratings G1 and G2 (and G3, if present) and detector D is rotated through a sequence of orientations about axis SCN, parallel to the y-axis, while object BDY remains stationary. A sequence of x-ray exposures is obtained, when the apparatus is stationary during this sequence of orientations. Since no apparatus realignment is needed between steps, the exposures may be taken in reasonably rapid sequence. FIG. 4a is drawn using the detector sparse array configuration of FIG. 4b; however, it also may be used with the sparse array configuration of FIG. 4d. The sparse detector arrays of the configurations of FIGS. 4b,d then allow the use of small inexpensive CCD arrays, to create the associated large mosaic layouts of FIGS. 4c,e, respectively.

The configuration of FIG. 4a consists of multiple replications of the configuration of FIG. 1 into a fanned periodic arrangement of pyramidal geometries. X-rays that form an image within each such pyramidal replication are confined within each of the 2D-fanned replications to propagation within a four-sided canted pyramid. All such canted pyramids have the common focal spot S at their apexes, which provides x-ray illumination for all of them. Each canted pyramid has an associated small CCD array as its base. All such pyramidal replications have the same parameters as each other, whereupon all gratings G1 and G2 (and G3, if used) and CCD arrays occupy associated common planes. Thus, grating(s) G1 occupy plane G1P, gratings G2 occupy plane G2P, and the array of detector arrays occupies plane DP. Each pyramid has its own axis $C_L$ that passes through focal spot S and the center of each associated CCD, and these various axes $C_L$ are no-longer perpendicular to these planes, as they are with the geometry of FIG. 1. Instead, all such axes $C_L$ fan out in 2D from the common point on focal spot S. (In an alternative embodiment the various axes $C_L$ are all each locally perpendicular to the associated detector array and grating, and the gratings are configured in a piece-wise planar arrangement.) The rotational scan of the apparatus shown in FIG. 4a is such that object BDY (not shown in FIG. 4a) passes between planes G2P and DP.

Given a requirement for CCD edge connections, the array of CCD arrays occupying the common detector plane DP is sparse, i.e. there are gaps between the CCD arrays. The array of grating G2 segments thus formed (shown on FIG. 4a on grating G2 plane G2P) is also sparse, although the array of grating G1 segments may or may not be sparse. The whole arrangement is then scanned in steps across stationary object BDY, whereupon a sequence of sparse image mosaic segments is recorded for each step. The step-wise scan is rotational on a y-directed axis SCN that passes through focal spot S. The final image is then stitched together (as discussed in Sect. V.5) to form the (no-longer sparse) final image mosaic.

As with the image mosaic discussed in Sect. V.5, it is necessary to maintain accurate phase continuity of the pixel periods and parallelism of the individual CCD's with each other. Said phase continuity and parallelism may be obtained by assembling the various CCD arrays on a large single Ronchi ruling via methods outlined in Sect. V.5. If grating G3 is included, its sparse array of grating segments is similar to the layout shown on FIG. 4b, and it may be used in place of the Ronchi ruling. Similar phase continuity and parallelism is obtained for the individual grating G2 segments (and G3 segments) that all occupy common planes by fabricating said grating segments all on the same wafer as part of their common lithography (see, Sect. V.4). To prevent additional object dosage, gaps between the grating segments on each such grating plane are covered with a thick x-ray absorbing layer XAL, as shown on FIG. 4a, whether or not grating G2 is a binary absorption or phase grating. Thus, within each such a pyramid, each grating G2 segment is surrounded by said layer XAL, to provide a sparse periodic array of x-ray transmitting windows, so that the geometric shadow from focal spot S made by said windows illuminates only the associated CCD detector array.

All such pyramidal replications may be aligned at the same time. A single alignment laser illuminates with laser light each pyramid via x-ray transmitting mirror XTM and 2D-periodic diffraction grating ODF that diffracts the laser light. Diffraction grating ODF is located on laser optical axis LCL at the point of reflection of focal spot S. Optical diffraction grating ODF then replicates, via Fraunhofer diffraction, a fanned set of laser-light diffraction orders, wherein each such diffraction order now propagates along each of the various fanned $C_L$ axes, so that each order acts the same as the others for each replication. With careful design and alignment of grating ODF, the three orders $FD_0$ and $FD_{\pm 1}$ generated by each order incident on grating G1 from grating ODF then passes through different adjacent grating G2 segments.

Two different layouts of CCD arrays on the detector plane of FIG. 4a are useful. One configuration, is shown in FIG. 4b. It consists of two columns of CCD arrays, with said columns aligned along the y axis. As shown on FIG. 4b, even numbered arrays $D_2$, $D_4$, . . . occupy the left-hand column, while odd numbered arrays $D_1$, $D_3$, . . . occupy the right-hand column. The scanning motion moves all detectors from left to the right, in an incremental fashion, across object BDY. FIG. 4c shows the sequence of positions occupied by each detector during pauses in the incremental scan wherein the detectors are stationary, and an x-ray exposure is taken. Thus, detector array $D_1$ first occupies position $D_1(1)$, next occupies position $D_1(2)$, and so forth. Similarly, detector $D_2$ first occupies position $D_2(1)$, next occupies position $D_2(2)$, and so forth. Given the staggered positioning of these detectors, as shown on FIG. 4b, then a sequence of many such steps provides the set of positions shown in FIG. 4c so that all portions of the final contiguous mosaic image are covered by at least one detector during the scan. The detectors are positioned on the detector plane and the rotational scan step size is chosen so that said covering has a small overlap (shown highly exaggerated in FIG. 4c) of detector positions by a few detector pixels at the detector edges. Said overlap is kept minimal by a careful layout of the arrays and a careful choice of the step size. Overlapped image segments may be averaged together when the final image mosaic is stitched together.

The detector array configuration of FIG. 4b requires many steps in its scan to cover the image. The scan can be shortened by instead using the detector plane layout of FIG. 4d. It differs from that of FIG. 4b. in that it contains many columns of detector arrays. FIG. 4d shows only the upper left hand corner of the layout, which extends to the right and downward off of the Figure. FIG. 4e shows the sequence of positions occupied by each detector during pauses in the incremental scan wherein the detectors are stationary and an exposure is obtained. Unlike the arrangement of FIG. 4b, a scan using the layout of FIG. 4d is completed with only three steps. Thus, detector $D_1$ sequentially occupies positions $D_1(1)$, $D_1(2)$, and $D_1(3)$. Similarly, detector $D_2$ sequentially occupies positions $D_2(1)$, $D_2(2)$, and $D_2(3)$. Given the sparse checkerboard positioning of detectors shown on FIG. 4d, it is seen that the area covered at $D_1(3)$ overlaps that of $D_2(1)$. Thus, a sequence of only three steps provides the set of positions shown in FIG. 4e, and the whole image area is again covered by at least one detector during the three-step scan. As with the arrangement of FIG. 4b, the positional overlap of the array positions is kept minimal.

Figure 2:
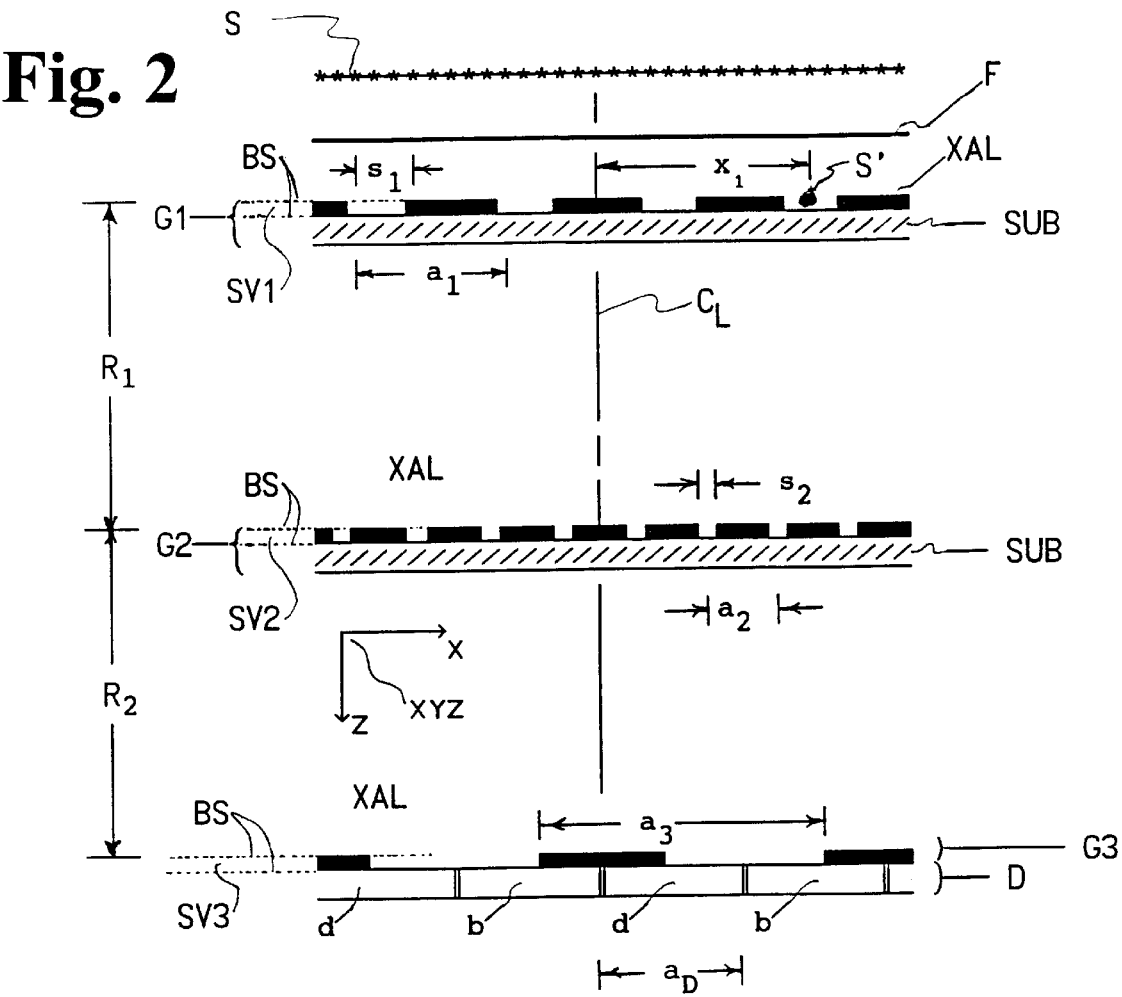
FIG. 2 shows a horizontally expanded elevation (x-z) view of a thin slice through the Invention taken along x-ray axis $C_L$, giving fine details of gratings G1, G2 and G3. The Figure is not drawn to scale. While anode A is sloping with respect to the z-axis in FIG. 1, here the horizontal scale expansion renders it as nearly horizontal. Grating substrate SUB and x-ray absorbing layer thickness are also highly exaggerated. X-ray point source S', located on grating G1 at a distance $x_1$ from $C_L$, is a fictitious source. Point source S' is used in Sects. III.2–III.5 for calculating patterns Q, Q', P and P'. The configuration shown is for amplitude-interferometric mode, and optional grating G3 is shown present, configured at u=2, v=2. Grating G3 is shown laminated directly to the surface of detector D. Portions of slab-volumes SV1, SV2, and SV3 are also shown as the volumes between three mutually-parallel pairs of substantially planar bounding surfaces BS (shown as dotted lines). When grating G3 is absent, the front surface of detector D occupies slab-volume SV3.

The configuration shown FIG. 5 is appropriate for a CT (or CAT) scan, wherein a 3D image of object BDY may be synthesized via computed tomography [Meredith and Massey, 1977; Hendee, 1995]. Suitable parameters for it are given as Embodiments 5 and 7, discussed in Sect. V.1. It can use either a scanned single detector array, as per FIG. 1, or with a scanned segmented detector array, as per FIGS. 4a,b,d. In FIG. 5, the whole apparatus, including gratings G1, G2, (and G3, if included), x-ray tube T and detector D is scanned rotationally around stationary object BDY, about an axis SCN passing through object BDY. The detector's x-y 2D periodic planar pixel array extends in the y-direction (perpendicular to the plane of FIG. 5), parallel to axis SCN for some distance (whether detector D is either a single large 2D-periodic array or sparse array of small 2D-periodic arrays). To access portions of object BDY not included by a single rotational scan, the scan is augmented by an additional axial positional scan translationally along axis SCN, in a manner similar to that of a usual CT or CAT scanning x-ray system. The arrangement of FIG. 5 then differs from that of a usual CT scan machine in that the latter generally uses rather tight source collimation to minimize x-ray scatter by object BDY, e.g. by scanning a thin fan shaped x-ray beam, confined to a plane that is perpendicular to the rotation axis, or a pencil shaped x-ray beam [Hendee, 1995, FIG. 2]. However, the elimination of scatter-induced blur by the Invention's added components, all simultaneously co-aligned and rotating together, allows a very much larger number of paths through object BDY to be recorded simultaneously by the Invention (relative to the number simultaneously recorded by a normal CT scanning apparatus). The total time required for completing a scan is then considerably reduced by the Invention.

VI. Industrial applicability

The Invention has a wide range of application within the radiological and radiographical imaging industry, in general. It is ideally suited for a variety of applications in the medical imaging industry. It may be used for diagnostic imaging purposes and for interventional radiography. In particular, it is useful for imaging biological soft-tissue, and for mammography, angiography, and for whole-body CT scans. It may be used to image radio-passive (rather than radio-active) tracers in diseased tissue.

What is claimed is:

1. Apparatus for producing an image that describes the internal structure of an object, comprising
    a source of x-rays,
    an x-ray image detector;
    improved by its further comprising
        three very-thin slab-shaped volumes, SV1, SV2, and SV3, each with substantially-planar slab faces oriented relative to each other to be substantially-mutually-parallel, and each containing an associated very-thin material structure that interacts with x-rays, and
        means for limiting the energy-bandwidth of detected x-rays;
        wherein said three contained structures are positioned between said source and said detector so that x-rays from said source propagate in the sequential order, first through said structure within slab-volume SV1, next through said structure within slab-volume SV2, next through said object, next into slab-volume SV3, and then are detected; and
        wherein the directions x and y are both parallel to the substantially-parallel faces of said three slab-volumes; and
        wherein said material structures within slab-volumes SV1, and SV2 are fabricated to be spatially-periodic within their associated useful x-direction widths, respectively with associated spatial periods $a_{1x}$ and $a_{2x}$, and oriented within the apparatus so that each structure's respective periodicity-direction that is associated with said respective period lies in the direction x; and
        wherein the perpendicular distance between slab-volume SV1 and slab-volume SV2 is $R_1$ and the perpendicular distance between slab-volume SV2 and slab-volume SV3 is $R_2$; and
        wherein b, q, and p are positive integers; and
        wherein $a_{1x}$ is accurately related to $a_{2x}$ by $$a_{1x} = b\ a_{2x}(R_1+R_2)(q\ p\ R_2)^{-1};$$

and
        wherein, when said object is absent, and for x-rays with at least one specific energy value that lies within said energy-bandwidth, and throughout the associated useful x-direction width of said material structure within slab-volume SV3, then the two structures respectively within slab-volumes SV1 and SV2 acting together but not separately project onto slab-volume SV3 an x-ray intensity distribution that is substantially spatially-periodic in direction x with the spatial period $a_{Px}$ and has a substantial spatial intensity variation; and
        wherein when the greatest common integer divisor of b and q is 1, then the period $a_{Px}$ is accurately related to $a_{2x}$ by $$a_{Px} = a_{2x}\ (R_1+R_2)(q\ p\ R_1)^{-1}.$$

2. Apparatus of claim 1 wherein, when said object is absent, and for said x-rays with said specific energy value that lies within said energy-bandwidth, then each of the two structures respectively within slab-volumes SV1 and SV2, acting alone with the other absent, projects onto slab-volume SV3 an x-ray intensity distribution that is different from said spatial distribution projected by said two structures acting together; and
    wherein any associated residual spatial periodicity in direction x of either of said two distributions projected by said two structures acting alone has a diminished spatial intensity variation relative to said spatial distribution projected by said two structures acting together, and/or has a dominant spatial period that is different from $a_{Px}$.

3. Apparatus of claim 1 wherein b and q are both equal to 1.

4. Apparatus of claim 1 wherein slab-volume SV1 is located near said x-ray source.

5. Apparatus of claim 1 further comprised of means for controlling the energy spectrum of x-rays that are projected onto slab-volume SV3.

6. Apparatus of claim 1 wherein a material structure within a slab-volume is spatially periodic with the spatial period $a_{SV}$ in an associated periodicity-direction when the effects of said structure's x-ray interaction properties are left substantially unchanged except at said structure's edges if said structure is spatially translated in said associated periodicity-direction by a distance that is an integral multiple of the period $a_{SV}$; and wherein said periodicity-direction for said structure provides a locally minimum spatial period measured in some fixed direction under an infinitesimal rotation of said structure within its containing slab-volume in which said structure's periodicity-direction rotates relative to said fixed direction with an axis of said infinitesimal rotation that is perpendicular to said substantially-planar mutually-parallel slab faces.

7. Apparatus of claim 6 wherein when a material structure within a slab-volume is spatially periodic with the spatial period $a_{SV}$, then said structure is also spatially periodic with a longer spatial period that is an integral multiple of $a_{SV}$.

8. Apparatus of claim 7 wherein the periods $a_{1x}$ and $a_{2x}$ are the shortest fabricated periods for which the respective structures within slab-volumes SV1 and SV2 are spatially-periodic.

9. Apparatus of 8 wherein said source emits x-rays dominantly from a spatially small but finite-size spatial region S, and wherein $W_S$ is the approximate x-direction width of said finite-size spatial region S within which said dominant emission of x-rays occurs, and wherein the distance $a_{1x}$ is substantially smaller than the distance $W_S$.

10. Apparatus of claim 1 further comprised of a thin substrate that provides structural support for a spatially-periodic material structure within a slab-volume;

wherein said substrate is made from a material that is minimally absorbing of light and x-rays, and wherein said substrate has a substantially constant thickness.

11. Apparatus of claim 1 wherein the directions x and y are substantially perpendicular to each other.

12. Apparatus of claim 1 wherein said structure within slab-volume SV1 is fabricated and configured to be additionally spatially-periodic within its associated useful y-direction width with period $a_{1y}$ and with the associated additional periodicity-direction lying in the direction y; and wherein said structure within slab-volume SV2 is fabricated and configured to be additionally spatially-periodic within its associated useful y-direction width with period $a_{2y}$ and with the additional associated periodicity-direction lying in the direction y; and wherein $a_{1y}$ is accurately related to $a_{2y}$ by $$a_{1y} = b\ a_{2y}(R_1+R_2)(q\ p\ R_2)^{-1};$$

and wherein, when said object is absent, and for x-rays with at least one energy value that lies within said energy-bandwidth and throughout the associated useful y-direction width of said material structure within slab-volume SV3, then the structures within slab-volumes SV1 and SV2 acting together but not separately project onto slab-volume SV3 an x-ray intensity distribution that is additionally substantially spatially-periodic in direction y with the spatial period $a_{Py}$; and wherein when the greatest common integer divisor of b and q is 1, then the period $a_{Py}$ is accurately related to $a_{2y}$ by $$a_{Py} = a_{2y}(R_1+R_2)(q\ p\ R_1)^{-1}.$$

13. Apparatus of claim 12 wherein $a_{2y}$ is approximately equal to $a_{2x}$.

14. Apparatus of claim 12 wherein a material structure within a particular slab-volume is spatially-periodic with the spatial period $a_{SVx}$ in the associated periodicity-direction x and is also spatially-periodic with the spatial period $a_{SVy}$ in the associated periodicity-direction y; and wherein $x_{SV}$ and $y_{SV}$ are position coordinate values associated respectively with directions x and y that specify points on said particular spatially-periodic structure; and wherein $f(t;a_{SV})$ is a periodic function of dummy variable t that is parameterized by the period $a_{SV}$; and wherein j is an arbitrary integer; and wherein the function $f(t;a_{SV})$ has the periodic property given by $$f(t;a_{SV}) f(t+ja_{SV};a_{SV});$$

and wherein g is a constant; and wherein the spatial dependence of the transmission properties of x-rays through particular said spatially-periodic material structure at coordinate values $x_{SV}$ and $y_{SV}$ can be evaluated approximately by using the function $$g \pm f(x_{SV};a_{SVx}) f(y_{SV};a_{SVy});$$

and wherein, when said particular slab-volume is slab-volume SV1, then the associations $a_{SVx}=a_{1x}$ and $a_{SVy}=a_{1y}$ hold; and wherein, when said particular slab-volume is slab-volume SV2, then the associations $a_{SVx}=a_{2x}$ and $a_{SVy}=a_{2y}$ hold.

15. Apparatus of claim 12 wherein a material structure within a particular slab-volume is spatially-periodic with the spatial period $a_{SVx}$ in the associated periodicity-direction x and is also spatially-periodic with the spatial period $a_{SVy}$ in the associated periodicity-direction y; and wherein $x_{SV}$ and $y_{SV}$ are position coordinate values associated respectively with directions x and y that specify points on said particular spatially-periodic structure; and wherein $f(t;a_{SV})$ is a periodic function of dummy variable t that is parameterized by the period $a_{SV}$; and wherein j is an arbitrary integer; and wherein the function $f(t;a_{SV})$ has the periodic property given by $$f(t;a_{SV}) = f(t+ja_{SV};a_{SV});$$

and wherein g is a constant; and wherein the spatial dependence of the transmission properties of x-rays through said particular spatially-periodic material structure at coordinate values $x_{SV}$ and $y_{SV}$ can be evaluated approximately by using the function $$g \pm f(x_{SV};a_{SVx}) f(y_{SV};a_{SVy}) \pm f[x_{SV}+(a_{SVx}/2);a_{SVx}] f[y_{SV}+(a_{SVy})];$$

and wherein, when said particular slab-volume is slab-volume SV1, then the associations $a_{SV}=a_{1x}$ and $a_{SVy}=a_{1y}$ hold; and wherein, when said particular slab-volume is slab-volume SV2, then the associations $a_{SVx}=a_{2x}$ and $a_{SVy}=a_{2y}$ hold.

16. Apparatus of claim 1 wherein the structure within slab-volume SV1 is made from a material that absorbs x-rays and is configured so that its structure acts as a spatially-periodic x-ray mask.

17. Apparatus of claim 1 wherein the structure within slab-volume SV2 is made from a material that absorbs x-rays and is configured so that its structure acts as a spatially-periodic x-ray mask.

18. Apparatus of claim 1 wherein the two structures respectively within slab-volumes SV1 and SV2 are each made from a material that absorb x-rays and are each configured so that their structures act as spatially-periodic x-ray masks; and wherein, when said object is absent, and for said x-rays with said specific energy value that lies within said energy-bandwidth, then said two structures acting together but not separately project said spatially periodic x-ray intensity distribution onto slab-volume SV3 as a geometric x-ray shadow.

19. Apparatus of claim 1 wherein, when said object is absent, and for said x-rays with said specific energy value that lies within said energy-bandwidth, then the two structures respectively within slab-volumes SV1 and SV2 acting together but not separately project said spatially periodic x-ray intensity distribution onto slab-volume SV3 by wave interference of the electromagnetic waves associated with said x-rays via the fractional Talbot effect; and wherein the Talbot effect is special case of the fraction Talbot effect; and wherein the formation of spatially-periodic geometric shadows is a further special case of the Talbot effect.

20. Apparatus of claim 19 wherein n and m are positive integers; and wherein the greatest common integer divisor of n and m is 1; and wherein the average energy of said energy-bandwidth-limited x-rays projected onto slab-volume SV3 is $E_X$; and wherein the product hc is Planck's constant times the speed of light; and wherein $a_{2x}$ is approximately equal to the value given by $$(m/n)^{1/2}(hc\ R_1\ R_2/E_X)^{1/2}(R_1+R_2)^{-1/2}.$$

21. Apparatus of claim 19 wherein the energy spectrum of said energy-bandwidth-limited x-rays includes a multiplicity of component energy values; and wherein the average energy of said bandwidth limited x-rays projected onto slab-volume SV3 is $E_X$; and wherein said multiplicity of component energy values includes component energy values that are both substantially above and substantially below $E_X$; and wherein said multiplicity of component energy values may be comprised of a continuum of energy values; and wherein, when said object is absent, then the spatial distribution of x-ray intensities projected onto slab-volume SV3 by x-rays with component energy values substantially above $E_X$ is substantially different from the spatial distribution of x-ray intensities projected onto slab-volume SV3 by x-rays with component energy values substantially below $E_X$.

22. Apparatus of claim 21 wherein $E_X$ is approximately equal to the energy of an x-ray absorption edge of some chemical element, and wherein said chemical element is present within said object, and wherein said presence of said chemical element within said object is anisotropic.

23. Apparatus of claim 1 wherein a material structure within a selected slab-volume is divided into discrete portions; and wherein each of said discrete portions of material within said slab-volume has an associated finite surface-projected area formed by perpendicularly projecting boundaries of said discrete portion on to a slab face of said selected slab-volume; and wherein each of said discrete portions of material within said selected slab-volume has a thickness measured perpendicularly to said slab face that is approximately locally constant throughout said associated surface-projected area; and wherein the thicknesses of discrete portions encountered in passing spatially along a straight line through various discrete portions step in a spatially periodic fashion among different discrete values; and wherein said different discrete values include at least one significant finite value and possibly, but not necessarily, include the value approximate-zero; and wherein the thickness of each said discrete portion provides an approximately locally-constant magnitude for the interaction of x-rays with said material when said x-ray propagation is along a single very thin path that is incident on a discrete portion's associated surface-projected area; and wherein said possible approximately zero-thickness portions of material provide negligible interaction with x-rays when said x-rays are incident along said very thin path on an approximately zero-thickness portion's associated surface-projected area.

24. Apparatus of claim 23 wherein slab-volume SV2 is a selected slab-volume that is divided into discrete portions; and wherein said structure within slab-volume SV2 is made from a material that refracts x-rays; and wherein said refraction induces a phase shift of the electromagnetic field amplitudes of x-rays incident on slab-volume SV2 that occurs in addition to the phase shift experienced by propagation of said x-rays the same distance in vacuum; and wherein said phase shift may be negative; and wherein said phase shift for x-rays incident on a discrete portion's associated surface-projected area is approximately locally constant and approximately proportional to the associated thickness of said discrete portion; and wherein the quantity $m_*$ is an integer that is greater than 1; and wherein the quantity $n_*$ is a positive integer; and wherein the integers $n_*$ and $m_*$ have a greatest common integer divisor of 1; and wherein there is an imaginary line-segment with the length $a_{2x}$ oriented in the direction x on slab-volume SV2 that thereby spans one x-direction period of said structure within slab-volume SV2; and wherein said x-directed line-segment starts and ends on boundaries of said surface-projected areas; and wherein said x-directed line-segment crosses through $m_*$ of said surface-projected areas; and wherein, in crossing surface-projected area boundaries between associated discrete portions, said x-directed line-segment is divided approximately equally into $m_*$ x-directed line-segment fractions by said area boundaries; and wherein each of said x-directed line-segment fractions has approximately the length $a_{2x}/M_*$; and wherein said crossed associated discrete portions are numbered sequentially and monotonically starting with the value 0 by the associated integer index $j_x$ in passing from one end of said x-directed line-segment to the other end; and wherein said indices $j_x$ form a monotonic integer sequence starting at the value 0 and ending with the value $m_*-1$; and wherein index $j_x$ assumes only discrete values that are greater than $-1$ and are less than $m_*$; and wherein index $j_x$ assumes any one such discrete value once and only once in said sequence; and wherein each value of index $j_x$ has an associated accompanying index $k_x$; and wherein said association of index $j_x$ with index $k_x$ associates index $k_x$ with said numbered discrete portion; and wherein said accompanying index $k_x$ also has only $m_*$ possible discrete values; and wherein said sequence of values for index $j_x$ and said association of each index $j_x$ with index $k_x$ provides an associated sequence of values for $k_x$; and wherein the set of discrete values assumed by the index $k_x$ is the same set of discrete values assumed by the integer $j_x$ so that index $k_x$ assumes only discrete values that are greater than $-1$ and are less than $m_*$, and so that index $k_x$ assumes any one value within said set once and only once; and wherein the relationship between $k_x$ and $j_x$ is $j_x=[(n_*k_x)$ modulo $m_*]$; and wherein said relationship between $k_x$ and $j_x$ provides that said sequence of values for $j_x$ and said associated sequence of values for $k_x$ are either the same sequence as each other or are a permutation of each other; and wherein each and every discrete portion of said structure within slab-volume SV2 has an associated pair of indices $j_x$ and $k_x$ that are arranged so that the values of the indices $j_x$ and $k_x$ are associated with said discrete portions and have a spatially periodic arrangement, and so that the associated sequences of $j_x$ and $k_x$ values, encountered on any two such x-directed imaginary line-segments that are each of length $a_{2x}$ and are each starting and ending on boundaries of said surface-projected areas, are the same as each other when said two x-directed line-segments are aligned on the same straight line and spaced from each other by a distance that is an integral multiple of $a_{2x}$; and wherein the product hc is Planck's constant times the speed of light; and wherein the quantity $r_*$ is a chosen non-zero integer; and wherein the energy $E_*$ is defined by $$E_* = (m_*/n_*) hc\, R_1 R_2\, (R_1+R_2)^{-1} a_{2x}^{-1};$$

and wherein $\phi_*$ is a spatially constant phase shift.

25. Apparatus of claim 24 wherein, when x-rays with the approximate energy $E_*$ propagate along a single very thin path through slab-volume SV2, and when said very thin path is through a surface-projected area with associated index $k_x$, then said x-rays obtain a value for said refraction-induced phase shift that occurs in addition to the phase shift experienced in vacuum has a value that is approximately equal to the value given in radians by $\pi\, n_*\, r_*\, [k_x - (k_x^2 m_*^{-1})] - \phi_*$.

26. Apparatus of claim 24 wherein the integer $m_*$ is even, and wherein the value of $\phi_*$ in radians is approximately equal to $$\pi\, n_*\, r_*\, m_*/4.$$

27. Apparatus of claim 24 wherein the integer $m_*$ is odd, and wherein the value of $\phi_*$ in radians is approximately equal to $$\pi\, n_*\, r_*\, (m_*-1)^2 (4m_*)^{-1}.$$

28. Apparatus of claim 24 wherein $a_{2x}$ is approximately equal to $$(m_*/n_*)^{1/2} (hc\, R_1\, R_2/E_X)^{1/2} (R_1+R_2)^{-1/2}.$$

29. Apparatus of claim 24 wherein n is a positive integer, and wherein $a_{2x}$ is approximately equal to $$(m_*/n)^{1/2} (hc\, R_1\, R_2/E_X)^{1/2} (R_1+R_2)^{-1/2}.$$

30. Apparatus of claim 24 wherein n is a positive integer, and wherein $a_{2x}$ is approximately equal to $$(2/n)^{1/2} (hc\, R_1\, R_2/E_X)^{1/2} (R_1+R_2)^{-1/2}.$$

31. Apparatus of claim 24 wherein said structure within slab-volume SV2 is fabricated and configured to be additionally spatially-periodic within its associated useful y-direction width with period $a_{2y}$ and with the additional associated periodicity-direction lying in the direction y; and wherein there is an imaginary line-segment with the length $a_{2y}$ oriented in the direction y on slab-volume SV2 that thereby spans one y-direction period of said structure within slab-volume SV2; and wherein said y-directed line-segment starts and ends on boundaries of said surface-projected areas; and wherein said y-directed line-segment crosses through $m_*$ of said surface-projected areas; and wherein, in crossing surface-projected area boundaries between associated discrete portions, said y-directed line-segment is divided approximately equally into $m_*$ y-directed line-segment fractions by said area boundaries; and wherein each said y-directed line-segment fraction has approximately the length $a_{2y}/m_*$; and wherein said crossed associated discrete portions are numbered sequentially and monotonically starting with the value 0 by the associated integer index $j_y$ in passing from one end of said y-directed line-segment to the other end; and wherein said indices $j_y$ form a monotonic integer sequence starting the value 0 and ending with the value $m_*-1$; and wherein index $j_y$ assumes only discrete values that are greater than $-1$ and are less than $m_*$; and wherein index $j_y$ assumes any one such discrete value once and only once in said sequence; and wherein each value of index $j_y$ has an associated accompanying index $k_y$; and wherein said association of index $j_y$ with index $k_y$ associates index $k_y$ with said numbered discrete portion; and wherein said accompanying index $k_y$ also has only $m_*$ possible discrete values; and wherein said sequence of values for index $j_y$ and said association of each index $j_y$ with index $j_y$ provides an associated sequence of values for $k_y$; and wherein the set of discrete values assumed by the index $k_y$ is the same set of discrete values assumed by the integer $j_y$, so that index $k_y$ assumes only discrete values that are greater than $-1$ and are less than $m_*$, and so that index $k_y$ assumes any one value within said set once and only once; and wherein the relationship between $k_y$ and $j_y$ is $j_y=[(n_* k_y)$ modulo $m_*]$; and wherein said relationship between $k_y$ and $j_y$ provides that said sequence of values for $j_y$ and said associated sequence of values for $k_y$ are either the same sequence as each other or are a permutation of each other; and wherein each and every discrete portion of said structure within slab-volume SV2 each has an additional associated pair of indices $j_y$ and $k_y$, so that each and every discrete portion of said structure within slab-volume SV2 thereby has four associated indices $j_x$, $k_x$, $j_y$, and $k_y$; and wherein the indices $j_y$ and $k_y$ are arranged so that the values of the indices $j_y$ and $k_y$ are associated with said discrete portions in a spatially periodic arrangement, and so that the associated sequences of $j_y$ and $k_y$ values, encountered on any two such y-directed imaginary line-segments that are each of length $a_{2y}$ and are each starting and ending on boundaries of said surface-projected areas, are the same as each other when said two y-directed line-segments are aligned on the same straight line and spaced from each other by a distance that is an integral multiple of $a_{2y}$; and wherein, when x-rays with the approximate energy $E_*$ propagate along a single very thin path through slab-volume SV2, and when said very thin path is through a surface-projected area with associated indices $k_x$ and $k_y$, then said x-rays obtain a value for said refraction-induced phase shift that occurs in addition to the phase shift experienced in vacuum has a value that is approximately equal to the value given in radians by $$\pi\, n_*\, r_*[k_x-(k_x^2\, m_*^{-1})+k_y-(k_y^2\, m_*^{-1})]-2\phi_*.$$

32. Apparatus of claim 1 wherein v is a positive integer.

33. Apparatus of claim 32 wherein said x-ray image detector is comprised of a spatially-periodic array of detector-pixels whose front surface is substantially planar; and wherein the detector-pixel front surfaces interact with x-rays in a manner that results in the detection and measurement of the spatial distribution of the intensity of said x-rays incident on said image detector; and wherein said array of detector-pixels is spatially periodic in direction x so that centroids of the front surfaces of adjacent detector-pixels within said spatially-periodic array are periodically spaced from each other in the direction y by the distance $a_{Dx}$; and wherein u is a positive even integer.

34. Apparatus of claim 33 wherein $a_{Dx}$ is accurately related to $a_{Px}$ by $a_{Dx}=(v/u)\, a_{Px}$; and wherein the spatial phase of said spatially periodic x-ray intensity distribution projected, when said object is absent, onto slab-volume SV3 with period $a_{Px}$ is carefully aligned with the phase of said detector-pixel array.

35. Apparatus of claim 33 wherein u equals 2 and v equals 1.

36. Apparatus of claim 33 wherein the front surface of said spatially-periodic array of detector-pixels is said spatially-periodic structure within slab-volume SV3.

37. Apparatus of claim 33 wherein said array of detector-pixels is also spatially periodic in direction y so that centroids of the front surfaces of adjacent detector-pixels within said spatially-periodic array are periodically spaced from each other in the direction y by the distance $a_{Dy}$.

38. Apparatus of claim 37 wherein said structure within slab-volume SV2 is fabricated and configured to be additionally spatially-periodic within its associated useful y-direction width with period $a_{2y}$ and with the additional associated periodicity-direction lying in the direction y; and wherein, when said object is absent, and for x-rays with at least one energy value that lies within said energy-bandwidth and throughout the associated useful y-direction width of said material structure within slab-volume SV3, then the structures within slab-volumes SV1 and SV2 acting together but not separately project onto slab-volume SV3 an x-ray intensity distribution that is additionally substantially spatially-periodic in direction y with the spatial period $a_{Py}$; and wherein when the greatest common integer divisor of b and q is 1, then the period $a_{Py}$ is accurately related to $a_{2y}$ by $$a_{Py}=a_{2y}(R_1+R_2)(q\, p\, R_1)^{-1},$$

and wherein $a_{Dy}$ is accurately related to $a_{Py}$ by $a_{Dy}=(v/u)\, a_{Py}$; and wherein the spatial phase of said spatially periodic x-ray intensity distribution projected when said object is absent onto slab-volume SV3 with period $a_{Py}$ is carefully aligned with the phase of said detector-pixel array.

39. Apparatus of claim 32 wherein said structure within slab-volume SV3 is spatially-periodic in direction x with the spatial period $a_{3x}$; and wherein said structure is oriented within the apparatus so that the periodicity-direction associated with spatial period $a_{3x}$ lies in the direction x; and wherein a is accurately related to $a_{Px}$ by $a_{3x}=v\, a_{Px}$; and wherein the spatial phase of said spatially periodic x-ray intensity distribution projected when said object is absent onto slab-volume SV3 with period $a_{Px}$ is carefully aligned with the phase of said spatially-periodic structure within slab-volume SV3; and wherein $a_{3y}$ is a distance measured in direction y.

40. Apparatus of claim 39 wherein said structure within slab-volume SV3 acts as a spatially-periodic mask; and wherein the spatial profile of the intensity distribution of x-rays projected onto slab-volume SV3 is masked by said structure within slab-volume SV3; and wherein said x-ray image-detector measures said masked profile.

41. Apparatus of claim 40 wherein said structure within slab-volume SV3 is made from a material that absorbs x-rays and is configured so that its spatially-periodic structure acts as said spatially-periodic mask.

42. Apparatus of claim 39 wherein said structure within slab-volume SV3 is made from a fluor material that absorbs x-rays and that responds to said x-ray absorption by the emission of light; and wherein said x-ray image detector images the spatial profile of the distribution of light emission by said fluor material.

43. Apparatus of claim 39 wherein said structure within slab-volume SV3 is fabricated and configured to be additionally spatially-periodic within its associated useful y-direction width with period $a_{3y}$ and with the additional additional periodicity-direction lying in the direction y.

44. Apparatus of claim 43 wherein said structure within slab-volume SV2 is fabricated and configured to be additionally spatially-periodic within its associated useful y-direction width with period $a_{2y}$ and with the additional associated periodicity-direction lying in the direction y; and wherein, when said object is absent, and for x-rays with at least one specific energy value that lies within said energy-bandwidth, and throughout the associated useful x-direction width of said material structure within slab-volume SV3, then the two structures respectively within slab-volumes SV1 and SV2 acting together but not separately project onto slab-volume SV3 an x-ray intensity distribution that is substantially spatially-periodic in direction y with the spatial period $a_{Py}$; and wherein $a_{3y}$ is accurately related to $a_{Py}$ by $a_{3y} = v\, a_{Py}$; and wherein the spatial phase of said spatially periodic x-ray intensity distribution projected when said object is absent onto slab-volume SV3 with period $a_{Py}$ is carefully aligned with the phase of said detector-pixel array.

45. Apparatus of claim 39 wherein said image that describes the internal structure of said object is divided into image-pixels; and wherein each image-pixel has an associated gray-scale for any produced image; and wherein the quantity w is a positive integer; and wherein $a_{Rx}$ is accurately related to $a_{3x}$ by $a_{Rx} = w\, a_{3x}$; and wherein $a_{Ry}$ is accurately related to $a_{3y}$ by $a_{Ry} = w\, a_{3y}$; and wherein each image-pixel is associated with an $a_{Rx}$-by-$a_{Ry}$ area on a slab face of slab-volume SV3; and wherein each image-pixel has dimensions scaled similarly in directions x and y, and has a width and height that are scaled similarly from the associated distances $a_{Rx}$ and $a_{Ry}$; and wherein each image-pixel-associated $a_{Rx}$-by-$a_{Ry}$ area on said slab face of slab-volume SV3 is subdivided into a multiplicity of labeled component areas that includes at least one associated b-labeled area and that includes at least one associated d-labeled area, and also may include other labeled component areas; and wherein said specific names for said labels are inconsequential, as long as they are applied consistently to produce the same apparatus; and wherein said other component areas may include one associated c-labeled area, and also may include additional associated b-labeled, c-labeled, and d-labeled areas; and wherein the b-labels, c-labels, and d-labels within any two $a_{Rx}$-by-$a_{Ry}$ areas on said slab face of slab-volume SV3 are configured to have the same geometric arrangement of said component area labels as each other when the centroids of the two $a_{Rx}$-by-$a_{Ry}$ areas are spaced from each other in the direction x by a distance that is an integral multiple of $a_{3x}$; and wherein said x-ray image detector is segmented into detector-pixels; and wherein said x-ray image detector measures simultaneously and independently the intensity of x-rays incident on each detector-pixel; and wherein said x-ray image detector is segmented and positioned so that simultaneously and independently some of its various detector-pixels measure the intensities of x-rays incident only on associated b-labeled areas and some of its various detector-pixels measure the intensities of x-rays incident only on associated d-labeled areas; and wherein each of said gray-scales is computed as a function of the measured intensity of x-rays incident on at least one associated b-labeled area and of the measured intensity of x-rays incident on at least one associated d-labeled area; and wherein said gray-scale computation function also may depend on measured intensities of x-rays incident on additional associated b-labeled areas and also may depend on measured intensities incident on additional associated d-labeled areas; and wherein said apparatus further includes means for performing said computation.

46. Apparatus of claim 45 wherein said gray-scale computation function includes a weighted linear combination of said measured intensities; and wherein at least one weight factor in said linear combination is negative.

47. Apparatus of claim 45 wherein the b-labels, c-labels, and d-labels within any two $a_{Rx}$-by-$a_{Ry}$ areas on said slab face of slab-volume SV3 are configured to have the same geometric arrangement of said component area labels as each other when the centroids of the two $a_{Rx}$-by-$a_{Ry}$ areas are spaced from each other in the direction y by a distance that is an integral multiple of $a_{3y}$.

48. Apparatus of claim 45 for producing at least two different images of the same object;

wherein said two different images display different physical properties of said object; and wherein said x-ray image detector is segmented and positioned so that simultaneously and independently some of its various detector-pixels measure the intensities of x-rays incident only on b-labeled areas and some of its various detector-pixels measure the intensities of x-rays incident only on c-labeled areas and some of its various detector-pixels measure the intensities of x-rays incident only on d-labeled areas; and wherein each gray-scale for each image-pixel for the first of said two different images is computed as a function of the measured intensity of x-rays incident on at least one associated b-labeled area, and of the measured intensity of x-rays incident on at least one associated c-labeled area, and of of the measured intensity of x-rays incident on at least one associated d-labeled area; and wherein each gray-scale for each image-pixel for the second of said two different images is computed as a function of the measured intensity of x-rays incident on at least one associated b-labeled area, and of the measured intensity of x-rays incident on at least one associated c-labeled area, and of the measured intensity of x-rays incident on at least one associated d-labeled area; and wherein the function used for the first of said two different images is different from the function used for the second of said two images.

49. Apparatus of claim 48 wherein a third image is produced, and wherein said third image is colored, and wherein one color component of said third image is scaled from the gray-scales of the first image, and wherein a different color component of said third image is scaled from the gray-scales of the second image.

50. Apparatus of claim 39 for measuring the x-ray refractive-index-gradient structure of an object and for producing an image with edge-enhanced features;

wherein said refractive-index-gradient structure of said object induces a significant change to the intensity distribution of x-rays projected onto slab-volume SV3, relative to said distribution projected when said object is absent; and wherein the distance $a_{3x}$ has a sufficiently small value that the interaction of x-rays with said spatially-periodic structure within slab-volume SV3 provides, at least in part, means for detecting said significant change.

51. Apparatus of claim 39 further comprising means for adjusting the relative alignment of the spatially-periodic material structures within slab-volumes SV1, SV2, and SV3; wherein said means for adjusting the relative alignment of the spatially-periodic material structures within slab-volumes SV1, SV2, and SV3 comprises means for moving at least two of the three structures within slab-volumes SV1, SV2, and SV3, a laser that emits light, a telescope, a mirror, and an optical image detector;

wherein said telescope focuses said laser-emitted light; and wherein the focusing of said telescope is adjustable; and wherein said mirror transmits x-rays; and wherein said mirror reflects at least some of said laser-emitted light; and wherein said optical image detector detects and thereby measures the spatial profile of the intensity distribution of laser-emitted telescope-focused light that is incident upon it; and wherein said x-ray image detector may serve as said optical image detector; and wherein said mirror, said laser, and said telescope are positioned so that with appropriate focusing of said telescope said laser-emitted telescope-focused light propagates in the sequential order, first through said structure within slab-volume SV1, next through said structure within slab-volume SV2, next into slab-volume SV3, and then is detected; and wherein said spatially-periodic structures within slab-volumes SV1, SV2, and SV3 are each made from a material that also interacts with said laser-emitted telescope-focused light; and wherein with appropriate focusing of said telescope said propagation of laser-emitted telescope-focused light through said spatially-periodic material structure within slab-volume SV1 generates by diffraction Fraunhofer diffraction orders; and wherein laser-emitted telescope-focused light propagating in at least two of said Fraunhofer diffraction orders that are generated by diffraction of laser-emitted telescope-focused light by material within slab-volume SV1 is incident on said structure within slab-volume SV2; and wherein the propagation of the laser-emitted telescope-focused light in each of said at least two Fraunhofer diffraction orders through said spatially-periodic material structure within slab-volume SV2 generates by diffraction more Fraunhofer diffraction orders; and wherein laser-emitted telescope-focused light propagating in one of said Fraunhofer diffraction orders that is generated by diffraction of laser-emitted telescope-focused light by said structure within slab-volume SV2 is incident on a first incidence area on said structure within slab-volume SV3; and wherein laser-emitted telescope-focused light propagating in a second one of said Fraunhofer diffraction orders that is generated by diffraction of laser-emitted telescope-focused light by said structure within slab-volume SV2 is incident on a second incidence area on said structure within slab-volume SV3; and wherein said first and second incidence areas overlap; and wherein by said overlap said laser-emitted telescope-focused light incident within said overlap-area forms a spatially-periodic optical interference pattern on said structure within slab-volume SV3; and wherein said spatial periodicities of said optical interference pattern and of said spatially-periodic material structure within slab-volume SV3 together create a spatially-periodic moiré pattern, if and when their two associated spatial periods are incommensurate; and wherein said moiré pattern is imaged by said optical image detector; and wherein observations of said moiré pattern can be used to guide said relative alignment adjustments.

52. Apparatus of claim 51 further comprised of means for adjusting said laser's wavelength, wherein a small adjustment of said laser's wavelength improves said optical interference pattern's fringe visibility.

53. Apparatus of claim 51 wherein said laser-emitted telescope-focused light propagating in a third one of said Fraunhofer diffraction orders that is generated by diffraction of laser-emitted telescope-focused light by said spatially-periodic material structure within slab-volume SV2 is incident on a third incidence area on said structure within slab-volume SV3; and wherein said first, second, and third incidence areas all overlap on a common three-way overlap-area; and wherein by said overlap said laser-emitted telescope-focused light incident within said common three-way overlap-area forms said spatially-periodic optical interference pattern on slab-volume SV3.

54. Apparatus of claim 1 wherein said x-ray image detector is further comprised of a plurality of small x-ray image detectors;

wherein said plurality of small x-ray image detectors can acquire simultaneously a plurality of small images; and wherein said apparatus is further comprised of means for combining said plurality of small images to form said image that describes the internal structure of said object.

55. Apparatus of claim 54 wherein said small x-ray image detectors are relatively positioned in a spatially-periodic geometrical pattern.

56. Apparatus of claim 55 wherein said spatially-periodic geometrical pattern includes gaps between said small x-ray image detectors.

57. Apparatus of claim 1 further comprised of
a multiple replication of apparatus component sets;
wherein said replication provides a plurality of x-ray image detectors; and
wherein said replication excludes replication of said object; and
wherein said replication excludes replication of said x-ray source; and
wherein said replication includes, as needed, said contents of slab-volumes SV1, SV2, and SV3; and
wherein said replication of an apparatus component is performed in such a manner that may result simply in the spatial extension of said apparatus component; and
wherein said x-ray source provides a common source of x-ray illumination for said replicated apparatus components; and
wherein each of said sets of replicated components acquires a small image that is descriptive of a portion of the internal structure of said object; and
wherein said sets of replicated components can acquire a plurality of small images simultaneously with each other; and
wherein said apparatus is further comprised of
means for combining said plurality of small images to form said image that describes the internal structure of said object.

58. Apparatus of claim 1 further comprising
means for acquiring and recording a plurality of small images,
means for combining said plurality of small images to form said image that describes the internal structure of said object,
means for acquiring at least one of said small images subsequently in time from another one of said small images, and
means for changing the relative positioning of the apparatus and the object between said temporally subsequent acquisitions of said small images.

59. Apparatus of claim 58 wherein said means for changing said relative positioning of said apparatus and the object is selected from
means for rotationally repositioning said apparatus relative to said object,
means for translationally repositioning said apparatus relative to said object, and
means for rotationally and translationally repositioning said apparatus relative to said object.

60. Apparatus for producing an image that describes the internal structure of an object, comprising
a source of x-rays,
an x-ray image detector;
improved by its further comprising
three very-thin slab-shaped volumes, SV1, SV2, and SV3, each with substantially-planar slab faces oriented relative to each other to be substantially-mutually-parallel, and each containing an associated very-thin material structure that interacts with x-rays, and
means for limiting the energy-bandwidth of detected x-rays;
wherein said three contained structures are positioned between said source and said detector so that x-rays from said source propagate in the sequential, order first through said structure within slab-volume SV1, next through said structure within slab-volume SV2, next through said object, next into slab-volume SV3, and then are detected; and
wherein, when said object is absent, and for x-rays with at least one specific energy value that lies within said energy-bandwidth, and throughout the associated useful x-direction width of said material structure within slab-volume SV3, then the two structures respectively within slab-volumes SV1 and SV2 acting together but not separately project onto slab-volume SV3 an x-ray intensity distribution that is substantially spatially-periodic and has a substantial spatial intensity variation; and
wherein, when said object is absent, and for said x-rays with said specific energy value that lies within said energy-bandwidth, then each of the two structures respectively within slab-volumes SV1 and SV2, acting alone with the other absent, projects onto slab-volume SV3 an x-ray intensity distribution that is different from said spatial distribution projected by said two structures acting together; and
wherein any associated residual spatial periodicity of either of said two distributions projected by said two structures acting alone has a diminished spatial intensity variation relative to said spatial distribution projected by said two structures acting together, and/or has a dominant spatial period that is different from that projected by said two structures acting together.

61. Method for producing an image that describes the internal structure of an object, comprising
providing a source of x-rays, and
providing an x-ray image detector;
wherein said method is improved by its further comprising
providing three very-thin slab-shaped volumes, SV1, SV2, and SV3, each with substantially-planar slab faces oriented relative to each other to be substantially-mutually-parallel, and with each slab-volume containing an associated very-thin material structure that interacts with x-rays; and
positioning said three contained structures between said source and said detector; and
propagating x-rays from said source in the sequential order, first through said structure within slab-volume SV1, next through said structure within slab-volume SV2, next through said object, next into slab-volume SV3, and then detecting the x-rays; and
limiting the energy-bandwidth of the energy spectrum of x-rays that are detected; and
configuring and further positioning the two spatially-periodic structures respectively within slab-volumes SV1 and SV2
so that when said object is absent, and for x-rays with at least one specific energy value that lies within said energy-bandwidth, and throughout the associated useful x-direction width of said material structure within slab-volume SV3, then the two structures respectively within slab-volumes SV1 and SV2 acting together but not separately project onto slab-volume SV3 an x-ray intensity distribution that is substantially spatially-periodic, and
so that when said object is absent, and for said x-rays with said specific energy value that lies within said energy-bandwidth, then each of the two structures respectively within slab-volumes SV1 and SV2, acting alone with the other absent, projects onto slab-volume SV3 an x-ray intensity distribution that is different from said spatial distribution projected by said two structures acting together, and so that any associated residual spatial periodicity of either of said two distributions projected by said two structures acting alone has a diminished spatial intensity variation relative to said spatial distribution projected by said two structures acting together, and/or has a dominant spatial period that is different from that projected by said two structures acting together.

62. Method of claim 61 wherein said object includes portion of a human body, and wherein said image is used to diagnose a disorder of said human body.

63. Method of claim 61 further comprising fabricating the material structure within slab-volume SV2 to be spatially-periodic and with an appropriate structure, spatial period, and from an appropriate material; and adjusting the positional spacing between slab-volume SV1 and SV2; and adjusting the positional spacing between slab-volume SV2 and SV3; so that if, hypothetically, with said object absent, said structure within slab-volume SV1 were to be removed and were to be replaced by an infinitesimally-small source of x-rays located at some point within slab-volume SV1, with said x-rays emitted by said infinitesimally-small source having an energy that lies within said energy-bandwidth, then the structure within slab-volume SV2 would project x-rays from said infinitesimally-small source to form a spatially-periodic x-ray intensity pattern on slab-volume SV3, with said pattern having a significant spatially-periodic spatial intensity variation.

64. Method of claim 63 further comprising forming said spatially-periodic x-ray intensity pattern on slab-volume SV3 with x-rays from said infinitesimally-small source by using wave interference of the electromagnetic waves associated with said x-rays, and by using the fractional-Talbot-effect to provide said wave interference;

wherein the Talbot effect is included as special case of the fractional Talbot effect; and wherein the formation of spatially-periodic geometric shadows is included as a further special case of the Talbot effect.

65. Method of claim 64 further comprising controlling the average energy and the energy-bandwidth of x-rays that are detected, providing an appropriately chosen structure, spatial period, and appropriate material for the structure within slab-volume SV2, providing an appropriately chosen positional spacing between slab-volume SV1 and SV2, and providing an appropriately chosen positional spacing between slab-volume SV2 and SV3, so that aspects of the fractional Talbot effect obtain for the energy-bandwidth limited spectrum of x-rays that are detected.

66. Method of claim 64 further comprising controlling the average energy and energy-bandwidth of x-rays that are detected, providing the spectrum of said controlled energy-bandwidth-limited x-rays with a multiplicity of energy component values, providing an appropriately chosen structure, spatial period, and appropriate material for the structure within slab-volume SV2, providing an appropriately chosen positional spacing between slab-volume SV1 and SV2, and providing an appropriately chosen positional spacing between slab-volume SV2 and SV3, so that aspects of the fractional Talbot effect obtain for low energy x-rays within the energy-bandwidth limited spectrum of x-rays that are detected, and so that different aspects of the fractional Talbot effect obtain for high energy x-rays within the energy-bandwidth limited spectrum of x-rays that are detected.

67. Method of claim 61 further comprising fabricating each of the two structures respectively within slab-volumes SV1 and SV2 so that its structure is spatially periodic in at least one periodicity-direction, and adjusting the orientations of said two structures and associated slab-volumes SV1 and SV2 so that said at least one associated periodicity-direction for slab-volume SV1 and said at least one associated periodicity-direction for slab-volume SV2 are both substantially-parallel to said substantially mutually-parallel slab-faces of said slab-volumes and are substantially-parallel to each other.

68. Method of claim 67 further comprising fabricating the spatially-periodic material structure within slab-volume SV1 from a material that absorbs x-rays and further configuring said spatially-periodic material structure within slab-volume SV1 with a spatially-periodic distribution of x-ray transmitting portions and x-ray absorbing portions, so that the spatially-periodic material structure within slab-volume SV1 and said source of x-rays together act as a spatially-periodic source of x-rays, and further configuring the relationships between the structure and spatial period of the structure within slab-volume SV1, and the structure and spatial period of the structure within slab-volume SV2, the energy-bandwidth-limited x-ray spectrum, and the positional spacing between slab-volume SV1 and SV2, and the positional spacing between slab-volume SV2 and SV3, so that, when said object is absent, then x-rays emitted by said source and with some energy component within said energy-bandwidth-limited x-ray spectrum source and transmitted by a large multiplicity of x-ray transmitting portions of the spatially-periodic structure within slab-volume SV1 propagate through said structure within slab-volume SV2 to thereby project onto slab-volume SV3 an associated large multiplicity of spatially-periodic x-ray intensity patterns, that each have a spatial period and a spatial phase such that the large multiplicity of intensity patterns reinforce each other in phase, and so as to maintain by said in-phase reinforcement a substantial intensity spatial variation projected onto slab-volume SV3, and so as to form by said in-phase reinforcement a high-intensity spatially-periodic x-ray intensity pattern on slab-volume SV3.

69. Method of claim 61 further comprising fabricating each of the structures respectively within slab-volume SV1 and SV2 so that its structure is spatially periodic in at least two mutually-non-parallel periodicity-directions; and adjusting the orientations of said two contained fabricated spatially-periodic material structures and associated slab-volumes so that said associated first periodicity-directions of the structures respectively within slab-volume SV1 and SV2 are both substantially parallel to said substantially mutually-parallel to slab-faces of said slab-volumes and are substantially parallel to each other, and so that said associated second periodicity-directions of the structures respectively within slab-volume SV1 and SV2 are both substantially parallel to said substantially mutually-parallel to slab-faces of said slab-volumes and are substantially parallel to each other.

70. Method of claim 61 further comprising fabricating the structures respectively within slab-volumes SV1 and SV2, each from a material that absorbs x-rays, each with a spatially-periodic arrangement of x-ray transmitting portions and x-ray absorbing portions, and each with an appropriate spatial period, adjusting the positional spacing between slab-volume SV1 and SV2, and adjusting the positional spacing between slab-volume SV2 and SV3, so that the structure within slab-volume SV2 and said infinitesimally-small source of x-rays within slab-volume SV1 together project said spatially-periodic x-ray intensity pattern onto slab-volume SV3 as a spatially-periodic geometric x-ray shadow of said spatially-periodic material structure within slab-volume SV2.

71. Method of claim 61 further comprising fabricating the structure within slab-volume SV2, from a material that absorbs x-rays, and with a spatially-periodic arrangement of x-ray transmitting portions and x-ray absorbing portions.

72. Method of claim 61 further comprising fabricating the structure within a slab-volume with a spatially-periodic spatial-thickness-profile that has the approximate form of a periodic step-function.

73. Method of claim 61 further comprising fabricating a structure within a slab-volume from a material that refracts x-rays, and fabricating said structure within said slab-volume to be spatially-periodic in at least one periodicity-direction, so that it then acts as an x-ray phase grating.

74. Method of claim 73 further comprising fabricating said structure within said slab-volume from a material and with a typical thickness so as to diminish the absorption of x-rays by said said structure.

75. Method of claim 61 further comprising fabricating the spatially-periodic material structure within slab-volume SV1 from a material that absorbs x-rays, and configuring said spatially-periodic material structure within slab-volume SV1 with a spatially-periodic distribution of x-ray transmitting portions and x-ray absorbing portions, so that the spatially-periodic material structure within slab-volume SV1 and said source of x-rays together act as a spatially-periodic source of x-rays.

76. Method of claim 61 further comprising providing the spectrum of said energy-bandwidth-limited x-rays with a multiplicity of energy component values, projecting a first x-ray intensity pattern onto slab-volume SV3 when said object is present using low energy x-rays within said energy-bandwidth limited spectrum, and projecting a second x-ray intensity pattern onto slab-volume SV3 when said object is present using high energy x-rays within said energy-bandwidth limited spectrum, so that said first and second patterns are different from each other, and detecting the difference between said first and second patterns.

77. Method of claim 76 further comprising creating an image from said difference, and using said difference to provide information concerning the spatial distribution and material composition of said object.

78. Method of claim 76 further comprising configuring said energy-bandwidth-limited x-ray spectrum so that at least one of its low energy components has an energy below the energy of an x-ray absorption edge of some chemical element;

configuring said energy-bandwidth-limited x-ray spectrum so that at least one of its high energy components has an energy above the energy of an x-ray absorption edge of some chemical element; and obtaining said image for an object, wherein said chemical element is anisotropically distributed within said object.

79. Method of claim 61 further comprising configuring the x-ray energy bandwidth and the average x-ray energy, the parameters, periodicities, materials, structures, and structural configurations for the contents of slab-volumes SV1, SV2, and SV3, the spacing between slab-volumes SV1 and SV2, and the spacing between slab-volumes SV2 and SV3, so that, when said object is absent, then a substantially-spatially-periodic x-ray intensity distribution is projected onto slab-volume SV3 by the structures within slab-volumes SV1 and SV2 for x-rays with said energy-bandwidth-limited spectrum.

80. Method of claim 61 for measuring the x-ray refractive-index-gradient structure of an object and for producing an image with edge-enhanced features, further comprising diminishing the spatial period of said substantially spatially-periodic x-ray intensity distribution projected onto slab-volume SV3 when said object is absent for x-rays with said at least one specific energy, using the presence of said object and further using said refractive-index-gradient structure of said object to induce significant changes to an intensity distribution of x-rays projected onto slab-volume SV3, detecting said changes, and forming an image from the spatial distribution of said changes.

81. Method of claim 61 further comprising detecting x-rays by using at least part of said structure within slab-volume SV3 as at least one component of said x-ray image detector.

82. Method of claim 61 further comprising spatially masking image detection by said x-ray image detector by using said structure within slab-volume SV3 as a spatially-periodic mask.

83. Method of claim 82 further comprising configuring the spatially-periodic mask pattern of said structure within slab-volume SV3 by using a tiling algorithm.

84. Method of claim 61 further comprising fabricating the material structure within slab-volume SV3 to be spatially-periodic with an appropriate spatial period and with an appropriate spatial structure, and accurately relatively positioning said structures within slab-volumes SV1, SV2, and SV3, so that the spatial phase and period of said structure within slab-volume SV3 are accurately harmonically related to the spatial phase and period of said spatially-periodic x-ray intensity distribution projected by said two structures respectively within slab-volumes SV1 and SV2 acting together when said object is absent and with said at least one specific x-ray energy value that lies within said energy-bandwidth.

85. Method of claim 84 further comprising spatially masking said spatially-periodic x-ray intensity distribution projected by said two structures respectively within slab-volumes SV1 and SV2 acting together when said object is absent and with said at least one specific x-ray energy value that lies within said energy-bandwidth, by using said structure within slab-volume SV3 as a spatially-periodic mask, and segmenting said x-ray image detector into a spatially-periodic array of detector-pixels, accurately positioning said spatially-periodic array of detector-pixels relative to said spatially-periodic masking structure within slab-volume SV3, and providing an accurate harmonic relationship between the spatial periods of said spatially-periodic array of detector-pixels and of a spatially-periodic x-ray intensity distribution that hypothetically would be projected onto said detector in the absence of said structure within slab-volume SV3 and in the absence of said object by x-rays from said x-ray source and by said structures respectively within slab-volumes SV1 and SV2 all acting together.

86. Method of claim 84 for obtaining accurate relative positions and orientations for said structures that are contained within said slab-volumes, further comprising providing a source of light;

providing an optical image detector;

wherein said x-ray image detector may serve as said optical image detector; and fabricating the structures within slab-volumes SV1 and SV2 from a material such said structures within slab-volumes SV1 and SV2 transmit and diffract light;

propagating light in sequence through slab-volume SV1, through slab-volume SV2, and onto slab-volume SV3;

diffracting said light by said structures in slab-volumes SV1 and SV2;

forming a spatially-periodic optical-interference-pattern in said light on slab-volume SV3, wherein said optical-interference-pattern has a spatial period and periodicity-direction that are directly related to said spatial period and periodicity-direction of said spatially-periodic x-ray intensity distribution projected by said two structures respectively within slab-volumes SV1 and SV2 acting together when said object is absent and with said at least one specific x-ray energy value that lies within said energy-bandwidth; and forming a moiré pattern between said optical-interference-pattern and said spatially-periodic structure within slab-volume SV3; detecting said moiré pattern;

changing said moiré pattern by adjusting the relative positions and orientations of said structures; and detecting said changes;

adjusting the relative positions and orientations of said structures by using said detected changes as a guide; and guiding said adjustments to obtain accurate relative positions and orientations for said structures.

87. Method of claim 86 further comprising adjusting the wavelength of said light, and controlling the spectrum of said light, thereby improving said optical-interference-pattern's fringe visibility.

88. Method of claim 86 further comprising focusing said light prior to propagating it through slab-volume SV1, providing by said diffraction and by said focusing a multiplicity of optical foci near slab-volume SV3, and adjusting the relative spacings between slab-volumes SV1, SV2 and SV3 so that said foci coincide.

89. Method of claim 86 further comprising adjusting said relative positions and orientations of said structures by iterating various adjustment steps;

wherein said various adjustment steps include at least two of the following steps:

focusing said light prior to propagating it through slab-volume SV1 so that its optical focus lies near slab-volume SV1 and then adjusting the position of said structure within slab-volume SV2 as a step, focusing said light prior to propagating it through slab-volume SV1 so that its optical focus lies near slab-volume SV1 and then adjusting the orientation of said structure within slab-volume SV2 as a step, focusing said light prior to propagating it through slab-volume SV1 so that its optical focus lies near slab-volume SV2 and then adjusting the position of said structure within slab-volume SV1 as a step, focusing said light prior to propagating it through slab-volume SV1 so that its optical focus lies near slab-volume SV2 and then adjusting the orientation of said structure within slab-volume SV1 as a step, and adjusting the wavelength of said light as a step.

90. Method of claim 61 for removing x-ray-scatter-induced unsharpness from said image, further comprising segmenting said x-ray image detector into a spatially-periodic array of detector-pixels with an appropriate spatial period and with an appropriate spatial structure;

accurately relatively positioning said structures within slab-volumes SV1 and SV2 and said array of detector-pixels so that the spatial phase and period of said array of detector-pixels are accurately harmonically related to and are phase matched to the spatial phase and period of said spatially-periodic x-ray intensity distribution projected by said two structures respectively within slab-volumes SV1 and SV2 acting together when said object is absent and with said at least one specific x-ray energy value that lies within said energy-bandwidth;

selecting from said array as a spatially-periodic-set a first set of detector-pixels that are illuminated by x-rays in x-ray BRIGHT areas of said projected distribution;

selecting from said array as a spatially-periodic-set a second set of detector-pixels that are illuminated by x-rays in x-ray DARK areas of said projected distribution;

measuring x-ray intensities using said detector-pixel array with said object present;

subtracting intensities measured with said object present by said second set of detector-pixels from intensities measured with said object present by said first set of detector-pixels; and forming an image from said subtracted intensities.

91. Method of claim 90 wherein detector-pixels are selected from said array as spatially-periodic-sets, further comprising configuring said spatially-periodic-sets of detector-pixels via a tiling algorithm, and configuring said spatially-periodic-sets of detector-pixels so that different sets are disjoint, and configuring said spatially-periodic-sets of detector-pixels so that different sets of detector-pixels are spatially interlaced with each other, and configuring said spatially-periodic-sets of detector-pixels so that each set provides sparse spatially-periodic array of detector pixels.

92. Method of claim 90 for producing at least two different images of the same object, wherein said two different images display different physical properties of said object, further comprising selecting from said array as a spatially-periodic-set a third set of detector-pixels, using a first algorithm to provide a first image from x-ray intensities measured when said object is present by said first, second and third sets of detector pixels, and using a second algorithm to provide a second image from x-ray intensities measured when said object is present by said first, second and third sets of detector pixels, wherein said first algorithm is different from said second algorithm.

93. Method of claim 61 further comprising acquiring and recording data for a plurality of partial images, wherein each of said partial images describes a portion of the internal structure of said object; and synthesizing said partial images; thereby forming an image that describes the internal structure of said object.

94. Method of claim 93 further comprising configuring said x-ray image detector as of a plurality of partial-image detectors, and acquiring said data for said plurality of partial images by detecting x-rays with said plurality of partial-image detectors.

95. Method of claim 93 further comprising acquiring said data for said plurality of partial images as a sequence of temporally-spaced data-acquisition steps; and using the same x-ray image detector sequentially more than once during said temporal sequence of steps.

96. Method of claim 95 further comprising repositioning said structures that lie within slab-volumes SV1, SV2, and SV3, and said x-ray image detector relative to said object while maintaining the relative positioning of said structures that lie within slab-volumes SV1, SV2, and SV3, and said x-ray image detector, and performing said relative repositioning between data-acquisition steps as a step in said temporal sequence.

97. Method of claim 96 wherein said relative repositioning is comprised of rotating said structures that lie within slab-volumes SV1, SV2, and SV3, and said x-ray image detector, relative to said object.

98. Method of claim 96 wherein said relative repositioning is comprised of translating linearly said structures that lie within slab-volumes SV1, SV2, and SV3, and said x-ray image detector, relative to said object.

99. Method of claim 96 wherein said relative repositioning is comprised of simultaneously translating linearly and rotating said structures that lie within slab-volumes SV1, SV2, and SV3, and said x-ray image detector, relative to said object, thereby providing helical trajectories for the motions of said structures and detector.

100. Method of claim 93 for producing an image that describes the three-dimensional internal structure of an object, wherein said synthesizing is comprised of performing a tomographic transformation of acquired image data.

* * * * *